United States Patent
McGonagle et al.

(10) Patent No.: US 10,995,073 B2
(45) Date of Patent: May 4, 2021

(54) PARG INHIBITORY COMPOUNDS

(71) Applicant: CANCER RESEARCH TECHNOLOGY LIMITED, London (GB)

(72) Inventors: Alison E. McGonagle, Manchester (GB); Allan M. Jordan, Manchester (GB); Bodhan Waszkowycz, Manchester (GB); Colin P. Hutton, Manchester (GB); Ian D. Waddell, Manchester (GB); James R. Hitchin, Manchester (GB); Kate M. Smith, Manchester (GB); Niall M. Hamilton, Manchester (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 16/662,997

(22) Filed: Oct. 24, 2019

(65) Prior Publication Data
US 2020/0165208 A1 May 28, 2020

Related U.S. Application Data

(66) Division of application No. 15/533,819, Substitute for application No. PCT/GB2015/054064, filed on Dec. 17, 2015, now Pat. No. 10,508,086.

(30) Foreign Application Priority Data

Dec. 19, 2014 (GB) .................................... 1422771

(51) Int. Cl.
| | | |
|---|---|---|
| C07D 235/26 | (2006.01) | |
| C07D 403/04 | (2006.01) | |
| C07D 413/04 | (2006.01) | |
| A61K 31/4184 | (2006.01) | |
| C07D 413/14 | (2006.01) | |
| C07D 401/06 | (2006.01) | |
| C07D 403/06 | (2006.01) | |
| C07D 405/04 | (2006.01) | |
| C07D 405/06 | (2006.01) | |
| C07D 409/04 | (2006.01) | |
| C07D 413/06 | (2006.01) | |
| C07D 417/04 | (2006.01) | |
| C07D 417/14 | (2006.01) | |
| C07D 417/06 | (2006.01) | |

(Continued)

(52) U.S. Cl.
CPC ............ *C07D 235/26* (2013.01); *A61P 35/00* (2018.01); *C07D 307/85* (2013.01); *C07D 401/06* (2013.01); *C07D 403/04* (2013.01); *C07D 403/06* (2013.01); *C07D 405/04* (2013.01); *C07D 405/06* (2013.01); *C07D 409/04* (2013.01); *C07D 413/04* (2013.01); *C07D 413/06* (2013.01); *C07D 413/14* (2013.01); *C07D 417/04* (2013.01); *C07D 417/06* (2013.01); *C07D 417/14* (2013.01)

(58) Field of Classification Search
CPC .............. A61K 31/4184; C07D 235/26; C07D 403/04; C07D 413/04
See application file for complete search history.

(56) References Cited

U.S. PATENT DOCUMENTS

| | | |
|---|---|---|
| 4,429,126 A | 1/1984 | Ueda et al. |
| 5,472,961 A | 12/1995 | Gottschlich et al. |

(Continued)

FOREIGN PATENT DOCUMENTS

| | | |
|---|---|---|
| CN | 101429191 A | 5/2009 |
| DE | 19927415 A1 | 12/2000 |

(Continued)

OTHER PUBLICATIONS

Handke et al, machine translation of WO0076966, 2000, p. 1-30 (Year: 2000).*
Chang, Yu Mi et al., "Petasis reaction of activated quinolone and isoquinoline with various boronic acids," Tetrahedron Letters (Mar. 2, 2005); 46:3053-3056.
Osmialowski, Borys et al., "2-Acylamino—and 2,4-Bis(acylamino)pyrimidines as Supramolecular Synthons Analyzed by Multiple Noncovalent Interactions. DFT, X-ray Diffraction, and NMR Spectral Studies," The Journal of Organic Chemistry (Nov. 2, 2012); 77:9609-9619.

(Continued)

*Primary Examiner* — Karen Cheng
(74) *Attorney, Agent, or Firm* — Mintz, Levin, Cohn, Ferris, Glovsky & Popeo, P.C.

(57) ABSTRACT

The present invention relates to compounds of formula I that function as inhibitors of PARG (Poly ADP-ribose glycohydrolase) enzyme activity: wherein $R_{1a}$, $R_{1b}$, $R_{1c}$, $R_{1d}$, $R_{1e}$, W, $X_1$, $X_2$, $X_3$, $X_4$, $X_5$, $X_6$, $X_7$, c are each as defined herein. The present invention also relates to processes for the preparation of these compounds, to pharmaceutical compositions comprising them, and to their use in the treatment of proliferative disorders, such as cancer, as well as other diseases or conditions in which PARG activity is implicated.

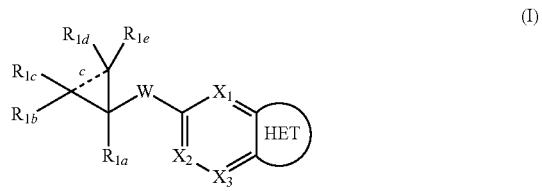

(I)

16 Claims, No Drawings

(51) Int. Cl.
*A61P 35/00* (2006.01)
*C07D 307/85* (2006.01)

(56) References Cited

U.S. PATENT DOCUMENTS

| | | |
|---|---|---|
| 7,994,202 B2 | 8/2011 | Atobe et al. |
| 2007/0049593 A1 | 3/2007 | Oka et al. |
| 2012/0329784 A1 | 12/2012 | Lallander et al. |
| 2014/0171363 A1 | 6/2014 | Barnes et al. |
| 2018/0194738 A1 | 7/2018 | McGonagle et al. |

FOREIGN PATENT DOCUMENTS

| | | |
|---|---|---|
| EP | 1719773 A1 | 11/2006 |
| RU | 2348635 C2 | 3/2009 |
| WO | 00/76966 A2 | 12/2000 |
| WO | 00/76966 A3 | 12/2000 |
| WO | WO0076966 * | 12/2000 |
| WO | 01/02369 A2 | 1/2001 |
| WO | 01/16108 A2 | 3/2001 |
| WO | 01/16108 A3 | 3/2001 |
| WO | 2003068743 A1 | 8/2003 |
| WO | 2004/083204 A1 | 9/2004 |
| WO | 2005/030212 A1 | 4/2005 |
| WO | 2005092890 A1 | 10/2005 |
| WO | 2007/014226 A2 | 2/2007 |
| WO | 2007/087488 A2 | 8/2007 |
| WO | 2009/047255 A1 | 4/2009 |
| WO | 2011/140325 A1 | 11/2011 |
| WO | 2011/140442 A1 | 11/2011 |
| WO | 2012/035078 A1 | 3/2012 |
| WO | 2012/080284 A2 | 6/2012 |
| WO | 2012/080284 A3 | 6/2012 |
| WO | 2012089721 1 | 7/2012 |
| WO | 2012160464 A2 | 12/2012 |
| WO | 2013/027168 A1 | 2/2013 |
| WO | 2013/067300 A1 | 5/2013 |
| WO | 2014026327 A1 | 2/2014 |
| WO | 2014028589 21 | 2/2014 |
| WO | 2014/106019 A2 | 7/2014 |
| WO | 2014/106019 A3 | 7/2014 |
| WO | 2015121209 A1 | 8/2015 |

OTHER PUBLICATIONS

Peng, Chin-Tzu et al., "The Synthesis of Some 6-N-Substituted Amido Derivatives of 4,6-Diaminquinaldine and a Study of their in vitro Antibacterial Activity," Journal of the American Chemical Society (Jan. 1, 1956); 78:3703-3708.
Rörsch, Florian et al., Structure-Activity Relationship of Nonacidic Quinazolinone Inhibitors of Human Microsomal Prostaglandin Synthase 1 (mPGES 1); Journal of Medicinal Chemistry (Apr. 26, 2012); 55(8):3792-3803.
Registry No. 1709761-66-9, 6-Quinolinesulfonamide, 2-(thylamino)-N-(1-methylcycloprpyl)-, EPO Data, entered STN: May 21, 2015.
Registry No. 1709660-65-0, 6-Quinolinesulfonamide, 2-amino-N-(1-methylcyclopropyl)-. EPO Data, entered STN: May 21, 2015.
Registry No. 1776414-48-2, 7-Quinolinesulfonamide, 1,2,3,4,-tetrahydro-N-(1-methylcycloprpyl)-, EPO Data, entered STN: Jun. 9, 2015.
Registry No. 1776626-70-0, 6-Quinolinesulfonamide, 2-(methylamino)-N-(1-methylcyclopropyl)-, EPO Data, entered STN: Jun. 9, 2015.
Registry No. 1776710-34-9, 6-Quinolinesolfonamide, 1.2.3.4.-tetrahyrdo-N-(1-methylcycloprophyl, EPO Data, entered STN: Jun. 9, 2015.
Registry No. 1777097-79-6, 6-Quinolinesulfonamide, 2-chloro-N-(1-methycyclopropyl)-, EPO Data, entered STN: Jun. 10, 2015.
UK Search Report dated Oct. 5, 2015 corresponding to priority application, GB1422098.2 filed on Dec. 12, 2014, 6 pages.
International Search Report dated Feb. 23, 2016 corresponding to International Patent Application No. PCT/GB2015/053883 filed on Dec. 11, 2015, 17 pages.

International Search Report dated Feb. 4, 2016 corresponding to International Patent Application No. PCT/GB2015/054064 filed on Dec. 17, 2015, 17 pages.
UK Search Report dated Oct. 1, 2015 corresponding to priority application, GB1422771.4 filed on Dec. 19, 2014, 5 pages.
Aldlab Chemicals Building Blocks (Nov. 2, 2014), Order No. Cat. AX103678857, see CHEMCATS Acc. No. 2132286836 for the compound having CAS Reg. No. 1411077-15-0; 18 pages.
Amé, Jean-Christophe, "Radiation-induced mitotic catastrophe in PARG-deficient cells," *Journal of Cell Science* (Accepted Feb. 24, 2009); 122:1990-2002.
Barber, Louise J. et al., "Secondary mutations in BRCA2 associated with clinical resistance to a PARP inhibitor," *J Pathol* (2013; accepted Oct. 24, 2012); 229:442-429.
Blen, Christian et al., "The Ups and Downs of Tannins as Inhibitors of Poly(ADP-Ribose)glycohydrolase," *Molecules* (Feb. 22, 2011) 16:1854-1877.
Caiafa, Paola et al., "Epigenetics: poly(ADP-ribosyl)ation of PARP-1 regulates genomic methylation patterns," *The FASEB Journal* (Mar. 2009; accepted for publication Oct. 23, 2008); 23:672-678.
Curtin, Nicola et al., "Therapeutic Applications of PARP Inhibitors: Anticancer Therapy and Beyond," *Mol Aspects Med.* (Dec. 2013; available in PMC Dec. 1, 2014); 34(6): .doi:10.106/j.mam.2013.01. 006 (71 pages).
Dahl, Markus et al., "Fine-Tuning of Smad Protein Function by Poly(ADP-Ribose) Polymerases and Poly(ADP-Ribose) Glycohydrolase during Transforming Growth Factor β Signaling," *PLOS ONE* (Aug. 18, 2014); 9(8):e103651 (19 pages).
Drost, R. et al., "Opportunities and hurdles in the treatment of BRCA1-related breast cancer," *Oncogene* (2014; published online Aug. 19, 2013) 33:3753-3763.
Erdélyi, Katalin et al., "Dual role of poly(ADP-ribose) glycohydrolase in the regulation of cell death in oxidatively stressed A549 cells," *FASEB J.* (Oct. 2009; accepted Jun. 4, 2009); 23(10):3553-3563.
Fathers, Catherine et al., "Inhibition of poly(ADP-ribose) glycohydrolase (PARG) specifically kills BRCA2-deficient tumor cells," *Cell Cycle* (Mar. 1, 2012); 11(5):990-997.
Fisher, Anna E. O. et al., "Poly(ADP-Ribose) Polymerase 1 Accelerates Single-Strand Break Repair in Concert with Poly(ADP-Ribose) Glycohydrolase," *Molecular and Cellular Biology* (Aug. 2007; published ahead of print Jun. 4, 2007); 27(15):5597-5604.
Frizzell, Kristine M. et al., "Global Analysis of Transcriptional Regulation by Poly(ADP-ribose) Polymerase-1 and Poly(ADP-ribose) Glycohydrolase in MCF-7 Human Breast Cancer Cells," *Journal of Biological Chemistry* (Dec. 4, 2009); 284(49):33926-33938.
Fujihara, H. et al., "*Poly(ADP-ribose)* Glycohydrolase Deficiency Sensitizes Mouse ES Cells to DNA Damaging Agents," *Current Cancer Drug Targets* (Accepted Sep. 17, 2009); 9:953-962.
Guastafierro, Tiziana et al., "ADP-ribose polymer depletion leads to nuclear Ctcf re-localization and chromatin rearrangement," *Biochem J.* (2013; published as BJ Immediate publication Nov. 2, 2012); 449:623-630.
Ji, Y et al., "Poly(ADP-ribosyl)ation of heterogeneous nuclear ribonucleaoproteins modulates splicing," *Nucleic Acids Research* (published online Apr. 3, 2009); 37(11):3501-3513.
Le May, Nicolas et al., "Poly(ADP-Ribose) Glycohydrolase Regulates Retinoic Acid Receptor-Mediated Gene Expression," *Molecular Cell* (Dec. 14, 2012); 48:785-798.
Mashimo, Masato et al., "Structure and function of the ARH family of ADP-ribose-acceptor hydrolases," *DNA Repair (Mast).* (Nov. 2014; available in PMC Nov. 1, 2015); 0:88-94. Doi:10.1016/j. dnarep.2014.03.005; 19 pages.
Mortusewicz, Oliver et al., "PARG is recruited to DNA damage sites through poly(ADP-ribose)—and PCNA-dependent mechanisms," *Nucleic Acids Research* (Mar. 11, 2011); 39(12):5045-5056.
Nakadate, Yusuke et al., "Silencing of poly(ADP-ribose) glycohydrolase sensitizes lung cancer cells to radiation through the abrogation of DNA damage checkpoint," Biochemical and Biophysical Research Communications (available online Nov. 6, 2013); 441:793-798.
Registry No. 1146895-94-4, 1H-Benzimidazole-5-sulfonamide, N-cyclopropyl-2, 3-dihydro-1, 3-dimethyl-2-oxo, May 15, 2009, 3 pages.

(56) References Cited

OTHER PUBLICATIONS

Registry No. 708996-44-5, 1H-Benzimidazole-5-sulfonamide, N-cyclopropyl-2, 3-dihydro-2-oxo-, Jul. 13, 2004, 1 page.

Shirai, Hidenori et al., "*Parg* deficiency confers radio-sensitization through enhanced cell death in mouse ES cells exposed to various forms of ionizing radiation," *Biochemical and Biophysical Research Communications* (available online Apr. 23, 2013); 435:100-106.

Shirai, H. et al., "PARG dysfunction enhances DNA double strand break formation in S-phase after alkylation DNA damage and augments different cell death pathways," *Cell Death and Disease* (accepted Mar. 1, 2013); 4:e656; doi:10.1038/cddis.2013.133; 10 pages.

Substance Record for SID 49925576 *Pubchem* (Jul. 10, 2008) NCBI XP55244188; 6 pages.

Substance Record for SID 105027706 *Pubchem* (Feb. 22, 2011) NCBI XP55244192; 6 pages.

Sun, Yanyan et al., "Tannic acid, an inhibitor of poly(ADP-ribose) glycohyrolase, sensitizes ovarian carcinoma cells to cisplatin", Anti-Cancer Drugs, (Revised form accepted May 23, 2012) 23(9):979-990.

Tani, Junichi et al., "Studies on biologically Active Halogenated Compounds. II. Chemical Modifications of 6-Amino-2-fluoromethyl-3-(*o-tolyl*)-4(*3H*)-quinazolinone and the CNS Depressant Activities of Related Compounds," *Chem. Pharm. Bull.* (Nov. 1, 1979); 27(11):2675-2687.

Zhou, Yiran et al., "Enhanced DNA Accessibility and Increased DNA Damage Induced by the Absence of Poly(ADP-ribose) Hydrolysis," Biochemistry (published on Web Jul. 23, 2010); 49(34):7360-7366.

Zhou, Yiran et al., "Synergistic cytotoxicity of N-methyl-N'-nitro-N-nitrosoguanidine and absence of poly(ADP-ribose) glycohydrolase involves chromatin decondensation," International Journal of Oncology (accepted Feb. 11, 2011); 39:121-127.

\* cited by examiner

PARG INHIBITORY COMPOUNDS

FIELD OF THE INVENTION

The present invention relates to certain compounds that function as inhibitors of PARG (Poly ADP-ribose glycohydrolase) enzyme activity. The present invention also relates to processes for the preparation of these compounds, to pharmaceutical compositions comprising them, and to their use in the treatment of proliferative disorders, such as cancer, as well as other diseases or conditions in which PARG activity is implicated.

BACKGROUND OF THE INVENTION

Cancer is caused by uncontrolled and unregulated cellular proliferation. The consequence of this often rapid proliferation is a high level of oxidative stress within the tumour which damages DNA and leads to a much-increased mutation rate. Tumour cells therefore engage and rely heavily upon DNA damage repair mechanisms.

Single-strand breaks (SSBs) are the commonest type of lesion arising in cells and PARG (Poly ADP-ribose glycohydrolase) together with PARP is involved along with a number of other proteins in single strand break repair (SSBR) and another repair mechanism called base excision repair (BER).

One of the earliest events during single strand DNA repair is the binding of PARP (poly ADP-ribose polymerase) to the break and the rapid synthesis of poly ADP-ribose (PAR) on PARP itself. This molecular structure serves as a signal to recruit other DNA repair proteins, initially XRCC1, which will then repair the break (Mortusewicz, Fouquerel et al. 2011). The signal initiated by these PAR chains is short-lived as they are rapidly degraded by the enzyme PAR glycohydrolase (PARG). When PARP is bound to PAR, its catalytic activity is reduced and therefore PARG activity helps to restore PARP to its catalytically active form (Curtin and Szabo 2013).

PARG exists as a single gene with isoforms that reside in the nucleus, mitochondria and cytosol. The only other known protein with glycohydrolase activity is ARH3 which is localised to the mitochondria (Mashimo, Kato et al. 2014). Although, known primarily for its direct role in DNA repair, PARG impacts PAR signalling in splicing, transcriptional and epigenetic pathways (Ji and Tulin 2009) (Le May, Iltis et al. 2012) (Dahl, Maturi et al. 2014) (Guastafierro, Catizone et al. 2013) (Caiafa, Guastafierro et al. 2009).

Cancer cells may become addicted to a specific DNA repair pathway when other mechanisms of DNA repair are non-functional. Tumours carrying mutations in proteins involved in double strand break repair are often more sensitive to PARP inhibitors of SSBR. There is already some evidence that PARG depletion inhibits SSBR and reduces survival of BRCA2-deficient cells (Fathers, Drayton et al. 2012). However, other tumour mutations may give rise to deficiencies in double strand DNA repair mechanisms (so-called "BRCA-ness") thereby sensitising tumour cells to PARG inhibition.

PARG depletion has been studied in a number of murine and human model systems. Murine cells that are null or depleted for PARG display an increased sensitivity to experimental and clinical DNA damaging agents. However, as deficiency in PARG doesn't sensitise to all agents (e.g. gemcitabine, camptothecin) this suggests a specificity for PARG function with certain pathways of DNA damage repair and chemo- and radiotherapies (Fujihara, Ogino et al. 2009) (Shirai, Fujimori et al. 2013) (Zhou, Feng et al. 2010) (Zhou, Feng et al. 2011).

In humans PARG depletion sensitises lung, cervical and pancreatic cancer cells to γ-irradiation or experimental DNA damaging agents (e.g. hydrogen peroxide, Methylmethanesulfonate) (Ame, Fouquerel et al. 2009) (Nakadate, Kodera et al. 2013) (Shirai, Poetsch et al. 2013).

PARP inhibitors are currently undergoing a raft of clinical trials where the concept of synthetic lethality or chemosensitisation is being explored. Clinical resistance to PARP inhibitors has already been described (Drost and Jonkers 2014) (Barber, Sandhu et al. 2013) and therefore there is a requirement that alternative inhibitors targeting the DNA damage repair machinery are found. As PARG depletion leads to reduced rates of SSBR to the same extent as depletion of PARP1, PARG inhibition may provide a therapeutic advantage in PARP inhibitor resistant cells (Fisher, Hochegger et al. 2007). Furthermore, depletion of PARG has been reported to lead to a markedly different gene expression pattern to that of PARP depletion in breast cancer cells (Frizzell, Gamble et al. 2009).

Although current models show that PARG depletion leads to PARP-dependent effects on DNA repair, recent research has shown a mechanistic differentiation from PARP inhibition. Following a genotoxic stimulus depletion of PARG, in contrast to PARP depletion, leads to a drop in NAD levels. This leads to lung cancer cell death that may be as a result of energy failure (Erdelyi, Bai et al. 2009).

Cell permeable PARG inhibitors have been limited to compounds such as Tannic acid or Gallotannin which have questionable specificity for PARG and limited bioavailability (Sun, Zhang et al. 2012) (Fathers, Drayton et al. 2012) (Blenn, Wyrsch et al. 2011).

An object of this invention is to provide specific cell permeable inhibitors of PARG.

SUMMARY OF THE INVENTION

In one aspect, the present invention provides a compound as defined herein, or a pharmaceutically acceptable salt or solvate thereof.

In another aspect, the present invention provides a pharmaceutical composition as defined herein which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the production of a PARG inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of a PARG inhibitory effect.

In another aspect, the present invention provides a method of inhibiting PARG in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

The present invention further provides a method of synthesising a compound, or a pharmaceutically acceptable salt or solvate thereof, as defined herein.

In another aspect, the present invention provides a compound as defined herein, or a pharmaceutically acceptable salt or solvate thereof, obtainable by, or obtained by, or directly obtained by a method of synthesis as defined herein.

In another aspect, the present invention provides novel intermediates as defined herein which are suitable for use in any one of the synthetic methods as set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(2-6C)alkenylene" means a linear divalent hydrocarbon radical of two to six carbon atoms or a branched divalent hydrocarbon radical of three to six carbon atoms, containing at least one double bond, for example, as in ethenylene, 2,4-pentadienylene, and the like.

"(2-6C)alkynylene" means a linear divalent hydrocarbon radical of two to six carbon atoms or a branched divalent hydrocarbon radical of three to six carbon atoms, containing at least one triple bond, for example, as in ethynylene, propynylene, and butynylene and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl.

"(3-8C)cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

"(3-8C)cycloalkyl-(1-6C)alkylene" means a (3-8C)cycloalkyl group covalently attached to a (1-6C)alkylene group, both of which are defined herein.

The term "halo" or "halogeno" refers to fluoro, chloro, bromo and iodo.

The term "heterocyclyl", "heterocyclic" or "heterocycle" means a non-aromatic saturated or partially saturated monocyclic, fused, bridged, or spiro bicyclic heterocyclic ring system(s). The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydro-triazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxo-imidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, $4^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5-or 6-membered monocyclic ring or a 9-or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

a benzene ring fused to a 5-or 6-membered ring containing 1, 2 or 3 ring heteroatoms;

a pyridine ring fused to a 5-or 6-membered ring containing 1, 2 or 3 ring heteroatoms;

a pyrimidine ring fused to a 5-or 6-membered ring containing 1 or 2 ring heteroatoms;

a pyrrole ring fused to a 5-or 6-membered ring containing 1, 2 or 3 ring heteroatoms;

a pyrazole ring fused to a 5-or 6-membered ring containing 1 or 2 ring heteroatoms;

a pyrazine ring fused to a 5-or 6-membered ring containing 1 or 2 ring heteroatoms;

an imidazole ring fused to a 5-or 6-membered ring containing 1 or 2 ring heteroatoms;

an oxazole ring fused to a 5-or 6-membered ring containing 1 or 2 ring heteroatoms;

an isoxazole ring fused to a 5-or 6-membered ring containing 1 or 2 ring heteroatoms;

a thiazole ring fused to a 5-or 6-membered ring containing 1 or 2 ring heteroatoms;

an isothiazole ring fused to a 5-or 6-membered ring containing 1 or 2 ring heteroatoms;

a thiophene ring fused to a 5-or 6-membered ring containing 1, 2 or 3 ring heteroatoms;

a furan ring fused to a 5-or 6-membered ring containing 1, 2 or 3 ring heteroatoms;
a cyclohexyl ring fused to a 5-or 6-membered heteroaromatic ring containing 1, 2 or 3 ring heteroatoms; and
a cyclopentyl ring fused to a 5-or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(1-6C)alkyl" means a heteroaryl group covalently attached to a (1-6C)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(1-6C)alkyl" means an aryl group covalently attached to a (1-6C)alkylene group, both of which are defined herein. Examples of aryl-(1-6C)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds of formula (I) shown below:

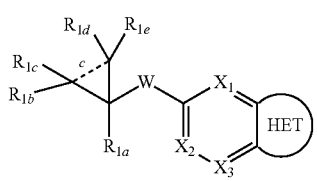

(I)

wherein:
bond c is absent or a single bond;
$R_{1a}$ is selected from hydrogen, fluoro, chloro, cyano, formyl, (1-2C)alkyl, (1-2C) haloalkyl, (2C)alkenyl, or (2C)alkynyl;
$R_{1b}$, $R_{1c}$, $R_{1d}$, and $R_{1e}$ are each independently selected from H, fluoro or methyl;
W is selected from —NH—S(O)$_y$—, —S(O), —NH—, —C(O)NH—, —NHC(O)—, —NH—S(O)(NH)—, S(O)(NH)—NH—, wherein y is 0, 1 or 2;
$X_1$ is selected from $CR_2$ or N; wherein $R_2$ is H or fluoro;
$X_2$ is selected from $CR_3$ or N; wherein $R_3$ is H or fluoro;
$X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or
$R_4$ is selected from a group of the formula:

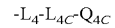
-L$_4$-L$_{4C}$-Q$_{4C}$ wherein
L$_4$ is absent or (1-3C)alkylene optionally substituted by (1-2C)alkyl or oxo;
L$_{4C}$ is absent or selected from O, S, SO, SO$_2$, N(R$_{4b}$), C(O), C(O)O, OC(O), C(O)N(R$_{4b}$), N(R$_{4b}$)C(O), N(R$_{4b}$)C(O)N(R$_{4c}$), S(O)$_2$N(R$_{4b}$), or N(R$_{4b}$)SO$_2$, wherein R$_{4b}$ and R$_{4c}$ are each independently selected from hydrogen or (1-2C)alkyl; and
Q$_{4C}$ is hydrogen, (1-6C)alkyl, (3-6C)cycloalkyl, aryl, heterocyclyl or heteroaryl; and wherein Q$_6$ is optionally substituted by one or more substituents selected from halo, trifluoromethyl, trifluoromethoxy, amino, cyano, hydroxy, amino, carboxy, carbamoyl, sulphamoyl, (1-4C)alkyl, NR$_{4d}$R$_{4e}$, OR$_{4d}$, C(O)R$_{4d}$, C(O)OR$_{4d}$, OC(O)R$_{4d}$, C(O)N(R$_{4e}$)R$_{4d}$, N(R$_{4e}$)C(O)R$_{4d}$, S(O)$_y$R$_{4d}$ (where y is 0, 1 or 2), SO$_2$N(R$_{4e}$)R$_{4d}$, N(R$_{4e}$)SO$_2$R$_{4d}$ or (CH$_2$)$_z$NR$_{4e}$R$_{4d}$ (where z is 1, 2 or 3), wherein R$_{4d}$ and R$_{4e}$ are each independently selected from H or (1-4C)alkyl;
HET is a fused 5-membered saturated, partially saturated or unsaturated heterocyclic ring of formula:

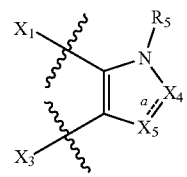

wherein
bond a is optionally a double bond;
R$_s$ is H, (1-4C)alkyl or a group of the formula:

-L$_1$-L$_5$-Q$_5$ wherein
L$_1$ is absent or selected from (1-3C)alkylene optionally substituted by (1-2C)alkyl or oxo, or a (2-3C)alkenylene or (2-3C)alkynylene linker that is optionally substituted by (1-2C)alkyl;
L$_5$ is absent or selected from C(O), C(O)O, OC(O), C(O)N(R$_a$), N(R$_a$)C(O), N(R$_a$)C(O)N(R$_b$), S(O)$_2$N(R$_a$), N(R$_a$)SO$_2$, wherein R$_a$ and R$_b$ are each independently selected from hydrogen or (1-2C)alkyl; and
Q$_5$ is selected from hydrogen, (1-4C)alkyl, aryl, 5-6 membered heteroaryl, (4-6C)cycloalkyl, (4-6C)cycloalkenyl, (2C)alkenyl or 5-6 membered heterocyclyl; and wherein Q$_5$ is optionally substituted by one or more substituents selected from (1-4C)alkyl, halo, amino, cyano, amino, carboxy, carbamoyl, sulphamoyl, trifluoromethoxy, haloalkyl, $NR_cR_d$, $OR_c$, $C(O)R_c$, $C(O)OR_c$, $OC(O)R_c$, $C(O)N(R_c)R_d$, $N(R_c)C(O)R_d$, $S(O)_yR_c$ (where y is 0, 1 or 2), $SO_2N(R_c)R_d$, $N(R_c)SO_2R_d$ or $(CH_2)_zNR_cR_d$ (where z is 1, 2 or 3), wherein $R_c$ and $R_d$ are each independently selected from H or (1-4C)alkyl; or $Q_5$ is optionally substituted by a group of the formula;

$-W_5-Y_5-Z_5$ wherein
   $W_5$ is absent or selected from (1-3C)alkylene optionally substituted by (1-2C)alkyl or oxo, or a (2-3C)alkenylene or (2-3C)alkynylene linker that is optionally substituted by (1-2C)alkyl;
   $Y_5$ is absent or selected from C(O), C(O)O, OC(O), $C(O)N(R_e)$, $N(R_e)C(O)$, $N(R_e)C(O)N(R_f)$, $S(O)_2N(R_e)$, $N(R_e)SO_2$, wherein $R_e$ and $R_f$ are each independently selected from hydrogen or (1-2C)alkyl; and
   $Z_5$ is selected from hydrogen, (1-4C)alkyl, phenyl, 5 or 6-membered heterocyclyl or a 5-6 membered heteroaryl; and wherein $Z_5$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl or sulphamoyl;

$X_4$ is selected from C(=O), C(=NH), C(=S), $CHR_{6c}$ or $N-R_{6N}$ when bond a is a single bond, or $CR_{6c}$ or N when bond a is a double bond;
   wherein
   $R_{6c}$ is selected from hydrogen, cyano, halo or a group of the formula:

$-L_6-L_{6C}-Q_{6C}$ wherein
   $L_6$ is absent or (1-3C)alkylene optionally substituted by (1-2C)alkyl or oxo;
   $L_{6C}$ is absent or selected from O, S, SO, $SO_2$, $N(R_g)$, C(O), C(O)O, OC(O), $C(O)N(R_g)$, $N(R_g)C(O)$, $N(R_g)C(O)N(R_h)$, $S(O)_2N(R_g)$, or $N(R_g)SO_2$, wherein $R_g$ and $R_h$ are each independently selected from hydrogen or (1-2C)alkyl; and
   $Q_{6C}$ is hydrogen, (1-4C)alkyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl, $NR_iR_j$, $OR_i$, $C(O)R_i$, $C(O)OR_i$, $OC(O)R_i$, $C(O)N(R_i)R_j$, $N(R_i)C(O)R_j$, $S(O)_yR_i$ (where y is 0, 1 or 2), $SO_2N(R_i)R_j$, $N(R_i)SO_2R_j$ or $(CH_2)_zNR_iR_j$ (where z is 1, 2 or 3), wherein $R_i$ and $R_j$ are each independently selected from H or (1-4C)alkyl;

$R_{6N}$ is selected from hydrogen or a group of the formula:

$-L_6-L_{6N}-Q_{6N}$ wherein
   $L_6$ is absent or (1-3C)alkylene optionally substituted by (1-2C)alkyl or oxo;
   $L_{6N}$ is absent or selected from O, S, SO, $SO_2$, $N(R_k)$, C(O), C(O)O, OC(O), $C(O)N(R_k)$, $N(R_k)C(O)$, $N(R_k)C(O)N(R_l)$, $S(O)_2N(R_k)$, or $N(R_k)SO_2$, wherein $R_k$ and $R_l$ are each independently selected from hydrogen or (1-2C)alkyl; and
   $Q_{6N}$ is hydrogen, cyano, (1-6C)alkyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl, $NR_mR_n$, $OR_m$, $C(O)R_m$, $C(O)OR_m$, $OC(O)R_m$, $C(O)N(R_m)R_n$, $N(R_m)C(O)R_n$, $S(O)_yR_m$ (where y is 0, 1 or 2), $SO_2N(R_m)R_n$, $N(R_m)SO_2R_n$ or $(CH_2)_zNR_mR_n$ (where z is 1, 2 or 3), wherein $R_m$ and $R_n$ are each independently selected from H or (1-4C)alkyl;

$X_5$ is selected from C(=O), C(=NH), C(=S), $CHR_{7c}$ or $N-R_{7N}$ when bond a is a single bond, or $CR_{7c}$ or N when bond a is a double bond;
   wherein
   $R_{7c}$ is selected from hydrogen, cyano, halo or a group of the formula:

$-L_7-L_{7C}-Q_{7C}$ wherein
   $L_7$ is absent or (1-3C)alkylene optionally substituted by (1-2C)alkyl or oxo;
   $L_{7C}$ is absent or selected from O, S, SO, $SO_2$, $N(R_o)$, C(O), C(O)O, OC(O), C(O)N(R), $N(R_o)C(O)$, $N(R_o)C(O)N(R_p)$, $S(O)_2N(R_o)$, or $N(R_o)SO_2$, wherein $R_o$ and $R_p$ are each independently selected from hydrogen or (1-2C)alkyl; and
   $Q_{7C}$ is hydrogen, cyano, (1-6C)alkyl, (2C)alkynyl, (2-3C)alkenyl, (3-6C)cycloalkyl, aryl, heterocyclyl or heteroaryl; and wherein $Q_{8C}$ is optionally substituted by one or more substituents selected from (1-4C)alkyl, halo, trifluoromethyl, trifluoromethoxy, amino, cyano, nitro, hydroxy, amino, carboxy, carbamoyl, sulphamoyl, $NR_qR_r$, $OR_q$, $C(O)R_q$, $C(O)OR_q$, $OC(O)R_q$, $C(O)N(R_q)R_r$, $N(R_q)C(O)R_r$, $S(O)_yR_q$ (where y is 0, or 2), $SO_2N(R_q)R_r$, $N(R_q)SO_2R_r$ or $(CH_2)_zNR_qR_r$ (where z is 1, 2 or 3), wherein $R_q$ and $R_r$ are each independently selected from H or (1-4C)alkyl; or
   $Q_{7C}$ is optionally substituted by a group of the formula:

$-W_{7C}-L_{7'}-Z_{7C}$ wherein
   $W_{7C}$ is absent or (1-3C)alkylene substituted by (1-2C)alkyl or oxo;
   $L_{7'}$ is absent or selected from C(O), C(O)O, OC(O), $C(O)N(R_s)$, $N(R_s)C(O)$, $N(R_s)C(O)N(R_t)$, $S(O)_2N(R_s)$, or $N(R_s)SO_2$, wherein $R_s$ and $R_t$ are each independently selected from hydrogen or (1-2C)alkyl; and
   $Z_{7C}$ is phenyl or 5-6 membered heteroaryl; each of which is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl or sulphamoyl;

$R_{7N}$ is selected from hydrogen or a group of the formula:

$-L_7-L_{7N}-Q_{7N}$ wherein
   $L_7$ is absent or (1-3C)alkylene optionally substituted by (1-2C)alkyl;
   $L_{7N}$ is absent or selected from O, S, SO, $SO_2$, $N(R_u)$, C(O), C(O)O, OC(O), $C(O)N(R_u)$, $N(R_u)C(O)$, $N(R_u)C(O)N(R_v)$, $S(O)_2N(R_u)$, or $N(R_u)SO_2$, wherein $R_u$ and $R_v$ are each independently selected from hydrogen or (1-2C)alkyl; and
   $Q_{7N}$ is hydrogen, cyano, (1-6C)alkyl, (2C)alkynyl, (2-3C)alkenyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl, $NR_wR_x$, $OR_w$, $C(O)R_w$, $C(O)OR_c$, $OC(O)R_w$, $C(O)N(R_w)R_x$, $N(R_w)C(O)R_x$, $S(O)_yR_w$ (where y is 0, 1 or 2), $SO_2N(R_w)R_x$, $N(R_w)SO_2R_x$ or $(CH_2)_zNR_wR_x$ (where z is 1, 2 or 3), wherein $R_w$ and $R_x$ are each independently selected from H or (1-4C)alkyl; or $Q_{7N}$ is optionally substituted by a group of the formula:

—$W_{7N}$-$L_7$-$Z_{7N}$ wherein
  $W_{7N}$ is absent or (1-3C)alkylene optionally substituted by (1-3C)alkyl;
  $L_{7'}$ is absent or selected from C(O), C(O)O, OC(O), C(O)N($R_y$), N($R_y$)C(O), N($R_y$)C(O)N($R_z$), $S(O)_2N(R_y)$, or N($R_y$)$SO_2$, wherein $R_y$ and $R_z$ are each independently selected from hydrogen or (1-2C)alkyl; and
  $Z_{7N}$ is phenyl or 5-6 membered heteroaryl; each of which is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl or sulphamoyl;

with the proviso that:
  (i) only one or two of $R_{1b-e}$ can be selected from any substituent other than H;
  (ii) only one or two of $X_1$, $X_2$ or $X_3$ can be N;
  (iii) Het may only comprise up to 2 ring nitrogen atoms; and
  (iv) only one of $X_4$ or $X_5$ can be selected from C(=O), C(=NH) or C(=S).

Particular compounds of the invention include, for example, compounds of the formula I, or pharmaceutically acceptable salts and/or solvates thereof, wherein, unless otherwise stated, each of c, $R_{1a}$, $R_{1b}$, $R_{1c}$, $R_{1d}$, $R_{1e}$, W, $X_1$, $X_2$, $X_3$, $X_4$, $X_5$, $R_5$ and any associated substituent groups has any of the meanings defined hereinbefore or in any of paragraphs (1) to (55) hereinafter:

(1) c is a single bond;
(2) $R_{1a}$ is selected from hydrogen, fluoro, cyano, formyl, (1-2C)alkyl, (1-2C)haloalkyl or (2C)alkynyl;
(3) $R_{1a}$ is selected from hydrogen, cyano, formyl, (1-2C)alkyl or (1-2C)haloalkyl;
(4) $R_{1a}$ is selected from hydrogen, cyano, methyl or $CF_3$;
(5) $R_{1a}$ is selected from hydrogen, cyano, methyl or fluoromethyl;
(6) $R_{1a}$ is selected from cyano, methyl or fluoromethyl;
(7) $R_{1a}$ is selected from methyl or fluoromethyl;
(8) $R_{1a}$ is methyl;
(9) $R_{1b}$, $R_{1c}$, $R_{1d}$ and $R_{1e}$ are independently selected from H, fluoro;
(10) $R_{1b}$, $R_{1c}$, $R_{1d}$ and $R_{1e}$ are H;
(11) W is selected from —NH—S(O)$_y$—, —S(O)—, —NH—, —C(O)NH— or —NHC(O)—, wherein y is 0, 1 or 2;
(12) W is selected from —NH—S(O)$_2$—, —S(O)$_2$—NH—, —C(O)NH— or —NHC(O)—;
(13) W is selected from —NH—S(O)$_2$— or —S(O)$_2$—NH—;
(14) W is —NH—S(O)$_2$—;
(15) $X_1$ is N or $CR_2$, wherein $R_2$ is H or fluoro;
(16) $X_1$ is N or CH;
(17) $X_1$ is CH;
(18) $X_2$ is N or $CR_3$, wherein $R_3$ is H or fluoro;
(19) $X_2$ is N or CH;
(20) $X_2$ is CH or CF;
(21) $X_2$ is CH;
(22) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or
$R_4$ is selected from a group of the formula:

-$L_4$-$L_{4C}$-$Q_{4C}$ wherein
$L_4$ is absent or (1-3C)alkylene optionally substituted by (1-2C)alkyl or oxo;
$L_4$ is absent or selected from O, S, SO, $SO_2$, N($R_{4b}$), C(O), C(O)O, OC(O), C(O)N($R_{4b}$), N($R_{4b}$)C(O), N($R_{4b}$)C(O)N($R_{4c}$), $S(O)_2N(R_{4b})$, or N($R_{4b}$)$SO_2$, wherein $R_{4b}$ and $R_{4c}$ are each independently selected from hydrogen or (1-2C)alkyl; and
$Q_{4C}$ is hydrogen, (1-6C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl, sulphamoyl, (1-4C)alkyl, $NR_{4d}R_{4e}$, $OR_{4d}$, $C(O)R_{4d}$, $C(O)OR_{4d}$, $OC(O)R_{4d}$, $C(O)N(R_{4e})R_{4d}$, $N(R_{4e})C(O)R_{4d}$, $S(O)_yR_{4d}$ (where y is 0, 1 or 2), $SO_2N(R_{4e})R_{4d}$, $N(R_{4e})SO_2R_{4d}$ or $(CH_2)_zNR_{4e}R_{4d}$ (where z is 1, 2 or 3), wherein $R_{4d}$ and $R_{4e}$ are each independently selected from H or (1-4C)alkyl;

(23) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or
$R_4$ is selected from a group of the formula:

-$L_4$-$L_{4C}$-$Q_{4C}$ wherein
$L_4$ is absent or (1-3C)alkylene optionally substituted by (1-2C)alkyl or oxo;
$L_4$ is absent or selected from O, S, SO, $SO_2$, N($R_{4b}$), C(O), C(O)O, OC(O), C(O)N($R_{4b}$), N($R_{4b}$)C(O), N($R_{4b}$)C(O)N($R_{4c}$), $S(O)_2N(R_{4b})$, or N($R_{4b}$)$SO_2$, wherein $R_{4b}$ and $R_{4c}$ are each independently selected from hydrogen or (1-2C)alkyl; and
$Q_{4C}$ is hydrogen, (1-6C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl or sulphamoyl;

(24) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or
$R_4$ is selected from a group of the formula:

-$L_4$-$L_{4C}$-$Q_{4C}$ wherein
$L_4$ is absent or (1-3C)alkylene optionally substituted by (1-2C)alkyl or oxo;
$L_{4C}$ is absent or selected from $SO_2$, N($R_{4b}$), C(O), C(O)O, OC(O), C(O)N($R_{4b}$), N($R_{4b}$)C(O), wherein $R_{4b}$ is selected from hydrogen or (1-2C)alkyl; and
$Q_{4C}$ is hydrogen, (1-6C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl, sulphamoyl, (1-4C)alkyl, $NR_{4d}R_{4e}$, $OR_{4d}$, $C(O)R_{4d}$, $C(O)OR_{4d}$, $OC(O)R_{4d}$, $C(O)N(R_{4e})R_{4d}$, $N(R_{4e})C(O)R_{4d}$, $S(O)_yR_{4d}$ (where y is 0, 1 or 2), $SO_2N(R_{4e})R_{4d}$, $N(R_{4e})SO_2R_{4d}$ or $(CH_2)_zNR_{4e}R_{4d}$ (where z is 1, 2 or 3), wherein $R_{4d}$ and $R_{4e}$ are each independently selected from H or (1-4C) alkyl;

(25) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or
$R_4$ is selected from a group of the formula:

$L_4$-$L_{4C}$-$Q_{4C}$ wherein
$L_4$ is absent or (1-3C)alkylene optionally substituted by (1-2C)alkyl or oxo;
$L_{4C}$ is absent or selected from $SO_2$, $N(R_{4b})$, $C(O)$, $C(O)O$, $OC(O)$, $C(O)N(R_{4b})$, $N(R_{4b})C(O)$, wherein $R_{4b}$ is selected from hydrogen or (1-2C)alkyl; and
$Q_{4C}$ is hydrogen, (1-6C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl or sulphamoyl;

(26) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or
$R_4$ is selected from a group of the formula:

-$L_4$-$L_{4C}$-$Q_{4C}$ wherein
$L_4$ is absent or (1-2C)alkylene optionally substituted by (1-2C)alkyl or oxo;
$L_{4C}$ is absent or selected from $C(O)O$, $OC(O)$, $C(O)N(R_{4b})$, $N(R_{4b})C(O)$, wherein $R_{4b}$ is selected from hydrogen or (1-2C)alkyl; and
$Q_{4C}$ is hydrogen, (1-4C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl or sulphamoyl;

(27) $X_3$ is selected form $CR_4$ or N; wherein $R_4$ is H, halo, cyano, (1-2C)alkyl, (1-2C)haloalkyl, (1-2C)alkoxy, (1-2C)haloalkoxy or (2C)alkynyl; or
$R_4$ is selected from a group of the formula:

-$L_{4C}$-$Q_{4C}$ wherein
$L_4$ is absent or selected from $C(O)N(R_{4b})$, wherein $R_{4b}$ is selected from hydrogen or (1-2C)alkyl; and
$Q_{4C}$ is hydrogen, (1-4C)alkyl, (3-6C)cycloalkyl, aryl, heterocyclyl or heteroaryl; and wherein $Q_{6C}$ is optionally substituted by one or more substituents selected from halo, trifluoromethyl, trifluoromethoxy, amino, cyano, hydroxy, amino, carboxy, carbamoyl or sulphamoyl;

(28) $X_3$ is selected form $CR_4$ or N; wherein $R_4$ is H, halo, cyano, (1-2C)alkyl, (1-2C)haloalkyl, or (2C)alkynyl;

(29) $X_3$ is selected form $CR_4$ or N; wherein $R_4$ is H, halo, (1-2C)alkyl or (1-2C)haloalkyl;

(30) $X_3$ is selected form $CR_4$ or N; wherein $R_4$ is H, fluoro, methyl or $CF_3$;

(31) $X_3$ is selected form $CR_4$ or N; wherein $R_4$ is H or fluoro;

(32) $X_3$ is CH or CF;

(33) $X_4$ is selected from C(=O), C(=NH), C(=S), $CHR_{6c}$ or N—$R_{6N}$ when bond a is a single bond, or $CR_{6c}$ or N when bond a is a double bond;
wherein
$R_{6c}$ is selected from hydrogen, cyano, halo or a group of the formula:

-$L_6$-$L_{6C}$-$Q_{6C}$ wherein
$L_6$ is absent or (1-3C)alkylene optionally substituted by (1-2C)alkyl or oxo;
$L_{6C}$ is absent or selected from O, S, SO, $SO_2$, $N(R_g)$, $C(O)$, $C(O)O$, $OC(O)$, $C(O)N(R_g)$, $N(R_g)C(O)$, $N(R_g)C(O)N(R_h)$, $S(O)_2N(R_g)$, or $N(R_g)SO_2$, wherein $R_g$ and $R_h$ are each independently selected from hydrogen or (1-2C)alkyl; and
$Q_{6C}$ is hydrogen, (1-4C)alkyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl or $NR_iR_j$, wherein $R_i$ and $R_j$ are each independently selected from H or (1-4C)alkyl;
$R_{6N}$ is selected from hydrogen or a group of the formula:

-$L_6$-$L_{6N}$-$Q_{6N}$ wherein
$L_6$ is absent or (1-3C)alkylene optionally substituted by (1-2C)alkyl or oxo;
$L_{6N}$ is absent or selected from O, S, SO, $SO_2$, $N(R_k)$, $C(O)$, $C(O)O$, $OC(O)$, $C(O)N(R_k)$, $N(R_k)C(O)$, $N(R_k)C(O)N(R_l)$, $S(O)_2N(R_k)$, or $N(R_k)SO_2$, wherein $R_k$ and $R_l$ are each independently selected from hydrogen or (1-2C)alkyl; and
$Q_{6N}$ is hydrogen, cyano, (1-6C)alkyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl or $NR_mR_n$, wherein $R_m$ and $R_n$ are each independently selected from H or (1-4C)alkyl;

(34) $X_4$ is selected from C(=O), C(=NH), C(=S), $CHR_{6c}$ or N—$R_{6N}$ when bond a is a single bond, or $CR_6$ or N when bond a is a double bond;
wherein
$R_{6c}$ is selected from hydrogen, cyano, halo or a group of the formula:

-$L_6$-$L_{6C}$-$Q_{6C}$ wherein
$L_6$ is absent or (1-3C)alkylene optionally substituted by (1-2C)alkyl or oxo;
$L_{6C}$ is absent or selected from O, S, SO, $SO_2$, $N(R_g)$, $C(O)$, $C(O)O$, $OC(O)$, $C(O)N(R_g)$, $N(R_g)C(O)$, $N(R_g)C(O)N(R_h)$, $S(O)_2N(R_g)$, or $N(R_g)SO_2$, wherein $R_g$ and $R_h$ are each independently selected from hydrogen or (1-2C)alkyl; and
$Q_{6C}$ is hydrogen, (1-4C)alkyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, carboxy, carbamoyl, sulphamoyl or $NR_iR_j$ wherein $R_i$ and $R_j$ are each independently selected from H or (1-4C)alkyl;
$R_{6N}$ is selected from hydrogen or a group of the formula:

-$L_6$-$Q_{6N}$ wherein
$L_6$ is absent or (1-3C)alkylene optionally substituted by (1-2C)alkyl or oxo;
$Q_{6N}$ is hydrogen, cyano, (1-4C)alkyl, (3-6C)cycloalkyl, aryl, heterocyclyl or 5- or 6-membered heteroaryl, each of which is optionally substituted by one or more substituents selected from (1-4C)alkyl, halo, trifluoromethyl, amino or cyano;

(35) $X_4$ is selected from $C(=O)$, $C(=NH)$, $C(=S)$, $CHR_6$ or $N-R_{6N}$ when bond a is a single bond, or $CR_{6c}$ or $N$ when bond a is a double bond;
wherein
$R_{6c}$ is selected from hydrogen, cyano, halo or a group of the formula:

$-L_6-L_{6C}-Q_{6C}$ wherein
$L_6$ is absent or (1-3C)alkylene optionally substituted by (1-2C)alkyl or oxo;
$L_{6C}$ is absent or selected from O, S, SO, $SO_2$, $N(R_g)$, $C(O)$, $C(O)O$, $OC(O)$, $C(O)N(R_g)$, $N(R_g)C(O)$, $N(R_g)C(O)N(R_h)$, $S(O)_2N(R_g)$, or $N(R_g)SO_2$, wherein $R_g$ and $R_h$ are each independently selected from hydrogen or (1-2C)alkyl; and
$Q_{6C}$ is hydrogen, (1-4C)alkyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, carboxy, carbamoyl, sulphamoyl or $NR_iR_j$, wherein R and $R_j$ are each independently selected from H or (1-4C)alkyl;

(36) $X_4$ is selected from $C(=O)$, $C(=NH)$, $C(=S)$, $CHR_{6Q}$ or $N-R_{6N}$ when bond a is a single bond, or $CR_{6c}$ or N when bond a is a double bond;
wherein
$R_{6c}$ is selected from hydrogen or a group of the formula:

$-L_6-L_{6C}-Q_{6C}$ wherein
$L_6$ is absent or (1-3C)alkylene optionally substituted by (1-2C)alkyl or oxo;
$L_{6C}$ is absent or selected from O, S, SO, $SO_2$, $N(R_g)$, $C(O)$, $C(O)O$, $OC(O)$, $C(O)N(R_g)$, $N(R_g)C(O)$, wherein $R_g$ is selected from hydrogen or (1-2C)alkyl; and
$Q_{6C}$ is hydrogen, (1-4C)alkyl, (3-6C)cycloalkyl, aryl, (3-6C)heterocyclyl or 5-or 6-membered heteroaryl, each of which is optionally substituted by one or more substituents selected from (1-4C)alkyl, halo, trifluoromethyl, trifluoromethoxy, amino, cyano, hydroxy, carboxy, carbamoyl, sulphamoyl or $NR_iR_j$, wherein $R_i$ and $R_j$ are each independently selected from H or (1-2C)alkyl;

(37) $X_4$ is selected from $C(=O)$, $C(=NH)$, $CHR_{6c}$ or $N-R_{6N}$ when bond a is a single bond, or $CR_6$ or N when bond a is a double bond;
wherein
$R_{6c}$ is selected from hydrogen or a group of the formula:

$-L_6-L_{6C}-Q_{6C}$ wherein
$L_6$ is absent or (1-3C)alkylene optionally substituted by (1-2C)alkyl or oxo;
$L_{6C}$ is absent or selected from O, S, $SO_2$, $N(R_g)$, $C(O)$, $C(O)O$, $C(O)N(R_g)$, $N(R_g)C(O)$, wherein $R_g$ is selected from hydrogen or (1-2C)alkyl; and
$Q_{6C}$ is hydrogen, (1-4C)alkyl, (3-6C)cycloalkyl, aryl, (3-6C)heterocyclyl or 5-or 6-membered heteroaryl, each of which is optionally substituted by one or more substituents selected from (1-4C)alkyl, halo, trifluoromethyl, amino or cyano;

(38) $X_4$ is selected from $C(=O)$ or $CHR_{6c}$ when bond a is a single bond, or $CR_{6c}$ when bond a is a double bond;
wherein
$R_{6c}$ is selected from hydrogen or a group of the formula:

$-L_6-L_{6C}-Q_{6C}$ wherein
$L_6$ is absent or (1-2C)alkylene optionally substituted by (1-2C)alkyl;
$L_{6C}$ is absent or selected from $C(O)O$ or $C(O)N(R_g)$, wherein $R_g$ is selected from hydrogen or (1-2C)alkyl; and
$Q_{6C}$ is hydrogen, (1-4C)alkyl, phenyl or 5-or 6-membered heteroaryl, each of which is optionally substituted by one or more substituents selected from (1-4C)alkyl, halo, trifluoromethyl, amino or cyano;

(39) $X_4$ is selected from $C(=O)$ when a is a single bond, or $CR_{6c}$ when bond a is a double bond;
wherein
$R_{6c}$ is selected from hydrogen or a group of the formula:

$-L_6-L_{6C}-Q_{6C}$ wherein
$L_6$ is absent or (1-2C)alkylene;
$L_{6C}$ is absent or selected from $C(O)O$ or $C(O)N(R_g)$, wherein $R_g$ is selected from hydrogen or methyl; and
$Q_{6C}$ is hydrogen, (1-4C)alkyl, phenyl or 5-or 6-membered heteroaryl, each of which is optionally substituted by one or more substituents selected from (1-2C)alkyl, halo, trifluoromethyl, amino or cyano;

(40) $X_5$ is selected from $C(=O)$, $C(=NH)$, $C(=S)$, $CHR_{7c}$ or $N-R_{7N}$ when bond a is a single bond, or $CR_{7c}$ or N when bond a is a double bond;
wherein
$R_{7c}$ is selected from hydrogen, cyano, halo or a group of the formula:

$-L_7-L_{7C}-Q_{7C}$ wherein
$L_7$ is absent or (1-3C)alkylene optionally substituted by (1-2C)alkyl or oxo;
$L_{7C}$ is absent or selected from O, S, SO, $SO_2$, $N(R_o)$, $C(O)$, $C(O)O$, $OC(O)$, $C(O)N(R_o)$, $N(R_o)C(O)$, wherein $R_o$ is selected from hydrogen or (1-2C) alkyl; and
$Q_{7C}$ is hydrogen, cyano, (1-6C)alkyl, (2C)alkynyl, (2-3C)alkenyl, (3-6C)cycloalkyl, aryl, heterocyclyl or heteroaryl; and wherein $Q_{8C}$ is optionally substituted by one or more substituents selected from (1-4C)alkyl, halo, trifluoromethyl, trifluoromethoxy, amino, cyano, nitro, hydroxy, amino, carboxy, carbamoyl, sulphamoyl, $NR_qR_r$, $OR_q$, wherein $R_q$ and $R_r$ are each independently selected from H or (1-4C) alkyl; or
$Q_{7C}$ is optionally substituted by a group of the formula:

$—W_{7C}-L_{7'}-Z_{7C}$ wherein
$W_{7C}$ is absent or (1-3C)alkylene substituted by (1-2C)alkyl or oxo;
$L_{7'}$ is absent or selected from $C(O)$, $C(O)O$, $OC(O)$, $C(O)N(R_s)$, $N(R_s)C(O)$, wherein $R_s$ is selected from hydrogen or (1-2C)alkyl; and
$Z_{7C}$ is phenyl or 5-6 membered heteroaryl; each of which is optionally substituted by one or more substituents selected from (1-4C)alkyl or halo;
$R_{7N}$ is selected from hydrogen or a group of the formula:

$-L_7-L_{7N}-Q_{7N}$ wherein
$L_7$ is absent or (1-3C)alkylene optionally substituted by (1-2C)alkyl;

$L_{7N}$ is absent or selected from O, S, SO, SO$_2$, N(R$_u$), C(O), C(O)O, OC(O), C(O)N(R$_u$) or N(R$_u$)C(O), wherein R$_u$ is selected from hydrogen or (1-2C)alkyl; and Q$_{7N}$ is hydrogen, cyano, (1-6C)alkyl, (2C)alkynyl, (2-3C)alkenyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl, NR$_w$R$_x$, OR$_w$, C(O)R$_w$, C(O)OR$_w$, OC(O)R$_w$, C(O)N(R$_w$)R$_x$, N(R$_w$)C(O)R$_x$, S(O)$_y$R$_w$ (where y is 0, 1 or 2), SO$_2$N(R$_w$)R$_x$, N(R$_w$)SO$_2$R$_x$ or (CH$_2$)$_z$NR$_w$R$_x$ (where z is 1, 2 or 3), wherein R$_w$ and R$_x$ are each independently selected from H or (1-4C)alkyl; or Q$_{7N}$ is optionally substituted by a group of the formula:

—W$_{7N}$-L$_7$-Z$_{7N}$ wherein
  W$_{7N}$ is absent or (1-3C)alkylene optionally substituted by (1-3C)alkyl;
  L$_7$ is absent or selected from C(O), C(O)O, OC(O), C(O)N(R$_y$) or N(R$_y$)C(O), wherein R$_y$ is selected from hydrogen or (1-2C)alkyl; and
  Z$_{7N}$ is phenyl or 5-6 membered heteroaryl; each of which is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl or sulphamoyl;

(41) X$_5$ is selected from C(=O), C(=NH), C(=S), CHR$_7$, or N—R$_{7N}$ when bond a is a single bond, or CR$_7$, or N when bond a is a double bond;

wherein
R$_{7c}$ is selected from hydrogen, cyano, halo or a group of the formula:

-L$_7$-L$_{7C}$-Q$_{7C}$ wherein
  L$_7$ is absent or (1-3C)alkylene optionally substituted by (1-2C)alkyl or oxo;
  L$_{7C}$ is absent or selected from O, S, SO, SO$_2$, N(R$_o$), C(O), C(O)O, OC(O), C(O)N(R$_o$), N(R$_o$)C(O), wherein R$_c$ is selected from hydrogen or (1-2C)alkyl; and
  Q$_{7C}$ is hydrogen, cyano, (1-6C)alkyl, (2C)alkynyl, (2-3C)alkenyl, (3-6C)cycloalkyl, aryl, heterocyclyl or heteroaryl; and wherein Q$_{8C}$ is optionally substituted by one or more substituents selected from (1-4C)alkyl, halo, trifluoromethyl, trifluoromethoxy, amino or cyano; or Q$_{7C}$ is optionally substituted by a group of the formula:

—W$_{7C}$—Z$_{7C}$ wherein
  W$_{7C}$ is absent or (1-3C)alkylene substituted by (1-2C)alkyl or oxo;
  Z$_{7C}$ is phenyl or 5-6 membered heteroaryl; each of which is optionally substituted by one or more substituents selected from (1-4C)alkyl or halo;
R$_{7N}$ is selected from hydrogen or a group of the formula:

-L$_7$-L$_{7N}$-Q$_{7N}$ wherein
  L$_7$ is absent or (1-3C)alkylene optionally substituted by (1-2C)alkyl;
  L$_{7N}$ is absent or selected from O, S, SO, SO$_2$, N(R$_u$), C(O), C(O)O, OC(O), C(O)N(R$_u$) or N(R$_u$)C(O), wherein R$_u$ is selected from hydrogen or (1-2C)alkyl; and
  Q$_{7N}$ is hydrogen, cyano, (1-6C)alkyl, (2C)alkynyl, (2-3C)alkenyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl, NR$_w$R$_x$, OR$_w$, C(O)R$_w$, C(O)OR$_w$, OC(O)R$_w$, C(O)N(R$_w$)R$_x$, N(R$_w$)C(O)R$_x$, wherein R$_w$ and R$_x$ are each independently selected from H or (1-4C)alkyl; or Q$_{7N}$ is optionally substituted by a group of the formula:

—W$_{7N}$—Z$_{7N}$ wherein
  W$_{7N}$ is absent or (1-3C)alkylene optionally substituted by (1-3C)alkyl;
  Z$_{7N}$ is phenyl or 5-6 membered heteroaryl; each of which is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl or sulphamoyl;

(42) X$_5$ is selected from C(=O), C(=NH), CHR$_{7c}$ or N—R$_{7N}$ when bond a is a single bond, or CR$_{7c}$ or N when bond a is a double bond;

wherein
R$_{7c}$ is selected from hydrogen, halo or a group of the formula:

-L$_7$-L$_{7C}$-Q$_{7C}$ wherein
  L$_7$ is absent or (1-3C)alkylene optionally substituted by (1-2C)alkyl or oxo;
  L$_{7C}$ is absent or selected from O, S, N(R$_o$), C(O), C(O)O, C(O)N(R$_o$), N(R$_o$)C(O), wherein R$_c$ is selected from hydrogen or (1-2C)alkyl; and
  Q$_{7C}$ is hydrogen, cyano, (1-6C)alkyl, (2C)alkynyl, (2-3C)alkenyl, (3-6C)cycloalkyl, aryl, heterocyclyl or heteroaryl; and wherein Q$_{8C}$ is optionally substituted by one or more substituents selected from (1-4C)alkyl, halo, trifluoromethyl, amino or cyano;

R$_{7N}$ is selected from hydrogen or a group of the formula:

-L$_7$-L$_{7N}$-Q$_{7N}$ wherein
  L$_7$ is absent or (1-3C)alkylene optionally substituted by (1-2C)alkyl;
  L$_7$N is absent or selected from O, S, N(R$_u$), C(O), C(O)O, C(O)N(R$_u$) or N(R$_u$)C(O), wherein R$_u$ is selected from hydrogen or (1-2C)alkyl; and
  Q$_{7N}$ is hydrogen, cyano, (1-6C)alkyl, (2C)alkynyl, (2-3C)alkenyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl, NR$_w$R$_x$, OR$_w$, C(O)R$_w$, C(O)OR$_w$, OC(O)R$_w$, C(O)N(R$_w$)R$_x$, N(R$_w$)C(O)R$_x$, wherein R$_w$ and R$_x$ are each independently selected from H or (1-4C)alkyl;

(43) $X_5$ is selected from C(=O), $CHR_{7c}$ or N—$R_{7N}$ when bond a is a single bond, or $CR_{7c}$ or N when bond a is a double bond;
wherein
$R_{7c}$ is selected from hydrogen, halo or a group of the formula:

-$L_7$-$L_{7C}$-$Q_{7C}$ wherein
  $L_7$ is absent or (1-3C)alkylene optionally substituted by (1-2C)alkyl or oxo;
  $L_{7C}$ is absent or selected from O, N($R_o$), C(O), C(O)O, C(O)N($R_o$), N($R_o$)C(O), wherein $R_c$ is selected from hydrogen or (1-2C)alkyl; and
  $Q_{7C}$ is hydrogen, cyano, (1-4C)alkyl, (2C)alkynyl, (2-3C)alkenyl, (3-6C)cycloalkyl, aryl, (3-6C)heterocyclyl or 5-or 6-membered heteroaryl; and wherein $Q_8c$ is optionally substituted by one or more substituents selected from (1-2C)alkyl, halo, trifluoromethyl, amino or cyano;
$R_{7N}$ is selected from hydrogen or a group of the formula:

-$L_7$-$Q_{7N}$ wherein
  $L_7$ is absent or (1-3C)alkylene optionally substituted by (1-2C)alkyl;
  $Q_{7N}$ is hydrogen, cyano, (1-6C)alkyl, (2C)alkynyl, (2-3C)alkenyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl, $NR_wR_x$, $OR_w$, C(O)$R_w$, C(O)O$R_w$, OC(O)$R_w$, C(O)N($R_w$)$R_x$, N($R_w$)C(O)$R_x$, wherein $R_w$ and $R_x$ are each independently selected from H or (1-2C)alkyl;

(44) $X_5$ is selected from C(=O), $CHR_7$, or N—$R_{7N}$ when bond a is a single bond, or $CR_{7c}$ or N when bond a is a double bond;
wherein
$R_{7c}$ is selected from hydrogen or a group of the formula:

-$L_7$-$L_{7C}$-$Q_{7C}$ wherein
  $L_7$ is absent or (1-3C)alkylene optionally substituted by methyl or oxo;
  $L_{7C}$ is absent or selected from C(O), C(O)O, C(O)N($R_o$), N($R_o$)C(O), wherein $R_c$ is selected from hydrogen or (1-2C)alkyl; and
  $Q_{7C}$ is hydrogen, cyano, (1-4C)alkyl, (2C)alkynyl, (2-3C)alkenyl, (3-6C)cycloalkyl, aryl, (3-6C)heterocyclyl or 5-or 6-membered heteroaryl; and wherein $Q_8c$ is optionally substituted by one or more substituents selected from (1-2C)alkyl, halo, trifluoromethyl, amino or cyano;
$R_{7N}$ is selected from hydrogen or a group of the formula:

-$L_7$-$Q_{7N}$ wherein
  $L_7$ is absent or (1-3C)alkylene optionally substituted by (1-2C)alkyl;
  $Q_{7N}$ is hydrogen, cyano, (1-6C)alkyl, (2C)alkynyl, (2-3C)alkenyl, (3-6C)cycloalkyl, aryl, heterocyclyl or heteroaryl, each of which is optionally substituted by one or more substituents selected from (1-2C)alkyl, halo, trifluoromethyl, trifluoromethoxy, amino, cyano, hydroxy, amino, carboxy, carbamoyl, sulphamoyl, $NR_wR_x$, $OR_w$, C(O)$R_w$, C(O)OR, C(O)N($R_w$)$R_x$, N($R_w$)C(O)$R_x$, wherein $R_w$ and $R_x$ are each independently selected from H or (1-2C)alkyl;

(45) $X_5$ is N—$R_{7N}$ when bond a is a single bond, or $CR_7$, or N when bond a is a double bond;
wherein
$R_{7c}$ is selected from hydrogen or a group of the formula:

-$L_7$-$L_{7C}$-$Q_{7C}$ wherein
  $L_7$ is absent or (1-2C)alkylene optionally substituted by methyl or oxo;
  $L_{7C}$ is absent or selected from C(O), C(O)O, C(O)N($R_o$), N($R_o$)C(O), wherein $R_o$ is selected from hydrogen or (1-2C)alkyl; and
  $Q_{7C}$ is hydrogen, (1-4C)alkyl, (2C)alkynyl, (3-6C)cycloalkyl, phenyl, (3-6C)heterocyclyl or 5-or 6-membered heteroaryl; and wherein $Q_{8C}$ is optionally substituted by one or more substituents selected from (1-2C)alkyl, halo, trifluoromethyl, amino or cyano;
$R_{7N}$ is selected from hydrogen or a group of the formula:

-$L_7$-$Q_{7N}$ wherein
  $L_7$ is absent or (1-2C)alkylene optionally substituted by (1-2C)alkyl;
  $Q_{7N}$ is hydrogen, (1-6C)alkyl, (2C)alkynyl, (3-6C)cycloalkyl, phenyl or 5-or 6-membered heteroaryl, each of which is optionally substituted by one or more substituents selected from (1-2C)alkyl, halo, trifluoromethyl, trifluoromethoxy, amino, cyano, hydroxy, $NR_wR_x$ or $OR_w$, wherein $R_w$ and $R_x$ are each independently selected from H or (1-2C)alkyl;

(46) $X_5$ is N—$R_{7N}$ when bond a is a single bond, or $CR_{7c}$ or N when bond a is a double bond;
wherein
$R_{7c}$ is selected from hydrogen or a group of the formula:

-$L_7$-$L_{7C}$-$Q_{7C}$ wherein
  $L_7$ is absent or (1-2C)alkylene optionally substituted by methyl or oxo;
  $L_{7C}$ is absent or selected from C(O), C(O)O, C(O)N($R_o$), N($R_o$)C(O), wherein $R_o$ is selected from hydrogen or (1-2C)alkyl; and
  $Q_{7C}$ is hydrogen, (1-4C)alkyl, (2C)alkynyl, (3-6C)cycloalkyl, phenyl, (4-6C)heterocyclyl or 5-or 6-membered heteroaryl; and wherein $Q_{8c}$ is optionally substituted by one or more substituents selected from (1-2C)alkyl, halo, trifluoromethyl, amino or cyano;
$R_{7N}$ is selected from hydrogen or a group of the formula:

-$L_7$-$Q_{7N}$ wherein
  $L_7$ is absent or (1-2C)alkylene;
  $Q_{7N}$ is (1-4C)alkyl, (2C)alkynyl, (3-6C)cycloalkyl, phenyl or 5-or 6-membered heteroaryl, each of which is optionally substituted by one or more substituents selected from (1-2C)alkyl, (1-2C)alkoxy, halo, trifluoromethyl, trifluoromethoxy or amino;

(47) $X_5$ is N—$R_{7N}$ when bond a is a single bond, or $CR_{7c}$ or N when bond a is a double bond;

wherein

R$_{7C}$ is selected from hydrogen or a group of the formula:

-L$_7$-L$_{7C}$-Q$_{7c}$ wherein
L$_7$ is absent or (1-2C)alkylene optionally substituted by methyl or oxo;
L$_{7C}$ c is absent or selected from C(O), C(O)O or C(O)N(R$_o$), wherein R$_o$ is selected from hydrogen or (1-2C)alkyl; and
Q$_{7C}$ is hydrogen, (1-4C)alkyl, (3-6C)cycloalkyl, phenyl, (4-6C)heterocyclyl or 5- or 6-membered heteroaryl; and wherein Q$_{8C}$ is optionally substituted by one or more substituents selected from (1-2C)alkyl, halo, trifluoromethyl, amino or cyano;

R$_{7N}$ is selected from hydrogen or a group of the formula:

-L$_7$-Q$_{7N}$ wherein
L$_7$ is absent or (1-2C)alkylene;
Q$_{7N}$ is (1-4C)alkyl, (2C)alkynyl, (3-6C)cycloalkyl, phenyl or 5- or 6-membered heteroaryl, each of which is optionally substituted by one or more substituents selected from (1-2C)alkyl, halo, trifluoromethyl, trifluoromethoxy or amino;

(48) R$_5$ is H, (1-4C)alkyl or a group of the formula:

-L$_1$-L$_5$-Q$_5$ wherein
L$_1$ is absent or selected from (1-3C)alkylene optionally substituted by (1-2C)alkyl or oxo;
L$_5$ is absent or selected from C(O), C(O)O, OC(O), C(O)N(R$_a$), N(R$_a$)C(O), wherein R$_a$ and R$_b$ are each independently selected from hydrogen or (1-2C)alkyl; and
Q$_5$ is selected from hydrogen, (1-4C)alkyl, aryl, 5-6 membered heteroaryl, (4-6C)cycloalkyl, (4-6C)cycloalkenyl, (2C)alkenyl or 5-6 membered heterocyclyl;
and wherein Q$_5$ is optionally substituted by one or more substituents selected from (1-4C)alkyl, halo, amino, cyano, carboxy, carbamoyl, sulphamoyl, trifluoromethoxy, haloalkyl, NR$_c$R$_d$, OR$_c$, C(O)R$_c$, C(O)OR$_c$, OC(O)R$_c$, C(O)N(R$_c$)R$_d$, N(R)C(O)R$_d$, wherein R$_c$ and R$_d$ are each independently selected from H or (1-4C)alkyl;
or Q$_5$ is optionally substituted by a group of the formula;

—W$_5$—Y$_5$—Z$_5$ wherein
W$_5$ is absent or selected from (1-3C)alkylene optionally substituted by (1-2C)alkyl or oxo;
Y$_5$ is absent or selected from C(O), C(O)O, OC(O), C(O)N(R$_e$), N(R$_e$)C(O, wherein R$_e$ is selected from hydrogen or (1-2C)alkyl; and
Z$_5$ is selected from hydrogen, (1-4C)alkyl, phenyl, 5 or 6-membered heterocyclyl or a 5-6 membered heteroaryl; and wherein Z$_5$ is optionally substituted by one or more substituents selected from (1-4C)alkyl, halo, (1-4C)haloalkyl, (1-4C)haloalkoxy, (1-4C) alkoxy, (1-4C)alkylamino, amino, cyano, hydroxyl, carboxy, carbamoyl or sulphamoyl;

(49) R$_5$ is H, (1-4C)alkyl or a group of the formula:
L$_1$-L$_5$-Q$_5$
wherein
L$_1$ is absent or selected from (1-3C)alkylene optionally substituted by (1-2C)alkyl or oxo;
L$_5$ is absent or selected from C(O), C(O)O, OC(O), C(O)N(R$_a$), N(R$_a$)C(O), wherein R$_a$ and R$_b$ are each independently selected from hydrogen or (1-2C)alkyl; and
Q$_5$ is selected from hydrogen, (1-4C)alkyl, aryl, 5-6 membered heteroaryl, (4-6C)cycloalkyl, (4-6C)cycloalkenyl, (2C)alkenyl or 5-6 membered heterocyclyl;
and wherein Q$_5$ is optionally substituted by one or more substituents selected from (1-4C)alkyl, halo, amino, cyano, carboxy, carbamoyl, sulphamoyl, trifluoromethoxy, haloalkyl, NR$_c$R$_d$, OR$_e$ or C(O)R$_c$, wherein R$_c$ and R$_d$ are each independently selected from H or (1-2C)alkyl;
or Q$_5$ is optionally substituted by a group of the formula;

—W$_5$—Y$_5$—Z$_5$ wherein
W$_5$ is absent or selected from (1-3C)alkylene optionally substituted by (1-2C)alkyl or oxo;
Y$_5$ is absent or selected from C(O), C(O)O, OC(O), C(O)N(R$_e$), N(R$_e$)C(O, wherein R$_e$ is selected from hydrogen or (1-2C)alkyl; and
Z$_5$ is selected from hydrogen, (1-4C)alkyl, phenyl, 5 or 6-membered heterocyclyl or a 5-6 membered heteroaryl; and wherein Z$_5$ is optionally substituted by one or more substituents selected from (1-2C)alkyl, halo, (1-2C)haloalkyl, (1-2C)haloalkoxy, (1-2C) alkoxy, (1-2C)alkylamino, amino, cyano, hydroxyl, carboxy, carbamoyl or sulphamoyl;

(50) R$_5$ is H, (1-4C)alkyl or a group of the formula:

-L$_1$-L$_5$-Q$_5$ wherein
L$_1$ is absent or selected from (1-3C)alkylene optionally substituted by (1-2C)alkyl or oxo;
L$_5$ is absent or selected from C(O), C(O)O, OC(O), C(O)N(R$_a$), N(R$_a$)C(O), wherein R$_a$ and R$_b$ are each independently selected from hydrogen or (1-2C)alkyl; and
Q$_5$ is selected from hydrogen, (1-4C)alkyl, aryl, 5-6 membered heteroaryl, (4-6C)cycloalkyl, (2C)alkenyl or 5-6 membered heterocyclyl;
and wherein Q$_5$ is optionally substituted by one or more substituents selected from (1-2C)alkyl, halo, amino, cyano, carboxy, carbamoyl, sulphamoyl, trifluoromethoxy, haloalkyl, NR$_c$R$_d$, OR$_e$ or C(O)R$_c$, wherein R$_c$ and R$_d$ are each independently selected from H or (1-2C)alkyl;
or Q$_5$ is optionally substituted by a group of the formula;

—W$_5$—Y$_5$—Z$_5$ wherein
W$_5$ is absent or selected from (1-3C)alkylene optionally substituted by (1-2C)alkyl or oxo;
Y$_5$ is absent or selected from C(O), C(O)O, C(O)N(R$_e$), N(R$_e$)C(O, wherein R$_e$ is selected from hydrogen or (1-2C)alkyl; and
Z$_5$ is selected from hydrogen, (1-4C)alkyl, phenyl, 5 or 6-membered heterocyclyl or a 5-6 membered heteroaryl; and wherein Z$_5$ is optionally substituted by one or more substituents selected from (1-2C)alkyl, halo, CF$_3$ (1-2C)alkoxy, amino, cyano, hydroxyl, carboxy, carbamoyl or sulphamoyl;

(51) R$_5$ is H, (1-4C)alkyl or a group of the formula:

-L$_1$-L$_5$-Q$_5$ wherein
L$_1$ is absent or selected from (1-3C)alkylene optionally substituted by (1-2C)alkyl or oxo;
L$_5$ is absent or selected from C(O), C(O)O, C(O)N(R$_a$), N(R$_a$)C(O), wherein R$_a$ and R$_b$ are each independently selected from hydrogen or methyl; and
Q$_5$ is selected from hydrogen, (1-4C)alkyl, aryl, 5-6 membered heteroaryl, (4-6C)cycloalkyl, (2C)alkenyl or 5-6 membered heterocyclyl;
and wherein Q$_5$ is optionally substituted by one or more substituents selected from (1-2C)alkyl, halo, haloalkyl, amino, cyano, carboxy, carbamoyl, CF$_3$, NR$_c$R$_d$, OR$_c$ or C(O)R$_c$, wherein R$_c$ and R$_d$ are each independently selected from H or (1-2C)alkyl;
or Q$_5$ is optionally substituted by a group of the formula;

—W$_5$—Y$_5$—Z$_5$ wherein
W$_5$ is absent or selected from (1-3C)alkylene optionally substituted by (1-2C)alkyl or oxo;
Y$_5$ is absent or selected from C(O), C(O)O, C(O)N(R$_e$), N(R$_e$)C(O, wherein R$_e$ is selected from hydrogen or (1-2C)alkyl; and
Z$_5$ is selected from hydrogen, (1-4C)alkyl, phenyl, 5 or 6-membered heterocyclyl or a 5-6 membered heteroaryl; and wherein Z$_5$ is optionally substituted by one or more substituents selected from (1-2C)alkyl, halo or CF$_3$.

(52) R$_5$ is H, (1-4C)alkyl or a group of the formula:

-L$_1$-L$_5$-Q$_5$ wherein
L$_1$ is absent or selected from (1-2C)alkylene optionally substituted by (1-2C)alkyl or oxo;
L$_5$ is absent or selected from C(O), C(O)O, C(O)N(R$_a$), N(R$_a$)C(O), wherein R$_a$ and R$_b$ are each independently selected from hydrogen or methyl; and
Q$_5$ is selected from hydrogen, (1-4C)alkyl, phenyl, 5-6 membered heteroaryl, (4-6C)cycloalkyl, (2C)alkenyl or 5-6 membered heterocyclyl;
and wherein Q$_5$ is optionally substituted by one or more substituents selected from (1-2C)alkyl, halo, amino, cyano, carboxy, carbamoyl, CF$_3$, NR$_c$R$_d$, OR$_c$ or C(O)R$_c$, wherein R$_c$ and R$_d$ are each independently selected from H or (1-2C)alkyl;

(53) R$_5$ is 5-6 membered heteroaryl, optionally substituted by one or more substituents selected from (1-2C)alkyl, halo, haloalkyl, amino, cyano, carboxy, carbamoyl, CF$_3$, NR$_c$R$_d$, OR$_c$ or C(O)R$_C$, wherein R$_t$ and R$_d$ are each independently selected from H or (1-2C)alkyl;
or said heteroaryl is optionally substituted by a group of the formula;

—W$_5$—Y$_5$—Z$_5$ wherein
W$_5$ is absent or selected from (1-2C)alkylene optionally substituted by (1-2C)alkyl or oxo;
Y$_5$ is absent or selected from C(O), C(O)O, C(O)N(R$_e$), N(R$_e$)C(O, wherein R$_e$ is selected from hydrogen or (1-2C)alkyl; and
Z$_5$ is selected from hydrogen, (1-4C)alkyl, phenyl, 5 or 6-membered heterocyclyl or a 5-6 membered heteroaryl; and wherein Z$_5$ is optionally substituted by one or more substituents selected from (1-2C)alkyl, halo or CF$_3$;

(54) R$_5$ is 5-or 6-membered heteroaryl, optionally substituted by one or more substituents selected from (1-2C) alkyl, halo, amino, cyano, carboxy, carbamoyl, CF$_3$, CHF$_2$, NR$_c$R$_d$, OR$_c$ or C(O)R$_c$, wherein R$_e$ and R$_d$ are each independently selected from H or (1-2C)alkyl;

(55) R$_5$ is a thiadiazole or oxadiazole, optionally substituted by one or more substituents selected from (1-2C)alkyl, halo, amino, cyano, carboxy, carbamoyl, CF$_3$, CHF$_2$, NR$_c$R$_d$, OR$_c$ or C(O)R$_c$, wherein R$_e$ and R$_d$ are each independently selected from H or (1-2C)alkyl.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5-or 6-membered heteroaryl ring comprising one, two or three heteroatoms selected from N, O or S.

Suitably, a heterocyclyl group is a 4-, 5-or 6-membered heterocyclyl ring comprising one, two or three heteroatoms selected from N, O or S. Most suitably, a heterocyclyl group is a 5-or 6-membered ring comprising one, two or three heteroatoms selected from N, O or S [e.g. morpholinyl (e.g. 4-morpholinyl), oxetane, methyloxetane (e.g. 3-methyloxetane), pyrrolidinone (e.g. pyrrolidin-2-one)].

Suitably an aryl group is phenyl.

Suitably, R$_{1a}$ is as defined in any one of paragraphs (2) to (8) above. Most suitably, R$_{1a}$ is methyl.

Suitably, R$_{1b}$, R$_{1c}$, R$_{1d}$ and R$_{1e}$ are defined as in paragraphs (9) and (10) above. Most suitably, R$_{1b}$, R$_{1c}$, R$_{1d}$ and R$_{1e}$ are H.

Suitably, W is as defined in any one of paragraphs (11) to (14) above. Most preferably, W is as defined in paragraph (14).

Suitably, X$_1$ is as defined in any one of paragraphs (15) to (17) above. Most preferably, X$_1$ is as defined in paragraph (17).

Suitably, X$_2$ is as defined in any one of paragraphs (18) to (21) above. Most preferably, X$_2$ is as defined in paragraph (21).

Suitably, X$_3$ is as defined in any one of paragraphs (22) to (32) above. Most preferably, X$_3$ is as defined in paragraph (32).

Suitably, X$_4$ is as defined in any one of paragraphs (33) to (39) above. Most preferably, X$_4$ is as defined in paragraph (39).

Suitably, X$_5$ is as defined in any one of paragraphs (40) to (47) above. Most preferably, X$_5$ is as defined in paragraph (47).

Suitably, X$_6$ is as defined in any one of paragraphs (48) to (55) above. Most preferably, X$_6$ is as defined in paragraph (55).

In an embodiment, the compound of the present invention is not one of the following compounds:
6-[(cyclopropylamino)sulfonyl]-2,3-dihydro-2-methyl-N-[4-(1-pyrrolidinyl)phenyl]-1H-indole-1-carboxamide;
6-[(cyclopropylamino)sulfonyl]-2,3-dihydro-N-(4-methoxyphenol)-2-methyl-1H-indole-1-carboxamide;
N-[1,1'-biphenyl]-4-yl-6-[(cyclopropylamino)sulfonyl]-2,3-dihydro-2-methyl-1H-indole-1-carboxamide;
6-[(cyclopropylamino)sulfonyl]-2,3-dihydro-2-methyl-N-[4-(4-morpholinyl)phenyl]-1H-indole-1-carboxamide;
6-[(cyclopropylamino)sulfonyl]-2,3-dihydro-N-(4-ethoxyphenol)-2-methyl-1H-indole-1-carboxamide;
N-(1,1-dimethylethyl)-1H-indole-6-sulfonamide;
3-(1-cyclohexen-1-yl)-N-(1,1-dimethylethyl)-1H-indole-6-sulfonamide;
3-cyclohexyl-N-(1,1-dimethylethyl)-1H-indole-6-sulfonamide;

2-bromo-3-cyclohexyl-N-(1,1-dimethylethyl)-1H-indole-6-sulfonamide;
2-(2-amino-4-methylphenyl)-3-cyclohexyl-N-(1,1-dimethylethyl)-1H-indole-6-sulfonamide;
6-[(cyclopropylamino)sulfonyl]-1-(1-methylethyl)-1H-indazole-4-carboxylic acid methyl ester; or
6-[(cyclopropylamino)sulfonyl]-1-(1-methylethyl)-1H-indazole-4-carboxylic acid.

In a particular group of compounds of the invention, c is a single bond and W is —NH—S(O)$_2$—, i.e. the compounds have the structural formula IIa (a sub-definition of formula I) shown below:

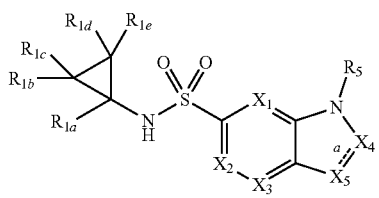

IIa wherein a, $X_1$, $X_2$, $X_3$, $X_4$, $X_5$, $R_5$, $R_{1a}$, $R_{1b}$, $R_{1c}$, $R_{1d}$, and $R_{1e}$ each have any one of the meanings defined herein; or a pharmaceutically acceptable salt, hydrate and/or solvate thereof.

In an embodiment of the compounds of formula IIa:
$R_{1a}$ is as defined in any one of paragraphs (2) to (8);
$R_{1b}$, $R_{1c}$, $R_{1d}$ and $R_{1e}$ are as defined in any one of paragraphs (9) and (10);
$X_1$ is as defined in any one of paragraphs (15) to (17) above;
$X_2$ is as defined in any one of paragraphs (18) to (21) above;
$X_3$ is as defined in any one of paragraphs (22) to (32) above;
$X_4$ is as defined in any one of paragraphs (33) to (39) above;
$X_s$ is as defined in any one of paragraphs (40) to (47) above; and
$R_5$ is as defined in any one of paragraphs (48) and (55).

In an embodiment of the compounds of formula IIa:
$R_{1a}$ is as defined in paragraph (8) above;
$R_{1b}$, $R_{1c}$, $R_{1d}$ and $R_{1e}$ are as defined in paragraph (10) above;
$X_1$ is as defined in paragraph (17) above;
$X_2$ is as defined in paragraph (21) above;
$X_3$ is as defined in paragraph (32) above;
$X_4$ is as defined in paragraph (39) above;
$X_5$ is as defined in paragraph (47) above; and
$R_5$ is as defined in paragraph (55).

In a particular group of compounds of the invention, c is a single bond, W is NH—S(O)$_2$—, $R_{1b}$, $R_{1c}$, $R_{1d}$ and $R_{1e}$ are H, and $X_1$ is H, i.e. the compounds have the structural formula IIb (a sub-definition of formula I) shown below:

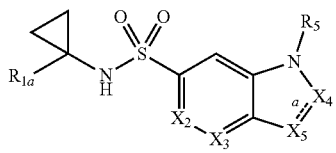

IIb wherein a, $X_2$, $X_3$, $X_4$, $X_5$, $R_5$ and $R_{1a}$ each have any one of the meanings defined herein; or a pharmaceutically acceptable salt, hydrate and/or solvate thereof.

In an embodiment of the compounds of formula IIa:
$R_{1a}$ is as defined in any one of paragraphs (2) to (8);
$X_2$ is as defined in any one of paragraphs (18) to (21) above;
$X_3$ is as defined in any one of paragraphs (22) to (32) above;
$X_4$ is as defined in any one of paragraphs (33) to (39) above;
$X_s$ is as defined in any one of paragraphs (40) to (47) above; and
$R_5$ is as defined in any one of paragraphs (48) and (55).

In an embodiment of the compounds of formula IIa:
$R_{1a}$ is as defined in paragraph (8) above;
$X_2$ is as defined in paragraph (21) above;
$X_3$ is as defined in paragraph (32) above;
$X_4$ is as defined in paragraph (39) above;
$X_5$ is as defined in paragraph (47) above; and
$R_5$ is as defined in paragraph (55).

In a particular group of compounds of the invention, c is a single bond, W is NH—S(O)$_2$—, $R_{1b}$, $R_{1c}$, $R_{1d}$ and $R_{1e}$ are H, and $X_1$, $X_2$ and $X_3$ are H, i.e. the compounds have the structural formula IIc a sub-definition of formula I) shown below:

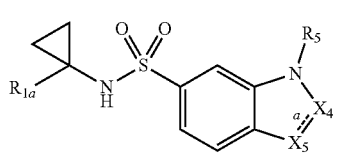

IIc wherein a, $X_4$, $X_5$, $R_5$ and $R_{1a}$ each have any one of the meanings defined herein; or a pharmaceutically acceptable salt, hydrate and/or solvate thereof.

In an embodiment of the compounds of formula IIa:
$R_{1a}$ is as defined in any one of paragraphs (2) to (8);
$X_4$ is as defined in any one of paragraphs (33) to (39) above;
$X_5$ is as defined in any one of paragraphs (40) to (47) above; and
$R_5$ is as defined in any one of paragraphs (48) and (55).

In an embodiment of the compounds of formula IIa:
$R_{1a}$ is as defined in paragraph (8) above;
$X_4$ is as defined in paragraph (39) above;
$X_5$ is as defined in paragraph (47) above; and
$R_5$ is as defined in paragraph (55).

In another particular group of compounds of the invention compound, HET is a compound of Formula (III), (IV) or (V):

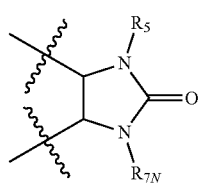

III

-continued

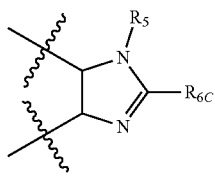

IV

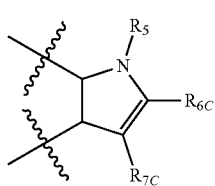

V

In another particular group of compounds of the invention compound, HET is a compound of Formula (III):

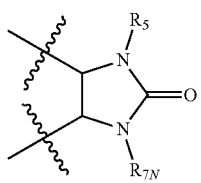

III

In a particular group of compounds of the invention, c is a single bond, W is NH—S(O)$_2$—, R$_{1b}$, R$_{1c}$, R$_{1d}$ and R$_{1e}$ are H, X$_1$, X$_2$ and X$_3$ are H, a is a single bond, X$_4$ is C═O and X$_5$ is N—R$_{7N}$ i.e. the compounds have the structural formula IId (a sub-definition of formula I) shown below:

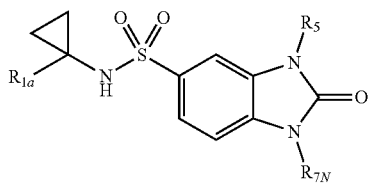

IId wherein R$_5$, R$_{7N}$ and R$_{1a}$ each have any one of the meanings defined herein; or a pharmaceutically acceptable salt, hydrate and/or solvate thereof.

In an embodiment of the compounds of formula IIa:
R$_{1a}$ is as defined in any one of paragraphs (2) to (8);
R$_{7N}$ is as defined in any one of paragraphs (40) to (47) above; and
R$_5$ is as defined in any one of paragraphs (48) to (55).
In an embodiment of the compounds of formula IIa:
R$_{1a}$ is as defined in paragraph (8) above;
R$_{7N}$ is as defined in paragraph (47) above; and
R$_5$ is as defined in paragraph (55).
Particular compounds of the present invention include any of the compounds exemplified in the present application, or a pharmaceutically acceptable salt or solvate thereof, and, in particular, any of the following:
1-[(2,6-dichlorophenyl)methyl]-3-methyl-N-(1-methylcyclopropyl)-2-oxo-benzimidazole-5-sulfonamide;
1-(cyclopropylmethyl)-3-methyl-N-(1-methylcyclopropyl)-2-oxo-benzimidazole-5-sulfonamide;
1-benzyl-3-methyl-N-(1-methylcyclopropyl)-2-oxo-benzimidazole-5-sulfonamide; 1-(cyclopropylmethyl)-N-(1-methylcyclopropyl)-2-oxo-3-phenyl-benzimidazole-5-sulfonamide;
3-methyl-N-(1-methylcyclopropyl)-2-oxo-1-(3-pyridylmethyl)benzimidazole-5-sulfonamide;
1-[(2,2-difluorocyclopropyl)methyl]-3-methyl-N-(1-methylcyclopropyl)-2-oxo-benzimidazole-5-sulfonamide;
1-isobutyl-3-methyl-N-(1-methylcyclopropyl)-2-oxo-benzimidazole-5-sulfonamide;
3-methyl-N-(1-methylcyclopropyl)-1-[(2-methylcyclopropyl)methyl]-2-oxo-benzimidazole-5-sulfonamide;
3-methyl-N-(1-methylcyclopropyl)-1-[(1-methylcyclopropyl)methyl]-2-oxo-benzimidazole-5-sulfonamide;
3-methyl-N-(1-methylcyclopropyl)-1-[(3-methyloxetan-3-yl)methyl]-2-oxo-benzimidazole-5-sulfonamide;
1-(cyclobutylmethyl)-3-methyl-N-(1-methylcyclopropyl)-2-oxo-benzimidazole-5-sulfonamide;
1-(cyclohexylmethyl)-3-methyl-N-(1-methylcyclopropyl)-2-oxo-benzimidazole-5-sulfonamide;
3-methyl-N-(1-methylcyclopropyl)-2-oxo-1-(4-pyridylmethyl)benzimidazole-5-sulfonamide;
N-(1-methylcyclopropyl)-1-[2-(2-oxooxazolidin-3-yl)acetyl]indoline-6-sulfonamide;
1-(2,2-dimethylpropyl)-3-methyl-N-(1-methylcyclopropyl)-2-oxo-benzimidazole-5-sulfonamide;
1-(cyclopentylmethyl)-3-methyl-N-(1-methylcyclopropyl)-2-oxo-benzimidazole-5-sulfonamide;
3-methyl-N-(1-methylcyclopropyl)-2-oxo-1-prop-2-ynyl-benzimidazole-5-sulfonamide;
1-allyl-3-methyl-N-(1-methylcyclopropyl)-2-oxo-benzimidazole-5-sulfonamide;
1-(2-cyclopropylethyl)-3-methyl-N-(1-methylcyclopropyl)-2-oxo-benzimidazole-5-sulfonamide;
3-methyl-N-(1-methylcyclopropyl)-1-[(5-methyl-2-furyl)methyl]-2-oxo-benzimidazole-5-sulfonamide;
N-(1-methylcyclopropyl)-1-[2-(2-oxoimidazolidin-1-yl)acetyl]indoline-6-sulfonamide;
2-[3-methyl-5-[(1-methylcyclopropyl)sulfamoyl]-2-oxo-benzimidazol-1-yl]ethyl acetate;
3-methyl-N-(1-methylcyclopropyl)-1-[(1-methylpyrazol-3-yl)methyl]-2-oxo-benzimidazole-5-sulfonamide;
3-acetyl-1-methyl-N-(1-methylcyclopropyl)-2-oxo-benzimidazole-5-sulfonamide;
N-(1-methylcyclopropyl)-1-[2-(3-methyl-2-oxo-imidazolidin-1-yl)acetyl]indoline-6-sulfonamide;
1-methyl-N-(1-methylcyclopropyl)-2-oxo-3-(3-thienyl)benzimidazole-5-sulfonamide;
3-benzoyl-1-methyl-N-(1-methylcyclopropyl)-2-oxo-benzimidazole-5-su fonamide;
3-(cyclohexanecarbonyl)-1-methyl-N-(1-methylcyclopropyl)-2-oxo-benzimidazole-5-sulfonamide;
1-methyl-3-(4-methylbenzoyl)-N-(1-methylcyclopropyl)-2-oxo-benzimidazole-5-sulfonamide;
1-methyl-3-(3-methylbenzoyl)-N-(1-methylcyclopropyl)-2-oxo-benzimidazole-5-sulfonamide;
1-methyl-3-(2-methylbenzoyl)-N-(1-methylcyclopropyl)-2-oxo-benzimidazole-5-sulfonamide;
N-ethyl-3-methyl-6-[(1-methylcyclopropyl)sulfamoyl]-2-oxo-benzimidazole-1-carboxamide;
3-methyl-N-(1-methylcyclopropyl)-1-(m-tolylmethyl)-2-oxo-benzimidazole-5-sulfonamide;
3-methyl-N-(1-methylcyclopropyl)-2-oxo-1-(p-tolylmethyl)benzimidazole-5-sulfonamide;
1-[(2-methoxyphenyl)methyl]-3-methyl-N-(1-methylcyclopropyl)-2-oxo-benzimidazole-5-sulfonamide;

1-[(3-methoxyphenyl)methyl]-3-methyl-N-(1-methylcyclopropyl)-2-oxo-benzimidazole-5-sulfonamide;
1-[(4-methoxyphenyl)methyl]-3-methyl-N-(1-methylcyclopropyl)-2-oxo-benzimidazole-5-sulfonamide;
1-[(3-chlorophenyl)methyl]-3-methyl-N-(1-methylcyclopropyl)-2-oxo-benzimidazole-5-sulfonamide;
1-[(4-chlorophenyl)methyl]-3-methyl-N-(1-methylcyclopropyl)-2-oxo-benzimidazole-5-sulfonamide;
1-[(2-fluorophenyl)methyl]-3-methyl-N-(1-methylcyclopropyl)-2-oxo-benzimidazole-5-sulfonamide;
1-[(3-fluorophenyl)methyl]-3-methyl-N-(1-methylcyclopropyl)-2-oxo-benzimidazole-5-sulfonamide;
1-[(4-fluorophenyl)methyl]-3-methyl-N-(1-methylcyclopropyl)-2-oxo-benzimidazole-5-sulfonamide;
1-[(2-cyanophenyl)methyl]-3-methyl-N-(1-methylcyclopropyl)-2-oxo-benzimidazole-5-sulfonamide;
1-[(3-cyanophenyl)methyl]-3-methyl-N-(1-methylcyclopropyl)-2-oxo-benzimidazole-5-sulfonamide;
1-[(4-cyanophenyl)methyl]-3-methyl-N-(1-methylcyclopropyl)-2-oxo-benzimidazole-5-sulfonamide;
3-methyl-N-(1-methylcyclopropyl)-2-oxo-1-[[2-(trifluoromethyl)phenyl]methyl]benzimidazole-5-sulfonamide;
1-[(2,6-difluorophenyl)methyl]-3-methyl-N-(1-methylcyclopropyl)-2-oxo-benzimidazole-5-sulfonamide;
1-[(3,5-dichlorophenyl)methyl]-3-methyl-N-(1-methylcyclopropyl)-2-oxo-benzimidazole-5-sulfonamide;
1-[(3,5-dimethylphenyl)methyl]-3-methyl-N-(1-methylcyclopropyl)-2-oxo-benzimidazole-5-sulfonamide;
1-[(3,5-dimethoxyphenyl)methyl]-3-methyl-N-(1-methylcyclopropyl)-2-oxo-benzimidazole-5-sulfonamide;
1-[(3,5-difluorophenyl)methyl]-3-methyl-N-(1-methylcyclopropyl)-2-oxo-benzimidazole-5-sulfonamide;
3-(2-furyl)-1-methyl-N-(1-methylcyclopropyl)-2-oxo-benzimidazole-5-su fonamide;
1-methyl-N-(1-methylcyclopropyl)-2-oxo-3-thiazol-2-yl-benzimidazole-5-sulfonamide;
3-(5-formyl-2-thienyl)-1-methyl-N-(1-methylcyclopropyl)-2-oxo-benzimidazole-5-sulfonamide;
N,3-dimethyl-6-[(1-methylcyclopropyl)sulfamoyl]-2-oxo-benzimidazole-1-carboxamide;
6-fluoro-1,3-dimethyl-N-(1-methylcyclopropyl)-2-oxo-benzimidazole-5-sulfonamide;
3-methyl-N-(1-methylcyclopropyl)-2-oxo-1-phenyl-benzimidazole-5-sulfonamide;
1-[(4-cyano-3-fluoro-phenyl)methyl]-3-methyl-N-(1-methylcyclopropyl)-2-oxo-benzimidazole-5-sulfonamide;
4-[[3-methyl-5-[(1-methylcyclopropyl)sulfamoyl]-2-oxo-benzimidazol-1-yl]methyl]benzamide;
N-methyl-5-[[3-methyl-5-[(1-methylcyclopropyl)sulfamoyl]-2-oxo-benzimidazol-1-yl]methyl]-1,2,4-oxadiazole-3-carboxamide;
3-[[3-methyl-5-[(1-methylcyclopropyl)sulfamoyl]-2-oxo-benzimidazol-1-yl]methyl]benzamide;
3-methyl-N-(1-methylcyclopropyl)-1-[(5-nitro-2-furyl)methyl]-2-oxo-benzimidazole-5-sulfonamide;
N-[4-[[3-methyl-5-[(1-methylcyclopropyl)sulfamoyl]-2-oxo-benzimidazol-1-yl]methyl]phenyl]acetamide;
3-methyl-N-(1-methylcyclopropyl)-1-[(2-methylpyrazol-3-yl)methyl]-2-oxo-benzimidazole-5-sulfonamide;
3-methyl-N-(1-methylcyclopropyl)-1-[(2-methylthiazol-5-yl)methyl]-2-oxo-benzimidazole-5-sulfonamide;
ethyl 3-methyl-6-[(1-methylcyclopropyl)sulfamoyl]-2-oxo-benzimidazole-1-carboxylate;
(E)-3-[5-[3-methyl-6-[(1-methylcyclopropyl)sulfamoyl]-2-oxo-benzimidazol-1-yl]-2-furyl]prop-2-enoic acid;
1-methyl-N-(1-methylcyclopropyl)-2-oxo-3-(5-methyl-1,3,4-thiadiazol-2-yl)-2-oxo-benzimidazole-5-sulfonamide;
(E)-3-[2-[3-methyl-6-[(1-methylcyclopropyl)sulfamoyl]-2-oxo-benzimidazol-1-yl]thiazol-5-yl]prop-2-enoic acid;
3-[2-[3-methyl-6-[(1-methylcyclopropyl)sulfamoyl]-2-oxo-benzimidazol-1-yl]thiazol-5-yl]propanoic acid;
N,N-dimethyl-3-[2-[3-methyl-6-[(1-methylcyclopropyl)sulfamoyl]-2-oxo-benzimidazol-1-yl]thiazol-5-yl]propanamide;
1-[(4-fluorophenyl)methyl]-N-(1-methylcyclopropyl)-2-oxo-3H-benzimidazole-5-sulfonamide;
1-[(4-fluorophenyl)methyl]-N-(1-methylcyclopropyl)-3-(5-methyl-1,3,4-thiadiazol-2-yl)-2-oxo-benzimidazole-5-sulfonamide;
N-methyl-3-[2-[3-methyl-6-[(1-methylcyclopropyl)sulfamoyl]-2-oxo-benzimidazol-1-yl]thiazol-5-yl]propanamide;
ethyl 3-[(4-fluorophenyl)methyl]-6-[(1-methylcyclopropyl)sulfamoyl]-2-oxo-benzimidazole-1-carboxylate;
1-[(4-fluorophenyl)methyl]-N-(1-methylcyclopropyl)-2-oxo-3-thiazol-2-yl-benzimidazole-5-sulfonamide;
1-methyl-N-(1-methylcyclopropyl)-2-oxo-3-(1,3,4-thiadiazol-2-yl)benzimidazole-5-sulfonamide;
1-methyl-N-(1-methylcyclopropyl)-2-oxo-3-[5-(trifluoromethyl)-1,3,4-thiadiazol-2-yl]benzimidazole-5-sulfonamide;
3-[5-(difluoromethyl)-1,3,4-thiadiazol-2-yl]-1-methyl-N-(1-methylcyclopropyl)-2-oxo-benzimidazole-5-sulfonamide;
N-(1-methylcyclopropyl)-3-(5-methyl-1,3,4-thiadiazol-2-yl)-2-oxo-1H-benzimidazole-5-sulfonamide;
3-(5-amino-1,3,4-thiadiazol-2-yl)-1-methyl-N-(1-methylcyclopropyl)-2-oxo-benzimidazole-5-sulfonamide;
1-(cyclopropylmethyl)-N-(1-methylcyclopropyl)-3-(5-methyl-1,3,4-thiadiazol-2-yl)-2-oxo-benzimidazole-5-sulfonamide;
N-(1-methylcyclopropyl)-3-(5-methyl-1,3,4-thiadiazol-2-yl)-1-[(2-methylthiazol-5-yl)methyl]-2-oxo-benzimidazole-5-sulfonamide;
1-[(2,5-dimethylpyrazol-3-yl)methyl]-N-(1-methylcyclopropyl)-3-(5-methyl-1,3,4-thiadiazol-2-yl)-2-oxo-benzimidazole-5-sulfonamide;
1-[2-(dimethylamino)ethyl]-N-(1-methylcyclopropyl)-3-(5-methyl-1,3,4-thiadiazol-2-yl)-2-oxo-benzimidazole-5-sulfonamide;
1-[(4-methoxyphenyl)methyl]-N-(1-methylcyclopropyl)-3-(5-methyl-1,3,4-thiadiazol-2-yl)-2-oxo-benzimidazole-5-sulfonamide;
1-[(2,4-dimethylthiazol-5-yl)methyl]-N-(1-methylcyclopropyl)-3-(5-methyl-1,3,4-thiadiazol-2-yl)-2-oxo-benzimidazole-5-sulfonamide;
3-[5-(difluoromethyl)-1,3,4-thiadiazol-2-yl]-1-[(2,4-dimethylthiazol-5-yl)methyl]-N-(1-methylcyclopropyl)-2-oxo-benzimidazole-5-sulfonamide;
1-[(2,4-dimethylthiazol-5-yl)methyl]-N-(1-methylcyclopropyl)-2-oxo-3H-benzimidazole-5-sulfonamide;
1-[(2,4-dimethylthiazol-5-yl)methyl]-N-(1-methylcyclopropyl)-2-oxo-3-(1,2,4-thiadiazol-5-yl)benzimidazole-5-sulfonamide;
1-[(2,4-dimethylthiazol-5-yl)methyl]-3-(1H-imidazol-5-yl)-N-(1-methylcyclopropyl)-2-oxo-benzimidazole-5-sulfonamide;
1-[(2,4-dimethylthiazol-5-yl)methyl]-N-(1-methylcyclopropyl)-2-oxo-3-(1H-pyrazol-4-yl)benzimidazole-5-sulfonamide;
1-[(2,4-dimethylthiazol-5-yl)methyl]-3-isothiazol-4-yl-N-(1-methylcyclopropyl)-2-oxo-benzimidazole-5-sulfonamide;

N-(1-methylcyclopropyl)-3-(5-methyl-1,3,4-oxadiazol-2-yl)-2-oxo-1H-benzimidazole-5-sulfonamide;
1-[(2,4-dimethylthiazol-5-yl)methyl]-N-(1-methylcyclopropyl)-2-oxo-3-thiazol-4-yl-benzimidazole-5-sulfonamide;
1-[(2,4-dimethylthiazol-5-yl)methyl]-N-(1-methylcyclopropyl)-3-(1-methylpyrazol-3-yl)-2-oxo-benzimidazole-5-sulfonamide;
1-[(2,4-dimethylthiazol-5-yl)methyl]-N-(1-methylcyclopropyl)-2-oxo-3-thiazol-5-yl-benzimidazole-5-sulfonamide;
1-methyl-N-(1-methylcyclopropyl)-2-oxo-3-(1,2,4-thiadiazol-5-yl)benzimidazole-5-sulfonamide;
1-[(2,4-dimethylthiazol-5-yl)methyl]-N-(1-methylcyclopropyl)-3-(5-methyl-1,3,4-oxadiazol-2-yl)-2-oxo-benzimidazole-5-sulfonamide;
N-(1-methylcyclopropyl)-3-(5-methyl-1,3,4-thiadiazol-2-yl)-2-oxo-1-prop-2-ynyl-benzimidazole-5-sulfonamide;
N-(1-methylcyclopropyl)-3-(5-methyl-1,3,4-thiadiazol-2-yl)-1-(oxazol-2-ylmethyl)-2-oxo-benzimidazole-5-sulfonamide;
N-(1-methylcyclopropyl)-3-(5-methyl-1,3,4-thiadiazol-2-yl)-2-oxo-1-(1H-pyrazol-4-ylmethyl)benzimidazole-5-sulfonamide;
N-(1-methylcyclopropyl)-1-[(5-methyl-2-furyl)methyl]-3-(5-methyl-1,3,4-thiadiazol-2-yl)-2-oxo-benzimidazole-5-sulfonamide;
N-(1-methylcyclopropyl)-3-(5-methyl-1,3,4-thiadiazol-2-yl)-1-[(5-methyl-2-thienyl)methyl]-2-oxo-benzimidazole-5-sulfonamide;
1-[(2,4-dimethylthiazol-5-yl)methyl]-3-(3-methoxy-1,2,4-thiadiazol-5-yl)-N-(1-methylcyclopropyl)-2-oxo-benzimidazole-5-sulfonamide;
1-[(2,4-dimethylthiazol-5-yl)methyl]-N-(1-methylcyclopropyl)-3-(4-methylthiazol-2-yl)-2-oxo-benzimidazole-5-sulfonamide;
1-[(2,4-dimethylthiazol-5-yl)methyl]-N-(1-methylcyclopropyl)-3-(5-methylthiazol-2-yl)-2-oxo-benzimidazole-5-sulfonamide;
3-(3-bromo-1,2,4-thiadiazol-5-yl)-1-[(2,4-dimethylthiazol-5-yl)methyl]-N-(1-methylcyclopropyl)-2-oxo-benzimidazole-5-sulfonamide;
1-[(2,4-dimethylthiazol-5-yl)methyl]-N-(1-methylcyclopropyl)-2-oxo-3-pyridazin-3-yl-benzimidazole-5-sulfonamide;
1-[(2,4-dimethylthiazol-5-yl)methyl]-N-(1-methylcyclopropyl)-2-oxo-3-(1,3,4-thiadiazol-2-yl)benzimidazole-5-sulfonamide;
1-[(2,4-dimethylthiazol-5-yl)methyl]-N-(1-methylcyclopropyl)-2-oxo-3-thiazol-2-yl-benzimidazole-5-sulfonamide;
ethyl 3-[(2,4-dimethylthiazol-5-yl)methyl]-6-[(1-methylcyclopropyl)sulfamoyl]-2-oxo-benzimidazole-1-carboxylate;
3-(cyclopenten-1-yl)-1-[(2,4-dimethylthiazol-5-yl)methyl]-N-(1-methylcyclopropyl)-2-oxo-benzimidazole-5-sulfonamide;
7-fluoro-1-methyl-N-(1-methylcyclopropyl)-3-(5-methyl-1,3,4-thiadiazol-2-yl)-2-oxo-benzimidazole-5-sulfonamide;
N-(1-methylcyclopropyl)-1-(5-methyl-1,3,4-thiadiazol-2-yl)indole-6-sulfonamide;
6-fluoro-1-methyl-N-(1-methylcyclopropyl)-3-(5-methyl-1,3,4-thiadiazol-2-yl)-2-oxo-benzimidazole-5-sulfonamide;
N-methyl-5-[[5-[(1-methylcyclopropyl)sulfamoyl]-3-(5-methyl-1,3,4-oxadiazol-2-yl)-2-oxo-benzimidazol-1-yl]methyl]-1,2,4-oxadiazole-3-carboxamide;
N-(1-methylcyclopropyl)-2-[(3-methylisoxazol-5-yl)methyl]-3-(5-methyl-1,3,4-thiadiazol-2-yl)benzimidazole-5-sulfonamide;
N-(1-methylcyclopropyl)-3-(5-methyl-1,3,4-thiadiazol-2-yl)benzimidazole-5-sulfonamide;
N-(1-methylcyclopropyl)-2-[(1-methylpyrazol-4-yl)methyl]-3-(5-methyl-1,3,4-thiadiazol-2-yl)benzimidazole-5-sulfonamide;
N-(1-methylcyclopropyl)-2-[2-(1-methylpyrazol-4-yl)ethyl]-3-(5-methyl-1,3,4-thiadiazol-2-yl)benzimidazole-5-sulfonamide;
2-methyl-N-(1-methylcyclopropyl)-3-(5-methyl-1,3,4-thiadiazol-2-yl)benzimidazole-5-sulfonamide;
1-methyl-N-(1-methylcyclopropyl)-3-(5-methyl-1,3,4-thiadiazol-2-yl)-2-oxo-7-(trifluoromethyl)benzimidazole-5-sulfonamide;
N-[[6-[(1-methylcyclopropyl)sulfamoyl]-1-(5-methyl-1,3,4-thiadiazol-2-yl)benzimidazol-2-yl]methyl]acetamide;
2-(2-aminoethyl)-N-(1-methylcyclopropyl)-3-(5-methyl-1,3,4-thiadiazol-2-yl)benzimidazole-5-sulfonamide;
3-benzyl-N-(1-methylcyclopropyl)-1-(5-methyl-1,3,4-thiadiazol-2-yl)indole-6-sulfonamide;
3-[(4-fluorophenyl)methyl]-N-(1-methylcyclopropyl)-1-(5-methyl-1,3,4-thiadiazol-2-yl)indole-6-sulfonamide;
3-cyclopropylmethyl-N-(1-methylcyclopropyl)-1-(5-methyl-1,3,4-thiadiazol-2-yl)indole-6-sulfonamide;
3-[(2,4-dimethylthiazol-5-yl)methyl]-N-(1-methylcyclopropyl)-1-(5-methyl-1,3,4-thiadiazol-2-yl)indole-6-sulfonamide;
3-(cyclopropanecarbonyl)-N-(1-methylcyclopropyl)-1-(5-methyl-1,3,4-thiadiazol-2-yl)indole-6-sulfonamide;
3-(4-fluorobenzoyl)-N-(1-methylcyclopropyl)-1-(5-methyl-1,3,4-thiadiazol-2-yl)indole-6-sulfonamide;
ethyl 3-[(2,4-dimethylthiazol-5-yl)methyl]-6-[(1-methylcyclopropyl)sulfamoyl]indole-1-carboxylate;
1-[3-(dimethylamino)propyl]-N-(1-methylcyclopropyl)-3-(5-methyl-1,3,4-oxadiazol-2-yl)-2-oxo-benzimidazole-5-sulfonamide;
1-(2-methoxyethyl)-N-(1-methylcyclopropyl)-3-(5-methyl-1,3,4-oxadiazol-2-yl)-2-oxo-benzimidazole-5-sulfonamide;
1-[3-(dimethylamino)propyl]-N-(1-methylcyclopropyl)-3-(5-methyl-1,3,4-thiadiazol-2-yl)-2-oxo-benzimidazole-5-sulfonamide;
N-(1-methylcyclopropyl)-1-[(1-methyl-3-piperidyl)methyl]-3-(5-methyl-1,3,4-thiadiazol-2-yl)-2-oxo-benzimidazole-5-sulfonamide;
1-[2-(dimethylamino)ethyl]-N-(1-methylcyclopropyl)-3-(5-methyl-1,3,4-oxadiazol-2-yl)-2-oxo-benzimidazole-5-sulfonamide;
N-(1-methylcyclopropyl)-3-(5-methyl-1,3,4-oxadiazol-2-yl)-1-[(1-methyl-2-piperidyl)methyl]-2-oxo-benzimidazole-5-sulfonamide;
N-(1-methylcyclopropyl)-3-(5-methyl-1,3,4-oxadiazol-2-yl)-1-[(1-methyl-3-piperidyl)methyl]-2-oxo-benzimidazole-5-sulfonamide;
N-(1-methylcyclopropyl)-3-(5-methyl-1,3,4-oxadiazol-2-yl)-2-oxo-1-[2-(1-piperidyl)ethyl]benzimidazole-5-sulfonamide;
N-(1-methylcyclopropyl)-3-(5-methyl-1,3,4-oxadiazol-2-yl)-1-(2-morpholinoethyl)-2-oxo-benzimidazole-5-sulfonamide;
N-(1-methylcyclopropyl)-3-(5-methyl-1,3,4-oxadiazol-2-yl)-2-oxo-1-(2-pyrrolidin-1-ylethyl)benzimidazole-5-sulfonamide;

N-(1-methylcyclopropyl)-1-[(1-methyl-2-piperidyl)methyl]-3-(5-methyl-1,3,4-thiadiazol-2-yl)-2-oxo-benzimidazole-5-sulfonamide;
3-acetyl-N-(1-methylcyclopropyl)-1-(5-methyl-1,3,4-thiadiazol-2-yl)indole-6-sulfonamide;
3-(cyclopropanecarbonyl)-1-[5-(difluoromethyl)-1,3,4-thiadiazol-2-yl]-N-(1-methylcyclopropyl)indole-6-sulfonamide;
3-[(4-fluorophenyl)methyl]-N-(1-methylcyclopropyl)-1-(5-methyl-1,3,4-thiadiazol-2-yl)indazole-6-sulfonamide;
1-(2-methoxyethyl)-N-(1-methylcyclopropyl)-3-(5-methyl-1,3,4-thiadiazol-2-yl)-2-oxo-benzimidazole-5-sulfonamide;
1-(3-methoxypropyl)-N-(1-methylcyclopropyl)-3-(5-methyl-1,3,4-thiadiazol-2-yl)-2-oxo-benzimidazole-5-sulfonamide;
N-(1-methylcyclopropyl)-3-(5-methyl-1,3,4-thiadiazol-2-yl)-2-oxo-1-[2-(1-piperidyl)ethyl]benzimidazole-5-sulfonamide;
1-(3-methoxypropyl)-N-(1-methylcyclopropyl)-3-(5-methyl-1,3,4-oxadiazol-2-yl)-2-oxo-benzimidazole-5-sulfonamide;
3-[5-[(1-methylcyclopropyl)sulfamoyl]-3-(5-methyl-1,3,4-oxadiazol-2-yl)-2-oxo-benzimidazol-1-yl]propanamide;
N-(1-methylcyclopropyl)-3-(5-methyl-1,3,4-thiadiazol-2-yl)-1-(2-morpholinoethyl)-2-oxo-benzimidazole-5-sulfonamide;
N-(1-methylcyclopropyl)-3-(5-methyl-1,3,4-thiadiazol-2-yl)-2-oxo-1-(2-pyrrolidin-1-ylethyl)benzimidazole-5-sulfonamide;
3-[5-[(1-methylcyclopropyl)sulfamoyl]-3-(5-methyl-1,3,4-thiadiazol-2-yl)-2-oxo-benzimidazol-1-yl]propanamide;
N-(1-methylcyclopropyl)-1-[(1-methylpyrrolidin-2-yl)methyl]-3-(5-methyl-1,3,4-thiadiazol-2-yl)-2-oxo-benzimidazole-5-sulfonamide;
N-[1-(fluoromethyl)cyclopropyl]-1-methyl-3-(5-methyl-1,3,4-thiadiazol-2-yl)-2-oxo-benzimidazole-5-sulfonamide;
N-(1-cyanocyclopropyl)-3-(5-methyl-1,3,4-thiadiazol-2-yl)-2-oxo-1H-benzimidazole-5-sulfonamide;
N-(1-cyanocyclopropyl)-1-ethyl-3-(5-methyl-1,3,4-thiadiazol-2-yl)-2-oxo-benzimidazole-5-sulfonamide;
1-ethyl-N-[1-(fluoromethyl)cyclopropyl]-3-(5-methyl-1,3,4-thiadiazol-2-yl)-2-oxo-benzimidazole-5-sulfonamide;
N-[1-(fluoromethyl)cyclopropyl]-1-(2-methoxyethyl)-3-(5-methyl-1,3,4-thiadiazol-2-yl)-2-oxo-benzimidazole-5-sulfonamide;
N-(1-cyanocyclopropyl)-1-(2-methoxyethyl)-3-(5-methyl-1,3,4-thiadiazol-2-yl)-2-oxo-benzimidazole-5-sulfonamide;
N-(1-cyanocyclopropyl)-3-[5-(difluoromethyl)-1,3,4-thiadiazol-2-yl]-1-(2-methoxyethyl)-2-oxo-benzimidazole-5-sulfonamide;
3-[5-(difluoromethyl)-1,3,4-thiadiazol-2-yl]-N-[1-(fluoromethyl)cyclopropyl]-1-(2-methoxyethyl)-2-oxo-benzimidazole-5-sulfonamide;
3-[5-(difluoromethyl)-1,3,4-thiadiazol-2-yl]-1-[(2,5-dimethylpyrazol-3-yl)methyl]-N-[1-(fluoromethyl)cyclopropyl]-2-oxo-benzimidazole-5-sulfonamide;
N-(1-cyanocyclopropyl)-3-[5-(difluoromethyl)-1,3,4-thiadiazol-2-yl]-1-[(2,5-dimethylpyrazol-3-yl)methyl]-2-oxo-benzimidazole-5-sulfonamide;
1-(cyanomethyl)-N-(1-methylcyclopropyl)-3-(5-methyl-1,3,4-thiadiazol-2-yl)-2-oxo-benzimidazole-5-sulfonamide;
3-[5-(difluoromethyl)-1,3,4-thiadiazol-2-yl]-6-fluoro-N-[1-(fluoromethyl)cyclopropyl]-1-(2-methoxyethyl)-2-oxo-benzimidazole-5-sulfonamide;
3-[5-(difluoromethyl)-1,3,4-thiadiazol-2-yl]-6-fluoro-1-(2-methoxyethyl)-N-(1-methylcyclopropyl)-2-oxo-benzimidazole-5-sulfonamide;
3-[5-(difluoromethyl)-1,3,4-thiadiazol-2-yl]-1-(2-methoxyethyl)-N-(1-methylcyclopropyl)-2-oxo-benzimidazole-5-sulfonamide;
3-[5-(difluoromethyl)-1,3,4-thiadiazol-2-yl]-1-[3-(dimethylamino)propyl]-N-[1-(fluoromethyl)cyclopropyl]-2-oxo-benzimidazole-5-sulfonamide;
6-fluoro-1-methyl-N-(1-methylcyclopropyl)-3-(3-methyl-1,2,4-thiadiazol-5-yl)-2-oxo-benzimidazole-5-sulfonamide;
6-fluoro-N-[1-(fluoromethyl)cyclopropyl]-1-methyl-3-(3-methyl-1,2,4-thiadiazol-5-yl)-2-oxo-benzimidazole-5-sulfonamide;
3-[5-(difluoromethyl)-1,3,4-thiadiazol-2-yl]-6-fluoro-1-methyl-N-(1-methylcyclopropyl)-2-oxo-benzimidazole-5-sulfonamide;
3-[5-(difluoromethyl)-1,3,4-thiadiazol-2-yl]-6-fluoro-N-[1-(fluoromethyl)cyclopropyl]-1-methyl-2-oxo-benzimidazole-5-sulfonamide;
N-[1-(fluoromethyl)cyclopropyl]-1-methyl-2-oxo-3-(1,2,4-thiadiazol-5-yl)benzimidazole-5-sulfonamide;
1-methyl-N-(1-methylcyclopropyl)-3-(3-methyl-1,2,4-thiadiazol-5-yl)-2-oxo-benzimidazole-5-sulfonamide;
N-[1-(fluoromethyl)cyclopropyl]-1-methyl-3-(3-methyl-1,2,4-thiadiazol-5-yl)-2-oxo-benzimidazole-5-sulfonamide;
1-(cyanomethyl)-N-[1-(fluoromethyl)cyclopropyl]-3-(5-methyl-1,3,4-thiadiazol-2-yl)-2-oxo-benzimidazole-5-sulfonamide;
1-(cyanomethyl)-N-(1-methylcyclopropyl)-3-(3-methyl-1,2,4-thiadiazol-5-yl)-2-oxo-benzimidazole-5-sulfonamide;
1-(cyanomethyl)-N-[1-(fluoromethyl)cyclopropyl]-3-(3-methyl-1,2,4-thiadiazol-5-yl)-2-oxo-benzimidazole-5-sulfonamide;
3-[5-(difluoromethyl)-1,3,4-thiadiazol-2-yl]-N-[1-(fluoromethyl)cyclopropyl]-1-methyl-2-oxo-benzimidazole-5-sulfonamide;
1-(2-methoxyethyl)-N-(1-methylcyclopropyl)-3-(3-methyl-1,2,4-thiadiazol-5-yl)-2-oxo-benzimidazole-5-sulfonamide;
N-[1-(fluoromethyl)cyclopropyl]-1-(2-methoxyethyl)-2-oxo-3-(1,2,4-thiadiazol-5-yl)benzimidazole-5-sulfonamide;
N-[1-(fluoromethyl)cyclopropyl]-1-(2-methoxyethyl)-3-(3-methyl-1,2,4-thiadiazol-5-yl)-2-oxo-benzimidazole-5-sulfonamide;
N-[1-(fluoromethyl)cyclopropyl]-1-(3-methoxypropyl)-3-(3-methyl-1,2,4-thiadiazol-5-yl)-2-oxo-benzimidazole-5-sulfonamide;
1-[2-(dimethylamino)ethyl]-N-[1-(fluoromethyl)cyclopropyl]-3-(3-methyl-1,2,4-thiadiazol-5-yl)-2-oxo-benzimidazole-5-sulfonamide;
N-[1-(fluoromethyl)cyclopropyl]-1-(3-methoxypropyl)-3-(5-methyl-1,3,4-thiadiazol-2-yl)-2-oxo-benzimidazole-5-sulfonamide;
1-[2-(dimethylamino)ethyl]-N-[1-(fluoromethyl)cyclopropyl]-3-(5-methyl-1,3,4-thiadiazol-2-yl)-2-oxo-benzimidazole-5-sulfonamide;
1-methyl-N-(1-methylcyclopropyl)-3-(5-methyl-1,3,4-oxadiazol-2-yl)-2-oxo-benzimidazole-5-sulfonamide;

1-ethyl-N-(1-methylcyclopropyl)-3-(5-methyl-1,3,4-oxadiazol-2-yl)-2-oxo-benzimidazole-5-sulfonamide;
1-(2-fluoroethyl)-N-(1-methylcyclopropyl)-3-(5-methyl-1,3,4-oxadiazol-2-yl)-2-oxo-benzimidazole-5-sulfonamide;
6-fluoro-N-(1-methylcyclopropyl)-3-(5-methyl-1,3,4-oxadiazol-2-yl)-2-oxo-1H-benzimidazole-5-sulfonamide;
3-[5-(difluoromethyl)-1,3,4-thiadiazol-2-yl]-N-[1-(fluoromethyl)cyclopropyl]-2-oxo-1-prop-2-ynyl-benzimidazole-5-sulfonamide;
6-fluoro-N-[1-(fluoromethyl)cyclopropyl]-3-(5-methyl-1,3,4-oxadiazol-2-yl)-2-oxo-1H-benzimidazole-5-sulfonamide;
3-[5-(difluoromethyl)-1,3,4-oxadiazol-2-yl]-1-methyl-N-(1-methylcyclopropyl)-2-oxo-benzimidazole-5-sulfonamide;
3-[5-(difluoromethyl)-1,3,4-oxadiazol-2-yl]-N-[1-(fluoramethyl)cyclopropyl]-1-methyl-2-oxa-benzimidazole-5-sulfonamide;
6-fluoro-1-methyl-N-(1-methylcyclopropyl)-3-(5-methyl-1,3,4-oxadiazol-2-yl)-2-oxo-benzimidazole-5-sulfonamide;
6-fluoro-1-(2-fluoroethyl)-N-(1-methylcyclopropyl)-3-(5-methyl-1,3,4-oxadiazol-2-yl)-2-oxo-benzimidazole-5-sulfonamide;
3-[5-(difluoromethyl)-1,3,4-oxadiazol-2-yl]-1-ethyl-6-fluoro-N-(1-methylcyclopropyl)-2-oxo-benzimidazole-5-sulfonamide;
3-[5-(difluoromethyl)-1,3,4-oxadiazol-2-yl]-1-ethyl-6-fluoro-N-[1-(fluoromethyl)cyclopropyl]-2-oxo-benzimidazole-5-sulfonamide;
3-[5-(difluoromethyl)-1,3,4-oxadiazol-2-yl]-1-ethyl-N-(1-methylcyclopropyl)-2-oxo-benzimidazole-5-sulfonamide;
3-[5-(difluoromethyl)-1,3,4-oxadiazol-2-yl]-1-ethyl-N-[1-(fluoromethyl)cyclopropyl]-2-oxo-benzimidazole-5-sulfonamide;
6-fluoro-N-[1-(fluoromethyl)cyclopropyl]-1-(2-methoxyethyl)-3-(6-methylpyridazin-3-yl)-2-oxo-benzimidazole-5-sulfonamide;
6-fluoro-N-[1-(fluoromethyl)cyclopropyl]-1-methyl-3-(6-methylpyridazin-3-yl)-2-oxo-benzimidazole-5-sulfonamide;
6-fluoro-1-methyl-N-(1-methylcyclopropyl)-3-(6-methylpyridazin-3-yl)-2-oxo-benzimidazole-5-sulfonamide;
6-fluoro-N-[1-(fluoromethyl)cyclopropyl]-1-methyl-2-oxo-3-[6-(trifluoromethyl)pyridazin-3-yl]benzimidazole-5-sulfonamide;
3-[5-(difluoromethyl)-1,3,4-thiadiazol-2-yl]-1-ethyl-6-fluoro-N-(1-methylcyclopropyl)-2-oxo-benzimidazole-5-sulfonamide;
3-[5-(difluoromethyl)-1,3,4-thiadiazol-2-yl]-1-ethyl-6-fluoro-N-[1-(fluoromethyl)cyclopropyl]-2-oxo-benzimidazole-5-sulfonamide;
3-[5-(difluoromethyl)-1,3,4-oxadiazol-2-yl]-6-fluoro-1-methyl-N-(1-methylcyclopropyl)-2-oxo-benzimidazole-5-sulfonamide;
3-[5-(difluoromethyl)-1,3,4-oxadiazol-2-yl]-6-fluoro-N-[1-(fluoromethyl)cyclopropyl]-1-methyl-2-oxo-benzimidazole-5-sulfonamide;
3-[5-(difluoromethyl)-1,3,4-oxadiazol-2-yl]-6-fluoro-1-(2-fluoroethyl)-N-(1-methylcyclopropyl)-2-oxo-benzimidazole-5-sulfonamide;
3-[5-(difluoromethyl)-1,3,4-oxadiazol-2-yl]-6-fluoro-1-(2-fluoroethyl)-N-[1-(fluoromethyl)cyclopropyl]-2-oxo-benzimidazole-5-sulfonamide;
3-[5-(difluoromethyl)-1,3,4-thiadiazol-2-yl]-6-fluoro-N-[1-(fluoromethyl)cyclopropyl]-2-oxo-1-prop-2-ynyl-benzimidazole-5-sulfonamide;
2-[3-[5-(difluoromethyl)-1,3,4-thiadiazol-2-yl]-6-fluoro-5-[[1-(fluoromethyl)cyclopropyl]sulfamoyl]-2-oxo-benzimidazol-1-yl]acetamide;
1-(cyanomethyl)-3-[5-(difluoromethyl)-1,3,4-thiadiazol-2-yl]-6-fluoro-N-[1-(fluoromethyl)cyclopropyl]-2-oxo-benzimidazole-5-sulfonamide;
3-[5-(Difluoromethyl)-1,3,4-thiadiazol-2-yl]-6-fluoro-1-(2-fluoroethyl)-N-[1-(fluoromethyl)cyclopropyl]-2-oxo-benzimidazole-5-sulfonamide;
3-[5-(Difluoromethyl)-1,3,4-thiadiazol-2-yl]-6-fluoro-1-(2-fluoroethyl)-N-(1-methylcyclopropyl)-2-oxo-benzimidazole-5-sulfonamide;
Ethyl 3-methyl-5-[(1-methylcyclopropyl)sulfamoyl]benzofuran-2-carboxylate;
or a pharmaceutically acceptable salt or solvate thereof.

The various functional groups and substituents making up the compounds of the formula I are typically chosen such that the molecular weight of the compound of the formula does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J.

March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including $^1$H, $^2$H(D), and $^3$H (T); C may be in any isotopic form, including $^{12}$C, $^{13}$C, and $^{14}$C; and O may be in any isotopic form, including $^{16}$O and $^{18}$O; and the like.

It is also to be understood that certain compounds of the formula I may exist in solvated as well as unsolvated forms such as, for example, hydrated forms. It is to be understood that the invention encompasses all such solvated forms that possess antiproliferative activity.

It is also to be understood that certain compounds of the formula I may exhibit polymorphism, and that the invention encompasses all such forms that possess antiproliferative activity.

Compounds of the formula I may exist in a number of different tautomeric forms and references to compounds of the formula I include all such forms. For the avoidance of doubt, where a compound can exist in one of several tautomeric forms, and only one is specifically described or shown, all others are nevertheless embraced by formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

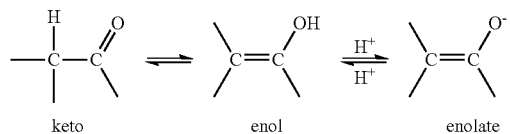

Compounds of the formula I containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4$^{th}$ Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of formula I may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the formula I and in-vivo cleavable amide derivatives that may be formed at a carboxy group or an amino group in a compound of the formula I.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$ alkylamine such as methylamine, a $(C_{1-4}$alkyl$)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of formula I will vary depending on the nature of $X_1$, $X_2$, $X_3$, $X_4$, $X_5$, W, $R_5$, $R_{1a}$, $R_{1b}$, $R_{1c}$, $R_{1d}$, and $R_{1e}$, and any substituent groups associated therewith. Suitable processes for their preparation are described further in the accompanying Examples.

Once a compound of formula I has been synthesised by any one of the processes defined herein, the processes may then further comprise the additional steps of:
(i) removing any protecting groups present;
(ii) converting the compound formula I into another compound of formula I;
(iii) forming a pharmaceutically acceptable salt, hydrate or solvate thereof; and/or
(iv) forming a prodrug thereof.

An example of (ii) above is when a compound of formula I is synthesised and then one or more of the groups of $X_1$, $X_2$, $X_3$, $X_4$, $X_5$, W, $R_5$, $R_{1a}$, $R_{1b}$, $R_{1c}$, $R_{1d}$, and $R_{1e}$, may be further reacted to change the nature of the group and provide an alternative compound of formula I. For example, the compound can be reacted to covert $R_1$ into a substituent group other than hydrogen.

The resultant compounds of formula I can be isolated and purified using techniques well known in the art.

In one aspect of the present invention, the compounds of formula I, or a pharmaceutically acceptable salt or solvate thereof, may be synthesised by a method comprising either:
a) reacting a compound of formula A:

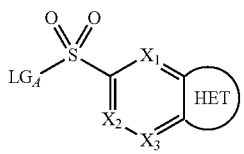

Formula A wherein $X_1$, $X_2$, $X_3$ and HET are as defined hereinabove, and $LG_A$ is a suitable leaving group;
with a compound of formula B:

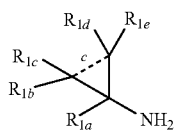

Formula B wherein $R_{1a}$, $R_{1b}$, $R_{1c}$, $R_{1d}$, $R_{1e}$ and c are as defined hereinabove;
b) reacting a compound of formula C:

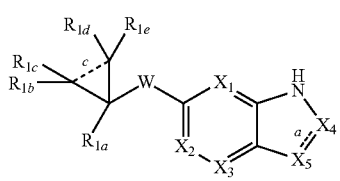

Formula C wherein $X_1$, $X_2$, $X_3$, $X_4$, $X_5$, W, $R_{1a}$, $R_{1b}$, $R_{1c}$, $R_{1d}$, $R_{1e}$, a and c are as defined hereinabove;
with a compound of formula D:

$R_5$-L    Formula D wherein $R_5$ is as defined hereinabove, and L is a suitable leaving group (e.g. halo, OMs) or a suitable coupling group (e.g. $CO_2H$);
c) reacting a compound of formula E:

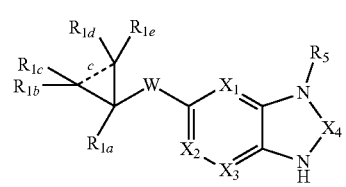

Formula E wherein $X_1$, $X_2$, $X_3$, $X_4$, W, $R_5$, $R_{1a}$, $R_{1b}$, $R_{1c}$, $R_{1d}$, $R_{1e}$ and c are as defined hereinabove; with a compound of formula F:

$R_{7N}$-LG    Formula F wherein $R_{7N}$ is as defined hereinabove, and LG is a suitable leaving group (e.g. halo, OMs);
d) reacting a compound of formula G:

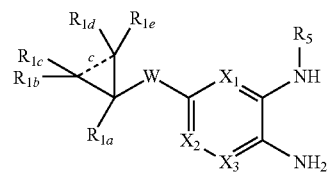

Formula G wherein $X_1$, $X_2$, $X_3$, W, $R_5$, $R_{1a}$, $R_{1b}$, $R_{1c}$, $R_{1d}$, $R_{1e}$ and c are as defined hereinabove;
with a compound of formula H:

$R_{6c}$-Q    Formula H wherein $R_{6c}$ is as defined in hereinabove, and Q is a suitable reagent for a condensation reaction (e.g. $CO_2H$);
e) optionally thereafter, and if necessary:
i) removing any protecting groups present;
ii) converting the compound formula I into another compound of formula I; and/or
iii) forming a pharmaceutically acceptable salt or solvate thereof.

Biological Activity

The PARG enzyme and cell assays described in accompanying Example section may be used to measure the pharmacological effects of the compounds of the present invention.

Although the pharmacological properties of the compounds of formula I vary with structural change, as expected, the compounds of the invention were found to be active in these PARG assays.

In general, the compounds of the invention demonstrate an $IC_{50}$ of 10 μM or less in the PARG enzyme assay described herein, with preferred compounds of the invention demonstrating an $IC_{50}$ of 1000 nM or less, or 500 nM or less, and the most preferred compounds of the invention demonstrating an $IC_{50}$ of 200 nM or less.

In general, the compounds of the invention demonstrate an $IC_{50}$ of 1 µM or less in the PARG cell assay described herein, with preferred compounds of the invention demonstrating an $IC_{50}$ of 500 nM or less and the most preferred compounds of the invention demonstrating an $IC_{50}$ of 200 nM or less.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of PARG.

The present invention therefore provides a method of inhibiting PARG enzyme activity in vitro or in vivo, said method comprising contacting a cell with an effective amount of a compound, or a pharmaceutically acceptable salt, hydrate or solvate thereof, as defined herein.

The present invention also provides a method of selectively inhibiting PARG enzyme activity over PARP1 or ARH3 enzyme activity in vitro or in vivo, said method comprising contacting a cell with an effective amount of a compound, or a pharmaceutically acceptable salt, hydrate or solvate thereof, as defined herein.

The present invention also provides a method of treating a disease or disorder in which PARG activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of PARG enzyme activity.

The present invention provides a compound, or a pharmaceutically acceptable salt, hydrate or solvate thereof, as defined herein for use in the treatment of a disease or disorder in which PARG activity is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of PARG enzyme activity.

The present invention provides a use of a compound, or a pharmaceutically acceptable salt, hydrate or solvate thereof, as defined herein in the manufacture of a medicament for the selective inhibition of PARG enzyme activity over PARP1 or ARH3 enzyme activity.

The present invention provides a use of a compound, or a pharmaceutically acceptable salt, hydrate or solvate thereof, as defined herein in the manufacture of a medicament for the treatment of a disease or disorder in which PARG activity is implicated.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers (by virtue of their inhibition of PARG enzyme activity).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Materials, Equipment, and General Experimental Details

General Experimental

Flash chromatography was performed using pre-packed silica gel cartridges (KP-Sil SNAP, Biotage, Hengoed UK or RediSep Rf, Isco). Thin layer chromatography was conducted with 5×10 cm plates coated with Merck Type 60 $F_{254}$ silica gel to a thickness of 0.25 mm. All reagents obtained from commercial sources were used without further purification. Anhydrous solvents were obtained from the Sigma-Aldrich Chemical Company Ltd. or Fisher Chemicals Ltd., and used without further drying. HPLC grade solvents were obtained from Fisher Chemicals Ltd. or Romil Ltd.

All compounds were >90% purity as determined by examination of both the LC-MS and $^1$H NMR spectra unless otherwise indicated. Where Cl or Br were present, expected isotopic distribution patterns were observed.

$^1$H NMR

Proton ($^1$H) NMR spectra were recorded on either a 300 MHz or 400 MHz Bruker spectrometer or ECX 300 MHz or ECX 400 MHz JEOL Spectrometer. Solutions were typically prepared in either deuterochloroform (CDCl$_3$) or deuterated dimethylsulfoxide (DMSO-d$_6$) with chemical shifts referenced to tetramethylsilane (TMS) or deuterated solvent as an internal standard. $^1$H NMR data are reported indicating the chemical shift (δ), the integration (e.g. 1H), the multiplicity (s, singlet; d, doublet; t, triplet; q, quartet; m, multiplet; br, broad; dd, doublet of doublets etc.) and the coupling constant (J) in Hz (app. implies apparent coupling on broadened signals). Deuterated solvents were obtained from the Sigma-Aldrich Chemical Company, Goss or Fluorochem.

Analytical LC-MS.

LC-MS analyses were performed using one of the following methods (denoted in Table 2):

LC-MS Method A

A Waters Acquity UPLC system fitted with BEH C18 1.7 μM columns (2.1×50 mm) and with UV diode array detection (210-400 nm). Positive and negative mass ion detection was performed using a Waters SQD detector. Analyses were performed with either buffered acidic or basic solvents and gradients as detailed below:
Low pH:
Solvent A—Water+10 mM ammonium formate+0.1% formic acid
Solvent B—Acetonitrile+5% water+0.1% formic acid High pH:
Solvent A—Water+10 mM ammonium hydrogen carbonate+0.1% ammonia solution
Solvent B—Acetonitrile+0.1% ammonia solution Gradient:

| Time | Flow rate (mL/min) | % Solvent A | % Solvent B |
|---|---|---|---|
| 0 | 0.6 | 95 | 5 |
| 1.2 | 0.6 | 5 | 95 |
| 1.7 | 0.6 | 5 | 95 |
| 1.8 | 0.6 | 95 | 5 |

LC-MS Method B

A Waters Acquity ZQD (ESI) UPLC system fitted with XBridge C18 2.1×50 mm, 2.5 μm or equivalent and with UV diode array detection (215-350 nm)
Low pH:
Solvent A—MeCN
Solvent B—0.1% Formic Acid (pH 3)
High pH:
Solvent A—MeCN
Solvent B—10 mM $NH_4HCO_3$ (pH 10)
Gradient:

| Time | Flow rate (mL/min) | % Solvent A | % Solvent B |
|---|---|---|---|
| 0 | 0.8 | 98 | 2 |
| 0.8 | 0.8 | 2 | 98 |
| 1.2 | 0.8 | 2 | 98 |
| 1.25 | 0.8 | 98 | 2 |

LC-MS Method C

Waters X Bridge C18: 50 mm×4.6 mm, 3.5 μm Column, UV diode array detection (214-350 nm)
High pH:
Solvent A—Water (0.01 mol/L $NH_4HCO_3$)
Solvent B—MeCN
Gradient:

| Time | Flow rate (mL/min) | % Solvent A | % Solvent B |
|---|---|---|---|
| 0 | 2 | 95 | 5 |
| 1.6 | 2 | 5 | 95 |
| 3 | 2 | 95 | 95 |

Preparative HPLC

Some compounds were purified by preparative HPLC using the following systems. A Waters FractionLynx MS autopurification system, with a Waters XBridge 5 μm C18, 100 mm×19 mm i.d. column, running at a flow rate of 20 mL/min with UV diode array detection (210-400 nm) and mass-directed collection using both positive and negative mass ion detection.

Purifications were performed using buffered acidic or basic solvent systems as appropriate. Compound retention times on the system were routinely assessed using a 30-50 μL test injection and a standard gradient, and then purified using an appropriately chosen focussed gradient as detailed below, based upon observed retention time.
Low pH:
Solvent A—Water+10 mM ammonium formate+0.1% formic acid
Solvent B—Acetonitrile+5% water+0.1% formic acid
High pH:
Solvent A—Water+10 mM ammonium formate+0.1% ammonia solution Solvent B—Acetonitrile+5% water+0.1% ammonia solution
Standard Gradient:

| Time | Flow rate (mL/min) | % Solvent A | % Solvent B |
|---|---|---|---|
| 0 | 20 | 90 | 10 |
| 0.3 | 20 | 90 | 10 |
| 8.5 | 20 | 2 | 98 |
| 12 | 20 | 2 | 98 |
| 12.5 | 0 | 2 | 98 |

Focussed Gradients:

| | | % Solvent B Retention time on standard gradient (min.) | | | | |
|---|---|---|---|---|---|---|
| Time | Flow rate (mL/min) | 0-5.2 | 4.9-6.6 | 6.3-7.5 | 7.3-9.5 | 9.3-12 |
| 0 | 20 | 10 | 10 | 10 | 10 | 10 |
| 0.25 | 20 | 10 | 10 | 10 | 10 | 10 |
| 0.35 | 20 | 10 | 20 | 35 | 45 | 60 |
| 10 | 20 | 45 | 55 | 65 | 75 | 98 |
| 12 | 20 | 98 | 98 | 98 | 98 | 98 |
| 12.5 | 0 | 98 | 98 | 98 | 98 | 98 |

A Gilson-GX281 autopurification system, with a Waters XBridge 5 μm C18, 100 mm×30 mm i.d. or Waters XSelect 5 μm C18, 150 mm×19 mm i.d running at a flow rate of 20 mL/min with UV detection (214 nm, 254 nm). Purifications were performed using buffered basic solvent systems as appropriate. Compound retention times on the system were routinely assessed using Analytical LC-MS test as a standard gradient, then purified using an appropriately chosen focussed gradient as detailed below, based upon observed retention time.

Column: Waters X-Bridge C18: 100 mm*30 mm 5 um
Mobile Phase: A: Water (0.05% Ammonia) $B_2$: Methanol
Focussed Gradients:

| Flow rate | Solvent $B_2$ (Prep-HPLC) Reference gradient (%) | | | | |
|---|---|---|---|---|---|
| (mL/min) | 0 (min) | 8 (min) | 8.2 (min) | 9 (min) | 12 (min) |
| 20 | 45 | 65 | 95 | 95 | 95 |
| 20 | 50 | 70 | 95 | 95 | 95 |
| 20 | 55 | 75 | 95 | 95 | 95 |

Column: Waters X-Select 5 μm C18, 150 mm×19 mm
Mobile Phase: A: Water (0.05% Ammonia) $B_2$: Methanol Focussed Gradients:
| Flow rate | Solvent B$_2$ (Prep-HPLC) Reference gradient (%) | | | | |
|---|---|---|---|---|---|
| (mL/min) | 0 (min) | 8 (min) | 8.2 (min) | 9 (min) | 12 (min) |
| 20 | 45 | 65 | 95 | 95 | 95 |
| 20 | 50 | 70 | 95 | 95 | 95 |
| 20 | 55 | 75 | 95 | 95 | 95 |
Column: Waters X-Select 5 μm C18, 150 mm×19 mm
Mobile Phase: A: Water (10 mmol NH$_4$HCO$_3$) B$_1$: Acetonitrile
Focussed Gradients:
| Flow rate | Solvent B$_1$ (Prep-HPLC) Reference gradient (%) | | | | |
|---|---|---|---|---|---|
| (mL/min) | 0 (min) | 8 (min) | 8.2 (min) | 9 (min) | 12 (min) |
| 20 | 30 | 50 | 95 | 95 | 95 |
| 20 | 35 | 55 | 95 | 95 | 95 |
| 20 | 40 | 60 | 95 | 95 | 95 |
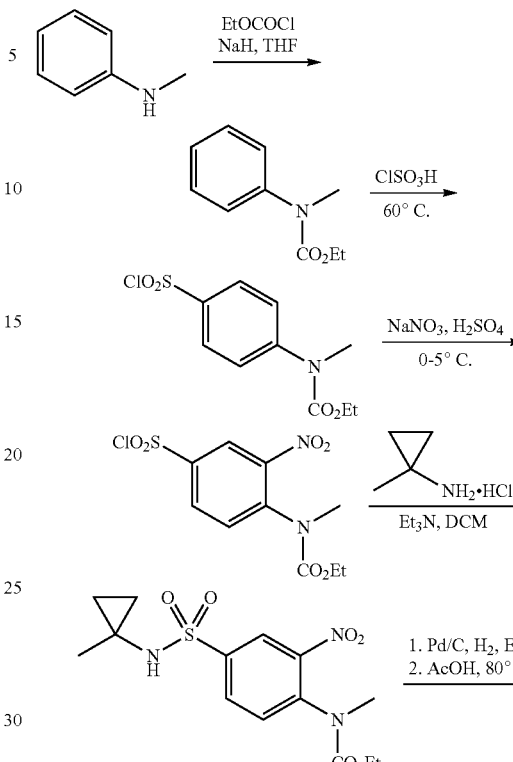
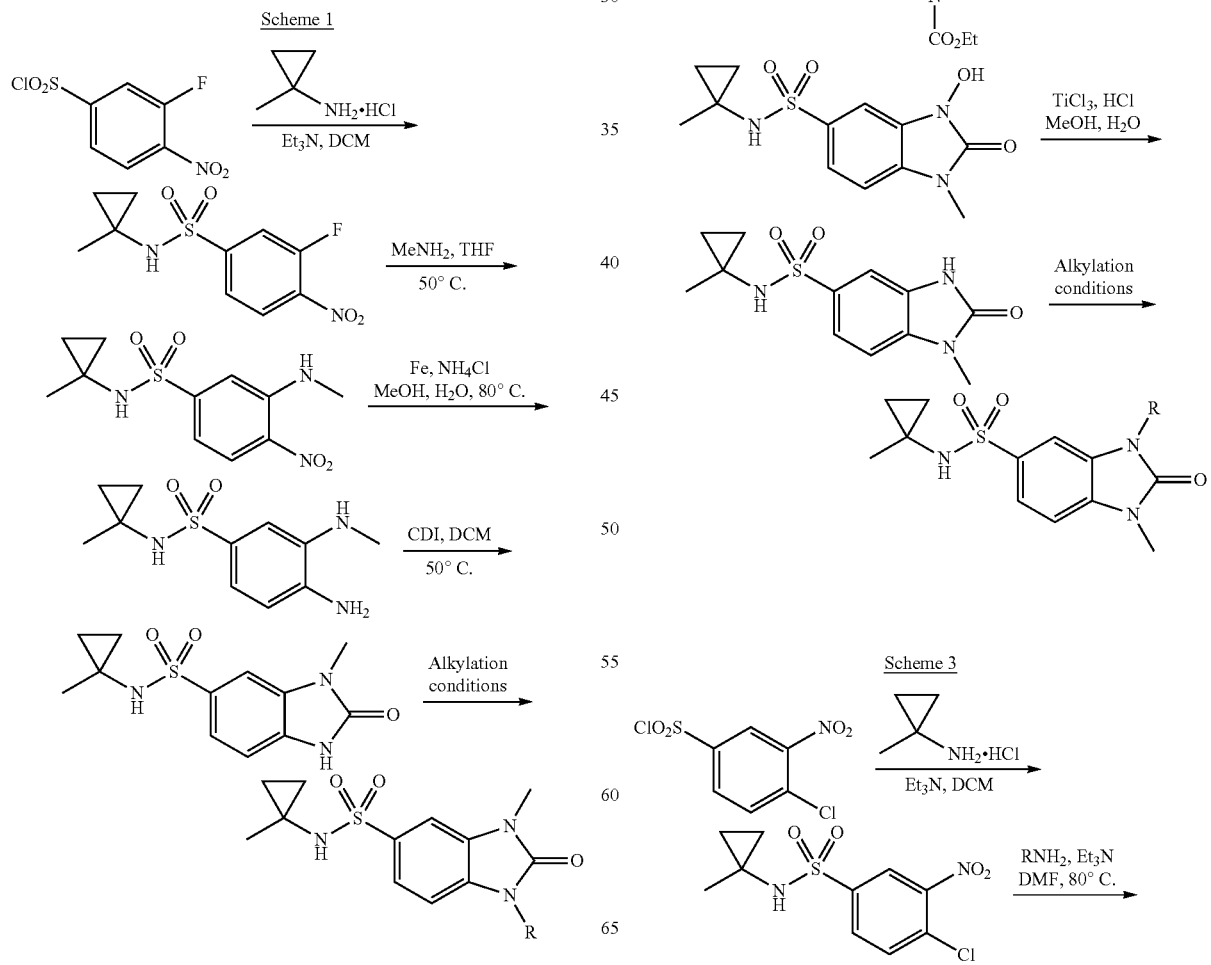

-continued
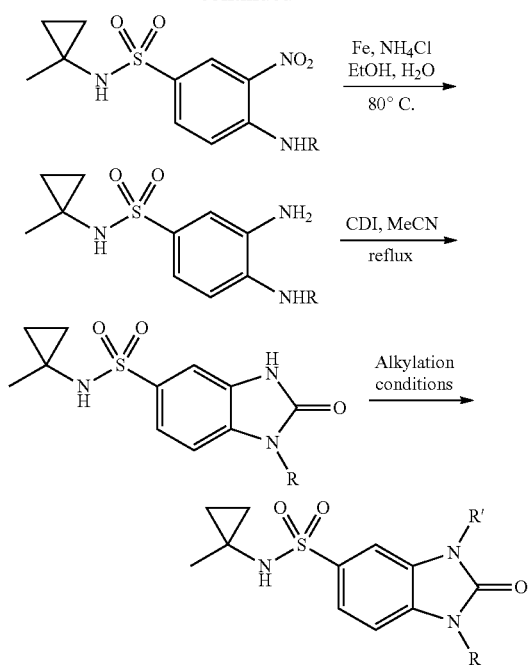
Scheme 4
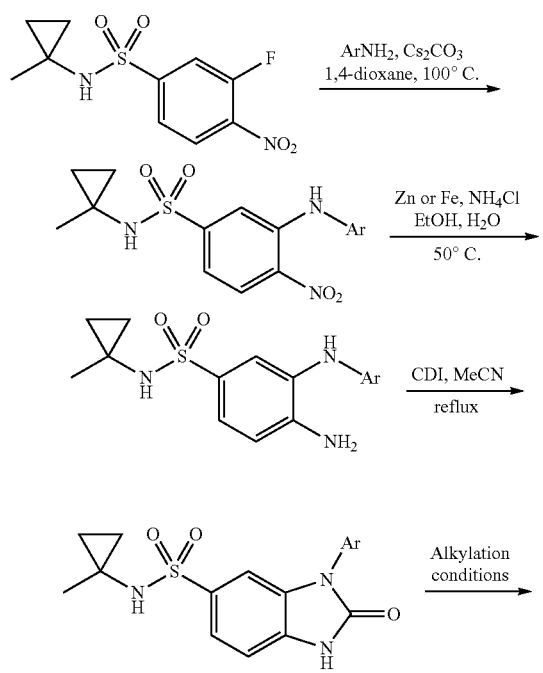
Scheme 5
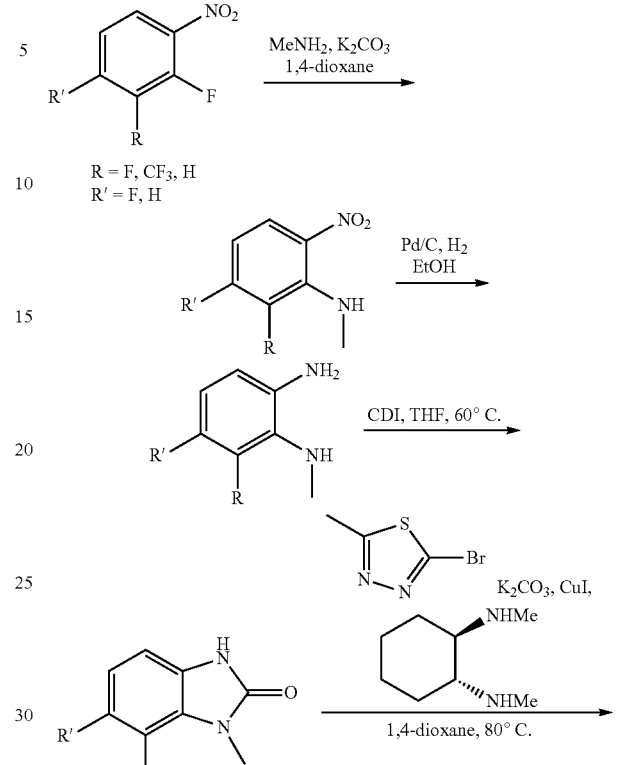
Scheme 6
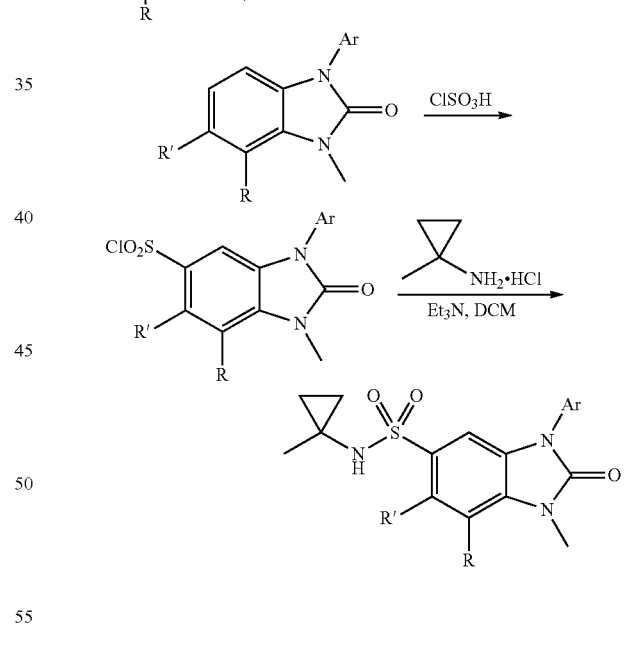
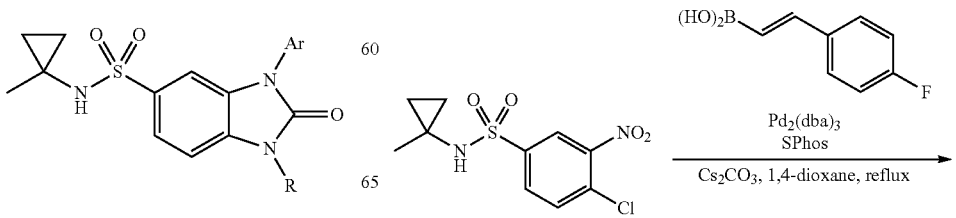

-continued
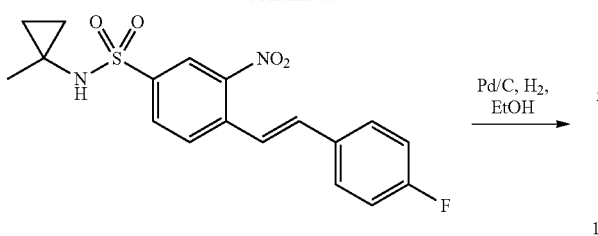
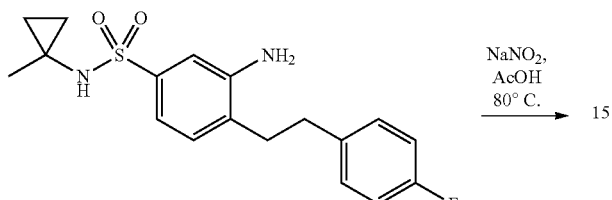
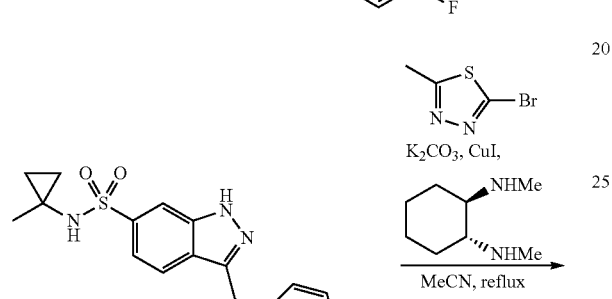
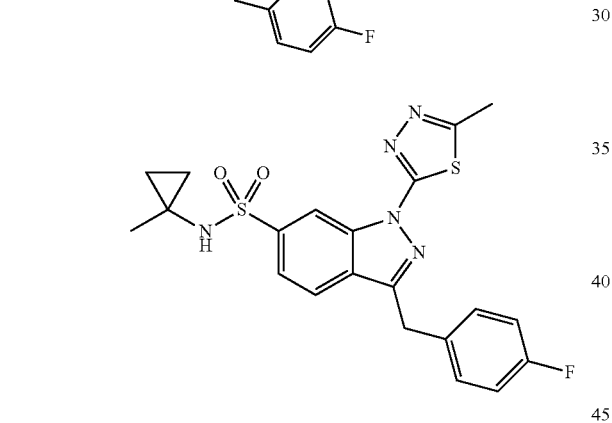
Scheme 7
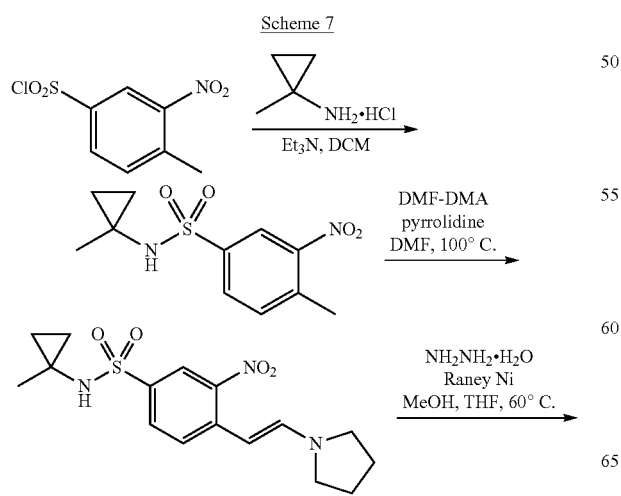
-continued
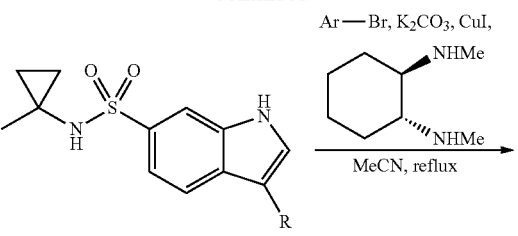
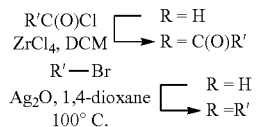
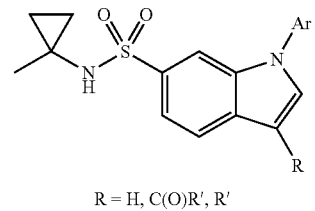
R = H, C(O)R', R'
Scheme 8
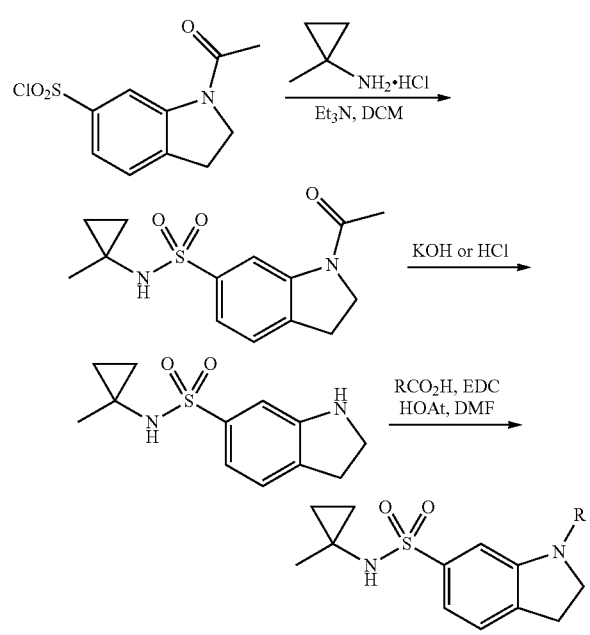
Scheme 9
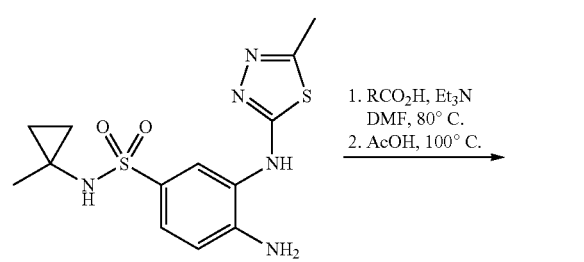

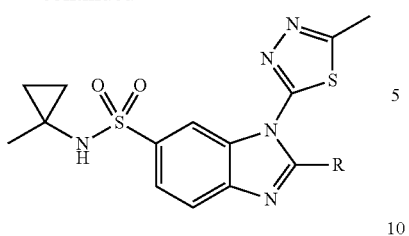
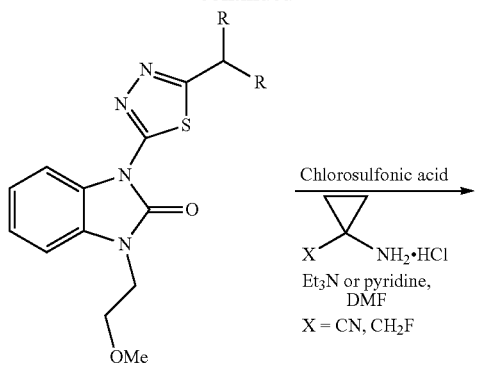
Scheme 10
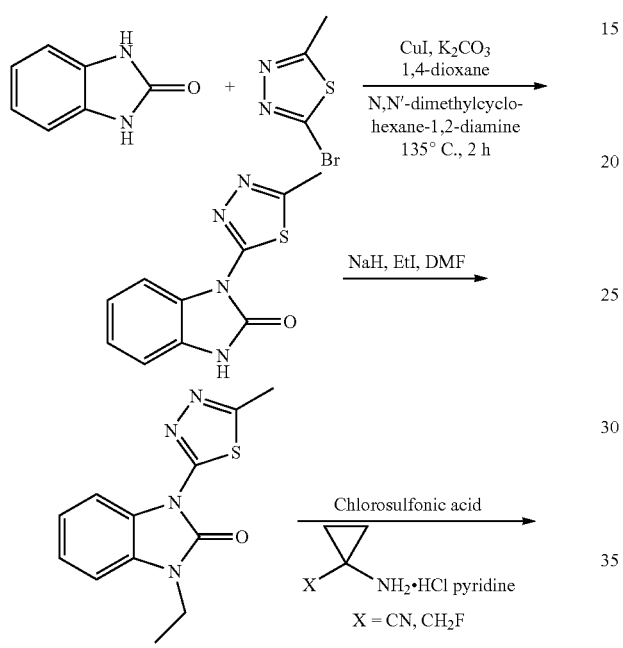
Scheme 11
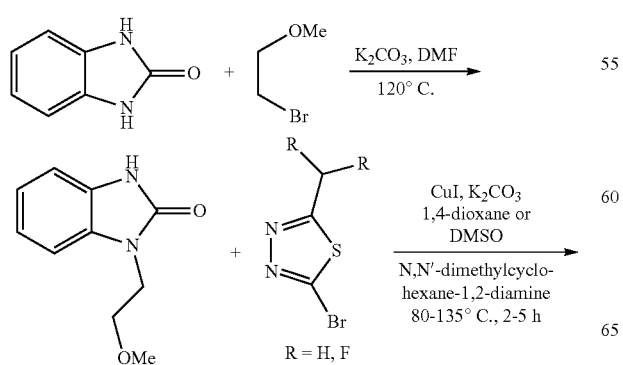
Scheme 12
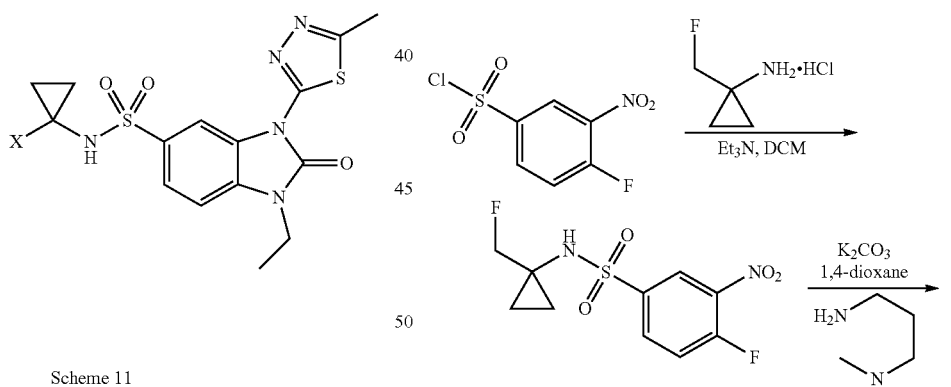
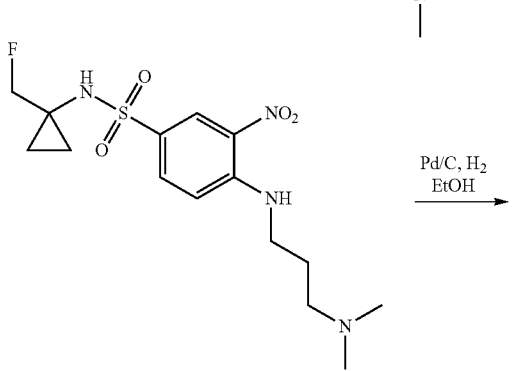

59
-continued

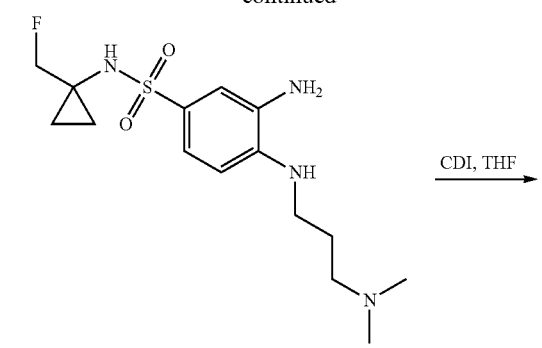

CDI, THF →

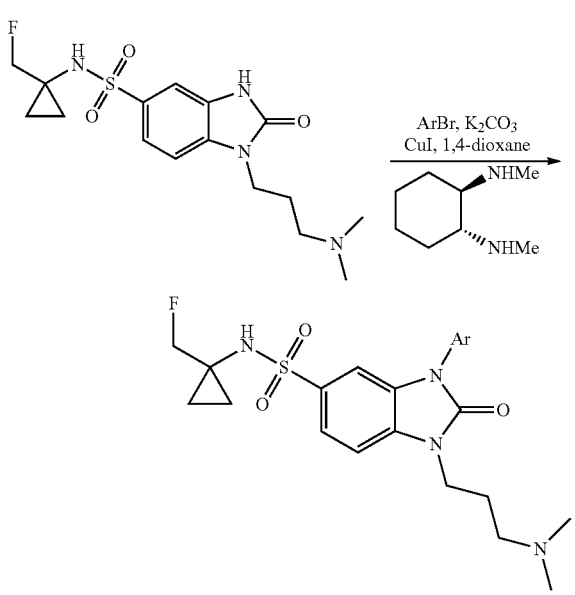

ArBr, K₂CO₃
CuI, 1,4-dioxane →

Scheme 13

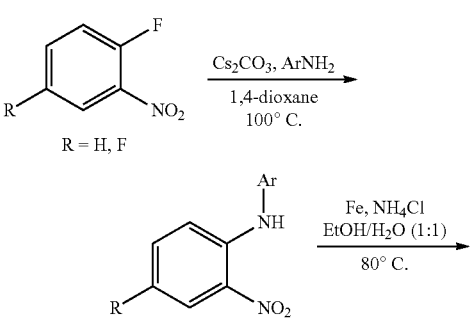

R = H, F

Cs₂CO₃, ArNH₂
1,4-dioxane
100° C. →

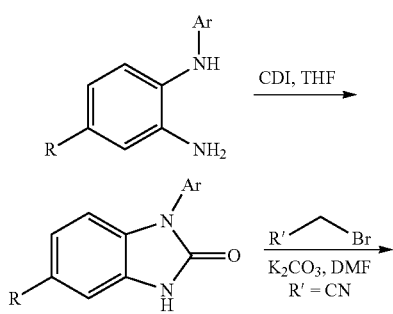

Fe, NH₄Cl
EtOH/H₂O (1:1)
80° C. →

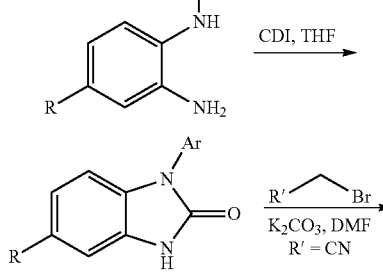

CDI, THF →

R'⌒Br
K₂CO₃, DMF
R' = CN →

60
-continued

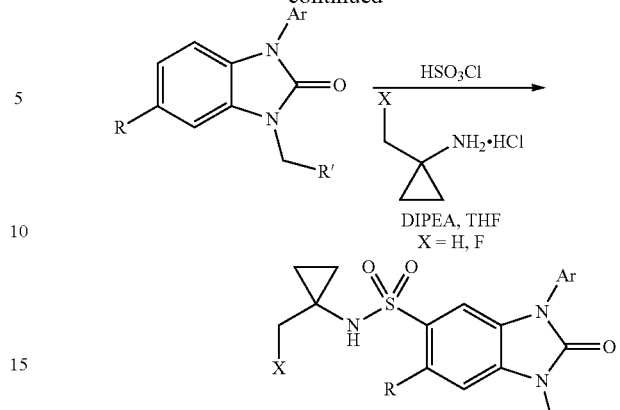

HSO₃Cl
DIPEA, THF
X = H, F →

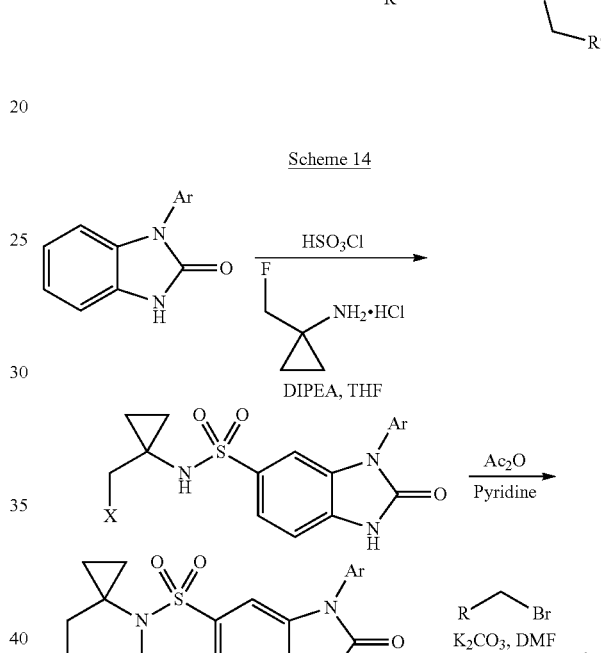

Scheme 14

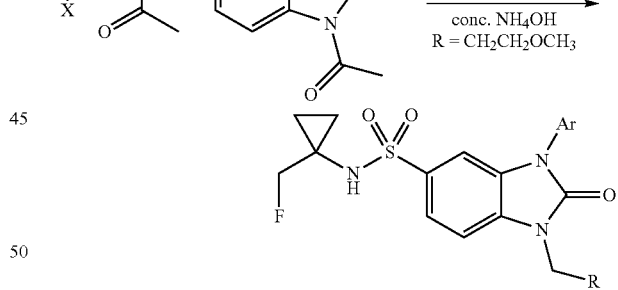

HSO₃Cl
DIPEA, THF →

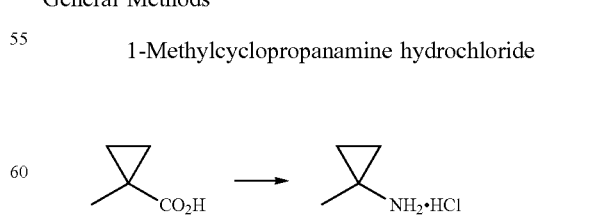

Ac₂O
Pyridine →

R⌒Br
K₂CO₃, DMF
conc. NH₄OH
R = CH₂CH₂OCH₃ →

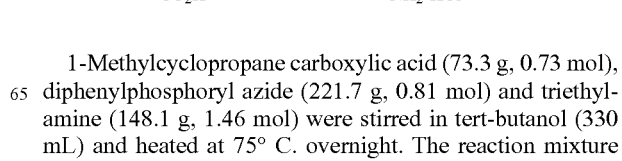

General Methods

1-Methylcyclopropanamine hydrochloride

1-Methylcyclopropane carboxylic acid (73.3 g, 0.73 mol), diphenylphosphoryl azide (221.7 g, 0.81 mol) and triethylamine (148.1 g, 1.46 mol) were stirred in tert-butanol (330 mL) and heated at 75° C. overnight. The reaction mixture was cooled to room temperature, poured into a mixture of ethyl acetate (750 mL) and water (1500 mL) and stirred for 15 min. The resulting precipitate was removed by filtration and the phases separated. The aqueous layer was extracted with ethyl acetate (2×750 mL) and the combined organic extracts were washed with water (750 mL), dried (MgSO$_4$) and concentrated to give a pale brown solid (88 g). The solid was suspended in dioxane (295 mL) and 4 M hydrochloric acid (366 mL) was added. The reaction mixture was stirred at room temperature for 2 h. Diethyl ether was added and the mixture chilled in a methanol/ice bath for 15 min. The precipitate was collected by filtration, washing with diethyl ether (2×220 mL) before drying the filter cake for 10 min to give 1-methylcyclopropanamine hydrochloride as a shiny white solid (40.5 g, 0.38 mol, 51%).

$^1$H NMR (CDCl$_3$) δ=1.32 (s, 3H), 0.75-0.68 (m, 2H), 0.60-0.51 (m, 2H) General procedures relating to Scheme 1:

Intermediate S1-A 3-Fluoro-N-(1-methylcyclopropyl)-4-nitrobenzenesulfonamide

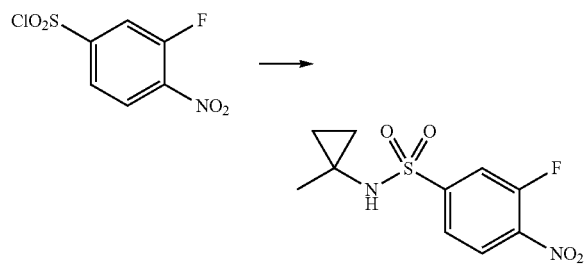

1-Methylcyclopropanamine hydrochloride (9.58 g, 89.1 mmol) was added to a stirred solution of 3-fluoro-4-nitrobenzene-1-sulfonyl chloride (19.4 g, 81.0 mmol) and triethylamine (22.6 mL, 161.9 mmol) in DCM (400 mL) over 15 min; exothermic reaction to 30° C. The reaction mixture was stirred for 1 h, and then concentrated. The residue was dissolved in ethyl acetate (400 mL) and washed with 1 M hydrochloric acid (2×400 mL), water (400 mL) and brine (400 mL), dried and concentrated to yield 3-fluoro-N-(1-methylcyclopropyl)-4-nitrobenzenesulfonamide (19 g, 69.3 mmol, 86%).

$^1$H NMR (300 MHz, CDCl$_3$) δ=8.19 (dd, J=7.0, 8.7 Hz, 1H), 7.88-7.78 (m, 2H), 5.09 (s, 1H), 1.30 (s, 3H), 0.92-0.72 (m, 2H), 0.68-0.50 (m, 2H)

Intermediate S1-B 3-(Methylamino)-N-(1-methylcyclopropyl)-4-nitrobenzenesulfonamide

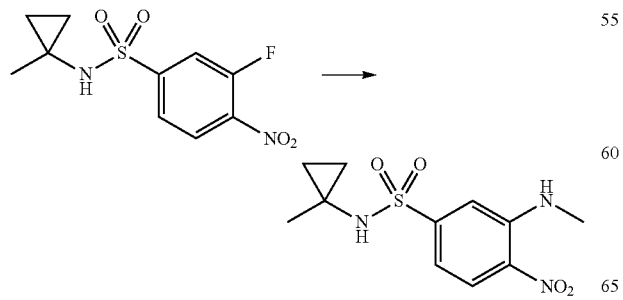

Methylamine (2M in THF) (100 mL, 200 mmol) was added to a stirred solution of 3-fluoro-N-(1-methylcyclopropyl)-4-nitrobenzenesulfonamide (17.3 g, 66.7 mmol) and triethylamine (14 mL, 100 mmol) in DCM (183 mL) over 15 min; exothermic reaction to 30° C. Once the addition was complete the reaction mixture was heated to 50° C. for 2 h. DCM (400 mL) and water (400 mL) were added, the layers separated and the aqueous phase re-extracted with DCM (2×200 mL). The combined organic layers were washed with brine (400 mL) and concentrated to yield 3-(methylamino)-N-(1-methylcyclopropyl)-4-nitrobenzenesulfonamide (19 g, 66.6 mmol, quant.).

$^1$H NMR (300 MHz, CDCl$_3$) δ=8.30 (d, J=8.9 Hz, 1H), 8.14 (s, 1H), 7.43 (d, J=2.0 Hz, 1H), 7.05 (dd, J=1.9, 8.9 Hz, 1H), 5.00 (s, 1H), 3.11 (d, J=4.2 Hz, 3H), 1.29 (s, 3H), 0.92-0.77 (m, 2H), 0.63-0.48 (m, 2H)

Intermediate S1-C 4-Amino-3-(methylamino)-N-(1-methylcyclopropyl)benzenesulfonamide

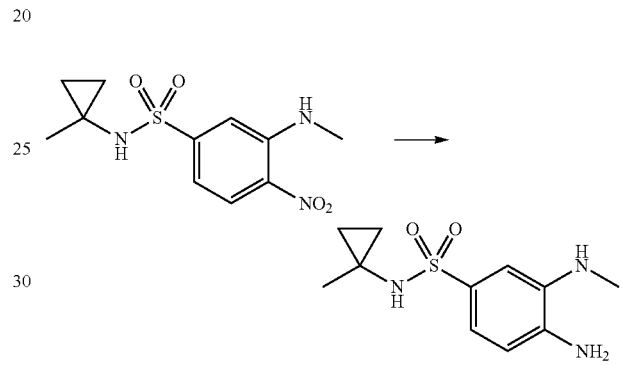

Ammonium chloride (19.3 g, 361 mmol) was dissolved in water (350 mL) and added to a solution of 3-(methylamino)-N-(1-methylcyclopropyl)-4-nitrobenzenesulfonamide (20.6 g, 72.2 mmol) in industrial methylated spirits (350 mL). Iron powder (20.2 g, 361 mmol) was added and the reaction mixture heated to 80° C. The reaction mixture was filtered through celite and concentrated to yield 4-amino-3-(methylamino)-N-(1-methylcyclopropyl)benzenesulfonamide (14.0 g, 54.8 mmol, 76%).

$^1$H NMR (300 MHz, CDCl$_3$) δ=7.25 (dd, J=2.1, 8.1 Hz, 1H), 7.13 (d, J=2.1 Hz, 1H), 6.72 (d, J=8.1 Hz, 1H), 5.01 (s, 1H), 3.73 (br. s., 2H), 2.89 (s, 3H), 1.18 (s, 3H), 0.89-0.71 (m, 2H), 0.51-0.34 (m, 2H)

Intermediate S1-D 3-Methyl-N-(1-methylcyclopropyl)-2-oxo-2,3-dihydro-1H-benzo[d]imidazole-5-sulfonamide

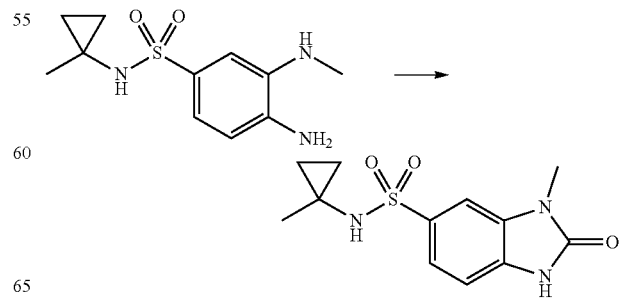

4-amino-3-(methylamino)-N-(1-methylcyclopropyl)benzenesulfonamide (14.0 g, 54.8 mmol) was dissolved in MeCN (420 mL) and warmed to 50° C. 1,2-Carbonyldiimidazole (17.8 g, 110 mmol) was added and stirred at 50° C. for 3 h. The reaction mixture was allowed to cool and was concentrated. The residue was dissolved in 2 M HCl (500 mL) and extracted with 5% MeOH in DCM (2×250 mL). The combined organic layers were concentrated and purified by silica gel flash column chromatography, eluent: 5% MeOH in DCM, to give 3-methyl-N-(1-methylcyclopropyl)-2-oxo-2,3-dihydro-1H-benzo[d]imidazole-5-sulfonamide (12.5 g, 44.4 mmol, 81%).

$^1$H NMR (300 MHz, DMSO-$d_6$) δ=12.31 (br. s., 1H), 8.05 (s, 1H), 7.64 (d, J=1.8 Hz, 1H), 7.59 (dd, J=1.9, 8.3 Hz, 1H), 7.29 (d, J=8.3 Hz, 1H), 3.53 (s, 3H), 1.06 (s, 3H), 0.65-0.59 (m, 2H), 0.42-0.35 (m, 2H)

General Procedures Relating to Scheme 2:

Intermediate S2-A Ethyl methyl(phenyl)carbamate

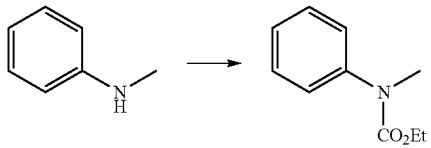

A solution of N-methylaniline (30 g, 0.28 mol) in DCM (100 mL) was treated with triethylamine (45 mL, 0.33 mol) and stirred for 20 min. Ethyl chloroformate (32 mL, 0.33 mol) was added over 25 min with ice bath cooling maintaining the temperature at <25° C. The reaction mixture was stirred at room temperature overnight, then poured into water (400 mL), acidified with 2 M HCl and extracted with EtOAc (700 mL). The organic layer was separated and washed with brine (400 mL), dried over $Na_2SO_4$ and evaporated to dryness to yield ethyl methyl(phenyl)carbamate (44 g, 0.25 mol, 88%).

$^1$H NMR (300 MHz, CDCl$_3$) δ=7.40-7.32 (m, 2H), 7.30-7.19 (m, 3H), 4.19 (q, J=7.1 Hz, 2H), 3.32 (s, 3H), 1.25 (t, J=7.1 Hz, 3H)

Intermediate S2-B Ethyl (4-(chlorosulfonyl)phenyl)(methyl)carbamate

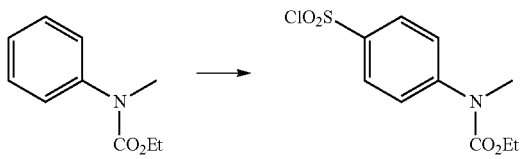 [SMILES: CCOC(=O)N(C)c1ccccc1 ; CCOC(=O)N(C)c1ccc(S(=O)(=O)Cl)cc1]

Ethyl methyl(phenyl)carbamate (22 g, 0.12 mol) was added dropwise with cooling to chlorosulfonic acid (80 mL, 1.20 mol) maintaining the temperature <20° C. The reaction mixture was heated to 60° C. and stirred for 3 h then allowed to cool overnight. The reaction mixture was added carefully to ice (400 mL) over 30 min. The resultant precipitate was stirred for 30 min, collected by filtration and washed with water. The product was dried in the vac oven to yield ethyl (4-(chlorosulfonyl)phenyl)(methyl)carbamate (31.7 g, 0.11 mol, 93%).

$^1$H NMR (300 MHz, CDCl$_3$) δ=8.01 (d, J=9.0 Hz, 2H), 7.58 (d, J=9.0 Hz, 2H), 4.27 (q, J=7.1 Hz, 2H), 3.41 (s, 3H), 1.33 (t, J=7.2 Hz, 3H)

Intermediate S2-C Ethyl (4-(chlorosulfonyl)-2-nitrophenyl)(methyl)carbamate

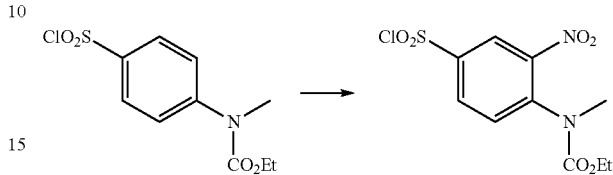

A solution of sodium nitrate (9.73 g, 0.114 mol) in sulfuric acid (80 mL) was added to a cold (0-5° C.) stirred solution of ethyl (4-(chlorosulfonyl)phenyl)(methyl)carbamate (30 g, 0.108 mol) in sulfuric acid (100 mL) over 30 min. The mixture was stirred at 0-5° C. for 2 h, then poured onto ice (500 mL) with stirring. The product was extracted with DCM (2×400 mL) and combined extracts were dried ($Na_2SO_4$) and passed through a silica plug, washing with DCM. The DCM solution was evaporated to dryness to yield ethyl (4-(chlorosulfonyl)-2-nitrophenyl)(methyl)carbamate (31.4 g, 0.097 mol, 90%).

$^1$H NMR (300 MHz, CDCl$_3$) δ=8.57 (d, J=2.3 Hz, 1H), 8.25 (dd, J=2.3, 8.6 Hz, 1H), 7.63 (d, J=8.7 Hz, 1H), 4.18 (br. s, 2H), 3.48-3.44 (m, 3H), 1.26 (br. s., 3H)

Intermediate S2-D Ethyl methyl(4-(N-(1-methylcyclopropyl)sulfamoyl)-2-nitrophenyl)carbamate

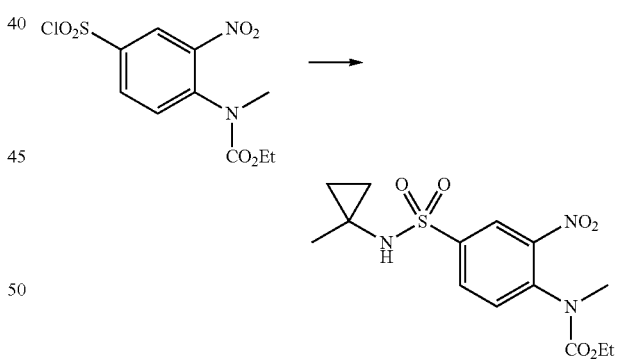

Triethylamine (19.5 mL, 141.0 mmol) was added to a solution of ethyl (4-(chlorosulfonyl)-2-nitrophenyl)(methyl)carbamate (15 g, 46.5 mmol) in DCM (450 mL) at 20° C. 1-Methylcyclopropanamine hydrochloride (5.1 g, 47.2 mmol) was added portionwise over 5 min. The reaction was stirred for 30 min and poured into 1 M HCl (150 mL). The organic layer was separated, washed with brine and evaporated to an orange to yield ethyl methyl(4-(N-(1-methylcyclopropyl)sulfamoyl)-2-nitrophenyl)carbamate (17.2 g, 48.1 mmol, quant.).

LCMS (high pH): RT 1.10 min, [M+H]$^+$ 358.5, 100% purity

Intermediate S2-E 3-Hydroxy-1-methyl-N-(1-methylcyclopropyl)-2-oxo-2,3-dihydro-1H-benzo[d]imidazole-5-sulfonamide

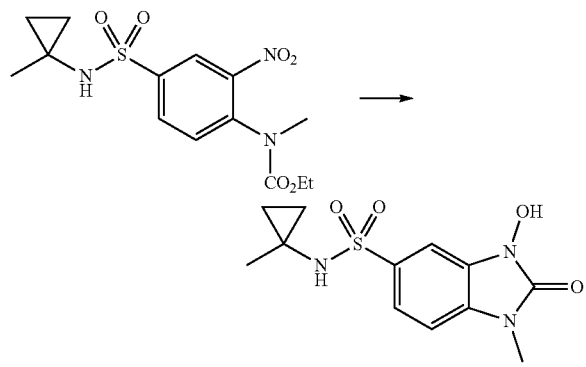

A solution of ethyl methyl(4-(N-(1-methylcyclopropyl)sulfamoyl)-2-nitrophenyl)carbamate (17.2 g, 48.1 mmol) in EtOH (350 mL) was charged to a 1 L autoclave. 5% Pd/C (1.7 g) was wetted with toluene and added to the autoclave. The vessel was sealed and charged with hydrogen to a pressure of 14 bar and stirred at 300 rpm for 3 h. The vessel was vented and the contents filtered washing with EtOH. The solvent was removed to leave the partially reduced intermediate. A solution of partially reduced intermediate (10 g, 77% purity, 23.5 mmol) in AcOH (150 mL) was heated to 80° C. for 2 h, and then allowed to cool overnight. The precipitate was filtered, washed with acetic acid and dried to yield 3-hydroxy-1-methyl-N-(1-methylcyclopropyl)-2-oxo-2,3-dihydro-1H-benzo[d]imidazole-5-sulfonamide (4.1 g, 13.8 mmol, 51%).

LCMS (high pH): RT 1.02 min, [M+H]$^+$ 298.1, 93% purity

Intermediate S2-F 1-Methyl-N-(1-methylcyclopropyl)-2-oxo-2,3-dihydro-1H-benzo[d]imidazole-5-sulfonamide

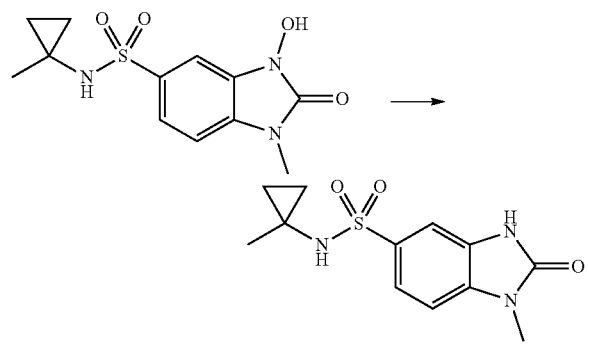

A solution of 3-hydroxy-1-methyl-N-(1-methylcyclopropyl)-2-oxo-2,3-dihydro-1H-benzo[d]imidazole-5-sulfonamide (9.75 g, 32.8 mmol) and ammonium acetate (63.2 g, 820 mmol) in MeOH (250 mL) and water (200 mL) was stirred at room temperature. A solution of TiCl$_3$ (30% in 2 M HCl) (70 mL, 164 mmol) was added in one portion and the mixture was stirred for 36 h. The MeOH was removed under reduced pressure, and the resulting suspension basified pH 8 with saturated aq. NaHCO$_3$. The suspension was filtered under vacuum and the resulting solid was placed in a warming tray to dry over three days. The off-white powdery solid was placed in a Soxhlet thimble and extracted with MeOH for 24 h. The MeOH was concentrated to ~100 mL, chilled in ice, and the resulting solid collected by suction filtration and air-dried, giving 2.40 g of product.

LCMS analysis of the material remaining in the Soxhlet thimble indicated that it still contained most of the desired product. The solid was stirred in DMSO (25 mL) and 2 M NaOH (25 mL) was added. The mixture was heated to 100° C. and filtered hot, rinsing the solid with cold water. As the filtrate cooled a white solid began to crystallise. The filtrate was acidified with 2 M HCl (25 mL) giving a thick white suspension. This was chilled in ice-water and the solid was collected by suction filtration to give further product. The residual solid from the filtration was treated with DMSO and aqueous NaOH as above, giving a second crop of the target after acidification. The two crops were combined to give 5.73 g of the product, identical by $^1$H NMR to that above. Total yield of 1-methyl-N-(1-methylcyclopropyl)-2-oxo-2,3-dihydro-1H-benzo[d]imidazole-5-sulfonamide (8.13 g, 28.9 mmol, 88%).

$^1$H NMR (300 MHz, DMSO-d$_6$) δ=11.23 (s, 1H), 7.88 (s, 1H), 7.49 (dd, J=1.8, 8.3 Hz, 1H), 7.35 (d, J=1.8 Hz, 1H), 7.25 (d, J=8.3 Hz, 1H), 3.32 (s, 3H), 1.01 (s, 3H), 0.66-0.51 (m, 2H), 0.42-0.26 (m, 2H) General procedures relating to Scheme 3:

Intermediate S3-A 4-Chloro-N-(1-methylcyclopropyl)-3-nitro-benzenesulfonamide

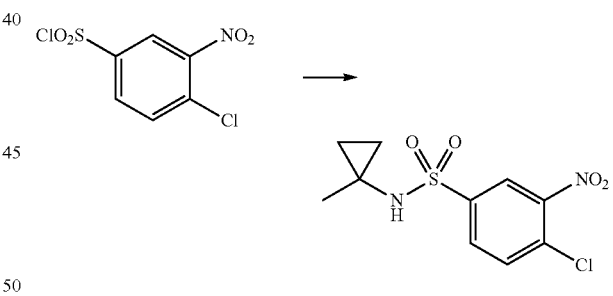

Triethylamine (1.63 mL, 11.72 mmol) was added dropwise to a stirring solution of 4-chloro-3-nitrobenzenesulfonyl chloride (1. g, 3.91 mmol) and 1-methylcyclopropanamine hydrochloride (0.46 g, 4.3 mmol) in DCM (20 mL). After 2 h saturated aq. NaHCO$_3$ (20 mL) was added and the mixture stirred for 5 min. The DCM layer was isolated by passing through a hydrophobic frit and the aqueous layer washed with DCM. The combined DCM extracts were concentrated under reduced pressure and purified by automated column chromatography, SiO$_2$, eluent 0-100% EtOAc in iso-hexane, to yield 4-chloro-N-(1-methylcyclopropyl)-3-nitro-benzenesulfonamide (1.07 g, 3.68 mmol, 94%).

$^1$H NMR (300 MHz, CDCl$_3$) δ=8.39 (d, J=2.2 Hz, 1H), 8.03 (dd, J=2.2, 8.5 Hz, 1H), 7.72 (d, J=8.5 Hz, 1H), 5.28 (s, 1H), 1.29 (s, 3H), 0.82-0.72 (m, 2H), 0.65-0.49 (m, 2H)

Intermediate S3-B1 4-[(4-Fluorophenyl)methylamino]-N-(1-methylcyclopropyl)-3-nitro-benzenesulfonamide

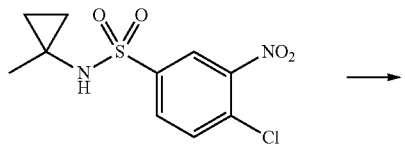

4-Fluorobenzylamine (1.87 mL, 16.4 mmol) was added dropwise to a stirring solution 4-chloro-N-(1-methylcyclopropyl)-3-nitro-benzenesulfonamide (3.97 g, 13.67 mmol) and triethylamine (2.85 mL, 20.5 mmol) in DMF (80 mL). The reaction mixture was heated at 80° C. for 2 h. Water (20 mL) and DCM (20 mL) were added and the mixture stirred for 5 min. The DCM layer was isolated by passing through a hydrophobic frit and the aqueous layer washed with DCM (2×10 mL). The combined organics were evaporated to dryness and the crude product purified by automated column chromatography, $SiO_2$, eluent 0-10% MeOH in DCM to yield 4-[(4-fluorophenyl)methylamino]-N-(1-methylcyclopropyl)-3-nitro-benzenesulfonamide (4.3 g, 11.3 mmol, 83%).

$^1$H NMR (300 MHz, CDCl$_3$) δ=8.75 (d, J=2.3 Hz, 1H), 8.68 (t, J=5.6 Hz, 1H), 7.82 (dd, J=2.3, 9.0 Hz, 1H), 7.36-7.29 (m, 2H), 7.15-7.04 (m, 2H), 6.90 (d, J=9.1 Hz, 1H), 4.58 (d, J=5.8 Hz, 2H), 1.27 (s, 3H), 0.88-0.70 (m, 2H), 0.60-0.42 (m, 2H)

The following intermediate was prepared in a similar manner:

Intermediate S3-B2 4-[(2,4-Dimethylthiazol-5-yl)methylamino]-N-(1-methylcyclopropyl)-3-nitro-benzenesulfonamide

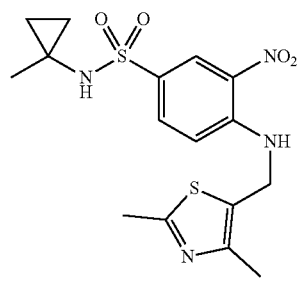 [SMILES: Cc1nc(C)c(CNc2ccc(S(=O)(=O)NC3(C)CC3)cc2[N+](=O)[O-])s1]

Prepared from 4-chloro-N-(1-methylcyclopropyl)-3-nitro-benzenesulfonamide, (dimethyl-1,3-thiazol-5-yl)methanamine and triethylamine.

LCMS (low pH): RT 1.07 min, [M+H]$^+$ 397.5, >95% purity

Intermediate S3-C1 3-Amino-4-[(4-fluorophenyl)methylamino]-N-(1-methylcyclopropyl)benzenesulfonamide

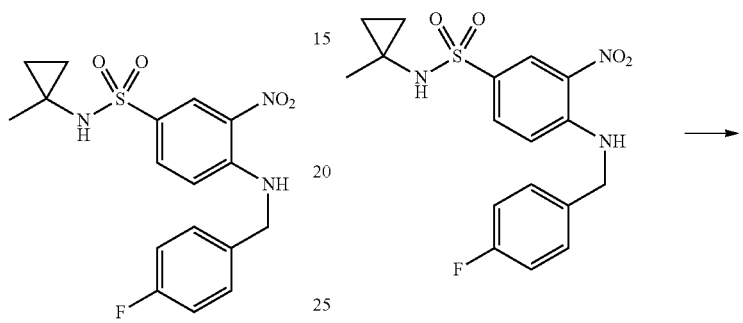

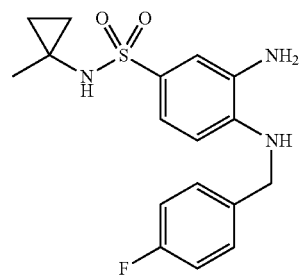

To a stirred suspension of iron (5.01 g, 89.73 mmol) in EtOH (25 mL) was added 4-[(4-fluorophenyl)methylamino]-N-(1-methylcyclopropyl)-3-nitro-benzenesulfonamide (6.81 g, 17.95 mmol), ammonium chloride (4.8 g, 89.73 mmol) and water (25 mL). The mixture was stirred for 2 h at 80° C. and then filtered through celite, washing with hot EtOH. The filtrate was concentrated under vacuum to a slurry and water (80 mL) and DCM (80 mL) were added. The organic layer was separated and the aqueous layer extracted with DCM (2×30 mL). The combined organics were passed through a hydrophobic frit and concentrated under vacuum. The crude product was purified by automated column chromatography, $SiO_2$, eluent 0-10% MeOH in DCM, to yield 3-amino-4-[(4-fluorophenyl)methylamino]-N-(1-methylcyclopropyl)benzenesulfonamide (3.34 g, 9.56 mmol, 53%).

$^1$H NMR (300 MHz, CDCl$_3$) δ=7.42-7.30 (m, 4H), 7.09-6.98 (m, 2H), 6.60 (d, J=8.3 Hz, 1H), 5.08 (br. s., 1H), 4.36 (s, 2H), 1.17 (s, 3H), 0.81-0.72 (m, 2H), 0.46-0.37 (m, 2H)

The following intermediate was prepared in a similar manner:

Intermediate S3-C2 3-Amino-4-[(2,4-dimethylthiazol-5-yl)methylamino]-N-(1-methylcyclopropyl) benzenesulfonamide

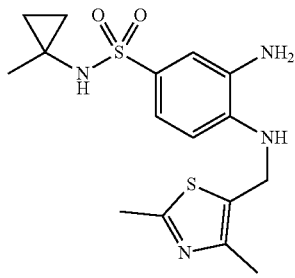

Prepared from 4-[(2,4-dimethylthiazol-5-yl)methylamino]-N-(1-methylcyclopropyl)-3-nitro-benzenesulfonamide, iron and ammonium chloride.

LCMS (low pH): RT 0.88 min, [M+H]$^+$, 367.6, 90% purity

Example 72 1-[(4-Fluorophenyl)methyl]-N-(1-methylcyclopropyl)-2-oxo-3H-benzimidazole-5-sulfonamide

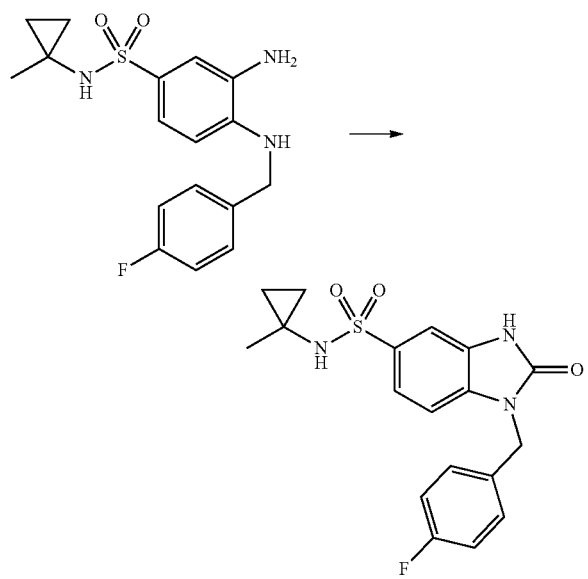

3-Amino-4-[(4-fluorophenyl)methylamino]-N-(1-methylcyclopropyl)benzenesulfonamide (3. g, 8.59 mmol) and 1,1'-carbonyldiimidazole (1.81 g, 11.16 mmol) in MeCN (40 mL) were heated to reflux under nitrogen for 4 h. The reaction mixture was allowed to cool to ambient temperature, with a precipitate forming. The reaction mixture was cooled to 0° C. with stirring and the precipitate was filtered and washed with ether to yield 1-[(4-fluorophenyl)methyl]-N-(1-methylcyclopropyl)-2-oxo-3H-benzimidazole-5-sulfonamide (2.94 g, 7.83 mmol, 91%).

$^1$H NMR (300 MHz, DMSO-d$_6$) δ=11.38 (s, 1H), 7.89 (s, 1H), 7.44 (dd, J=1.7, 8.2 Hz, 1H), 7.42-7.35 (m, 3H), 7.26 (d, J=8.3 Hz, 1H), 7.24-7.12 (m, 2H), 5.04 (s, 2H), 1.02 (s, 3H), 0.65-0.50 (m, 2H), 0.41-0.26 (m, 2H)

The following intermediate was prepared in a similar manner:

Example 89 1-[(2,4-Dimethylthiazol-5-yl)methyl]-N-(1-methylcyclopropyl)-2-oxo-3H-benzimidazole-5-sulfonamide

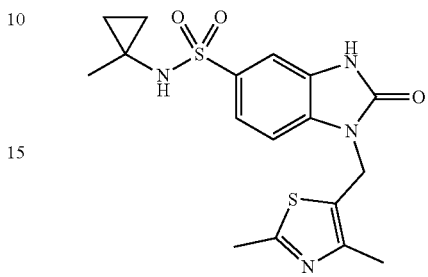

Prepared from 3-amino-4-[(2,4-dimethylthiazol-5-yl)methylamino]-N-(1-methylcyclopropyl)benzenesulfonamide and 1,1'-carbonyldiimidazole.

$^1$H NMR (300 MHz, DMSO-d$_6$) δ=11.36 (s, 1H), 7.90 (s, 1H), 7.49 (dd, J=1.8, 8.3 Hz, 1H), 7.36 (d, J=1.8 Hz, 1H), 7.26 (d, J=8.3 Hz, 1H), 5.16 (s, 2H), 2.50 (s, 3H), 2.43 (s, 3H), 1.02 (s, 3H), 0.66-0.50 (m, 2H), 0.40-0.29 (m, 2H)

General procedures relating to Scheme 4:

Intermediate S4-A1 N-(1-Methylcyclopropyl)-3-[(5-methyl-1,3,4-oxadiazol-2-yl)amino]-4-nitro-benzenesulfonamide

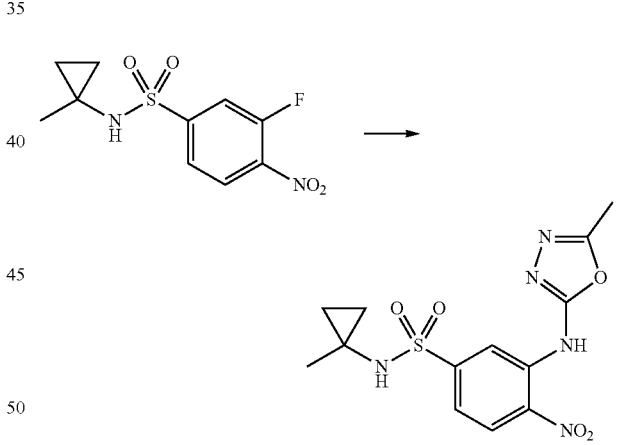

3-Fluoro-N-(1-methylcyclopropyl)-4-nitro-benzenesulfonamide (6.65 g, 25.5 mmol), 5-methyl-1,3,4-oxadiazol-2-amine (38.25 mmol) and caesium carbonate (24.9 g, 76.5 mmol) in 1,4-dioxane (60 mL) was heated to 100° C. for 4 h. After cooling, the solvent was removed under reduced pressure, and the residue was diluted with water (300 mL) and DCM (300 mL). The DCM layer was separated and the aqueous extracted with DCM (3×50 mL). The combined DCM extracts were dried and concentrated under reduced pressure to obtain crude compound which was purified by automated column chromatography, SiO$_2$, eluent 0-100% EtOAc in iso-hexane, to yield N-(1-methylcyclopropyl)-3-[(5-methyl-1,3,4-oxadiazol-2-yl)amino]-4-nitro-benzenesulfonamide (4 g, 11.3 mmol, 44% yield).

¹H NMR (300 MHz, CDCl₃) δ=9.27 (d, J=1.9 Hz, 1H), 8.43 (d, J=8.9 Hz, 1H), 7.66 (dd, J=2.0, 8.8 Hz, 1H), 2.55 (s, 3H), 1.33 (s, 3H), 0.91 (s, 2H), 0.61-0.56 (m, 2H)

The following intermediates were prepared in a similar manner:

Intermediate S4-A2 N-(1-Methylcyclopropyl)-3-[(5-methyl-1,3,4-thiadiazol-2-yl)amino]-4-nitro-benzenesulfonamide

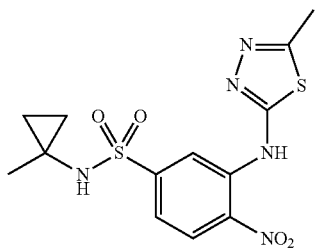

Prepared from 3-fluoro-N-(1-methylcyclopropyl)-4-nitro-benzenesulfonamide, 2-amino-5-methyl-1,3,4-thiadiazole and caesium carbonate.

¹H NMR (300 MHz, CDCl₃) δ=9.24 (d, J=2.0 Hz, 1H), 8.39 (d, J=8.9 Hz, 1H), 7.61 (dd, J=1.8, 8.8 Hz, 1H), 2.76 (s, 3H), 1.32 (s, 3H), 0.95-0.87 (m, 2H), 0.62-0.55 (m, 2H)

Intermediate S4-A3 3-[[5-(Difluoromethyl)-1,3,4-thiadiazol-2-yl]amino]-N-(1-methylcyclopropyl)-4-nitro-benzenesulfonamide

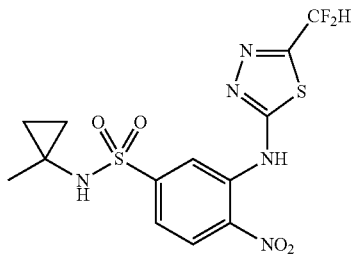

Prepared from 3-fluoro-N-(1-methylcyclopropyl)-4-nitro-benzenesulfonamide, 5-(difluoromethyl)-1,3,4-thiadiazol-2-amine and caesium carbonate.

LCMS (high pH): RT 1.00 min, [M+H]⁺ 406.5, 80% purity

Intermediate S4-A4 3-[(3-methoxy-1,2,4-thiadiazol-5-yl)amino]-N-(1-methylcyclopropyl)-4-nitro-benzenesulfonamide

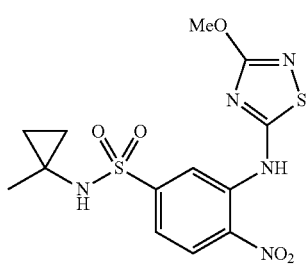

Prepared from 3-fluoro-N-(1-methylcyclopropyl)-4-nitro-benzenesulfonamide, 3-methoxy-1,2,4-thiadiazol-5-amine and caesium carbonate.

LCMS (high pH): RT 1.05 min, [M+H]⁺ 386.6, 82% purity

Intermediate S4-A5 3-Anilino-N-(1-methylcyclopropyl)-4-nitro-benzenesulfonamide

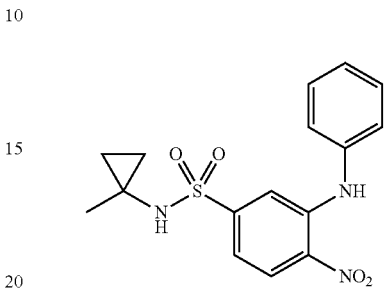

Prepared from 3-fluoro-N-(1-methylcyclopropyl)-4-nitro-benzenesulfonamide, aniline and triethylamine, the reaction mixture was heated at 80° C. overnight.

LCMS (high pH): RT 1.1 min, [M+H]⁺ 348.5, >95% purity

Intermediate S4-B1 4-Amino-N-(1-methylcyclopropyl)-3-[(5-methyl-1,3,4-oxadiazol-2-yl)amino]benzenesulfonamide

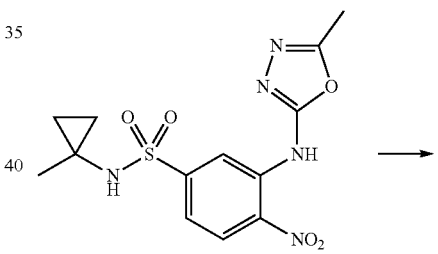

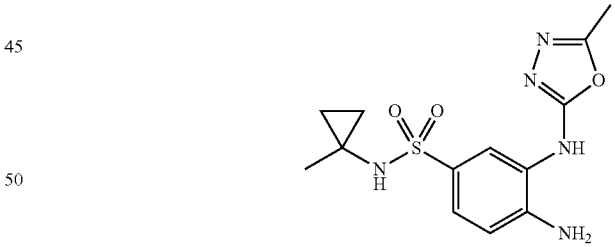

To a stirred suspension of zinc (1 g, 15.6 mmol) in EtOH (25 mL) was added N-(1-methylcyclopropyl)-3-[(5-methyl-1,3,4-oxadiazol-2-yl)amino]-4-nitro-benzenesulfonamide (1.1 g, 3.1 mmol), ammonium chloride (1.7 g, 31.2 mmol) and water (25 mL). The mixture was stirred overnight at 50° C. and filtered through celite, washing with hot ethanol. The filtrate was concentrated under vacuum and the residue was diluted with water (80 mL) and DCM (80 mL). The organic layer was separated and the aqueous layer extracted with DCM (2×30 mL). The combined organic layer was dried and concentrated to give the crude compound which was purified by flash column chromatography, SiO₂, eluent 0-10% MeOH in DCM, to yield 4-amino-N-(1-methylcyclopropyl)-

3-[(5-methyl-1,3,4-oxadiazol-2-yl)amino]benzenesulfonamide (920 mg, 2.84 mmol, 92% yield).

LCMS (high pH): RT 0.76 min, [M+H]$^+$ 324.5, 73% purity

The following intermediates were prepared in a similar manner:

Intermediate S4-B2 4-Amino-N-(1-methylcyclopropyl)-3-[(5-methyl-1,3,4-thiadiazol-2-yl)amino]benzenesulfonamide

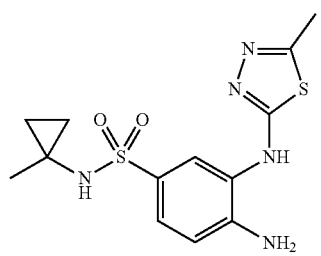

Prepared from N-(1-methylcyclopropyl)-3-[(5-methyl-1,3,4-thiadiazol-2-yl)amino]-4-nitro-benzenesulfonamide, ammonium chloride and iron.

$^1$H NMR (300 MHz, CDCl$_3$) δ=7.38 (dd, J=2.2, 8.4 Hz, 1H), 7.23 (d, J=2.2 Hz, 1H), 6.68 (d, J=8.3 Hz, 1H), 4.73 (s, 1H), 4.42 (d, J=5.5 Hz, 2H), 4.13-4.04 (m, 1H), 2.65 (s, 1H), 1.21 (s, 3H), 0.93-0.73 (m, 2H), 0.53-0.38 (m, 2H)

Intermediate S4-B3 4-Amino-3-[[5-(difluoromethyl)-1,3,4-thiadiazol-2-yl]amino]-N-(1-methylcyclopropyl)benzenesulfonamide

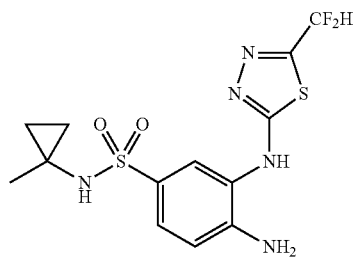 [SMILES: CC1(NS(=O)(=O)c2ccc([N+](=O)[O-])c(Nc3nnc(C(F)F)s3)c2)CC1]

Prepared from 3-[[5-(difluoromethyl)-1,3,4-thiadiazol-2-yl]amino]-N-(1-methylcyclopropyl)-4-nitro-benzenesulfonamide, ammonium chloride and iron. Used directly in synthesis of 3-[5-(difluoromethyl)-1,3,4-thiadiazol-2-yl]-N-(1-methylcyclopropyl)-2-oxo-1H-benzimidazole-5-sulfonamide as crude product.

Intermediate S4-B4 4-Amino-3-[(3-methoxy-1,2,4-thiadiazol-5-yl)amino]-N-(1-methylcyclopropyl)benzenesulfonamide

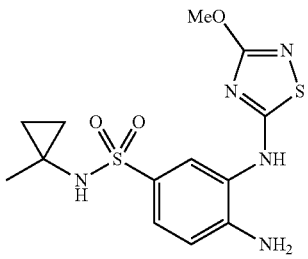 [SMILES: COc1nsc(Nc2cc(S(=O)(=O)NC3(C)CC3)ccc2[N+](=O)[O-])n1]

Prepared from 3-[(3-methoxy-1,2,4-thiadiazol-5-yl)amino]-N-(1-methylcyclopropyl)-4-nitro-benzenesulfonamide, ammonium chloride and iron.

LCMS (high pH): RT 0.93 min, [M+H]$^+$ 356.5, >90% purity

Intermediate S4-B5 4-Amino-3-anilino-N-(1-methylcyclopropyl)benzenesulfonamide

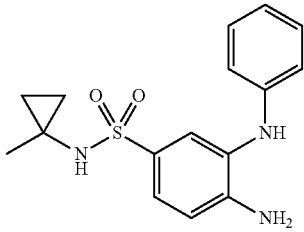 [SMILES: CC1(NS(=O)(=O)c2ccc([N+](=O)[O-])c(Nc3ccccc3)c2)CC1]

Prepared from 3-anilino-N-(1-methylcyclopropyl)-4-nitro-benzenesulfonamide, ammonium chloride and iron.

LCMS (low pH): RT 1.06 min, [M−H]$^-$ 316.5, >95% purity

Example 94 N-(1-Methylcyclopropyl)-3-(5-methyl-1,3,4-oxadiazol-2-yl)-2-oxo-1H-benzimidazole-5-sulfonamide

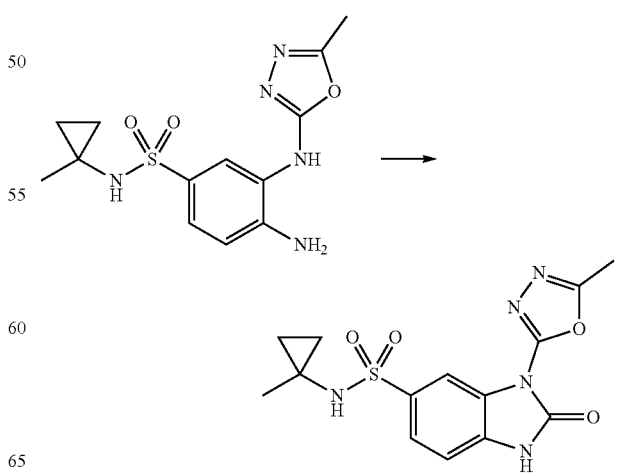

A solution of 1,1'-carbonyldiimidazole (1.41 g, 8.54 mmol) and 4-amino-N-(1-methylcyclopropyl)-3-[(5-methyl-1,3,4-oxadiazol-2-yl)amino]benzenesulfonamide (920 mg, 2.84 mmol) in MeCN (20 mL) was heated to reflux for 2 h. The solvent was evaporated to approximately 10 mL and cooled to ambient temperature. A precipitate formed which was filtered and stirred in 1 M HCl. After filtration, the solid was dried to afford N-(1-methylcyclopropyl)-3-(5-methyl-1,3,4-oxadiazol-2-yl)-2-oxo-1H-benzimidazole-5-sulfonamide (527 mg, 1.51 mmol, 62%).

$^1$H NMR (400 MHz, DMSO-$d_6$) δ=12.06 (s, 1H), 8.22 (s, 1H), 8.09 (s, 1H), 7.68-7.66 (m, 1H), 7.28 (d, J=8.4 Hz, 1H), 2.59 (s, 3H), 1.06 (s, 3H), 0.61-0.58 (m, 2H), 0.38-0.35 (m, 2H)

The following intermediates were prepared in a similar manner:

Example 80 N-(1-Methylcyclopropyl)-3-(5-methyl-1,3,4-thiadiazol-2-yl)-2-oxo-1H-benzimidazole-5-sulfonamide

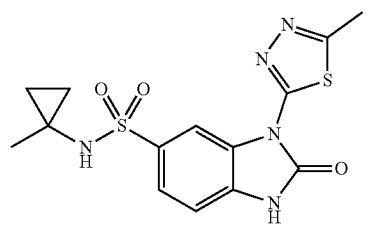

Prepared from 4-amino-N-(1-methylcyclopropyl)-3-[(5-methyl-1,3,4-thiadiazol-2-yl)amino]benzenesulfonamide and 1,1'-carbonyldiimidazole.

$^1$H NMR (400 MHz, DMSO-$d_6$) δ=12.31 (s, 1H), 8.73 (d, J=1.6 Hz, 1H), 8.14 (s, 1H), 7.72-7.7 (m, 1H), 7.35 (d, J=8.4 Hz, 1H), 2.74 (s, 3H), 1.07 (s, 3H), 0.62-0.59 (m, 2H), 0.38-0.34 (m, 2H)

Intermediate S4-C3 3-[5-(Difluoromethyl)-1,3,4-thiadiazol-2-yl]-N-(1-methylcyclopropyl)-2-oxo-1H-benzimidazole-5-sulfonamide

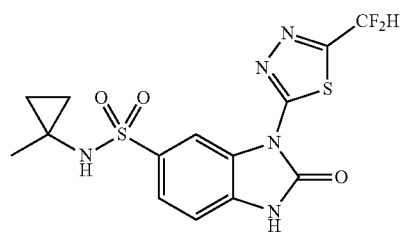 [SMILES: CC1(NS(=O)(=O)c2ccc3[nH]c(=O)n(-c4nnc(C(F)F)s4)c3c2)CC1]

Prepared from crude 4-amino-3-[[5-(difluoromethyl)-1,3,4-thiadiazol-2-yl]amino]-N-(1-methylcyclopropyl)benzenesulfonamide and 1,1'-carbonyldiimidazole.

LCMS (high pH): RT 0.99 min, [M+H]$^+$ 402.4, 83% purity

Intermediate S4-C4 3-(3-Methoxy-1,2,4-thiadiazol-5-yl)-N-(1-methylcyclopropyl)-2-oxo-1H-benzimidazole-5-sulfonamide

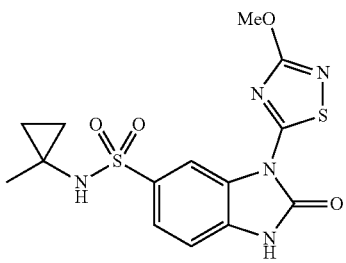 [SMILES: COc1nsc(-n2c(=O)[nH]c3ccc(S(=O)(=O)NC4(C)CC4)cc32)n1]

Prepared from 4-amino-3-[(3-methoxy-1,2,4-thiadiazol-5-yl)amino]-N-(1-methylcyclopropyl)benzenesulfonamide and 1,1'-carbonyldiimidazole.

LCMS (high pH): RT 0.81 min, [M+H]$^+$ 382.5, 70% purity

Intermediate S4-C5 N-(1-Methylcyclopropyl)-2-oxo-3-phenyl-1H-benzimidazole-5-sulfonamide

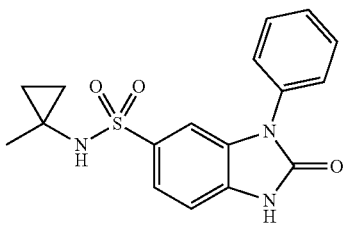 [SMILES: CC1(NS(=O)(=O)c2ccc3[nH]c(=O)n(-c4ccccc4)c3c2)CC1]

Prepared from 4-amino-3-anilino-N-(1-methylcyclopropyl)benzenesulfonamide and 1,1'-carbonyldiimidazole.

LCMS (high pH): RT 0.95 min, [M+H]$^+$ 344.5, >95 purity

Alkylation of 2-oxo-1H-benzimidazoles

Method A1

Sodium hydride (60% w/w) (1 eq) was added to a stirring solution of 2-oxo-1H-benzimidazole intermediate (Intermediate S1-D) (1 eq) in DMF. After 5 min alkyl halide (1 eq) was added and the reaction mixture stirred at ambient temperature for 1 h.

Method A2

Sodium hydride (60% w/w) (1.1 eq) was added to a stirring solution of 2-oxo-1H-benzimidazole intermediate (Intermediates S1-D, S2-F, S4-C5) (1 eq) in DMF. After 5 min alkyl halide, acyl chloride or alkyl isocyanate (1.1 eq) was added and the reaction mixture stirred at ambient temperature for 1 h.

For Examples 4, 11 and 12 the reaction mixture was stirred at ambient temperature overnight.

Method A3

Sodium hydride (60% w/w) (1.2 eq) was added to a stirring solution of 2-oxo-1H-benzimidazole intermediate (Intermediates S2-F, S3-D1, S3-D2, S4-C1) (1 eq) in DMF. After 20 min alkyl or aryl chloroformate, or alkyl halide (1.2 eq) was added and the reaction mixture stirred at ambient temperature for 2 h.

For Example 55 4-nitrophenyl chloroformate was used, after 2 h at ambient temperature methylamine (2 M in THF) (4 eq) was added and the reaction mixture was stirred at ambient temperature for 1 h, to yield the desired carboxamide product.

For Example 117 the reaction mixture was heated at 80° C. for 3 h.

Method A4

Sodium hydride (60% w/w) (1.02 eq) was added to a stirring solution of 2-oxo-1H-benzimidazole intermediate (Intermediate S1-D) (1 eq) in DMF. After 5 min alkyl halide or mesylate (1.05 eq) was added (when mesylates were used sodium iodide (0.2 eq) was added) and the reaction mixture stirred at ambient temperature overnight.

Method A5

2-Oxo-1H-benzimidazole intermediate (Intermediate S4-C2) (1 eq), potassium carbonate (4 eq), alkyl halide (1.4-1.5 eq), in DMF was heated at 50° C. for 0.5-1 h. When alkyl chlorides were used potassium iodide (1 eq) was added to the reaction mixture.

For Examples 89 and 100 the reaction mixture was stirred at ambient temperature overnight.

Method A6

2-Oxo-1H-benzimidazole intermediate (Intermediates S4-C1, S4-C2) (1 eq), caesium carbonate (3 eq), alkyl halide or mesylate (1.1 eq), potassium iodide (1.2 eq) in DMF was heated by microwave irradiation at 100° C. for 1 h.

Method A7

2-Oxo-1H-benzimidazole intermediate (Intermediates S4-C1, S4-C2) (1 eq), potassium tert-butoxide (3 eq), alkyl halide or mesylate (1.1 eq), potassium iodide (1.2 eq) in DMF was heated by microwave irradiation at 100° C. for 1 h.

Method A8

2-Oxo-1H-benzimidazole intermediate (Intermediates S4-C1, S4-C2) (1 eq), potassium carbonate (3 eq), alkyl halide or mesylate (1 eq), potassium iodide (1 eq) in DMF was stirred at ambient temperature for 48 h.

Method A9

2-Oxo-1H-benzimidazole intermediate (Intermediate S4-C2) (1 eq), potassium carbonate (2.2 eq), alkyl halide or mesylate (1.2 eq), potassium iodide (1 eq) in DMF was heated by microwave irradiation at 80° C. for 15 min.

Method A10

2-Oxo-1H-benzimidazole intermediate (Intermediate S1-D) (1 eq), diisopropyl azodicarboxylate (2 eq), alkyl alcohol (2 eq), PS—PPh$_3$ (2 eq) in CHCl$_3$ were heated at 40° C. for 1 h.

Method A11

2-Oxo-1H-benzimidazole intermediate (Intermediates S4-C1, S4-C2, S4-C3) (1 eq), diisopropyl azodicarboxylate (2 eq), alkyl alcohol (2 eq), PS—PPh$_3$ (2 eq) in DMF were heated at 80° C. for 2 h.

Method A12

2-Oxo-1H-benzimidazole intermediate (Intermediates S4-C2, S4-C4, S2-C5) (1 eq), diisopropyl azodicarboxylate (3 eq), alkyl alcohol (3 eq), PS—PPh$_3$ (4 eq) in DMF were heated at 80° C. for 2 h.

For Example 105 diisopropyl azodicarboxylate (1.5 eq) was used.

Method A13

Triethylamine (5 eq) was added to a mixture of 2-oxo-3H-benzimidazole intermediate (Intermediates S2-F, S3-D2) (1 eq), aryl boronic acid (2 eq) and copper (II) acetate (2 eq) in DCM (10 mL) with 4 Å molecular sieves, the reaction mixture was stirred at ambient temperature overnight.

Work-up for Method A13: DCM was added to the reaction mixture which was then filtered through celite, the organics were concentrated under reduced pressure and purified by prep. HPLC.

Method A14

A mixture of 2-oxo-3H-benzimidazole intermediate (Intermediates S2-F, S3-D1) (1 eq), copper (I) iodide (0.1 eq), aryl bromide (2 eq) and potassium carbonate (2 eq) in 1,4-dioxane was degassed with nitrogen for 5 min. trans-N,N'-Dimethylcyclohexane-1,2-diamine (0.2 eq) was added dropwise and the reaction mixture heated at reflux, under nitrogen, for 4 h.

Method A15

A mixture of 2-oxo-3H-benzimidazole intermediate (Intermediates S2-F, S3-D2) (1 eq), copper (I) iodide (0.2 eq), aryl bromide or iodide (4 eq) and potassium carbonate (4 eq) in 1,4-dioxane was degassed with nitrogen for 5 min. trans-N,N'-Dimethylcyclohexane-1,2-diamine (0.4 eq) was added dropwise and the reaction mixture heated at reflux, under nitrogen, for 4 h.

For Examples 107, 108 and 109 the reaction mixture was heated at 60° C. for 4 h.

For Example 90 aryl bromide (2 eq) was used.

Work-up for Methods A1-A3, A5, A10-A12, A14 & A15: DCM and water or saturated aq. NaHCO$_3$ were added to the reaction mixture, the organic phase was separated using a hydrophobic frit and the aqueous phase washed with DCM. The combined organics were concentrated under reduced pressure and purified by mass directed prep. HPLC or automated column chromatography, SiO$_2$.

Work-up for Methods A4, A6-9; the mixture was concentrated in vacuo and either purified directly or underwent the following work-up, water and ethyl acetate were added and the layers separated. The organic layer was washed with water and concentrated under reduced pressure. Purification by mass directed prep. HPLC or automated column chromatography gave the desired products.

Wittic Reaction and Acid Deprotection

Example 67 (E)-3-[5-[3-Methyl-6-[(1-methylcyclopropyl)sulfamoyl]-2-oxo-benzimidazol-1-yl]-2-furyl]prop-2-enoic acid

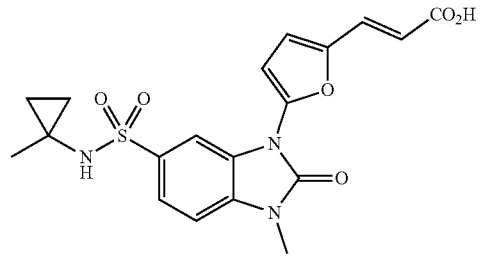

Step 1

Synthesis of 3-(5-formyl-2-furyl)-1-methyl-N-(1-methylcyclopropyl)-2-oxo-benzimidazole-5-sulfonamide, prepared from 1-methyl-N-(1-methylcyclopropyl)-2-oxo-3H-benzimidazole-5-sulfonamide and 5-bromo-2-furaldehyde using Method A14.

LCMS (high pH): RT 0.97 min, [M+H]$^+$ 376.5, >95 purity

Step 2

3-(5-Formyl-2-furyl)-1-methyl-N-(1-methylcyclopropyl)-2-oxo-benzimidazole-5-sulfonamide (500. mg, 1.33 mmol) and (carbethoxymethylene)triphenylphosphorane (464. mg, 1.33 mmol) in THF (20 mL) was heated at reflux, under nitrogen, for 4 h. The reaction mixture was allowed to cool and concentrated under reduced pressure, DCM (20 mL) and saturated aq. NaHCO$_3$ (20 mL) were added and the mixture stirred for 5 min. The DCM layer was isolated by passing through a hydrophobic frit, washing the aqueous layer with DCM (2×3 mL). The combined DCM layers were concentrated under reduced pressure and the residue purified by automated column chromatography, SiO$_2$, eluent 0-10% MeOH in DCM. The product contaminated with triphenylphosphine oxide was stirred in diethyl ether (100 mL) for 3 h and then filtered, to yield ethyl (E)-3-[5-[3-methyl-6-[(1-methylcyclopropyl)sulfamoyl]-2-oxo-benzimidazol-1-yl]-2-furyl]prop-2-enoate (242 mg, 0.53 mmol, 40%.

LCMS (high pH): RT 1.16 min, [M−H]$^-$ 444.5, >95 purity

Step 3

Ethyl (E)-3-[5-[3-methyl-6-[(1-methylcyclopropyl)sulfamoyl]-2-oxo-benzimidazol-1-yl]-2-furyl]prop-2-enoate (31.86 mg, 0.070 mmol) and lithium hydroxide (6.85 mg, 0.29 mmol) in THF (1 mL) and water (1 mL) were stirred at ambient temperature for 2 h. DCM (5 mL) was added followed by acidification with 2 M HCl to pH 1. The DCM layer was isolated by passing through a hydrophobic frit and the aqueous layer washed with DCM (2×3 mL). The combined DCM extracts were concentrated under reduced pressure and purified by prep. HPLC (low pH) to yield (E)-3-[5-[3-methyl-6-[(1-methylcyclopropyl)sulfamoyl]-2-oxo-benzimidazol-1-yl]-2-furyl]prop-2-enoic acid (8 mg, 0.0192 mmol, 27%).

The following example was prepared in a similar manner:

Example 69 (E)-3-[2-[3-methyl-6-[(1-methylcyclopropyl)sulfamoyl]-2-oxo-benzimidazol-1-yl]thiazol-5-yl]prop-2-enoic acid

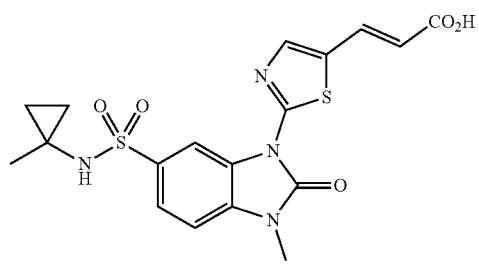 [SMILES: Cn1c(=O)n(-c2ncc(/C=C/C(=O)O)s2)c2cc(S(=O)(=O)NC3(C)CC3)ccc21]

Step 1, prepared from 1-methyl-N-(1-methylcyclopropyl)-2-oxo-3H-benzimidazole-5-sulfonamide and 2-bromothiazole-5-carbaldehyde using Method A14. Followed by Steps 2 and 3.

Hydrogenation

Example 70 3-[2-[3-Methyl-6-[(1-methylcyclopropyl)sulfamoyl]-2-oxo-benzimidazol-1-yl]thiazol-5-yl]propanoic acid

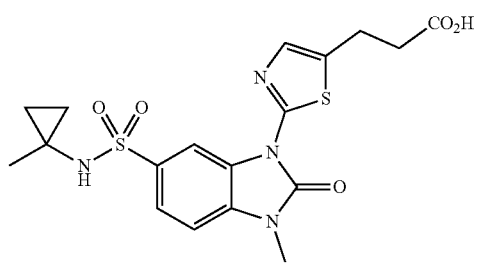 [SMILES: Cn1c(=O)n(-c2ncc(CCC(=O)O)s2)c2cc(S(=O)(=O)NC3(C)CC3)ccc21]

(E)-3-[2-[3-methyl-6-[(1-methylcyclopropyl)sulfamoyl]-2-oxo-enzimidazol-1-yl]thiazol-5-yl]prop-2-enoic acid (97.54 mg, 0.22 mmol) and palladium on activated carbon (100. mg, 0.32 mmol) in EtOH (4 mL) were purged under vacuum and stirred under an atmosphere of hydrogen at ambient temperature for 4 h. EtOH (20 mL) was added and the mixture stirred for 5 min before filtering through celite, washing with EtOH and DCM. The combined organics were concentrated under reduced pressure and purified by prep. HPLC (high pH) to yield 3-[2-[3-methyl-6-[(1-methylcyclopropyl)sulfamoyl]-2-oxo-benzimidazol-1-yl]thiazol-5-yl]propanoic acid (12 mg, 0.0275 mmol, 12%) as the ammonium salt.

Amide Formation

Example 71 N, N-Dimethyl-3-[2-[3-methyl-6-[(1-methylcyclopropyl)sulfamoyl]-2-oxo-benzimidazol-1-y]thiazol-5-y]propanamide

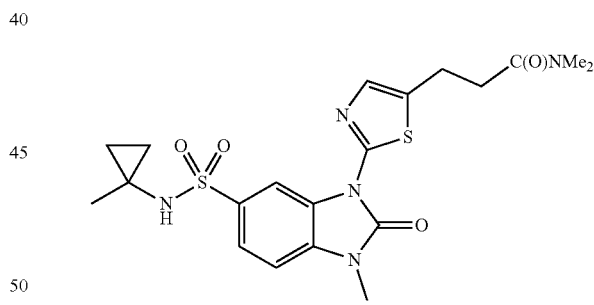

Lithium 3-[2-[3-methyl-6-[(1-methylcyclopropyl)sulfamoyl]-2-oxo-benzimidazol-1-yl]thiazol-5-yl]propanoate (100. mg, 0.23 mmol) was suspended in phosphorus oxychloride (3. mL, 32.19 mmol) and heated at 120° C. for 1 h. The excess POCl$_3$ was removed under reduced pressure and the residue taken up in DCM (5 mL). Dimethylamine solution (2 M in THF) (0.1 mL, 2 mmol) was added and the reaction mixture stirred at ambient temperature for 3 h. Saturated aq. NaHCO$_3$ (5 mL) was added and the mixture stirred for 5 min. The DCM layer was isolated by passing through a hydrophobic frit, concentrated under reduced pressure and purified by prep. HPLC (high pH) to yield N,N-dimethyl-3-[2-[3-methyl-6-[(1-methylcyclopropyl)sulfamoyl]-2-oxo-benzimidazol-1-yl]thiazol-5-yl]propanamide (6 mg, 0.0124 mmol, 5%).

Example 74 N-methyl-3-[2-[3-methyl-6-[(1-methyl-cyclopropyl)sulfamoyl]-2-oxo-benzimidazol-1-yl]thiazol-5-yl]propanamide

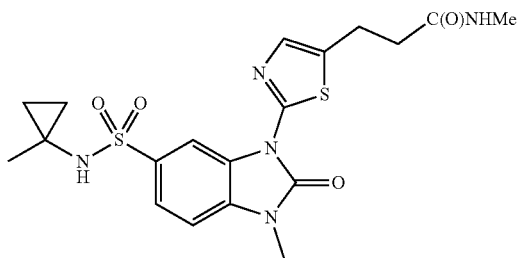

HATU (61.88 mg, 0.16 mmol) was added to a solution of lithium 3-[2-[3-methyl-6-[(1-methylcyclopropyl)sulfamoyl]-2-oxo-benzimidazol-1-yl]thiazol-5-yl]propanoate (60. mg, 0.1400 mmol) and N,N-diisopropylethylamine (0.07 mL, 0.41 mmol) in DMF (5 mL). After 10 min methylamine solution (2 M in THF) (0.2 mL, 0.41 mmol) was added and the reaction mixture stirred at ambient temperature overnight. DCM (10 mL) and saturated aq. NaHCO₃ (10 mL) were added and the mixture stirred for 5 min. The DCM layer was isolated by passing through a hydrophobic frit and the aqueous layer extracted with DCM (2×5 mL). The combined organics were concentrated under reduced pressure and the residue purified by prep. HPLC (high pH) to yield N-methyl-3-[2-[3-methyl-6-[(1-methylcyclopropyl)sulfamoyl]-2-oxo-benzimidazol-1-yl]thiazol-5-yl]propanamide (9 mg, 0.020 mmol, 15%).

Amine Deprotection

Example 81 3-(5-Amino-1,3,4-thiadiazol-2-yl)-1-methyl-N-(1-methylcyclopropyl)-2-oxo-benzimidazole-5-sulfonamide

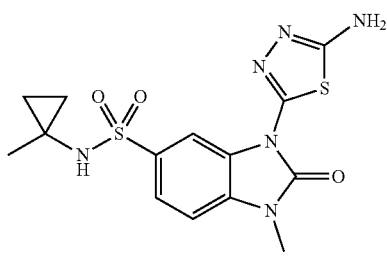 [SMILES: Cn1c(=O)n(-c2nnc(N)s2)c2cc(S(=O)(=O)NC3(C)CC3)ccc21]

Step 1

Synthesis of 3-[5-(2,5-dimethylpyrrol-1-yl)-1,3,4-thiadiazol-2-yl]-1-methyl-N-(1-methylcyclopropyl)-2-oxo-benzimidazole-5-sulfonamide, prepared from 1-methyl-N-(1-methylcyclopropyl)-2-oxo-2,3-dihydro-1H-benzo[d]imidazole-5-sulfonamide and 2-bromo-5-(2,5-dimethylpyrrol-1-yl)-1,3,4-thiadiazole (1.1 eq) using Method A15.

LCMS (high pH): RT 1.28 min, [M+H]⁺ 459.5, >95 purity

Step 2

3-[5-(2,5-Dimethylpyrrol-1-yl)-1,3,4-thiadiazol-2-yl]-1-methyl-N-(1-methylcyclopropyl)-2-oxo-benzimidazole-5-sulfonamide (30. mg, 0.070 mmol), hydroxylamine hydrochloride (68.17 mg, 0.98 mmol) and sodium hydroxide (26.16 mg, 0.65 mmol) in EtOH (4 mL) and water (4 mL) was heated at reflux for 3 days. The mixture was allowed to cool and concentrated under reduced pressure. To the residue was added DCM (10 mL), saturated aq. NaHCO₃ (10 mL) and water (5 mL) and the mixture stirred for 5 min. The mixture was passed through a hydrophobic frit and the aqueous washed with DCM, the combined DCM extracts were concentrated under reduced pressure and purified by prep. HPLC (high pH) to yield 3-(5-amino-1,3,4-thiadiazol-2-yl)-1-methyl-N-(1-methylcyclopropyl)-2-oxo-benzimidazole-5-sulfonamide (4.2 mg, 0.0104 mmol, 16%).

General Procedures Relating to Scheme 5:

Intermediate S5-A1
2-Fluoro-N-methyl-6-nitroaniline

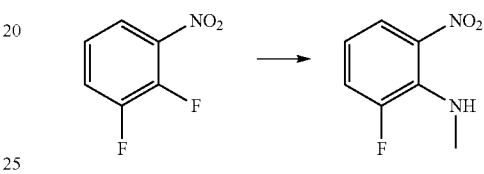

To a stirred solution of 2,3-difluoronitrobenzene (3.45 mL, 31.43 mmol) and potassium carbonate (8.69 g, 62.86 mmol) in 1,4-dioxane (50 mL) under nitrogen was added methylamine solution (33% w/w in EtOH) (6.87 mL, 62.86 mmol) and the resulting mixture was stirred at ambient temperature overnight. The reaction mixture was poured into EtOAc (250 mL) and water (250 mL). The organic phase was collected and the aqueous extracted with EtOAc (250 mL). The combined organics were washed with water (200 mL), dried over sodium sulfate and evaporated to dryness to yield 2-fluoro-N-methyl-6-nitro-aniline (5.40 g, 31.7 mmol, quant.).

¹H NMR (300 MHz, DMSO-d₆) δ=7.86 (dt, J=1.6, 8.7 Hz, 1H), 7.75 (br. s., 1H), 7.44 (dddd, J=0.8, 1.6, 7.9, 14.5 Hz, 1H), 6.70-6.62 (m, 1H), 3.11 (dd, J=5.4, 7.7 Hz, 3H)

The following intermediates were prepared in a similar manner:

Intermediate S5-A2
2-(Trifluoromethyl)-N-methyl-6-nitroaniline

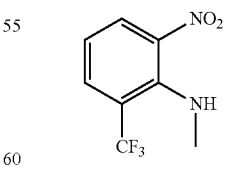

Prepared from 2-fluoro-1-nitro-3-(trifluoromethyl)benzene and methylamine (33% w/w in EtOH).

¹H NMR (300 MHz, DMSO-d₆) δ=8.01 (dd, J=1.7, 8.3 Hz, 1H), 7.80 (dd, J=1.7, 7.7 Hz, 1H), 6.86 (app. t, J=7.8 Hz, 1H), 6.65 (q, J=5.5 Hz, 1H), 2.71 (dd, J=0.8, 5.3 Hz, 3H)

Intermediate S5-A3
5-Fluoro-N-methyl-2-nitroaniline

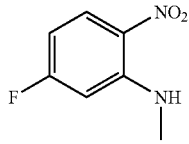

Prepared from 2,4-difluoronitrobenzene and methylamine (40% w/w in H$_2$O).

$^1$H NMR (300 MHz, DMSO-d$_6$) δ=8.33 (br. s., 1H), 8.16 (dd, J=6.3, 9.5 Hz, 1H), 6.78 (dd, J=2.7, 12.3 Hz, 1H), 6.53 (ddd, J=2.7, 7.6, 9.5 Hz, 1H), 2.93 (d, J=4.9 Hz, 3H)

Intermediate S5-B1
3-Fluoro-N2-methyl-benzene-1,2-diamine

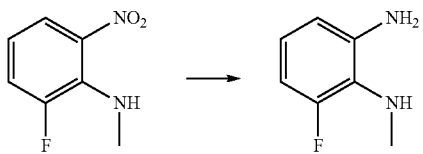

2-Fluoro-N-methyl-6-nitroaniline (5.40 g, 31.7 mmol) was dissolved in EtOH (150 mL), the mixture was then vacuum purged with nitrogen 3 times. Palladium on activated carbon (3.38 g, 31.7 mmol) was then added to the reaction mixture and the resulting suspension vacuum purged with nitrogen 3 times. The reaction mixture was then vacuum purged with hydrogen 3 times and then stirred under a positive pressure of hydrogen for 4 h. The reaction mixture was vacuum purged with nitrogen and filtered through a pad of celite. The cake was washed with EtOH and the combined filtrates combined. The solvent was removed in vacuo to yield 3-fluoro-N2-methyl-benzene-1,2-diamine (4.15 g, 29.6 mmol, 93%).

$^1$H NMR (300 MHz, DMSO-d$_6$) δ=6.65-6.46 (m, 1H), 6.40 (td, J=1.3, 7.7 Hz, 1H), 6.30 (ddd, J=1.5, 8.1, 11.7 Hz, 1H), 4.90 (s, 2H), 3.92 (br. s., 1H), 2.70 (dd, J=2.5, 5.7 Hz, 3H)

The following intermediates were prepared in a similar manner:

Intermediate S5-B2
N2-Methyl-3-(trifluoromethyl)benzene-1,2-diamine

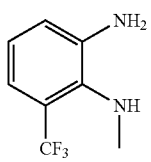

Prepared from N-methyl-2-nitro-6-(trifluoromethyl)aniline, palladium on carbon and hydrogen.

$^1$H NMR (300 MHz, DMSO-d$_6$) δ=6.94-6.85 (m, 2H), 6.79-6.72 (m, 1H), 5.11 (s, 2H), 3.63 (q, J=5.8 Hz, 1H), 2.59 (d, J=5.9 Hz, 3H)

Intermediate S5-B3
4-Fluoro-N2-methyl-benzene-1,2-diamine

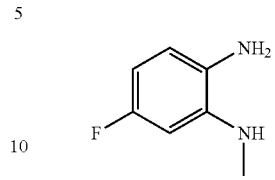

Prepared from 5-fluoro-N-methyl-2-nitro-aniline, palladium on carbon and hydrogen.

$^1$H NMR (300 MHz, DMSO-d$_6$) δ=6.52-6.41 (m, 1H), 6.20-6.11 (m, 2H), 4.90 (d, J=6.0 Hz, 1H), 4.28 (s, 2H), 2.69 (d, J=5.0 Hz, 3H)

Intermediate S5-C1
4-Fluoro-3-methyl-1H-benzimidazol-2-one

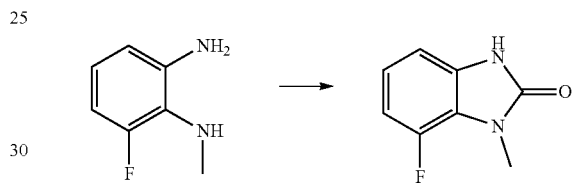

To a stirred solution of 3-fluoro-N2-methyl-benzene-1,2-diamine (4.20 g, 29.97 mmol) in THF (50 mL) under nitrogen was added 1,1'-carbonyldiimidazole (5.34 g, 32.96 mmol) and the reaction mixture was stirred at 60° C. overnight. The solvent was removed in vacuo and the residue suspended in DCM (50 mL). The mixture was stirred for 15 min and then filtered. The filter-cake was washed with DCM (2×10 mL) and collected to yield 4-fluoro-3-methyl-1H-benzimidazol-2-one (2.90 g, 17.5 mmol, 58%).

$^1$H NMR (300 MHz, DMSO-d$_6$) δ=11.10 (br. s., 1H), 7.00-6.80 (m, 3H), 3.42 (d, J=1.8 Hz, 3H)

The following intermediates were prepared in a similar manner:

Intermediate S5-C2
3-Methyl-4-(trifluoromethyl)-1H-benzimidazol-2-one

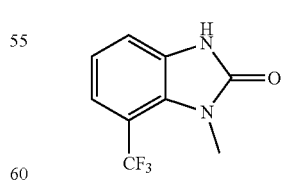

Prepared from N2-methyl-3-(trifluoromethyl)benzene-1,2-diamine and 1,1'-carbonyldiimidazole.

$^1$H NMR (300 MHz, DMSO-d$_6$) δ=11.47 (br. s., 1H), 7.35 (dd, J=1.4, 8.1 Hz, 1H), 7.30 (d, J=7.9 Hz, 1H), 7.16 (app. td, J=0.8, 8.0 Hz, 1H), 3.40 (q, J=2.4 Hz, 3H)

Intermediate S5-C3
5-Fluoro-3-methyl-1H-benzimidazol-2-one

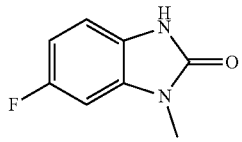

Prepared from 4-fluoro-N2-methyl-benzene-1,2-diamine and 1,1'-carbonyldiimidazole.

$^1$H NMR (300 MHz, DMSO-d$_6$) δ=10.86 (br. s., 1H), 7.06 (dd, J=2.6, 9.2 Hz, 1H), 6.93 (dd, J=4.6, 8.5 Hz, 1H), 6.78 (ddd, J=2.5, 8.5, 10.0 Hz, 1H), 3.26 (s, 3H)

Intermediate S5-D1 4-Fluoro-3-methyl-1-(5-methyl-1,3,4-thiadiazol-2-yl)benzimidazol-2-one

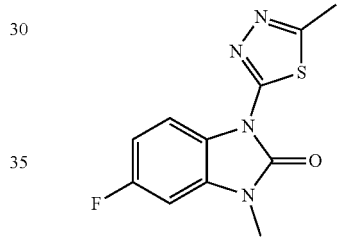

A stirred suspension of 4-fluoro-3-methyl-1H-benzimidazol-2-one (200. mg, 1.2 mmol), 2-bromo-5-methyl-1,3,4-thiadiazole (646.6 mg, 3.61 mmol), potassium carbonate (499.1 mg, 3.61 mmol), and copper (I) iodide (45.85 mg, 0.24 mmol) in 1,4-dioxane (8 mL) was purged with nitrogen for 5 min. trans-N,N'-Dimethylcyclohexane-1,2-diamine (94.91 uL, 0.60 mmol) was then added to the reaction mixture and then heated at 80° C. under nitrogen for 16 h. The reaction mixture was filtered (hot) through celite and the cake was washed with 1,4-dioxane (2×5 mL). The combined filtrates were distilled to dryness and the crude product was purified by automated column chromatography, SiO$_2$ (RediSep 24 g) eluent 0-100% EtOAc in iso-hexane to yield 4-fluoro-3-methyl-1-(5-methyl-1,3,4-thiadiazol-2-yl)benzimidazol-2-one (130 mg, 0.49 mmol, 41%).

$^1$H NMR (300 MHz, DMSO-d$_6$) δ=8.17 (dd, J=1.5, 7.4 Hz, 1H), 7.31-7.18 (m, 2H), 3.58 (d, J=2.1 Hz, 3H), 2.73 (s, 3H)

The following intermediates were prepared in a similar manner:

Intermediate S5-D2 3-Methyl-1-(5-methyl-1,3,4-thiadiazol-2-yl)-4-(trifluoromethyl)benzimidazol-2-one

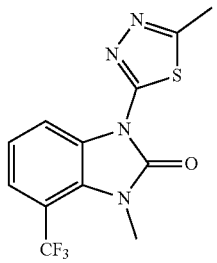 [SMILES: Cc1nnc(-n2c(=O)n(C)c3c(C(F)(F)F)cccc32)s1]

Prepared from 3-methyl-4-(trifluoromethyl)-1H-benzimidazol-2-one and 2-bromo-5-methyl-1,3,4-thiadiazole.

$^1$H NMR (300 MHz, DMSO-d$_6$) δ=8.73 (d, J=8.1 Hz, 1H), 7.68 (d, J=8.1 Hz, 1H), 7.47 (app. t, J=8.1 Hz, 1H), 3.55 (q, J=2.4 Hz, 3H), 2.75 (s, 3H)

Intermediate S5-D3 5-Fluoro-3-methyl-1-(5-methyl-1,3,4-thiadiazol-2-yl)benzimidazol-2-one Prepared from 5-fluoro-3-methyl-1H-benzimidazol-2-one and 2-bromo-5-methyl-1,3,4-thiadiazole.

$^1$H NMR (300 MHz, DMSO-d$_6$) δ=8.27 (dd, J=4.9, 8.8 Hz, 1H), 7.40 (dd, J=2.5, 8.9 Hz, 1H), 7.10 (ddd, J=2.6, 8.8, 10.0 Hz, 1H), 3.44 (s, 3H), 2.73 (s, 3H)

Intermediate S5-E1 7-Fluoro-1-methyl-3-(5-methyl-1,3,4-thiadiazol-2-yl)-2-oxo-benzimidazole-5-sulfonyl chloride

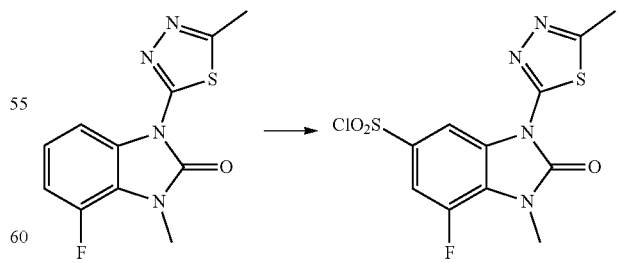

Chlorosulfonic acid (6. mL, 90.1 mmol) was added to solid 4-fluoro-3-methyl-1-(5-methyl-1,3,4-thiadiazol-2-yl)benzimidazol-2-one (110. mg, 0.42 mmol) in an ice bath with stirring, and the resulting mixture was stirred at ambient temperature for 2 h. The reaction mixture was poured into ice (60 g) and stirred for 15 min before being filtered. The resulting solid was dried under vacuum for 2 h at 40° C. to yield 7-fluoro-1-methyl-3-(5-methyl-1,3,4-thiadiazol-2-yl)-2-oxo-benzimidazole-5-sulfonyl chloride (125 mg, 0.345 mmol, 83%).

$^1$H NMR (300 MHz, DMSO-d$_6$) δ=8.47 (d, J=1.4 Hz, 1H), 7.34 (dd, J=1.3, 11.3 Hz, 1H), 3.57 (d, J=2.0 Hz, 3H), 2.75 (s, 3H), 1.24 (s, 1H)

The following intermediates were prepared in a similar manner:

Intermediate S5-E2 1-Methyl-3-(5-methyl-1,3,4-thiadiazol-2-yl)-2-oxo-7-(trifluoromethyl)benzimidazole-5-sulfonyl chloride

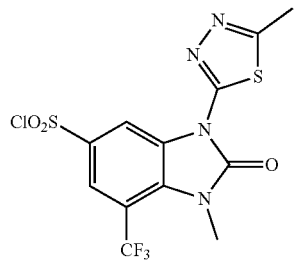 [SMILES: Cc1nnc(-n2c(=O)n(C)c3c(C(F)(F)F)cc(S(=O)(=O)Cl)cc32)s1]

Prepared from 3-methyl-1-(5-methyl-1,3,4-thiadiazol-2-yl)-4-(trifluoromethyl)benzimidazol-2-one and chlorosulfonic acid.

$^1$H NMR (300 MHz, DMSO-d$_6$) δ=8.97 (d, J=1.7 Hz, 1H), 7.84 (d, J=1.6 Hz, 1H), 3.55 (q, J=2.4 Hz, 3H), 2.76 (s, 3H)

Intermediate S5-E3 6-Fluoro-1-methyl-3-(5-methyl-1,3,4-thiadiazol-2-yl)-2-oxo-benzimidazole-5-sulfonyl chloride

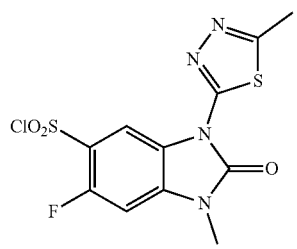 [SMILES: Cc1nnc(-n2c(=O)n(C)c3cc(F)c(S(=O)(=O)Cl)cc32)s1]

Prepared from 5-fluoro-3-methyl-1-(5-methyl-1,3,4-thiadiazol-2-yl)benzimidazol-2-one and chlorosulfonic acid.

$^1$H NMR (300 MHz, DMSO-d$_6$) δ=8.63 (d, J=6.4 Hz, 1H), 7.30 (d, J=9.6 Hz, 1H), 3.43 (s, 3H), 2.73 (s, 3H), 1.23 (s, 1H)

Example 114 7-Fluoro-1-methyl-N-(1-methylcyclopropyl)-3-(5-methyl-1,3,4-thiadiazol-2-yl)-2-oxo-benzimidazole-5-sulfonamide

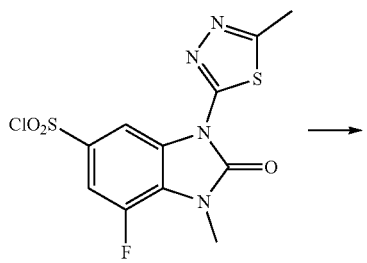

To a stirred solution of 7-fluoro-1-methyl-3-(5-methyl-1,3,4-thiadiazol-2-yl)-2-oxo-benzimidazole-5-sulfonyl chloride (50. mg, 0.14 mmol) and 1-methylcyclopropanamine hydrochloride (14.83 mg, 0.14 mmol) in DCM (4 mL) under nitrogen was added triethylamine (38.31 uL, 0.28 mmol), the reaction mixture was stirred at ambient temperature overnight. The solvent was removed in vacuo and the resulting crude product was purified by prep. HPLC, low pH, to yield 7-fluoro-1-methyl-N-(1-methylcyclopropyl)-3-(5-methyl-1,3,4-thiadiazol-2-yl)-2-oxo-benzimidazole-5-sulfonamide (40 mg, 0.10 mmol, 73%).

The following examples were prepared in a similar manner:

Example 123 1-Methyl-N-(1-methylcyclopropyl)-3-(5-methyl-1,3,4-thiadiazol-2-yl)-2-oxo-7-(trifluoromethyl)benzimidazole-5-sulfonamide

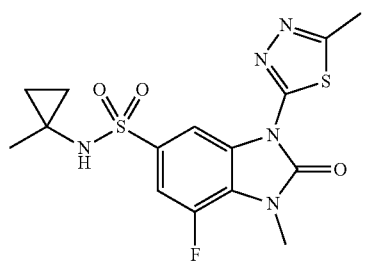

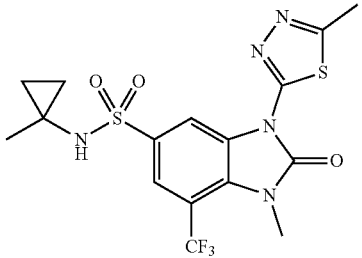

Prepared from 1-methyl-3-(5-methyl-1,3,4-thiadiazol-2-yl)-2-oxo-7-(trifluoromethyl)benzimidazole-5-sulfonyl chloride and 1-methylcyclopropanamine hydrochloride.

Example 116 6-Fluoro-1-methyl-N-(1-methylcyclopropyl)-3-(5-methyl-1,3,4-thiadiazol-2-yl)-2-oxo-benzimidazole-5-sulfonamide

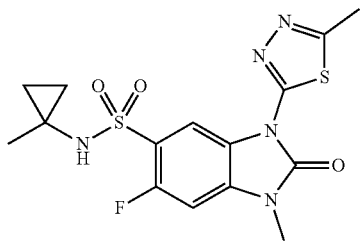

Prepared from 6-fluoro-1-methyl-3-(5-methyl-1,3,4-thiadiazol-2-yl)-2-oxo-benzimidazole-5-sulfonyl chloride and 1-methylcyclopropanamine hydrochloride. One-pot sulfonyl chloride formation/sulfonamide synthesis

Example 56 6-Fluoro-1,3-dimethyl-N-(1-methylcyclopropyl)-2-oxo-benzimidazole-5-sulfonamide

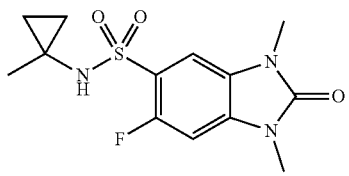 [SMILES: Cn1c(=O)n(C)c2cc(S(=O)(=O)NC3(C)CC3)c(F)cc21]

Step 1

Iodomethane (0.82 mL, 13.15 mmol) was added to a mixture of 5-fluoro-1,3-dihydro-2H-benzimidazol-2-one (500. mg, 3.29 mmol) and potassium carbonate (1.81 g, 13.15 mmol) in DMF (25 mL), and the reaction mixture stirred at ambient temperature for 16 h. DCM (30 mL) and water (60 mL) were added and the mixture stirred for 5 min. The DCM layer was isolated by passing through a hydrophobic frit and the aqueous washed with DCM (2×50 mL). The combined DCM extracts were concentrated under reduced pressure to yield 5-fluoro-1,3-dimethyl-benzimidazol-2-one (556 mg, 2.99 mmol, 91%).

$^1$H NMR (300 MHz, CDCl$_3$) δ=6.91-6.71 (m, 3H), 3.42 (s, 3H), 3.41 (s, 3H)

Step 2

Chlorosulfonic acid (3.33 mL, 50.06 mmol) was added dropwise to 5-fluoro-1,3-dimethyl-benzimidazol-2-one (250. mg, 1.39 mmol) and stirred at ambient temperature for 2 h. The reaction mixture was added dropwise to a stirring slurry of ice/water (approx 30 mL). After the addition was complete DCM (20 mL) was added and the mixture stirred for 5 min. The DCM layer was isolated by passing through a hydrophobic frit and the aqueous phase washed with DCM (2×4 mL). The DCM extracts were combined and under stirring a mixture of 1-methylcyclopropanamine hydrochloride (179.12 mg, 1.67 mmol) and triethylamine (0.77 mL, 5.55 mmol) in DCM (5 mL) was added dropwise. After 1 h at ambient temperature water (30 mL) was added and the mixture stirred for 5 min. The DCM layer was isolated by passing through a hydrophobic frit and the aqueous layer washed with DCM (2×4 mL). The combined DCM extracts were concentrated under reduced pressure and the residue purified by prep. HPLC (high pH) to yield 6-fluoro-1,3-dimethyl-N-(1-methylcyclopropyl)-2-oxo-benzimidazole-5-sulfonamide (25 mg, 0.0798 mmol, 6%).

General Procedures Relating to Scheme 6:

Intermediate S6-A 4-[(E)-2-(4-Fluorophenyl)vinyl]-N-(1-methylcyclopropyl)-3-nitro-benzenesulfonamide

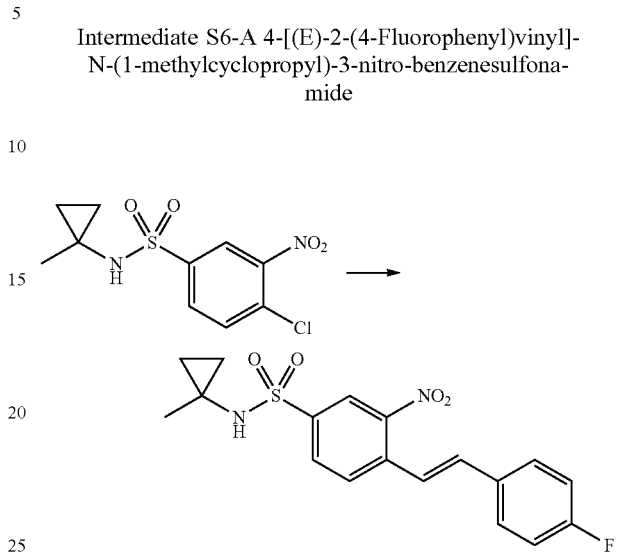

A mixture of 4-chloro-N-(1-methylcyclopropyl)-3-nitro-benzenesulfonamide (400. mg, 1.38 mmol), trans-2-(4-fluorophenyl)vinylboronic acid (342.52 mg, 2.06 mmol), caesium carbonate (896.59 mg, 2.75 mmol) and tris(dibenzylideneacetone)dipalladium(0) (63. mg, 0.07 mmol) in 1,4-dioxane (15 mL) was degassed with nitrogen. Dicyclohexyl(2',6'-dimethoxybiphenyl-2-yl)phosphane (56.49 mg, 0.14 mmol) was then added and the reaction mixture heated at reflux for 5 h. The mixture was allowed to cool and concentrated under reduced pressure. EtOAc (20 mL) and saturated aq. NaHCO$_3$ (20 mL) was added and the mixture stirred for 5 min. The EtOAc layer was separated and the aqueous layer washed with EtOAc. The combined EtOAc extracts were passed through a hydrophobic frit and concentrated under reduced pressure and purified by automated column chromatography, SiO$_2$, eluent 0-100% EtOAc in iso-hexane, to yield 4-[(E)-2-(4-fluorophenyl)vinyl]-N-(1-methylcyclopropyl)-3-nitro-benzenesulfonamide (436 mg, 1.16 mmol, 84%).

$^1$H NMR (300 MHz, CDCl$_3$) δ=8.46 (d, J=2.0 Hz, 1H), 8.07 (dd, J=2.5, 8.3 Hz, 1H), 7.91 (d, J=8.4 Hz, 1H), 7.62-7.49 (m, 3H), 7.18-7.06 (m, 3H), 5.09 (s, 1H), 1.30 (s, 3H), 0.85-0.79 (m, 2H), 0.60-0.53 (m, 2H)

Intermediate S6-B 3-Amino-4-[2-(4-fluorophenyl)ethyl]-N-(1-methylcyclopropyl)benzenesulfonamide

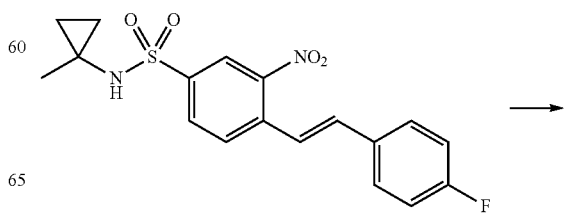

-continued

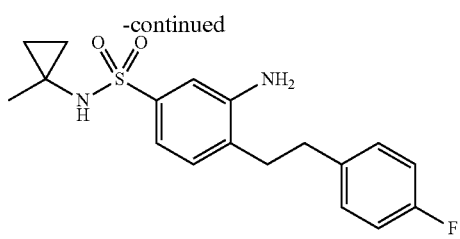

4-[(E)-2-(4-Fluorophenyl)vinyl]-N-(1-methylcyclopropyl)-3-nitro-benzenesulfonamide (270. mg, 0.72 mmol) and 5% palladium on activated carbon (100. mg, 0.94 mmol) in EtOH (10 mL) was heated to 60° C. overnight under an atmosphere of hydrogen. The reaction mixture was filtered through celite and the filter cake washed with MeOH, DCM and EtOAc. The combined organics were concentrated under reduced pressure. EtOAc (15 mL) and saturated aq. NaHCO$_3$ (15 mL) was added and the mixture stirred for 5 min. The EtOAc layer was separated and the aqueous layer washed with EtOAc. The combined EtOAc extracts were concentrated under reduced pressure and purified by automated column chromatography, SiO$_2$, eluent 0-100% EtOAc in iso-hexane, to yield 3-amino-4-[2-(4-fluorophenyl)ethyl]-N-(1-methylcyclopropyl)benzenesulfonamide (213 mg, 0.61 mmol, 85%).

LCMS (high pH): RT 1.18 min, [M+H]$^+$ 349.3, >90% purity

Intermediate S6-C 3-[(4-Fluorophenyl)methyl]-N-(1-methylcyclopropyl)-1H-indazole-6-sulfonamide

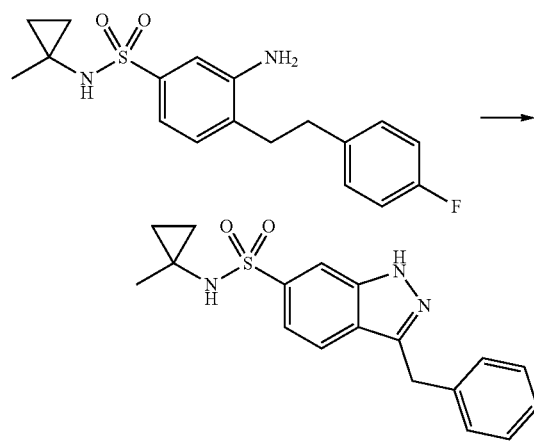

Sodium nitrite (0.06 g, 0.9200 mmol) was added portionwise to a stirring solution of 3-amino-4-[2-(4-fluorophenyl)ethyl]-N-(1-methylcyclopropyl)benzenesulfonamide (213. mg, 0.61 mmol) in AcOH (100 mL). After addition was complete the reaction mixture was heated to 80° C. for 3 h. The reaction mixture was allowed to cool and concentrated under reduced pressure. EtOAc (150 mL) and water (100 mL) was added and the mixture stirred for 5 min. The EtOAc layer was separated and the aqueous layer washed with EtOAc. The combined EtOAc extracts were passed through a hydrophobic frit and concentrated under reduced pressure. The residue was sonicated in cold diethyl ether causing precipitation and the solid filtered to yield 3-[(4-fluorophenyl)methyl]-N-(1-methylcyclopropyl)-1H-indazole-6-sulfonamide (110 mg, 0.31 mmol, 50%).

$^1$H NMR (300 MHz, CDCl$_3$) δ=8.19-8.15 (m, 1H), 7.65-7.58 (m, 1H), 7.58-7.50 (m, 1H), 7.32-7.24 (m, 2H), 7.04-6.94 (m, 2H), 5.37 (br. s., 1H), 4.38 (s, 2H), 1.19 (s, 3H), 0.80-0.73 (m, 2H), 0.49-0.42 (m, 2H)

Example 146 3-[(4-Fluorophenyl)methyl]-N-(1-methylcyclopropyl)-1-(5-methyl-1,3,4-thiadiazol-2-yl)indazole-6-sulfonamide

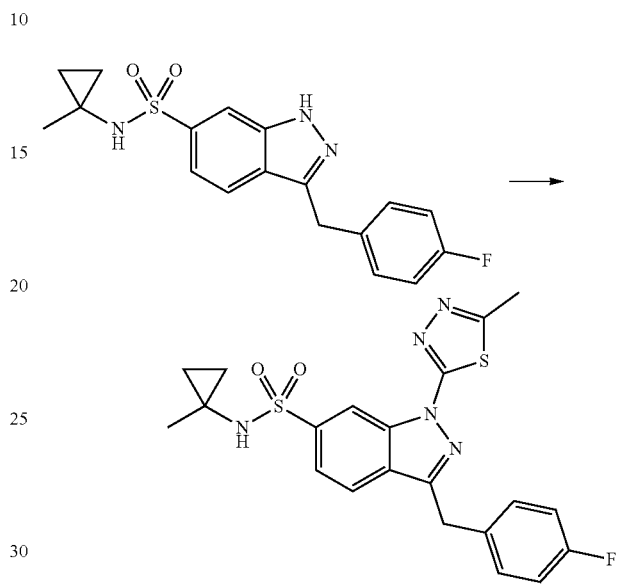

A mixture of 3-[(4-fluorophenyl)methyl]-N-(1-methylcyclopropyl)-1H-indazole-6-sulfonamide (45. mg, 0.13 mmol), 2-bromo-5-methyl-1,3,4-thiadiazole (0.04 mL, 0.31 mmol), copper (I) iodide (2.38 mg, 0.01 mmol) and potassium carbonate (43.26 mg, 0.31 mmol) in MeCN (2 mL) was degassed with nitrogen. (+/−)-trans,1,2-Diaminocyclohexane (3.0 μL, 0.03 mmol) was added and the reaction mixture heated at reflux for 2 h. The reaction mixture was allowed to cool, DCM (5 mL) and saturated aq. NaHCO$_3$ were added and the mixture stirred for 5 min. The DCM layer was isolated and the aqueous washed with DCM. The combined DCM extracts were concentrated under reduced pressure and purified by automated column chromatography, SiO$_2$, eluent 0-100% EtOAc in iso-hexane, and then by prep. HPLC (high pH) to yield 3-[(4-fluorophenyl)methyl]-N-(1-methylcyclopropyl)-1-(5-methyl-1,3,4-thiadiazol-2-yl)indazole-6-sulfonamide (4 mg, 0.0078 mmol, 6%).

General Procedures Relating to Scheme 7:

Intermediate S7-A 4-Methyl-N-(1-methylcyclopropyl)-3-nitro-benzenesulfonamide

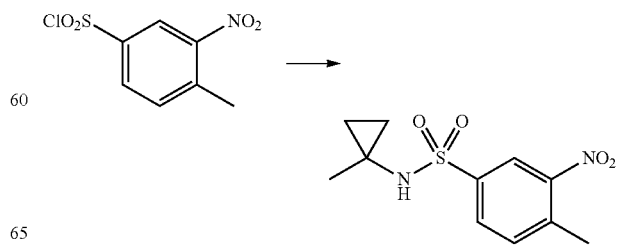

Triethylamine (2.36 mL, 16.98 mmol) was added dropwise to a solution of 4-methyl-3-nitrobenzenesulfonyl chloride (1. g, 4.24 mmol) and 1-methylcyclopropanamine hydrochloride (547.85 mg, 5.09 mmol) in DCM (20 mL) at 0° C. After addition was complete the ice bath was removed and the mixture allowed to stir at ambient temperature for 3 h. DCM (30 mL) and saturated aq. NaHCO₃ (50 mL) were added and the mixture was stirred for 5 min. The DCM layer was isolated by passing through a hydrophobic frit, washing the aqueous layer with DCM. The combined DCM layers were concentrated under reduced pressure and the residue purified by automated column chromatogrpahy SiO₂, eluent 0-100% EtOAc in iso-hexane to yield 4-methyl-N-(1-methylcyclopropyl)-3-nitro-benzenesulfonamide (1.09 g, 4.03 mmol, 95%).

¹H NMR (300 MHz, CDCl₃) δ=8.47 (d, J=2.0 Hz, 1H), 8.00 (dd, J=2.0, 8.1 Hz, 1H), 7.52 (d, J=8.1 Hz, 1H), 5.02 (br. s, 1H), 2.70 (s, 3H), 1.28 (s, 3H), 0.82-0.76 (m, 2H), 0.58-0.51 (m, 2H)

Intermediate S7-B N-(1-Methylcyclopropyl)-3-nitro-4-[(E)-2-pyrrolidin-1-ylvinyl]benzenesulfonamide

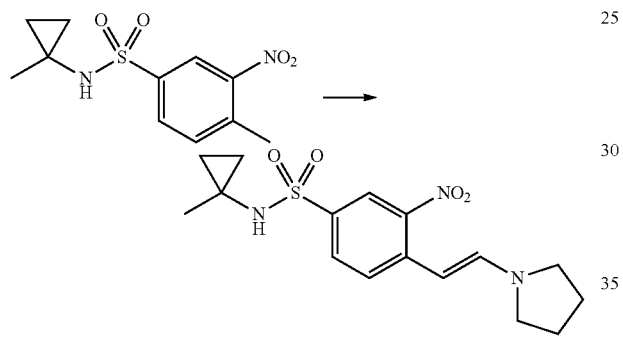

1,1-Dimethoxy-N,N-dimethylmethanamine (0.18 mL, 1.33 mmol) was added to a stirring solution of 4-methyl-N-(1-methylcyclopropyl)-3-nitro-benzenesulfonamide (300. mg, 1.11 mmol) and pyrrolidine (0.11 mL, 1.33 mmol) in DMF (5 mL) and the reaction mixture heated at 100° C., under nitrogen, for 3 h. The reaction mixture was allowed to cool and concentrated under reduced pressure. The residue was sonicated in cold diethyl ether and a precipitate formed, the solid was filtered to yield N-(1-methylcyclopropyl)-3-nitro-4-[(E)-2-pyrrolidin-1-ylvinyl]benzenesulfonamide (331 mg, 0.94 mmol, 85%).

¹H NMR (300 MHz, CDCl₃) δ=8.36 (d, J=2.1 Hz, 1H), 7.68 (dd, J=2.0, 8.5 Hz, 1H), 7.54 (d, J=8.8 Hz, 1H), 7.48 (d, J=13.6 Hz, 1H), 5.94 (d, J=13.1 Hz, 1H), 4.87 (s, 1H), 3.51-3.32 (m, 4H), 2.07-1.91 (m, 4H), 1.26 (s, 3H), 0.85-0.78 (m, 2H), 0.55-0.47 (m, 2H)

Intermediate S7-C
N-(1-Methylcyclopropyl)-1H-indole-6-sulfonamide

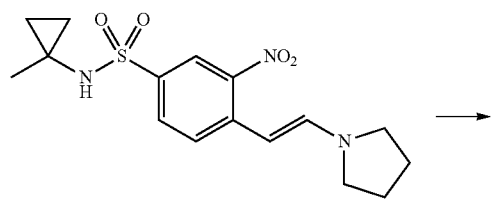

-continued

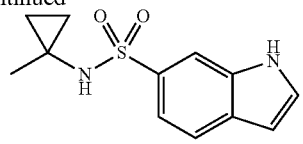

Hydrazine hydrate (1.88 mL, 51.36 mmol) was added to a stirring mixture of N-(1-methylcyclopropyl)-3-nitro-4-[(E)-2-pyrrolidin-1-ylvinyl]benzenesulfonamide (3.61 g, 10.27 mmol) and Raney nickel (2.13 mL, 323.64 mmol) in MeOH (25 mL) and THF (25 mL) and heated at 60° C. for 3 h. The reaction mixture was allowed to cool and DCM (10 mL) was added. The mixture was stirred for 5 min then filtered through celite washing with MeOH and DCM. The combined filtrate was concentrated under reduced pressure and the residue purified by automated column chromatography, 0-100% EtOAc in iso-hexane to yield N-(1-methylcyclopropyl)-1H-indole-6-sulfonamide (2.17 g, 8.15 mmol, 79%).

¹H NMR (300 MHz, DMSO-d₆) δ=11.56 (br. s., 1H), 7.91-7.87 (m, 1H), 7.82 (s, 1H), 7.70 (d, J=8.4 Hz, 1H), 7.61 (dd, J=2.1, 3.1 Hz, 1H), 7.40 (dd, J=1.6, 8.4 Hz, 1H), 6.57-6.53 (m, 1H), 1.00 (s, 3H), 0.61-0.54 (m, 2H), 0.36-0.25 (m, 2H)

Example 115 N-(1-Methylcyclopropyl)-1-(5-methyl-1,3,4-thiadiazol-2-yl)indole-6-sulfonamide

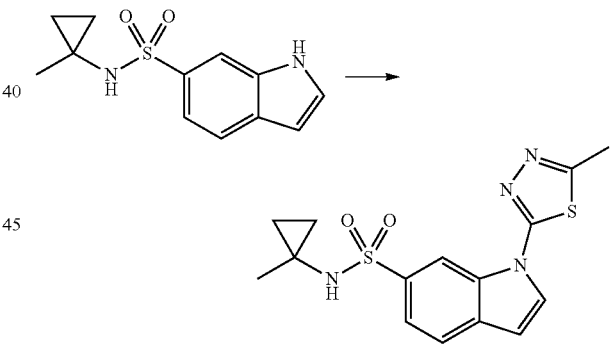

A mixture of N-(1-methylcyclopropyl)-1H-indole-6-sulfonamide (40. mg, 0.16 mmol), 2-bromo-5-methyl-1,3,4-thiadiazole (57.22 mg, 0.32 mmol), copper (I) iodide (3.04 mg, 0.02 mmol) and potassium carbonate (55.21 mg, 0.40 mmol) in MeCN (2 mL) was degassed with nitrogen. (+/−)-trans-1,2-Diaminocyclohexane (3.8 μL, 0.03 mmol) was added and the reaction mixture heated at reflux for 2 h. The reaction mixture was allowed to cool, DCM (5 mL) and saturated aq. NaHCO₃ were added and the mixture stirred for 5 min. The DCM layer was isolated and the aqueous washed with DCM. The combined DCM extracts were concentrated under reduced pressure and the residue purified by automated column chromatogrpahy SiO₂, eluent 0-100% EtOAc in iso-hexane, and then by prep. HPLC (high pH) to yield N-(1-methylcyclopropyl)-1-(5-methyl-1,3,4-thiadiazol-2-yl)indole-6-sulfonamide (6 mg, 0.017 mmol, 11%).

Intermediate S7-D1 3-Acetyl-N-(1-methylcyclopropyl)-1H-indole-6-sulfonamide

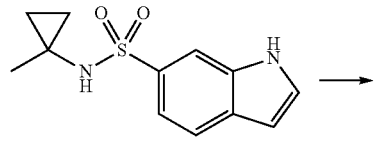

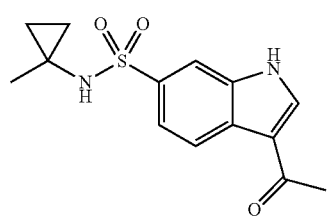

Tetrachlorozirconium (139.65 mg, 0.60 mmol) was added to a solution of N-(1-methylcyclopropyl)-1H-indole-6-sulfonamide (100. mg, 0.40 mmol) and acetyl chloride (0.03 mL, 0.40 mmol) in DCM (4 mL). After stirring at ambient temperature for 3 h EtOAc (10 mL) and water (10 mL) were added and the mixture stirred for 5 min. The EtOAc layer was isolated and the aqueous layer extracted with EtOAc. The combined extracts were concentrated under reduced pressure and the residue purified by automated column chromatography, $SiO_2$, eluent 0-100% EtOAc in iso-hexane to yield 3-acetyl-N-(1-methylcyclopropyl)-1H-indole-6-sulfonamide (60 mg, 0.18 mmol, 46%).

$^1$H NMR (300 MHz, DMSO-$d_6$) δ=12.32 (br. s., 1H), 8.55 (s, 1H), 8.31 (d, J=8.3 Hz, 1H), 7.95 (s, 1H), 7.93 (dd, J=0.8, 1.7 Hz, 1H), 7.60 (dd, J=1.6, 8.4 Hz, 1H), 2.49 (s, 3H), 1.00 (s, 3H), 0.62-0.53 (m, 2H), 0.36-0.29 (m, 2H)

The following intermediates were prepared in a similar manner:

Intermediate S7-D2 3-(Cyclopropanecarbonyl)-N-(1-methylcyclopropyl)-1H-indole-6-sulfonamide

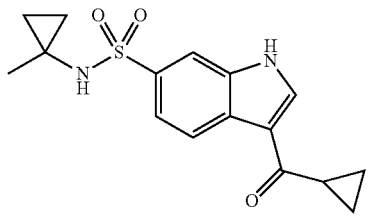 [SMILES: CC1(NS(=O)(=O)c2ccc3c(C(=O)C4CC4)c[nH]c3c2)CC1]

Prepared from N-(1-methylcyclopropyl)-1H-indole-6-sulfonamide and cyclopropanecarbonyl chloride.

LCMS (high pH): RT 0.98 min, [M+H]$^+$ 319.3, 93% purity

Intermediate S7-D3 3-(4-Fluorobenzoyl)-N-(1-methylcyclopropyl)-1H-indole-6-sulfonamide

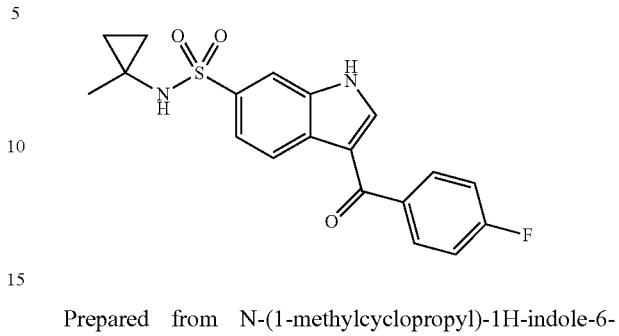

Prepared from N-(1-methylcyclopropyl)-1H-indole-6-sulfonamide and 4-fluorobenzoylchloride.

LCMS (high pH): RT 1.09 min, [M+H]$^+$ 373.3, 100% purity

Example 144 3-Acetyl-N-(1-methylcyclopropyl)-1-(5-methyl-1,3,4-thiadiazol-2-yl)indole-6-sulfonamide

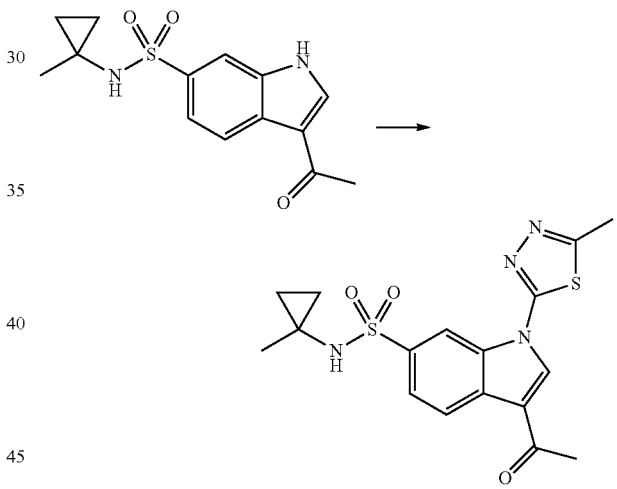

A stirring mixture of 3-acetyl-N-(1-methylcyclopropyl)-1H-indole-6-sulfonamide (60. mg, 0.21 mmol), 2-bromo-5-methyl-1,3,4-thiadiazole (0.04 mL, 0.41 mmol), copper (I) iodide (3.91 mg, 0.02 mmol) and potassium carbonate (85.1 mg, 0.62 mmol) in MeCN (4 mL) was degassed with nitrogen. (+/−)-trans,1,2-Diaminocyclohexane (4.9 μL, 0.040 mmol) was added and the mixture heated at reflux for 2 h. The reaction mixture was allowed to cool, DCM (5 mL) and saturated aq. NaHCO$_3$ were added and the mixture stirred for 5 min. The DCM layer was isolated and the aqueous washed with DCM. The combined DCM extracts were concentrated under reduced pressure and the residue purified by automated column chromatography, SiO$_2$, 0-100% EtOAc in iso-hexane, and then by prep. HPLC (high pH) to yield 3-acetyl-N-(1-methylcyclopropyl)-1-(5-methyl-1,3,4-thiadiazol-2-yl)indole-6-sulfonamide (4.4 mg, 0.0108 mmol, 5%).

The following examples were prepared in a similar manner:

Example 130 3-(Cyclopropanecarbonyl)-N-(1-methylcyclopropyl)-1-(5-methyl-1,3,4-thiadiazol-2-yl)indole-6-sulfonamide

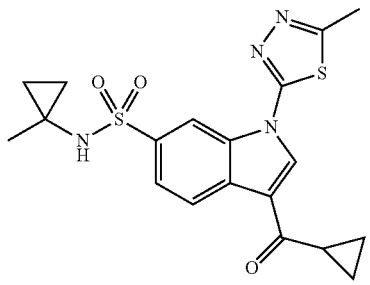 [SMILES: Cc1nnc(-n2cc(C(=O)C3CC3)c3ccc(S(=O)(=O)NC4(C)CC4)cc32)s1]

Prepared from 3-(cyclopropanecarbonyl)-N-(1-methylcyclopropyl)-1H-indole-6-sulfonamide and 2-bromo-5-methyl-1,3,4-thiadiazole.

Example 145 3-(Cyclopropanecarbonyl)-1-[5-(difluoromethyl)-1,3,4-thiadiazol-2-yl]-N-(1-methylcyclopropyl)indole-6-sulfonamide

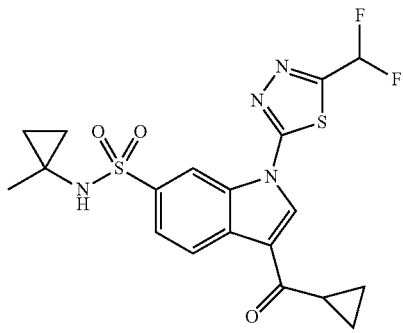 [SMILES: CC1(NS(=O)(=O)c2ccc3c(C(=O)C4CC4)cn(-c4nnc(C(F)F)s4)c3c2)CC1]

Prepared from 3-(cyclopropanecarbonyl)-N-(1-methylcyclopropyl)-1H-indole-6-sulfonamide and 2-bromo-5-(difluoromethyl)-1,3,4-thiadiazole.

Example 131 3-(4-Fluorobenzoyl)-N-(1-methylcyclopropyl)-1-(5-methyl-1,3,4-thiadiazol-2-yl)indole-6-sulfonamide

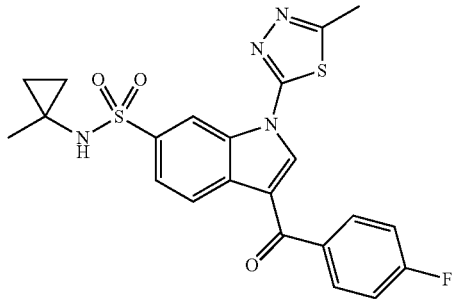 [SMILES: Cc1nnc(-n2cc(C(=O)c3ccc(F)cc3)c3ccc(S(=O)(=O)NC4(C)CC4)cc32)s1]

Prepared from 3-(4-fluorobenzoyl)-N-(1-methylcyclopropyl)-1H-indole-6-sulfonamide and 2-bromo-5-methyl-1,3,4-thiadiazole.

Intermediate S7-E1 3-Benzyl-N-(1-methylcyclopropyl)-1H-indole-6-sulfonamide

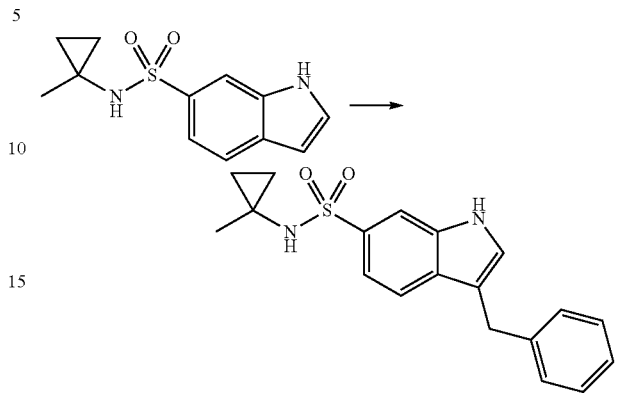

A solution of N-(1-methylcyclopropyl)-1H-indole-6-sulfonamide (200. mg, 0.80 mmol), benzyl bromide (0.19 mL, 1.6 mmol) and silver oxide (370.3 mg, 1.6 mmol) in 1,4-dioxane (6 mL) was heated at 100° C. for 6 h. The reaction mixture was allowed to cool and concentrated under reduced pressure. DCM (10 mL) and saturated aq. NaHCO$_3$ (10 mL) were added and the mixture stirred for 5 min. The DCM layer was isolated by passing through a hydrophobic frit and the aqueous layer washed with DCM. The combined DCM extracts were concentrated under reduced pressure and the crude product purified by prep. HPLC (high pH) to yield 3-benzyl-N-(1-methylcyclopropyl)-1H-indole-6-sulfonamide (109 mg, 0.32 mmol, 40%).

$^1$H NMR (300 MHz, DMSO-d$_6$) δ=11.37 (br. s., 1H), 7.83 (br. s, 1H), 7.60 (d, J=8.4 Hz, 1H), 7.42 (d, J=2.1 Hz, 1H), 7.34 (dd, J=1.8, 8.5 Hz, 1H), 7.32-7.13 (m, 5H), 4.07 (s, 2H), 0.99 (s, 3H), 0.59-0.45 (m, 2H), 0.33-0.25 (m, 2H)

The following intermediates were prepared in a similar manner:

Intermediate S7-E2 3-[(4-Fluorophenyl)methyl]-N-(1-methylcyclopropyl)-1H-indole-6-sulfonamide

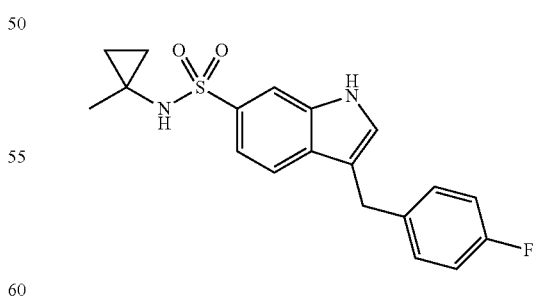

Prepared from N-(1-methylcyclopropyl)-1H-indole-6-sulfonamide and 4-fluorobenzyl bromide.

$^1$H NMR (300 MHz, DMSO-d$_6$) δ=11.38 (br. s., 1H), 7.89-7.79 (m, 2H), 7.60 (d, J=8.2 Hz, 1H), 7.43 (d, J=2.4 Hz, 1H), 7.41-7.29 (m, 3H), 7.13-7.05 (m, 2H), 4.06 (s, 2H), 1.00 (s, 3H), 0.59-0.51 (m, 2H), 0.33-0.27 (m, 2H)

Intermediate S7-E3 3-[(2,4-Dimethylthiazol-5-yl)methyl]-N-(1-methylcyclopropyl)-1H-indole-6-sulfonamide

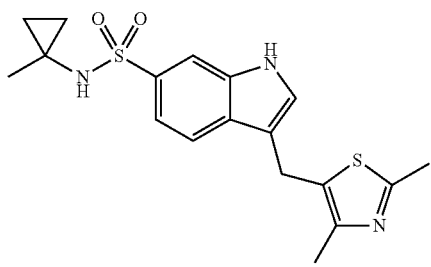

Prepared from N-(1-methylcyclopropyl)-1H-indole-6-sulfonamide and 5-(chloromethyl)-2,4-dimethyl-thiazole hydrochloride.

$^1$H NMR (300 MHz, DMSO-$d_6$) δ=11.40 (br. s, 1H), 7.84 (d, J=1.0 Hz, 2H), 7.59 (d, J=8.5 Hz, 1H), 7.43 (br. s, 1H), 7.38 (dd, J=1.6, 8.4 Hz, 1H), 4.15 (s, 2H), 2.47 (s, 3H), 2.34 (s, 3H), 1.05-0.94 (m, 3H), 0.66-0.50 (m, 2H), 0.35-0.28 (m, 2H)

Intermediate S7-E4 3-(Cyclopropylmethyl)-N-(1-methylcyclopropyl)-1H-indole-6-sulfonamide

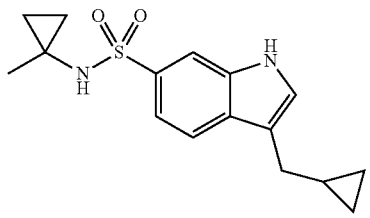 [SMILES: CC1(NS(=O)(=O)c2ccc3c(CC4CC4)c[nH]c3c2)CC1]

Prepared from N-(1-methylcyclopropyl)-1H-indole-6-sulfonamide and 1-(bromomethyl)cyclopropane. Crude product taken into next reaction.

LCMS (high pH): RT 1.19 min, [M+H]$^+$ 305.3, 65% purity.

Example 126 3-Benzyl-N-(1-methylcyclopropyl)-1-(5-methyl-1,3,4-thiadiazol-2-yl)indole-6-sulfonamide

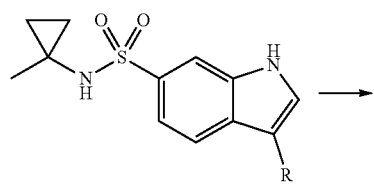

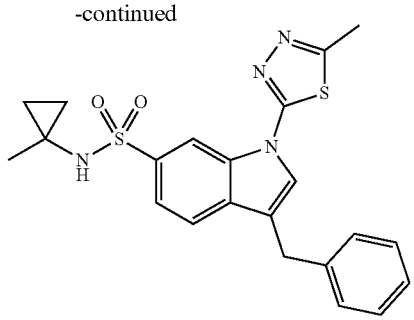

A suspension of 3-benzyl-N-(1-methylcyclopropyl)-1H-indole-6-sulfonamide (80. mg, 0.23 mmol), 2-bromo-5-methyl-1,3,4-thiadiazole (84.15 mg, 0.47 mmol), copper (I) iodide (4.48 mg, 0.02 mmol) and potassium carbonate (81.19 mg, 0.59 mmol) in MeCN (3 mL) was degassed with nitrogen. (+/−)-trans,1,2-Diaminocyclohexane (0.01 mL, 0.05 mmol) was added and the reaction mixture heated at reflux for 2 h. The reaction mixture was allowed to cool, DCM (5 mL) and saturated aq. NaHCO$_3$ were added and the mixture stirred for 5 min. The DCM layer was isolated and the aqueous washed with DCM. The combined DCM extracts were concentrated under reduced pressure and the residue purified by automated column chromatography, SiO$_2$, 0-100% EtOAc in iso-hexane, and then by prep. HPLC (high pH) to yield 3-benzyl-N-(1-methylcyclopropyl)-1-(5-methyl-1,3,4-thiadiazol-2-yl)indole-6-sulfonamide (26 mg, 0.059 mmol, 25%).

The following examples were prepared in a similar manner:

Example 127 3-[(4-Fluorophenyl)methyl]-N-(1-methylcyclopropyl)-1-(5-methyl-1,3,4-thiadiazol-2-yl)indole-6-sulfonamide

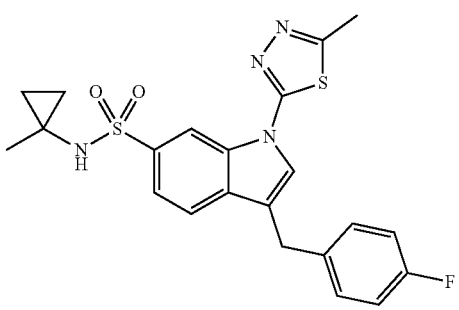 [SMILES: Cc1nnc(-n2cc(Cc3ccc(F)cc3)c3ccc(S(=O)(=O)NC4(C)CC4)cc32)s1]

Prepared from 3-[(4-fluorophenyl)methyl]-N-(1-methylcyclopropyl)-1H-indole-6-sulfonamide and 2-bromo-5-methyl-1,3,4-thiadiazole.

Example 129 3-[(2,4-Dimethylthiazol-5-yl)methyl]-N-(1-methylcyclopropyl)-1-(5-methyl-1,3,4-thiadiazol-2-yl)indole-6-sulfonamide

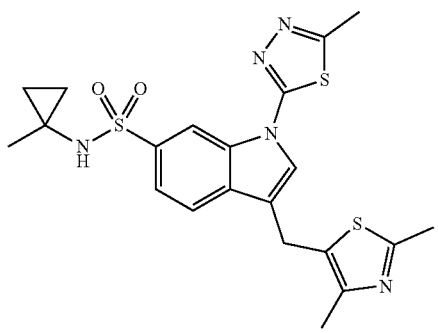

Prepared from 3-[(2,4-dimethylthiazol-5-yl)methyl]-N-(1-methylcyclopropyl)-1H-indole-6-sulfonamide and 2-bromo-5-methyl-1,3,4-thiadiazole.

Example 128 3-(Cyclopropylmethyl)-N-(1-methylcyclopropyl)-1-(5-methyl-1,3,4-thiadiazol-2-yl)indole-6-sulfonamide

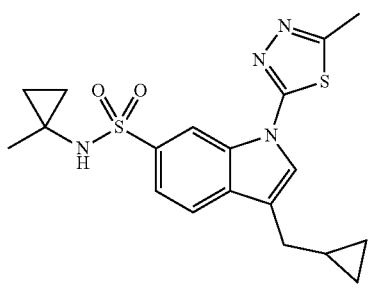 [SMILES: Cc1nnc(-n2cc(CC3CC3)c3ccc(S(=O)(=O)NC4(C)CC4)cc32)s1]

Prepared from 3-(cyclopropylmethyl)-N-(1-methylcyclopropyl)-1H-indole-6-sulfonamide and 2-bromo-5-methyl-1,3,4-thiadiazole.

Example 132 Ethyl 3-[(2,4-dimethylthiazol-5-yl)methyl]-6-[(1-methylcyclopropyl)sulfamoyl]indole-1-carboxylate

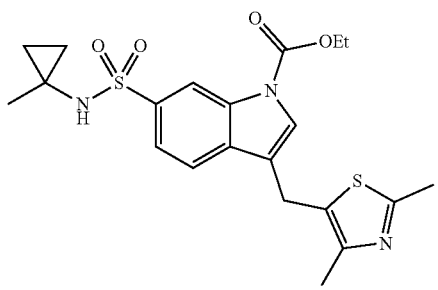

Sodium hydride (60% w/w) (5.9 mg, 0.15 mmol) was added to a stirring solution of ethyl chloroformate (0.02 mL, 0.16 mmol) in DMF (2 mL). After 5 min 3-[(2,4-dimethylthiazol-5-yl)methyl]-N-(1-methylcyclopropyl)-1H-indole-6-sulfonamide (50. mg, 0.13 mmol) was added and the reaction mixture stirred at ambient temperature for 1 h. Water (1 mL) was added and the mixture concentrated under reduced pressure. DCM (5 mL) and saturated aq. NaHCO$_3$ (5 mL) were added and the mixture stirred for 5 min. The DCM layer was separated by passing through a hydrophobic frit and the aqueous layer washed with DCM (2×2 mL). The combined DCM extracts were concentrated under reduced pressure and the residue purified by prep. HPLC (low pH) to yield ethyl 3-[(2,4-dimethylthiazol-5-yl)methyl]-6-[(1-methylcyclopropyl)sulfamoyl]indole-1-carboxylate (12 mg, 0.024 mmol, 18%).

General Procedures Relating to Scheme 8:

Intermediate S8-A 1-Acetyl-N-(1-methylcyclopropyl)indoline-6-sulfonamide

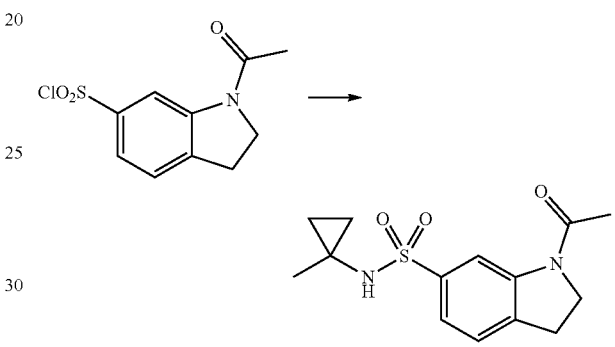

A suspension of 1-acetyl-2,3-dihydro-1H-indole-6-sulfonyl chloride (Enamine) (3. g, 9.82 mmol) in DCM (60 mL) was treated with 1-methylcyclopropanamine hydrochloride (1.58 g, 14.73 mmol) and triethylamine (4.09 mL, 29.46 mmol) and the reaction mixture stirred at ambient temperature for 1 h. The reaction mixture was diluted with 2 M HCl (60 mL) stirred vigorously for 20 min and the layers were separated. The aqueous phase was re-extracted with DCM (60 mL), the combined organics dried over MgSO$_4$ and concentrated to dryness to yield 1-acetyl-N-(1-methylcyclopropyl)indoline-6-sulfonamide (1.7 g, 5.78 mmol, 56%).

LCMS (high pH): RT 0.92 min, [M+H]$^+$ 295.5, 96% purity

Intermediate S8-B N-(1-Methylcyclopropyl)indoline-6-sulfonamide

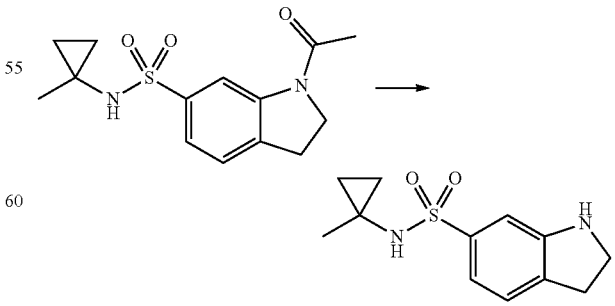

A solution of 1-acetyl-N-(1-methylcyclopropyl)indoline-6-sulfonamide (356. mg, 1.21 mmol) in THF (4 mL) and water (2 mL) was treated with potassium hydroxide (678.52 mg, 12.09 mmol) and the reaction mixture heated by microwave irradiation at 100° C. for 30 min. The THF was removed under vacuum and the resulting aqueous carefully brought to pH 7 with 2 M HCl with stirring and cooling. The neutral mixture was stirred in an ice bath for 20 min and then the precipitate was collected by filtration, washed with cold water (2×3 mL) and oven-dried to yield N-(1-methylcyclopropyl)indoline-6-sulfonamide (203 mg, 0.81 mmol, 67%).

$^1$H NMR (300 MHz, DMSO-$d_6$) δ=7.78 (s, 1H), 7.14 (d, J=7.6 Hz, 1H), 6.94 (dd, J=1.7, 7.5 Hz, 1H), 6.82 (d, J=1.7 Hz, 1H), 5.94 (s, 1H), 3.48 (dt, J=1.9, 8.8 Hz, 2H), 2.97 (t, J=8.7 Hz, 2H), 1.07 (s, 3H), 0.71-0.54 (m, 2H), 0.43-0.26 (m, 2H)

Intermediate S8-C1
2-(3-Methyl-2-oxo-imidazolidin-1-yl)acetic acid

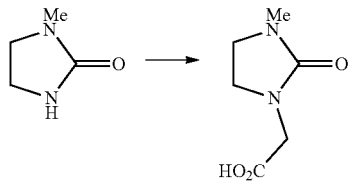 [SMILES: CN1CCNC1=O ; CN1CCN(CC(=O)O)C1=O]

Step 1

To a suspension of 1-methylimidazolidin-2-one (1. g, 9.99 mmol) was added sodium hydride (60% w/w) (439.47 mg, 10.99 mmol) and the reaction mixture was stirred at ambient temperature for 1 h and then at 40° C. for 2 h. tert-Butyl bromoacetate (1.47 mL, 9.99 mmol) was added and the mixture was stirred at ambient temperature for 16 h. Water was added and the mixture extracted with ethyl acetate (3×200 mL). The organic solution was washed with water, dried over MgSO$_4$ and evaporated to dryness in vacuo. The residue was purified by automated column chromatography, SiO$_2$, eluent 0-100% EtOAc in iso-hexane to yield tert-butyl 2-(3-methyl-2-oxo-imidazolidin-1-yl)acetate (0.86 g, 4.01 mmol, 40%).

Step 2 tert-Butyl 2-(3-methyl-2-oxo-imidazolidin-1-yl)acetate (800. mg, 3.73 mmol) was stirred in HCl (4 M in dioxane) (15. mL, 60 mmol) at ambient temperature for 4 h. Excess solvent was removed in vacuo and the residue taken up in 1,4-dioxane (20 mL). The solution was evaporated to dryness in vacuo to yield 2-(3-methyl-2-oxo-imidazolidin-1-yl)acetic acid (600 mg, 3.79 mmol, quant.)

$^1$H NMR (300 MHz, DMSO-$d_6$) δ=12.65 (br. s., 1H), 3.78 (s, 2H), 3.38-3.21 (m, 4H), 2.65 (s, 3H)

The following intermediates were prepared in a similar manner:

Intermediate S8-C2
2-(2-Oxoimidazolidin-1-yl)acetic acid

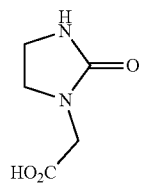

Prepared from 2-imidazolidone, tert-butyl bromoacetate and HCl (4 M in 1,4-dioxane).

$^1$H NMR (300 MHz, DMSO-$d_6$) δ=12.62 (br. s., 1H), 6.42 (br. s., 1H), 3.76 (s, 2H), 3.44-3.36 (m, 2H), 3.31-3.19 (m, 2H)

Intermediate S8-C3 2-(2-Oxooxazolidin-3-yl)acetic acid

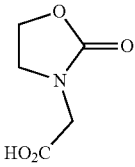

Prepared from oxazolidinone, tert-butyl bromoacetate and HCl (4 M in 1,4-dioxane).

$^1$H NMR (300 MHz, DMSO-$d_6$) δ=12.95 (br. s., 1H), 4.34-4.26 (m, 2H), 3.90 (s, 2H), 3.71-3.49 (m, 2H)

Example 25 N-(1-Methylcyclopropyl)-1-[2-(3-methyl-2-oxo-imidazolidin-1-yl)acetyl]indoline-6-sulfonamide

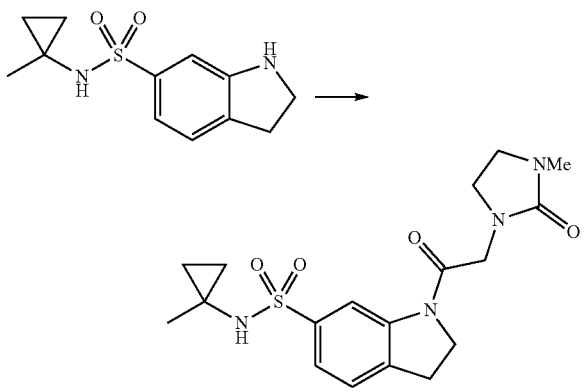

To a solution of 2-(3-methyl-2-oxo-imidazolidin-1-yl)acetic acid (125.39 mg, 0.79 mmol) in DMF (4 mL) was added 1-hydroxy-7-azabenzotriazole (107.91 mg, 0.79 mmol) and 1-(3-dimethylaminopropyl)-3-ethylcarbodiimide hydrochloride (151.98 mg, 0.79 mmol). The reaction mixture was stirred for 30 min. 2 mL of the above solution was added to N-(1-methylcyclopropyl)indoline-6-sulfonamide (50. mg, 0.20 mmol) and the mixture stirred at ambient temperature for 2 h. The reaction mixture was diluted with water and extracted with EtOAc, dried over MgSO$_4$ and evaporated to dryness. The crude product was purified by prep. HPLC to yield N-(1-methylcyclopropyl)-1-[2-(3-methyl-2-oxo-imidazolidin-1-yl)acetyl]indoline-6-sulfonamide (10.01 mg, 0.0255 mmol, 13%).

The following examples were prepared in a similar manner:

Example 21 N-(1-Methylcyclopropyl)-1-[2-(2-oxo-imidazolidin-1-yl)acetyl]indoline-6-sulfonamide

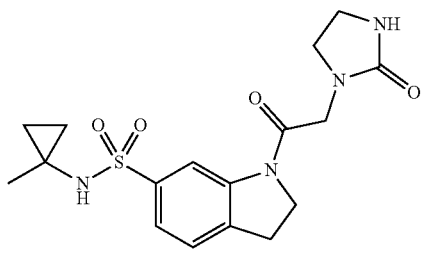 [SMILES: CC1(NS(=O)(=O)c2ccc3c(c2)N(C(=O)CN2CCNC2=O)CC3)CC1]

Prepared from N-(1-methylcyclopropyl)indoline-6-sulfonamide and 2-(2-oxoimidazolidin-1-yl)acetic acid.

Example 14 N-(1-Methylcyclopropyl)-1-[2-(2-oxooxazolidin-3-yl)acetyl]indoline-6-sulfonamide

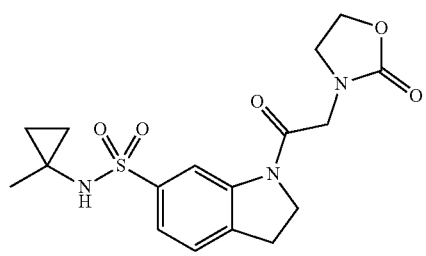 [SMILES: CC1(NS(=O)(=O)c2ccc3c(c2)N(C(=O)CN2CCOC2=O)CC3)CC1]

Prepared from N-(1-methylcyclopropyl)indoline-6-sulfonamide and 2-(2-oxooxazolidin-3-yl)acetic acid.

General Procedure Relating to Scheme 9:

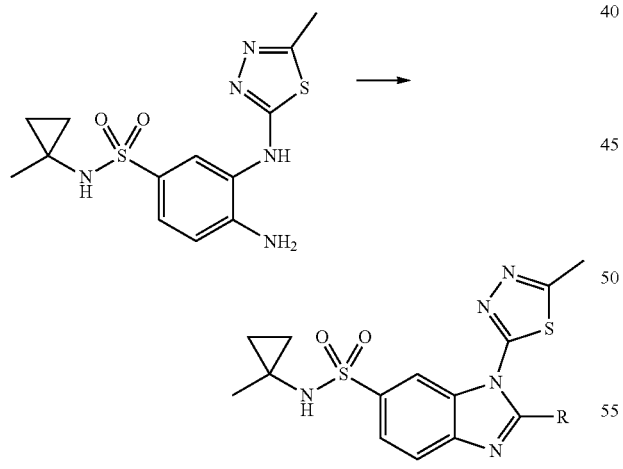

Step 1

1-(3-Dimethylaminopropyl)-3-ethylcarbodiimide hydrochloride (2.5 eq) was added to a solution of substituted carboxylic acid (2.5 eq) and triethylamine (6 eq) in DMF (8 mL). After 10 min at ambient temperature 4-amino-N-(1-methylcyclopropyl)-3-[(5-methyl-1,3,4-thiadiazol-2-yl)amino]benzenesulfonamide (1 eq) was added and the reaction mixture heated at 80° C. for 2 h. The reaction mixture was allowed to cool, DCM (10 mL) and saturated aq. NaHCO$_3$ (10 mL) were added and the mixture stirred for 5 min. The DCM layer was isolated by passing through a hydrophobic frit and the aqueous layer washed with DCM. The combined DCM extracts were concentrated under reduced pressure and purified by prep. HPLC (high pH) to yield the intermediate amide.

Step 2

The intermediate amide was taken up in AcOH (4 mL) and heated at 100° C. for 1 h. The reaction mixture was allowed to cool and concentrated under reduced pressure. DCM (8 mL) and saturated aq. NaHCO$_3$ (8 mL) were added and the mixture stirred for 5 min. The DCM layer was isolated by passing through a hydrophobic frit and the aqueous layer washed with DCM. The combined DCM extracts were concentrated under reduced pressure and purified by automated column chromatography, SiO$_2$, eluent 0-5% MeOH in DCM to yield the desired benzimidazole product.

For Example 119, formic acid was used as solvent and reagent and heated at reflux for 3 h, resulting in complete conversion to the desired benzimidazole.

Intermediate S5-D4 3-Methyl-1-(5-methyl-1,3,4-thiadiazol-2-yl)benzimidazol-2-one

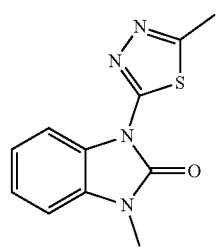 [SMILES: Cc1nnc(-n2c(=O)n(C)c3ccccc32)s1]

Prepared from 3-methyl-1H-benzimidazol-2-one and 2-bromo-5-methyl-1,3,4-thiadiazole.

$^1$H NMR (300 MHz, DMSO-d$_6$) δ=8.28-8.33 (m, 1H), 7.24-7.40 (m, 3H), 3.45 (s, 3H), 2.73 (s, 3H)

Example 156 N-[1-(Fluoromethyl)cyclopropyl]-1-methyl-3-(5-methyl-1,3,4-thiadiazol-2-yl)-2-oxo-benzimidazole-5-sulfonamide

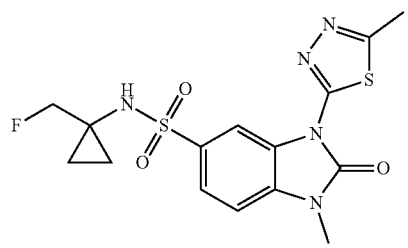 [SMILES: Cc1nnc(-n2c(=O)n(C)c3ccc(S(=O)(=O)NC4(CF)CC4)cc32)s1]

1-Methyl-3-(5-methyl-1,3,4-thiadiazol-2-yl)benzimidazol-2-one (75 mg, 0.30 mmol) was added in portions to chlorosulfonic acid (35.5 mg, 0.300 mmol) under stirring. After addition was complete the mixture was stirred for a further 3 h and then added carefully to a stirring slurry of ice (10 g) and 10% MeOH/DCM (10 mL). After 5 min of stirring the DCM layer was separated and the aqueous layer extracted with 10% MeOH/DCM (10 mL). The combined DCM layers were passed through a hydrophobic frit and concentrated to dryness. The resulting white solid was added to a stirring mixture of 1-(fluoromethyl)cyclopropan-1-amine hydrochloride (38 mg, 0.30 mmol) and N,N-diisopropylethylamine (39 mg, 0.30 mmol) in DMF (3 mL). After stirring for 3 h the mixture was added to a stirring mixture of 10% MeOH/DCM (10 mL) and saturated aqueous ammonium chloride (10 mL). After 5 min of stirring the DCM layer was separated and the aqueous layer extracted with 10% MeOH/DCM (10 mL). The combined DCM extracts were passed through a hydrophobic frit and purified by prep HPLC (low pH) yielding N-[1-(fluoromethyl)cyclopropyl]-1-methyl-3-(5-methyl-1,3,4-thiadiazol-2-yl)-2-oxo-benzimidazole-5-sulfonamide (5 mg, 0.013 mmol, 4.1%) as a white solid.

Example 157 N-(1-Cyanocyclopropyl)-3-(5-methyl-1,3,4-thiadiazol-2-yl)-2-oxo-1H-benzimidazole-5-sulfonamide

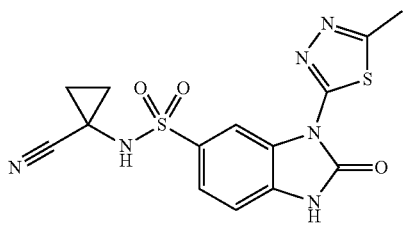 [SMILES: Cc1nnc(-n2c(=O)[nH]c3ccc(S(=O)(=O)NC4(C#N)CC4)cc32)s1]

3-(5-Methyl-1,3,4-thiadiazol-2-yl)-1H-benzimidazol-2-one (75 mg, 0.300 mmol) was added in portions to stirring chlorosulfonic acid (35.5 mg, 0.30 mmol). After stirring for 2 h the solution was added carefully in drops to a stirring slurry of ice (~10 mL) and 10% MeOH/DCM (10 mL). After stirring for 5 min the DCM layer was separated and the aqueous layer extracted with 10% MeOH/DCM (10 mL). The combined DCM extracts were passed through a hydrophobic frit and concentrated to dryness leaving a white powder. This powder was added to a mixture of 1-amino-1-cyclopropanecarbonitrile hydrochloride (36 mg, 0.30 mmol) in pyridine (3 mL) and stirred for 16 h. The reaction mixture was added to a stirring mixture of 10% MeOH/DCM (30 mL) and 1N HCL (aq) (30 mL). After 5 min the DCM layer was separated and the aqueous layer extracted with 10% MeOH/DCM (20 mL). The combined DCM extracts were passed through a hydrophobic frit, concentrated to dryness and purified by column chromatography (Hex→EtOAc) yielding N-(1-cyanocyclopropyl)-3-(5-methyl-1,3,4-thiadiazol-2-yl)-2-oxo-1H-benzimidazole-5-sulfonamide (60 mg, 0.159 mmol, 52.3%) as a white solid.

Example 158 N-(1-Cyanocyclopropyl)-1-ethyl-3-(5-methyl-1,3,4-thiadiazol-2-yl)-2-oxo-benzimidazole-5-sulfonamide Intermediate S10-A 1-(5-Methyl-1,3,4-thiadiazol-2-yl)-1H-benzo[d]imidazol-2(3H)-one

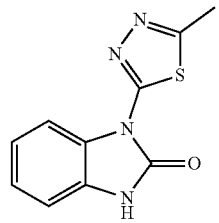 [SMILES: Cc1nnc(-n2c(=O)[nH]c3ccccc32)s1]

A stirring mixture of 2-hydroxybenzimidazole (500 mg, 3.73 mmol), 2-bromo-5-methyl-1,3,4-thiadiazole (801 mg, 4.47 mmol), copper iodide (71 mg, 0.37 mmol) and potassium carbonate (1030 mg, 7.46 mmol) in 1,4-dioxane (10 mL) was degassed by bubbling nitrogen through the mixture for 5 min. Trans-N,N'-dimethylcyclohexane-1,2-diamine (118 µL, 0.745 mmol) was added and the mixture heated to 135° C. for 2 h in a microwave. The mixture was added to 10% MeOH/DCM (200 mL) and saturated aqueous sodium bicarbonate (200 mL) and the mixture stirred for 5 min. The DCM layer was separated and the aqueous extracted with 10% MeOH/DCM (100 mL). The combined DCM extracts were concentrated under reduced pressure and purified by column chromatography (DCM→10% MeOH/DCM) yielding 3-(5-methyl-1,3,4-thiadiazol-2-yl)-1H-benzimidazol-2-one (612 mg, 2.64 mmol, 70.7%) as a white solid.

$^1$H NMR (300 MHz, DMSO-$d_6$) δ=11.98-11.67 (m, 1H), 8.26 (s, 1H), 7.29-7.13 (m, 3H), 2.72 (s, 3H)

Intermediate S10-B 1-Ethyl-3-(5-methyl-1,3,4-thiadiazol-2-yl)benzimidazol-2-one

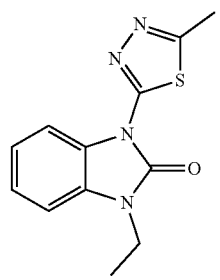 [SMILES: CCn1c(=O)n(-c2nnc(C)s2)c2ccccc21]

Sodium hydride, 60% dispersion in mineral oil (103 mg, 2.58 mmol) was added in portions to a stirring solution of 3-(5-methyl-1,3,4-thiadiazol-2-yl)-1H-benzimidazol-2-one (0.3 g, 1.29 mmol) in DMF (10 mL). After 30 min iodoethane (0.21 mL, 2.58 mmol) was added. After 16 h saturated aqueous sodium bicarbonate solution (10 mL) and EtOAc (10 mL) was added and the mixture stirred for 5 min. The EtOAc layer was separated and the aqueous layer extracted with EtOAc (10 mL). The combined EtOAc extracts were passed through a hydrophobic frit and concentrated under reduced pressure and purified by column chromatography (Hex→EtOAc) yielding 1-ethyl-3-(5-methyl-1,3,4-thiadiazol-2-yl)benzimidazol-2-one (261 mg, 1.00 mmol, 77.6%) as a yellow solid.

¹H NMR (300 MHz, DMSO-d₆) δ=7.19 (dd, J=3.2, 5.8 Hz, 2H), 7.05 (dd, J=3.2, 5.7 Hz, 2H), 4.01 (q, J=7.2 Hz, 2H), 2.73 (s, 2H), 1.29 (t, J=7.2 Hz, 3H)

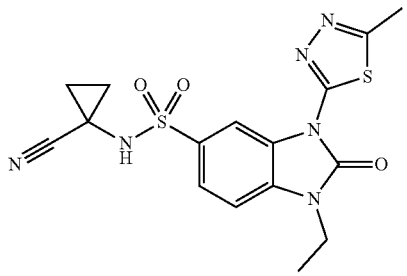 [SMILES: CCn1c(=O)n(-c2nnc(C)s2)c2cc(S(=O)(=O)NC3(C#N)CC3)ccc21]

1-Ethyl-3-(5-methyl-1,3,4-thiadiazol-2-yl)benzimidazol-2-one (100 mg, 0.38 mmol) was added in portions to chlorosulfonic acid (45 mg, 0.38 mmol) with stirring. After 3 h the solution was added to a stirring slurry of ice (10 mL) causing a precipitate to form. The precipitate was filtered and dried on the frit and then added to a stirring mixture of 1-amino-1-cyclopropanecarbonitrile hydrochloride (46 mg, 0.38 mmol) in pyridine (4 mL). This was stirred for 3 h and then EtOAc (10 mL) and 1M HCl solution (aq) (10 mL) was added and the mixture stirred for 5 min. The EtOAc layer was separated and the aqueous layer extracted with EtOAc (10 mL). The combined EtOAc extracts were passed through a hydrophobic frit, concentrated to dryness and purified by prep HPLC (low pH) yielding N-(1-cyanocyclopropyl)-1-ethyl-3-(5-methyl-1,3,4-thiadiazol-2-yl)-2-oxo-benzimidazole-5-sulfonamide (12 mg, 0.030 mmol, 7.7%) as a white solid.

Example 159 1-Ethyl-N-[1-(fluoromethyl)cyclopropyl]-3-(5-methyl-1,3,4-thiadiazol-2-yl)-2-oxo-benzimidazole-5-sulfonamide

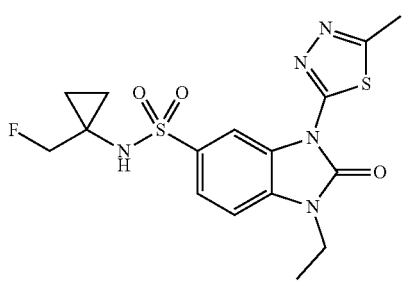 [SMILES: CCn1c(=O)n(-c2nnc(C)s2)c2cc(S(=O)(=O)NC3(CF)CC3)ccc21]

1-Ethyl-3-(5-methyl-1,3,4-thiadiazol-2-yl)benzimidazol-2-one (100 mg, 0.380 mmol) was added in portions to chlorosulfonic acid (45 mg, 0.380 mmol) under stirring. After 3 h the solution was added to a stirring slurry of ice (10 g) causing a precipitate to form. The precipitate was filtered off and dried on the frit and then added to a stirring mixture of 1-(fluoromethyl)cyclopropan-1-amine hydrochloride (48 mg, 0.38 mmol) in pyridine (3 mL). This was stirred for 3 h and then EtOAc (10 mL) and 1M HCL solution (aq) (10 mL) was added and the mixture stirred for 5 min. The EtOAc layer was separated and the aqueous layer extracted with EtOAc (10 mL). The combined EtOAc extracts were passed through a hydrophobic frit, concentrated to dryness and purified by prep HPLC (low pH) yielding 1-ethyl-N-[1-(fluoromethyl)cyclopropyl]-3-(5-methyl-1,3,4-thiadiazol-2-yl)-2-oxo-benzimidazole-5-sulfonamide (10 mg, 0.024 mmol, 6.3%) as a white solid.

Example 160 N-[1-(Fluoromethyl)cyclopropyl]-1-(2-methoxyethyl)-3-(5-methyl-1,3,4-thiadiazol-2-yl)-2-oxo-benzimidazole-5-sulfonamide Intermediate S11-A 1-(2-methoxyethyl)-1H-benzo[d]imidazol-2(3H)-one

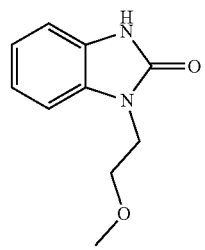

2-Bromoethyl methylether (2.52 mL, 26.84 mmol) was added to a stirring mixture of 2-hydroxybenzimidazole (3.0 g, 22.4 mmol) and potassium carbonate (6.18 g, 44.7 mmol) in DMF (10 mL) and heated to 120° C. in a microwave for 1 h. The mixture was allowed to cool and added to DCM (300 mL), saturated aqueous sodium bicarbonate solution (200 mL) and water (100 mL) and the mixture stirred for 5 min. The DCM layer was isolated by passing through a hydrophobic frit and the aqueous layer extracted with DCM. The combined DCM extracts were concentrated under reduced pressure and purified by column chromatography (Hex→EtOAc) yielding 3-(2-methoxyethyl)-1H-benzimidazol-2-one (951 mg, 4.95 mmol, 22.1%) as a white solid.

¹H NMR (300 MHz, DMSO-d₆) δ=10.99-10.65 (m, 1H), 7.13 (d, J=4.3 Hz, 1H), 7.05-6.92 (m, 3H), 3.94 (t, J=5.6 Hz, 2H), 3.58 (t, J=5.6 Hz, 2H), 3.23 (s, 3H)

Intermediate S11-B1 1-(2-methoxyethyl)-3-(5-methyl-1,3,4-thiadiazol-2-yl)-1H-benzo[d]imidazol-2(3H)-one

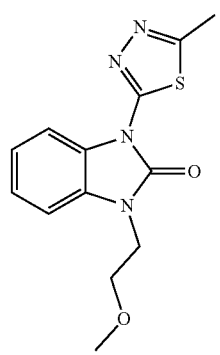 [SMILES: COCCn1c(=O)n(-c2nnc(C)s2)c2ccccc21]

A stirring mixture of 3-(2-methoxyethyl)-1H-benzimidazol-2-one (0.2 g, 1.04 mmol), 2-bromo-5-methyl-1,3,4-thiadiazole (466 mg, 2.6 mmol), copper iodide (20 mg, 0.100 mmol) and potassium carbonate (575 mg, 4.16 mmol) in 1,4-dioxane (10 mL) was degassed by bubbling nitrogen through the mixture for 5 min. Trans-N,N'-dimethylcyclohexane-1,2-diamine (0.03 mL, 0.21 mmol) was added and the mixture heated to 135° C. for 2 h in a microwave. The mixture was added to 10% MeOH/DCM (200 mL) and saturated aqueous sodium bicarbonate (200 mL) added and the mixture stirred for 5 min. The DCM layer was separated and the aqueous extracted with 10% MeOH/DCM (100 mL). The combined DCM extracts were passed through a hydrophobic frit, concentrated under reduced pressure and purified by column chromatography (Hex→EtOAc) yielding 1-(2-methoxyethyl)-3-(5-methyl-1,3,4-thiadiazol-2-yl)benzimidazol-2-one (107 mg, 0.369 mmol, 35.4%) as a white solid.

$^1$H NMR (300 MHz, DMSO-d$_6$) δ=8.38-8.28 (m, 1H), 7.43 (s, 1H), 7.30 (s, 2H), 4.14 (t, J=5.3 Hz, 2H), 3.68 (t, J=5.3 Hz, 2H), 3.24 (s, 3H), 2.73 (s, 3H)

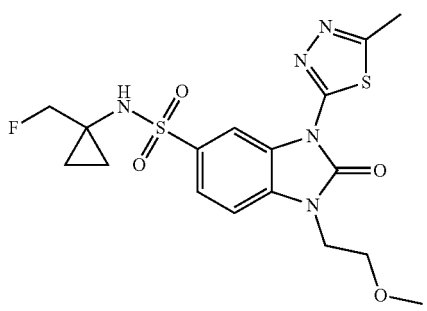 [SMILES: COCCn1c(=O)n(-c2nnc(C)s2)c2cc(S(=O)(=O)NC3(CF)CC3)ccc21]

1-(2-Methoxyethyl)-3-(5-methyl-1,3,4-thiadiazol-2-yl) benzimidazol-2-one (70 mg, 0.2400 mmol) was added in portions to chlorosulfonic acid (28 mg, 0.240 mmol) under stirring. After 3 h the solution was added to a stirring slurry of ice (10 g) and 10% MeOH/DCM (10 mL). After 5 min of stirring the DCM layer was separated and the aqueous layer extracted with 10% MeOH/DCM (10 mL). The combined DCM extracts were passed through a hydrophobic frit and concentrated under reduced pressure. The resulting white solid was added to a stirring mixture of 1-(fluoromethyl)cyclopropan-1-amine hydrochloride (30 mg, 0.240 mmol) and triethylamine (24.4 mg, 0.240 mmol) in DMF (3 mL). After 3 h 10% MeOH/DCM (10 mL) and 2M HCL solution (aq) (10 mL) was added and the mixture stirred for 5 min. The DCM layer was separated and the aqueous layer extracted with 10% MeOH/DCM (10 mL). The combined DCM layers were passed through a hydrophobic frit, concentrated to dryness and purified by prep HPLC (low pH) yielding N-[1-(fluoromethyl)cyclopropyl]-1-(2-methoxyethyl)-3-(5-methyl-1,3,4-thiadiazol-2-yl)-2-oxo-benzimidazole-5-sulfonamide (8 mg, 0.018 mmol, 7.5%) as a white solid.

Example 161 N-(1-Cyanocyclopropyl)-1-(2-methoxyethyl)-3-(5-methyl-1,3,4-thiadiazol-2-yl)-2-oxo-benzimidazole-5-sulfonamide

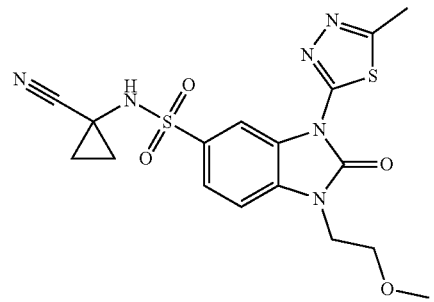 [SMILES: COCCn1c(=O)n(-c2nnc(C)s2)c2cc(S(=O)(=O)NC3(C#N)CC3)ccc21]

1-(2-Methoxyethyl)-3-(5-methyl-1,3,4-thiadiazol-2-yl) benzimidazol-2-one (112 mg, 0.380 mmol) was added in portions to chlorosulfonic acid (45 mg, 0.380 mmol) under stirring. After 3 h the solution was added to a stirring slurry of ice (10 g) and 10% MeOH/DCM (10 mL). The DCM layer was separated and the aqueous layer extracted with 10% MeOH/DCM (10 mL). The combined DCM extracts were passed through a hydrophobic frit and concentrated to dryness and added to a stirring mixture of 1-amino-1-cyclopropanecarbonitrile hydrochloride (46 mg, 0.380 mmol) in pyridine (4 mL). After 3 h 10% MeOH/DCM (30 mL) and 2M HCL solution (aq) (30 mL) was added and the mixture stirred for 5 min. The DCM layer was separated and the aqueous layer extracted with 10% MeOH/DCM (20 mL). The combined DCM extracts were passed through a hydrophobic frit, concentrated to dryness and purified by column chromatography (DCM→10% MeOH/DCM) yielding N-(1-cyanocyclopropyl)-1-(2-methoxyethyl)-3-(5-methyl-1,3,4-thiadiazol-2-yl)-2-oxo-benzimidazole-5-sulfonamide (15 mg, 0.0345 mmol, 9.0%) as a white solid.

Example 162 N-(1-Cyanocyclopropyl)-3-[5-(difluoromethyl)-1,3,4-thiadiazol-2-yl]-1-(2-methoxyethyl)-2-oxo-benzimidazole-5-sulfonamide Intermediate S11-B2 1-(5-(Difluoromethyl)-1,3,4-thiadiazol-2-yl)-3-(2-methoxyethyl)-1H-benzo[d]imidazol-2(3H)-one

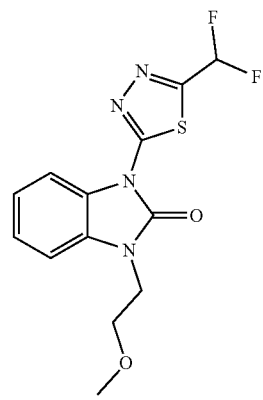 [SMILES: COCCn1c(=O)n(-c2nnc(C(F)F)s2)c2ccccc21]

A stirring mixture of 3-(2-methoxyethyl)-1H-benzimidazol-2-one (0.22 g, 1.14 mmol), 2-bromo-5-(difluoromethyl)-1,3,4-thiadiazole (0.27 g, 1.25 mmol), copper iodide (22 mg, 0.110 mmol) and potassium carbonate (0.47 g, 3.41 mmol) in DMSO (5 mL) was degassed by bubbling nitrogen through the mixture for 5 min. Trans-N,N-dimethylcyclohexane-1,2-diamine (0.04 mL, 0.230 mmol) was added and the mixture heated to 80° C. for 5 h. Similar work-up as described for Intermediate S11-B1 yielded 1-[5-(difluoromethyl)-1,3,4-thiadiazol-2-yl]-3-(2-methoxyethyl)benzimidazol-2-one (0.211 g, 0.647 mmol, 57.0%) as a white solid.

$^1$H NMR (300 MHz, DMSO-d$_6$) δ=8.41-8.30 (m, 1H), 7.82-7.30 (m, 4H), 4.17 (s, 2H), 3.69 (s, 2H), 3.25 (s, 3H)

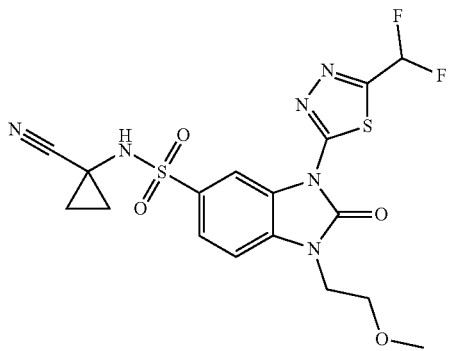 [SMILES: COCCn1c(=O)n(-c2nnc(C(F)F)s2)c2cc(S(=O)(=O)NC3(C#N)CC3)ccc21]

Using the method described in Example 161, 1-[5-(difluoromethyl)-1,3,4-thiadiazol-2-yl]-3-(2-methoxyethyl) benzimidazol-2-one (125 mg, 0.380 mmol) yielded N-(1-cyanocyclopropyl)-3-[5-(difluoromethyl)-1,3,4-thiadiazol-2-yl]-1-(2-methoxyethyl)-2-oxo-benzimidazole-5-sulfonamide (20 mg, 0.0412 mmol, 10.7%) as a white solid.

Example 163 3-[5-(Difluoromethyl)-1,3,4-thiadiazol-2-yl]-N-[1-(fluoromethyl)cyclopropyl]-1-(2-methoxyethyl)-2-oxo-benzimidazole-5-sulfonamide

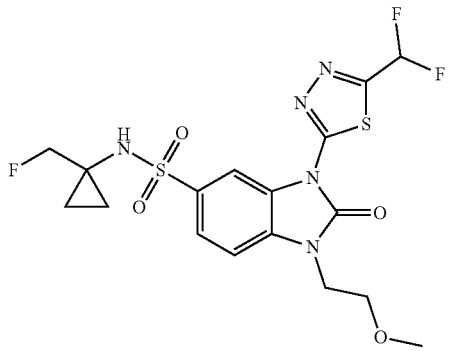 [SMILES: COCCn1c(=O)n(-c2nnc(C(F)F)s2)c2cc(S(=O)(=O)NC3(CF)CC3)ccc21]

Using the method described in Example 160, 1-[5-(difluoromethyl)-1,3,4-thiadiazol-2-yl]-3-(2-methoxyethyl) benzimidazol-2-one (79 mg, 0.240 mmol) yielded 3-[5-(difluoromethyl)-1,3,4-thiadiazol-2-yl]-N-[1-(fluoromethyl) cyclopropyl]-1-(2-methoxyethyl)-2-oxo-benzimidazole-5-sulfonamide (5 mg, 0.0105 mmol, 4.3%) as a white solid.

Example 164 3-[5-(Difluoromethyl)-1,3,4-thiadiazol-2-yl]-1-[(2,5-dimethylpyrazol-3-yl)methyl]-N-[1-(fluoromethyl)cyclopropyl]-2-oxo-benzimidazole-5-sulfonamide

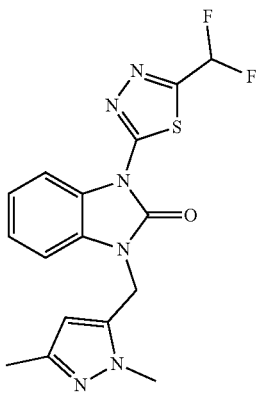 [SMILES: Cc1cc(Cn2c(=O)n(-c3nnc(C(F)F)s3)c3ccccc32)n(C)n1]

2-Hydroxybenzimidazole (3.0 g, 22.4 mmol), 5-(chloromethyl)-1,3-dimethyl-1H-pyrazole (1.82 mL, 24.6 mmol) and potassium carbonate (9.3 g, 67 mmol) in DMF (70 mL) was heated at 100° C. for 3 h. The mixture was added to saturated aqueous sodium bicarbonate solution (500 mL) and EtOAc (500 mL) and the mixture stirred for 5 min. The EtOAc layer was separated and the aqueous layer extracted with EtOAc (100 mL). The combined EtOAc extracts were passed through a hydrophobic frit and concentrated under reduced pressure and purified by column chromatography (Hex→EtOAc) yielding 3-[(2,5-dimethylpyrazol-3-yl) methyl]-1H-benzimidazol-2-one (3.1 g, 12.8 mmol, 57.2%) as yellow solid.

Using the method described for Intermediate S11-B2, (3-[(2,5-dimethylpyrazol-3-yl)methyl]-1H-benzimidazol-2-one) (0.4 g, 1.65 mmol) and 2-bromo-5-(difluoromethyl)-1,3,4-thiadiazole (0.36 g, 1.65 mmol) yielded 1-[5-(difluoromethyl)-1,3,4-thiadiazol-2-yl]-3-[(2,5-dimethylpyrazol-3-yl)methyl]benzimidazol-2-one (141 mg, 0.375 mmol, 22.7%) as a white solid.

$^1$H NMR (300 MHz, CHLOROFORM-d)=8.70-8.44 (m, 1H), 7.41-7.29 (m, 3H), 7.26-6.87 (m, 2H), 5.18 (s, 2H), 4.03-3.78 (m, 3H), 2.30-2.11 (m, 3H)

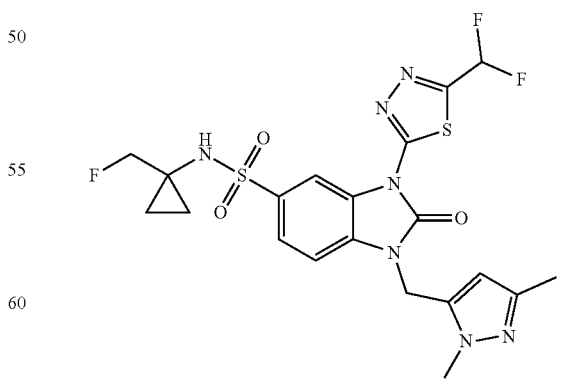

Using the method described in Example 160, 1-[5-(difluoromethyl)-1,3,4-thiadiazol-2-yl]-3-[(2,5-dimethylpyrazol-3-yl)methyl]benzimidazol-2-one (70 mg, 0.1900 mmol)

yielded 3-[5-(difluoromethyl)-1,3,4-thiadiazol-2-yl]-1-[(2,5-dimethylpyrazol-3-yl)methyl]-N-[1-(fluoromethyl)cyclopropyl]-2-oxo-benzimidazole-5-sulfonamide (20 mg, 0.038 mmol, 20.4%) as a white solid.

Example 165 N-(1-Cyanocyclopropyl)-3-[5-(difluoromethyl)-1,3,4-thiadiazol-2-yl]-1-[(2,5-dimethylpyrazol-3-yl)methyl]-2-oxo-benzimidazole-5-sulfon id

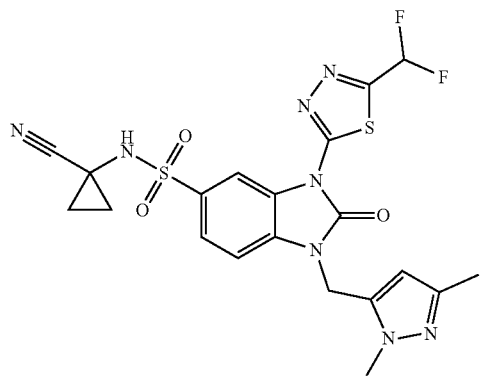 [SMILES: Cc1cc(Cn2c(=O)n(-c3nnc(C(F)F)s3)c3cc(S(=O)(=O)NC4(C#N)CC4)ccc32)n(C)n1]

1-[5-(Difluoromethyl)-1,3,4-thiadiazol-2-yl]-3-[(2,5-dimethylpyrazol-3-yl)methyl]benzimidazol-2-one (145 mg, 0.380 mmol) was added portion wise to chlorosulfonic acid (2.0 mL, 0.380 mmol) under stirring. After stirring for 3 h the solution was added to a stirring slurry of ice (~10 g) and 10% MeOH/DCM (10 mL). The DCM layer was separated and the aqueous layer extracted with 10% MeOH/DCM (10 mL). The combined DCM extracts were passed through a hydrophobic frit and concentrated to dryness and added to a stirring mixture of 1-amino-1-cyclopropanecarbonitrile hydrochloride (91 mg, 0.77 mmol) in pyridine (4 mL). This was stirred for 3 h and then 10% MeOH/DCM (30 mL) and 2M HCl solution (aq) (30 mL) was added and the mixture stirred for 5 min. The DCM layer was separated and the aqueous layer extracted with 10% MeOH/DCM (10 mL). The combined DCM layers were passed through a hydrophobic frit, concentrated to dryness and purified by column chromatography (DCM→10% MeOH/DCM) yielding N-(1-cyanocyclopropyl)-3-[5-(difluoromethyl)-1,3,4-thiadiazol-2-yl]-1-[(2,5-dimethylpyrazol-3-yl)methyl]-2-oxo-benzimidazole-5-sulfonamide (10 mg, 0.0192 mmol, 5.0%) as a white solid.

Example 166 1-(Cyanomethyl)-N-(1-methylcyclopropyl)-3-(5-methyl-1,3,4-thiadiazol-2-yl)-2-oxo-benzimidazole-5-sulfonamide

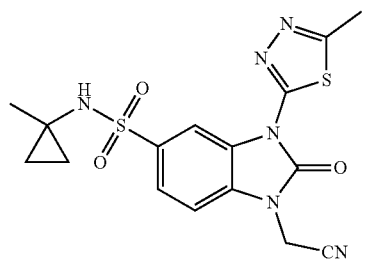

To a magnetically stirred solution of 3-(5-methyl-1,3,4-thiadiazol-2-yl)-N-(1-methylcyclopropyl)-2-oxo-2,3-dihydro-1H-benzo[d]imidazole-5-sulfonamide (150 mg, 0.41 mmol) and potassium carbonate (226.9 mg, 1.64 mmol) in DMF (4 mL) at 20° C. under nitrogen was added bromoacetonitrile (0.03 mL, 0.41 mmol), and the resulting mixture was agitated at ambient temperature for 12 h. The solvent was removed in vacuo and the resulting residue purified by prep. HPLC (high pH) to give the desired product as a white solid (30 mg; 18%)

Example 167 3-[5-(difluoromethyl)-1,3,4-thiadiazol-2-yl]-6-fluoro-N-[1-(fluoromethyl)cyclopropyl]-1-(2-methoxyethyl)-2-oxo-benzimidazole-5-sulfonamide Intermediate S5 A6
5-fluoro-N-(2-methoxyethyl)-2-nitro-aniline

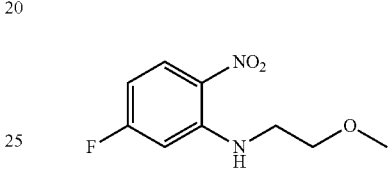

Methoxyethylamine (2.88 mL, 13.2 mmol) was added to a magnetically stirred solution of 2,4-difluoronitrobenzene (2.0 g, 12.6 mmol) and potassium carbonate (3.64 g, 26.4 mmol) in 1,4-dioxane (40 mL) at 5° C., and the resulting mixture was agitated at ambient temperature for 2 h. The mixture was poured into ice/water (40 mL), and the resulting yellow suspension was agitated for 15 min before being filtered. The filter cake was washed with water (2×20 mL) and dried under vacuum at 40° C. for 12 h to give the desired product as a yellow solid (2.78 g, 12.97 mmol, 103%).

$^1$H NMR (300 MHz, DMSO-d6) Shift=8.39-8.27 (m, 1H), 8.17 (dd, J=6.2, 9.5 Hz, 1H), 6.93 (dd, J=2.6, 12.3 Hz, 1H), 6.55 (ddd, J=2.6, 7, 9.7 Hz, 1H), 3.62-3.46 (m, 4H), 3.31 (s, 3H).

Intermediate S5 B6
4-fluoro-N2-(2-methoxyethyl)benzene-1,2-diamine

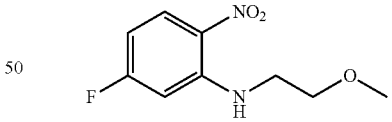

A solution of 5-fluoro-N-(2-methoxyethyl)-2-nitroaniline (2.6 g, 12.14 mmol) in ethanol (40 mL) was vacuum purged with nitrogen 3 times. Palladium on Activated Carbon (260 mg) was then added to the reaction mixture and the resulting suspension was vacuum purged with nitrogen 3 times. The reaction mixture was then vacuum purged with hydrogen 3 times and agitated under a positive pressure of hydrogen for 2 h. The mixture was vacuum purged with nitrogen and filtered through a pad of celite. The cake was washed with ethanol (2×10 mL) and the combined filtrates were evaporated to dryness to give the product as a mauve oil (2.25 g, 12.2 mmol, 100%).

$^1$H NMR (300 MHz, DMSO-d6) Shift=6.49 (dd, J=6.1, 8.3 Hz, 1H), 6.25 (dd, J=2.8, 11.7 Hz, 1H), 6.16 (dt, J=2.8, 8.6 Hz, 1H), 4.71 (t, J=5.1 Hz, 1H), 4.34 (br. s., 2H), 3.52 (t, J=5.6 Hz, 2H), 3.29 (s, 3H), 3.19 (q, J=5.6 Hz, 2H).

Intermediate S5 C6
5-fluoro-3-(2-methoxyethyl)-1H-benzimidazol-2-one

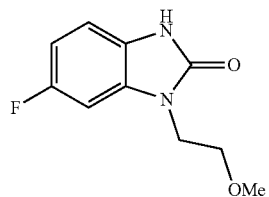 [SMILES: COCCn1c(=O)[nH]c2ccc(F)cc21]

To a magnetically stirred solution of 4-fluoro-N2-(2-methoxyethyl)benzene-1,2-diamine (2.3 g, 12.49 mmol) in THF (60 mL) at 20° C. under nitrogen was added 1,1'-carbonyldiimidazole (2.22 g, 13.73 mmol), and the resulting mixture was agitated at ambient temperature for 2 h. The solvent was removed in vacuo to give a residue, which was suspended in ether (40 mL) with agitation for 10 min. The mixture was then filtered and the filter cake washed with ether (3×20 mL) to give a solid, which was dried under vacuum for 4 h at 40° C. to give the desired product as a grey solid (1.04 g, 4.95 mmol, 39.6%).

$^1$H NMR (300 MHz, DMSO-d6) Shift=10.88 (s, 1H), 7.14-7.06 (m, 1H), 6.93 (dd, J=4.7, 8.5 Hz, 1H), 6.83-6.73 (m, 1H), 3.94 (t, J=5.5 Hz, 2H), 3.57 (t, J=5.5 Hz, 2H), 3.23 (s, 3H)

Intermediate S5 D6 1-[5-(difluoromethyl)-1,3,4-thiadiazol-2-yl]-5-fluoro-3-(2-methoxyethyl)benzimidazol-2-one

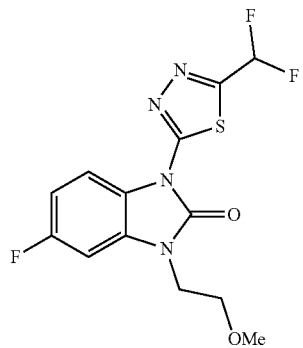 [SMILES: COCCn1c(=O)n(-c2nnc(C(F)F)s2)c2ccc(F)cc21]

A stirred mixture of 5-fluoro-3-(2-methoxyethyl)-1H-benzimidazol-2-one (140 mg, 0.67 mmol), 2-bromo-5-(difluoromethyl)-1,3,4-thiadiazole (157.5 mg, 0.73 mmol), copper iodide (12.7 mg, 0.07 mmol) and potassium carbonate (276.1 mg, 2.0 mmol) in DMSO (5 mL) was degassed with nitrogen for 5 min. Trans-N,N-dimethylcyclohexane-1,2-diamine (21.0 μL, 0.13 mmol) was added, and the resulting mixture was heated at 80° C. for 16 h. The reaction was cooled to ambient and partitioned between DCM (30 mL) and saturated sodium bicarbonate solution (30 mL). The resulting biphasic mixture was stirred for 5 min and the DCM layer was collected. The aqueous was back extracted with DCM (30 mL) and the combined DCM extracts were concentrated under reduced pressure to give a residue, which was purified by automated column chromatography (SiO$_2$; RediSep—12 g; 0 to 40% EtOAc in hexane) to afford the desired product as a white solid (130 mg, 0.37 mmol, 56.7%).

$^1$H NMR (300 MHz, DMSO-d6) Shift=8.33 (dd, J=4.8, 8.9 Hz, 1H), 7.81-7.41 (m, 2H), 7.15 (ddd, J=2.6, 8.9, 9.8 Hz, 1H), 4.16 (t, J=5.3 Hz, 2H), 3.67 (t, J=5.2 Hz, 2H), 3.25 (s, 3H).

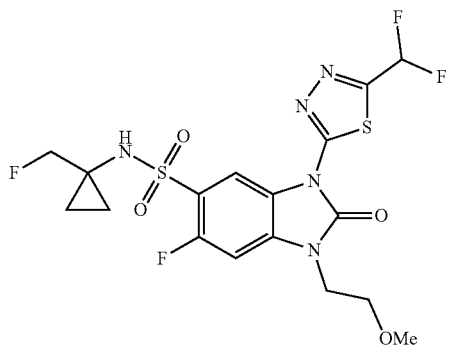 [SMILES: COCCn1c(=O)n(-c2nnc(C(F)F)s2)c2cc(S(=O)(=O)NC3(CF)CC3)c(F)cc21]

Using the method described in Example 160, 1-[5-(difluoromethyl)-1,3,4-thiadiazol-2-yl]-5-fluoro-3-(2-methoxyethyl)benzimidazol-2-one (120 mg, 0.34 mmol) yielded 3-[5-(difluoromethyl)-1,3,4-thiadiazol-2-yl]-6-fluoro-N-[1-(fluoromethyl)cyclopropyl]-1-(2-methoxyethyl)-2-oxo-benzimidazole-5-sulfonamide as a white solid (80 mg, 0.16 mmol, 47%).

Example 168 3-[5-(Difluoromethyl)-1,3,4-thiadiazol-2-yl]-6-fluoro-1-(2-methoxyethyl)-N-(1-methylcyclopropyl)-2-oxo-benzimidazole-5-sulfonamide

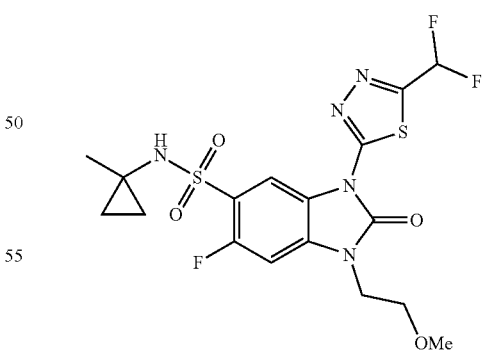

Using the method described in Example 160, 1-[5-(difluoromethyl)-1,3,4-thiadiazol-2-yl]-5-fluoro-3-(2-methoxyethyl)benzimidazol-2-one (120 mg, 0.34 mmol) yielded 3-[5-(difluoromethyl)-1,3,4-thiadiazol-2-yl]-6-fluoro-1-(2-methoxyethyl)-N-(1-methylcyclopropyl)-2-oxo-benzimidazole-5-sulfonamide as a white solid (82 mg, 0.17 mmol, 50%).

Example 169 3-[5-(Difluoromethyl)-1,3,4-thiadiazol-2-yl]-1-(2-methoxyethyl)-N-(1-methylcyclopropyl)-2-oxo-benzimidazole-5-sulfonamide

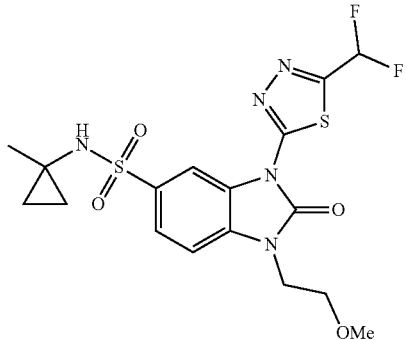 [SMILES: COCCn1c(=O)n(-c2nnc(C(F)F)s2)c2cc(S(=O)(=O)NC3(C)CC3)ccc21]

Using the method described in Example 160, 1-[5-(difluoromethyl)-1,3,4-thiadiazol-2-yl]-3-(2-methoxyethyl)benzimidazol-2-one (100 mg, 0.31 mmol) yielded 3-[5-(difluoromethyl)-1,3,4-thiadiazol-2-yl]-1-(2-methoxyethyl)-N-(1-methylcyclopropyl)-2-oxo-benzimidazole-5-sulfonamide as a white solid (80 mg, 0.17 mmol, 55%).

Example 170 3-[5-(Difluoromethyl)-1,3,4-thiadiazol-2-yl]-1-[3-(dimethylamino)propyl]-N-[1-(fluoromethyl)cyclopropyl]-2-oxo-benzimidazole-5-sulfonamide

Intermediate S12 A1 4-Fluoro-N-[1-(fluoromethyl)cyclopropyl]-3-nitro-benzenesulfonamide

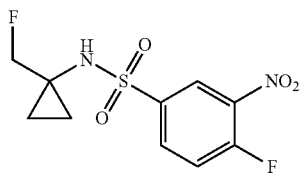 [SMILES: O=[N+]([O-])c1cc(S(=O)(=O)NC2(CF)CC2)ccc1F]

To a magnetically stirred solution of 4-fluoro-3-nitrobenzenesulfonyl chloride (2.97 mL, 20.87 mmol) and N,N-diisopropylethylamine (11.14 mL, 62.6 mmol) in THF (60 mL) at −78° C. under nitrogen was added 1-(fluoromethyl)cyclopropan-1-amine hydrochloride (2.75 g, 21.91 mmol), and the resulting mixture was agitated at −78° C. for 15 min and then −10° C. for 30 min before being warmed to ambient temperature and stirred overnight. The mixture was partitioned between EtOAc (60 mL) and water (40 mL). The organic phase was collected and the water back-extracted with EtOAc (40 mL). The combined organics were dried (NaSO$_4$) and distilled to dryness to give the crude, which was purified by automated column chromatography (SiO$_2$; RediSep—80 g; 0 to 20% EtOAc in hexane) to afford the desired product as a yellow solid (1.2 g, 4.11 mmol, 19.7%).

$^1$H NMR (300 MHz, DMSO-d6) Shift=8.83 (s, 1H), 8.47 (dd, J=2.4, 7.0 Hz, 1H), 8.17 (ddd, J=2.4, 4.1, 8.8 Hz, 1H), 7.83 (dd, J=8.8, 11.1 Hz, 1H), 4.32-4.09 (m, 2H), 0.81-0.73 (m, 4H)

Intermediate S12 B1 4-[2-(dimethylamino)ethylamino]-N-[1-(fluoromethyl)cyclopropyl]-3-nitro-benzenesulfonamide

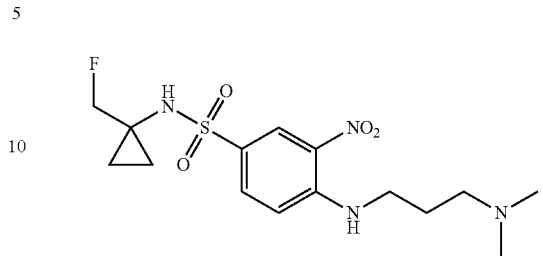

3-(Dimethylamino)-1-propylamine (0.38 mL, 3.01 mmol) was added to a stirred solution of 4-fluoro-N-[1-(fluoromethyl)cyclopropyl]-3-nitro-benzenesulfonamide (800 mg, 2.74 mmol) and potassium carbonate (832.3 mg, 6.02 mmol) in 1,4-dioxane (10 mL), and the resulting mixture was heated at 40° C. The mixture was partitioned between EtOAc (50 mL) and saturated potassium bicarbonate (50 mL) and the organic phase was collected and evaporated to dryness to give the desired product as an orange solid (800 mg, 2.14 mmol, 78.1%).

$^1$H NMR (300 MHz, DMSO-d6) Shift=9.08 (t, J=5.1 Hz, 1H), 8.43 (d, J=2.3 Hz, 1H), 8.36 (br. s., 1H), 7.76 (dd, J=2.1, 9.1 Hz, 1H), 7.23 (d, J=9.3 Hz, 1H), 4.34-4.08 (m, 2H), 3.51-3.41 (m, 2H), 2.36 (t, J=6.4 Hz, 2H), 2.17 (s, 6H), 1.77 (quin, J=6.4 Hz, 2H), 0.72 (s, 4H)

Intermediate S12 C1 3-amino-4-[3-(dimethylamino)propylamino]-N-[1-(fluoromethyl)cyclopropyl]benzenesulfonamide

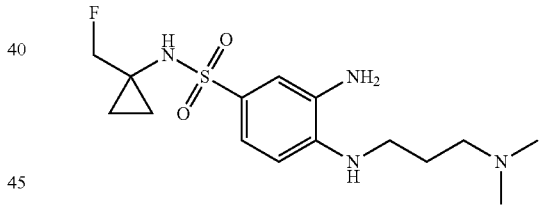

To a magnetically stirred solution of 4-[3-(dimethylamino)propylamino]-N-[1-(fluoromethyl)cyclopropyl]-3-nitro-benzenesulfonamide (1.0 g, 2.67 mmol) and ammonium chloride (714 mg, 13.35 mmol) in a 1:1 (v/v) mixture of ethanol (25 mL) and water (25 mL) at 20° C. was added iron powder (745.8 mg, 13.35 mmol), and the resulting mixture was agitated at 80° C. for 1 h. The mixture was filtered hot through celite, and the cake was washed with hot ethanol (2×20 mL). The combined filtrates were evaporated to dryness and the resulting residue was partitioned between DCM (50 mL) and saturated potassium bicarbonate (50 mL). The organic phase was collected and the aqueous phase back extracted with DCM (50 mL). The combined organics were dried and evaporated to dryness to give the desired product as a grey foam (700 mg, 2.03 mmol, 76.1%).

$^1$H NMR (300 MHz, DMSO-d6) Shift=7.83-7.77 (m, 1H), 7.00-6.87 (m, 2H), 6.45 (d, J=8.0 Hz, 1H), 5.20 (s, 1H), 4.91 (s, 2H), 4.29-4.04 (m, 2H), 3.18-3.05 (m, 2H), 2.31 (t, J=7.0 Hz, 2H), 2.14 (s, 6H), 1.73 (quin, J=7.0 Hz, 2H), 0.73-0.54 (m, 5H)

Intermediate S12 D1 1-[3-(dimethylamino)propyl]-N-[1-(fluoromethyl)cyclopropyl]-2-oxo-3H-benzimidazole-5-sulfonamide

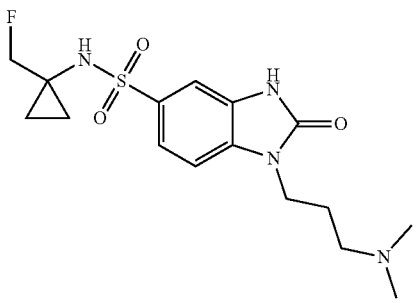 [SMILES: CN(C)CCCn1c(=O)[nH]c2cc(S(=O)(=O)NC3(CF)CC3)ccc21]

To a magnetically stirred solution of 3-amino-4-[3-(dimethylamino)propylamino]-N-[1-(fluoromethyl)cyclopropyl]benzenesulfonamide (500 mg, 1.45 mmol) in THF (20 mL) at 20° C. under nitrogen was added 1,1'-carbonyldiimidazole (282.4 mg, 1.74 mmol) and the resulting mixture was agitated at ambient temperature overnight. The mixture was distilled to dryness and the residue purified by automated column chromatography (SiO₂; SNAP—10 g; 0 to 20% MeOH in DCM) to afford the desired product as a white solid (320 mg, 0.86 mmol, 59.5%).

¹H NMR (300 MHz, DMSO-d6) Shift=11.23 (s, 1H), 8.27 (s, 1H), 7.47 (dd, J=1.7, 8.2 Hz, 1H), 7.34 (d, J=1.6 Hz, 1H), 7.30 (d, J=8.4 Hz, 1H), 4.26-4.05 (m, 2H), 3.85 (t, J=7.1 Hz, 2H), 2.22 (t, J=6.9 Hz, 2H), 2.12 (s, 6H), 1.77 (quin, J=6.9 Hz, 2H)

Nitrogen was bubbled through a mixture of 1-[3-(dimethylamino)propyl]-N-[1-(fluoromethyl)cyclopropyl]-2-oxo-3H-benzimidazole-5-sulfonamide (100 mg, 0.27 mmol), 2-bromo-5-(difluoromethyl)-1,3,4-thiadiazole (63.8 mg, 0.30 mmol), copper iodide (5.14 mg, 0.03 mmol) and potassium carbonate (111.9 mg, 0.81 mmol) in DMSO (5 mL) for 5 min. Trans-N,N'-dimethylcyclohexane-1,2-diamine (8.51 µL, 0.05 mmol) was then added to the reaction, and the resulting mixture was agitated at 80° C. for 2 h. The reaction was cooled to ambient and filtered through a plug of celite. The DMSO solution was then purified by preparatory HPLC (high pH) to give the desired product as a white solid (30 mg, 0.060 mmol, 22%).

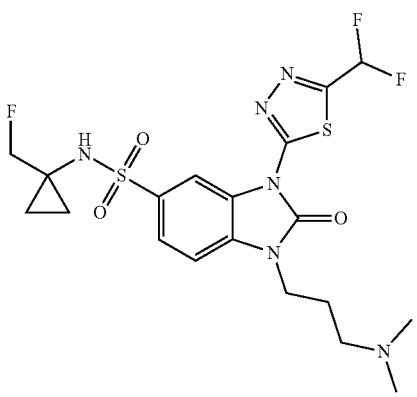 [SMILES: CN(C)CCCn1c(=O)n(-c2nnc(C(F)F)s2)c2cc(S(=O)(=O)NC3(CF)CC3)ccc21]

Example 171 6-Fluoro-1-methyl-N-(1-methylcyclopropyl)-3-(3-methyl-1,2,4-thiadiazol-5-yl)-2-oxo-benzimidazole-5-sulfonamide Intermediate S5 D7 5-fluoro-3-methyl-1-(3-methyl-1,2,4-thiadiazol-5-yl)benzimidazol-2-one

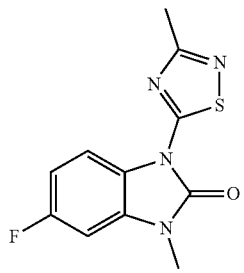

Prepared by the reaction of 5-fluoro-3-methyl-1H-benzimidazol-2-one (100 mg, 0.60 mmol) with 5-bromo-3-methyl-1,2,4-thiadiazole (118.5 mg, 0.66 mmol) to give the desired intermediate as a white solid (90 mg, 0.34 mmol. 56%).

¹H NMR (300 MHz, DMSO-d6) Shift=8.26 (dd, J=4.9, 8.8 Hz, 1H), 7.44 (dd, J=2.5, 8.9 Hz, 1H), 7.13 (ddd, J=2.5, 8.8, 10.0 Hz, 1H), 3.45 (s, 3H), 2.60 (s, 3H).

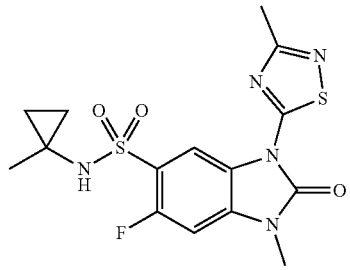 [SMILES: Cc1nsc(-n2c(=O)n(C)c3cc(F)c(S(=O)(=O)NC4(C)CC4)cc32)n1]

Prepared using the method described in Example 160 with 5-fluoro-3-methyl-1-(3-methyl-1,2,4-thiadiazol-5-yl)benzimidazol-2-one (80 mg, 0.303 mmol) to yield 6-fluoro-1-methyl-N-(1-methylcyclopropyl)-3-(3-methyl-1,2,4-thiadiazol-5-yl)-2-oxo-benzimidazole-5-sulfonamide as a white solid (30 mg, 0.075 mmol, 24%).

Example 172 6-Fluoro-N-[1-(fluoromethyl)cyclopropyl]-1-methyl-3-(3-methyl-1,2,4-thiadiazol-5-yl)-2-oxo-benzimidazole-5-sulfonamide

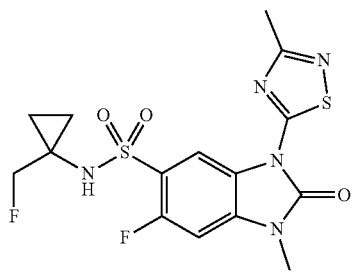 [SMILES: Cc1nsc(-n2c(=O)n(C)c3cc(F)c(S(=O)(=O)NC4(CF)CC4)cc32)n1]

Prepared using the method described in Example 160 with 5-fluoro-3-methyl-1-(3-methyl-1,2,4-thiadiazol-5-yl)benzimidazol-2-one (80 mg, 0.303 mmol) to yield 6-fluoro-N-[1-(fluoromethyl)cyclopropyl]-1-methyl-3-(3-methyl-1,2,4-thiadiazol-5-yl)-2-oxo-benzimidazole-5-sulfonamide as a white solid (30 mg, 0.072 mmol, 24%).

Example 173 3-[5-(Difluoromethyl)-1,3,4-thiadiazol-2-yl]-6-fluoro-1-methyl-N-(1-methylcyclopropyl)-2-oxo-benzimidazole-5-sulfonamide Intermediate S5 D8 1-[5-(difluoromethyl)-1,3,4-thiadiazol-2-yl]-5-fluoro-3-methyl-benzimidazol-2-one

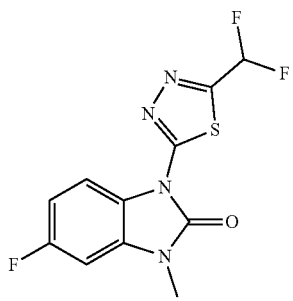 [SMILES: Cn1c(=O)n(-c2nnc(C(F)F)s2)c2ccc(F)cc21]

Prepared by the reaction of 5-fluoro-3-methyl-1H-benzimidazol-2-one (3.0 g, 18.01 mmol) with 2-bromo-5-(difluoromethyl)-1,3,4-thiadiazole (4.27 g, 19.9 mmol) to give the desired intermediate as a white solid (3.33 g, 12.0 mmol. 66%).

$^1$H NMR (300 MHz, DMSO-d6) Shift=8.27 (dd, J=4.8, 8.8 Hz, 1H), 7.80-7.36 (m, 2H), 7.11 (ddd, J=2.5, 8.9, 9 Hz, 1H), 343 (s, 3H)

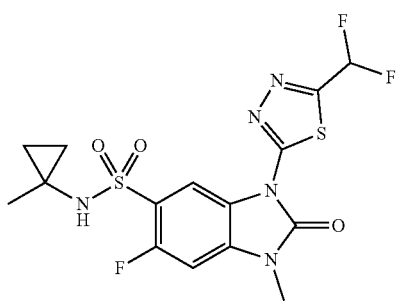 [SMILES: Cn1c(=O)n(-c2nnc(C(F)F)s2)c2cc(S(=O)(=O)NC3(C)CC3)c(F)cc21]

Prepared using the method described in Example 160 with 1-[5-(difluoromethyl)-1,3,4-thiadiazol-2-yl]-5-fluoro-3-methyl-benzimidazol-2-one (140 mg, 0.46 mmol) to yield 3-[5-(difluoromethyl)-1,3,4-thiadiazol-2-yl]-6-fluoro-1-methyl-N-(1-methylcyclopropyl)-2-oxo-benzimidazole-5-sulfonamide as a white solid (50 mg, 0.115 mmol, 25%).

Example 174 3-[5-(difluoromethyl)-1,3,4-thiadiazol-2-yl]-6-fluoro-N-[1-(fluoromethyl)cyclopropyl]-1-methyl-2-oxo-benzimidazole-5-sulfonamide

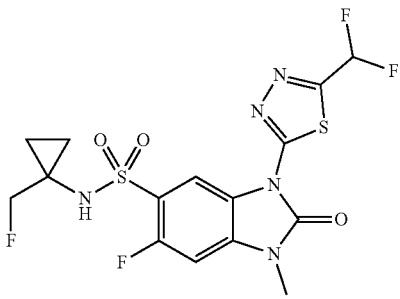 [SMILES: Cn1c(=O)n(-c2nnc(C(F)F)s2)c2cc(S(=O)(=O)NC3(CF)CC3)c(F)cc21]

Prepared using the method described in Example 160 with 1-[5-(difluoromethyl)-1,3,4-thiadiazol-2-yl]-5-fluoro-3-methyl-benzimidazol-2-one (140 mg, 0.46 mmol) to yield 3-[5-(difluoromethyl)-1,3,4-thiadiazol-2-yl]-6-fluoro-N-[1-(fluoromethyl)cyclopropyl]-1-methyl-2-oxo-benzimidazole-5-sulfonamide as a white solid (40 mg, 0.089 mmol, 19%).

Example 175 N-[1-(Fluoromethyl)cyclopropyl]-1-methyl-2-oxo-3-(1,2,4-thiadiazol-5-yl)benzimidazole-5-sulfonamide Intermediate S5 D9 1-methyl-3-(1,2,4-thiadiazol-5-yl)benzimidazol-2-one

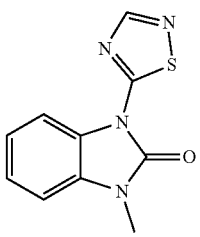 [SMILES: Cn1c(=O)n(-c2ncns2)c2ccccc21]

Prepared by the reaction of 3-methyl-1H-benzimidazol-2-one (150 mg, 1.01 mmol) with 5-bromo-1,2,4-thiadiazole (234 mg, 1.41 mmol) to give the desired intermediate as a white solid (190 mg, 0.81 mmol. 80%).

$^1$H NMR (300 MHz, DMSO-d6) Shift=8.77-8.70 (m, 1H), 8.35-8.28 (m, 1H), 7.47-7.25 (m, 3H), 3.48 (s, 3H)

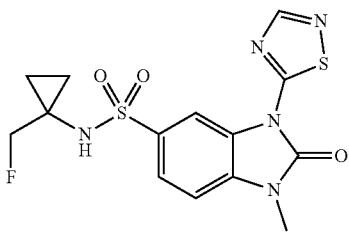 [SMILES: Cn1c(=O)n(-c2ncns2)c2cc(S(=O)(=O)NC3(CF)CC3)ccc21]

Prepared using the method described in Example 160 with 1-methyl-3-(1,2,4-thiadiazol-5-yl)benzimidazol-2-one (20 mg, 0.086 mmol) to yield N-[1-(fluoromethyl)cyclopropyl]-

1-methyl-2-oxo-3-(1,2,4-thiadiazol-5-yl)benzimidazole-5-sulfonamide as a white solid (15 mg, 0.039 mmol, 45%).

Example 176 1-Methyl-N-(1-methylcyclopropyl)-3-(3-methyl-1,2,4-thiadiazol-5-yl)-2-oxo-benzimidazole-5-sulfonamide Intermediate S5 D10 1-methyl-3-(3-methyl-1,2,4-thiadiazol-5-yl)benzimidazol-2-one

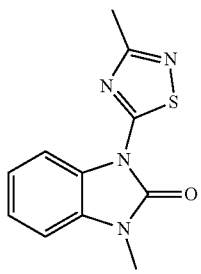 [SMILES: Cc1nsc(-n2c(=O)n(C)c3ccccc32)n1]

Prepared by the reaction of 3-methyl-1H-benzimidazol-2-one (150 mg, 1.01 mmol) with 5-bromo-3-methyl-1,2,4-thiadiazole (217 mg, 1.21 mmol) to give the desired intermediate as a white solid (150 mg, 0.60 mmol. 60%).
$^1$H NMR (300 MHz, DMSO-d6) Shift=8.34-8.27 (m, 1H), 7.44-7.27 (m, 3H), 3.47 (s, 3H), 2.61 (s, 3H)

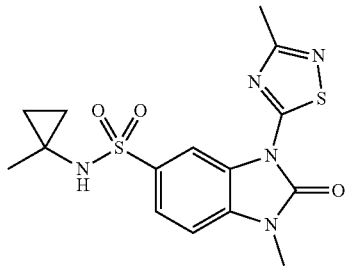 [SMILES: Cc1nsc(-n2c(=O)n(C)c3ccc(S(=O)(=O)NC4(C)CC4)cc32)n1]

Prepared using the method described in Example 160 with 1-methyl-3-(3-methyl-1,2,4-thiadiazol-5-yl)benzimidazol-2-one (95 mg, 0.386 mmol) to yield N-[1-(fluoromethyl)cyclopropyl]-1-methyl-2-oxo-3-(1,2,4-thiadiazol-5-yl)benzimidazole-5-sulfonamide as a white solid (4 mg, 0.01 mmol, 3%).

Example 177 1-Methyl-N-(1-methylcyclopropyl)-3-(3-methyl-1,2,4-thiadiazol-5-yl)-2-oxo-benzimidazole-5-sulfonamide

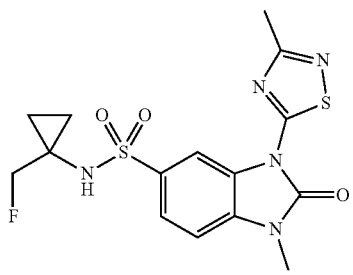 [SMILES: Cc1nsc(-n2c(=O)n(C)c3ccc(S(=O)(=O)NC4(CF)CC4)cc32)n1]

Prepared using the method described in Example 160 with 1-methyl-3-(3-methyl-1,2,4-thiadiazol-5-yl)benzimidazol-2-one (95 mg, 0.386 mmol) to yield 1-methyl-N-(1-methylcyclopropyl)-3-(3-methyl-1,2,4-thiadiazol-5-yl)-2-oxo-benzimidazole-5-sulfonamide as a white solid (20 mg, 0.05 mmol, 16%).

Example 178 1-(Cyanomethyl)-N-[1-(fluoromethyl)cyclopropyl]-3-(5-methyl-1,3,4-thiadiazol-2-yl)-2-oxo-benzimidazole-5-sulfonamide Intermediate S10 B3 2-[3-(5-methyl-1,3,4-thiadiazol-2-yl)-2-oxo-benzimidazol-1-yl]acetonitrile

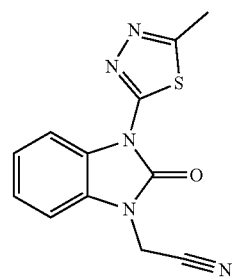 [SMILES: Cc1nnc(-n2c(=O)n(CC#N)c3ccccc32)s1]

Prepared by the reaction of 3-(5-methyl-1,3,4-thiadiazol-2-yl)-1H-benzimidazol-2-one (100 mg, 0.43 mmol) with bromoacetonitrile (72 mg, 0.603 mmol) to give the desired intermediate as a white solid (100 mg, 0.369 mmol, 86%).
$^1$H NMR (300 MHz, DMSO-d6) Shift=8.39-8.33 (m, 1H), 7.55 (dd, J=1.6, 7.3 Hz, 1H), 7.44-7.32 (m, 2H), 5.29 (s, 2H), 2.75 (s, 3H)

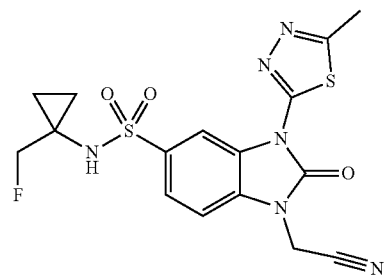 [SMILES: Cc1nnc(-n2c(=O)n(CC#N)c3ccc(S(=O)(=O)NC4(CF)CC4)cc32)s1]

Prepared using the method described in Example 160 with 2-[3-(5-methyl-1,3,4-thiadiazol-2-yl)-2-oxo-benzimidazol-1-yl]acetonitrile (90 mg, 0.332 mmol) to yield 1-(cyanomethyl)-N-[1-(fluoromethyl)cyclopropyl]-3-(5-methyl-1,3,4-thiadiazol-2-yl)-2-oxo-benzimidazole-5-sulfonamide as a white solid (20 mg, 0.047 mmol, 32%).

Example 179 1-(Cyanomethyl)-N-(1-methylcyclopropyl)-3-(3-methyl-1,2,4-thiadiazol-5-yl)-2-oxo-benzimidazole-5-sulfonamide Intermediate S13 A1 3-methyl-N-(2-nitrophenyl)-1,2,4-thiadiazol-5-amine

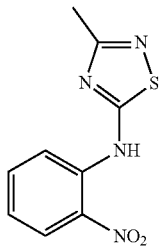 [SMILES: Cc1nsc(Nc2ccccc2[N+](=O)[O-])n1]

To a magnetically stirred solution of o-nitrofluorobenzene (1.87 mL, 17.72 mmol) and caesium carbonate (17.3 g, 53.15 mmol) in dioxane (20 mL) at 20° C. under nitrogen was added 3-methyl-1,2,4-thiadiazol-5-amine (4.08 g, 35.4 mmol), and the resulting mixture was agitated at 100° C. for 2 h. The mixture was cooled to ambient temperature and partitioned between water (150 mL) and EtOAc (200 mL). The organic phase was distilled to dryness and the resulting residue purified by automated column chromatography (SiO$_2$; RediSep—80 g; 0 to 40% EtOAc in hexane) to afford the desired product as a yellow solid (3.5 g, 14.81 mmol, 83.6%).

$^1$H NMR (300 MHz, DMSO-d6) Shift=10.93 (s, 1H), 8.32 (dd, J=0.9, 8.4 Hz, 1H), 8.08 (dd, J=1.5, 8.3 Hz, 1H), 7.77 (dt, J=1.6, 7.8 Hz, 1H), 7.31 (ddd, J=1.3, 7.3, 8.3 Hz, 1H), 2.37 (s, 3H)

Intermediate S13 B1 N2-(3-methyl-1,2,4-thiadiazol-5-yl)benzene-1,2-diamine

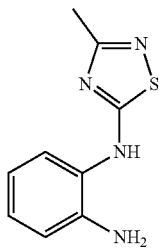

Iron powder (4.13 g, 74.1 mmol) and ammonium chloride (3.96 g, 74.1 mmol) were added to a stirred suspension of 3-methyl-N-(2-nitrophenyl)-1,2,4-thiadiazol-5-amine (3.50 g, 14.81 mmol) in ethanol (100 mL) and water (100 mL), and the resulting mixture was agitated at 80° C. for 1 h. The mixture was filtered (hot) through celite and the filter cake was washed with EtOH (2×40 mL). The combined filtrates were concentrated in vacuo to approximately 80 mL and then partitioned between EtOAc (200 mL) and water (50 mL). The EtOAc layer was collected and dried (Na$_2$SO$_4$) before being distilled to dryness to give the crude product as a brown solid (2.9 g, 14.1 mmol, 95%).

$^1$H NMR (300 MHz, DMSO-d6) Shift=9.75 (br. s., 1H), 7.30 (dd, J=1.3, 7.9 Hz, 1H), 7.00-6.89 (m, 1H), 6.77 (dd, J=1.2, 8.0 Hz, 1H), 6.60 (dt, J=1.4, 7.5 Hz, 1H), 5.03 (s, 2H), 2.31 (s, 3H)

Intermediate S13 C1 3-(3-methyl-1,2,4-thiadiazol-5-yl)-1H-benzimidazol-2-one

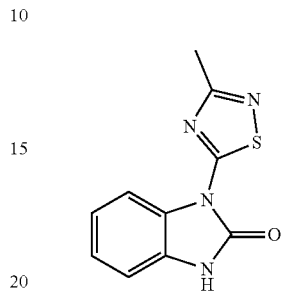

To a magnetically stirred solution of N2-(3-methyl-1,2,4-thiadiazol-5-yl)benzene-1,2-diamine (2.90 g, 14.1 mmol) in DMF (60 mL) at 20° C. under nitrogen was added 1,1'-carbonyldiimidazole (2.73 g, 16.9 mmol), and the resulting mixture was agitated at ambient overnight. The solvent was removed in vacuo to give a white solid, which was suspended in ether (40 mL). The mixture was agitated for 30 min and filtered to give the desired product as a white solid (2.20 g, 9.47 mmol, 67.4%).

$^1$H NMR (300 MHz, DMSO-d6) Shift=11.99 (br. s., 1H), 8.40-8.20 (m, 1H), 7.30-7.18 (m, 3H), 2.61 (s, 3H)

Intermediate S13 D 12-[3-(3-methyl-1,2,4-thiadiazol-5-yl)-2-oxo-benzimidazol-1-yl]acetonitrile

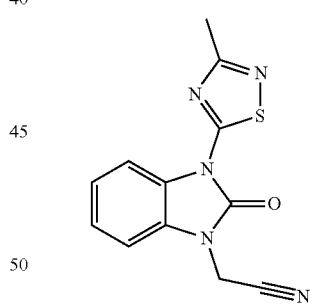

Bromoacetonitrile (0.04 mL, 0.60 mmol) was added to a magnetically stirred solution of 3-(3-methyl-1,2,4-thiadiazol-5-yl)-1H-benzimidazol-2-one (100 mg, 0.43 mmol) and potassium carbonate (178.52 mg, 1.29 mmol) in DMF (2 mL), and the resulting solution was stirred overnight. The solvent was removed in vacuo to give a yellow solid, which was purified by automated column chromatography (SiO$_2$; RediSep—4 g; 0 to 80% EtOAc in hexane) to afford the desired product as a white solid (105 mg, 0.38 mmol, 90%).

$^1$H NMR (300 MHz, DMSO-d6) Shift=8.40-8.33 (m, 1H), 7.61-7.54 (m, 1H), 7.48-7.30 (m, 2H), 5.31 (s, 2H), 2.63 (s, 3H)

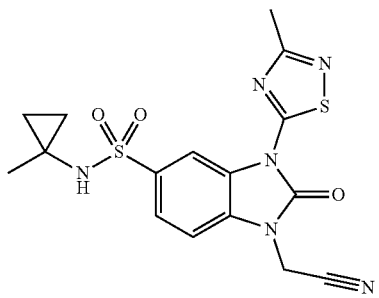 [SMILES: Cc1nsc(-n2c(=O)n(CC#N)c3ccc(S(=O)(=O)NC4(C)CC4)cc32)n1]

Prepared using the method described in Example 160 with 2-[3-(3-methyl-1,2,4-thiadiazol-5-yl)-2-oxo-benzimidazol-1-yl]acetonitrile (60 mg, 0.221 mmol) to yield 1-(cyanomethyl)-N-(1-methylcyclopropyl)-3-(3-methyl-1,2,4-thiadiazol-5-yl)-2-oxo-benzimidazole-5-sulfonamide as a white solid (20 mg, 0.049 mmol, 22%).

Example 180 1-(Cyanomethyl)-N-[1-(fluoromethyl)cyclopropyl]-3-(3-methyl-1,2,4-thiadiazol-5-yl)-2-oxo-benzimidazole-5-sulfonamide

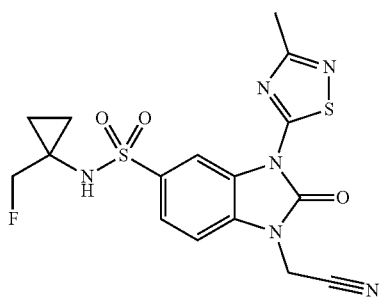 [SMILES: Cc1nsc(-n2c(=O)n(CC#N)c3ccc(S(=O)(=O)NC4(CF)CC4)cc32)n1]

Prepared using the method described in Example 160 with 2-[3-(3-methyl-1,2,4-thiadiazol-5-yl)-2-oxo-benzimidazol-1-yl]acetonitrile (60 mg, 0.221 mmol) to yield 1-(cyanomethyl)-N-[1-(fluoromethyl)cyclopropyl]-3-(3-methyl-1,2,4-thiadiazol-5-yl)-2-oxo-benzimidazole-5-sulfonamide as a white solid (20 mg, 0.047 mmol, 21%).

Example 181 3-[5-(Difluoromethyl)-1,3,4-thiadiazol-2-yl]-N-[1-(fluoromethyl)cyclopropyl]-1-methyl-2-oxo-benzimidazole-5-sulfonamide Intermediate S5 D11 1-[5-(difluoromethyl)-1,3,4-thiadiazol-2-yl]-3-methyl-benzimidazol-2-one

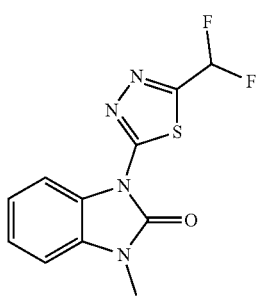 [SMILES: Cn1c(=O)n(-c2nnc(C(F)F)s2)c2ccccc21]

Prepared by the reaction of 3-methyl-1H-benzimidazol-2-one (150 mg, 1.01 mmol) with 2-bromo-5-(difluoromethyl)-1,3,4-thiadiazole (240 mg, 1.11 mmol) to give the desired intermediate as a white solid (130 mg, 0.46 mmol. 46%).

$^1$H NMR (300 MHz, DMSO-d6) Shift=8.38-8.31 (m, 1H), 7.83-7.29 (m, 4H), 3.49 (s, 3H)

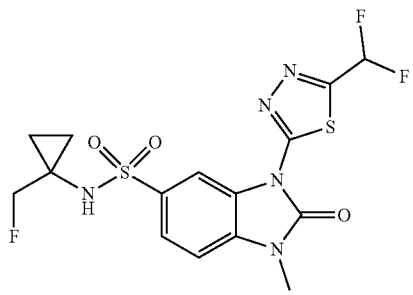 [SMILES: Cn1c(=O)n(-c2nnc(C(F)F)s2)c2cc(S(=O)(=O)NC3(CF)CC3)ccc21]

Prepared using the method described in Example 160 with 1-[5-(difluoromethyl)-1,3,4-thiadiazol-2-yl]-3-methyl-benzimidazol-2-one (110 mg, 0.39 mmol) to yield 1-(cyanomethyl)-N-[1-(fluoromethyl)cyclopropyl]-3-(5-methyl-1,3,4-thiadiazol-2-yl)-2-oxo-benzimidazole-5-sulfonamide as a white solid (60 mg, 0.14 mmol, 35%).

Example 182 1-(2-Methoxyethyl)-N-(1-methylcyclopropyl)-3-(3-methyl-1,2,4-thiadiazol-5-yl)-2-oxo-benzimidazole-5-sulfonamide Intermediate S11 B4 1-(2-methoxyethyl)-3-(3-methyl-1,2,4-thiadiazol-5-yl)benzimidazol-2-one

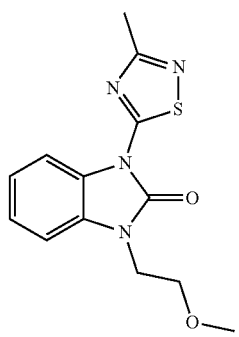 [SMILES: COCCn1c(=O)n(-c2nc(C)ns2)c2ccccc21]

Nitrogen was bubbled through a mixture of 1-[3-(dimethylamino)propyl]-N-[1-(fluoromethyl)cyclopropyl]-2-oxo-3H-benzimidazole-5-sulfonamide (100 mg, 0.27 mmol), 2-bromo-5-(difluoromethyl)-1,3,4-thiadiazole (63.84 mg, 0.30 mmol), copper iodide (5.14 mg, 0.03 mmol) and potassium carbonate (111.91 mg, 0.81 mmol) in 1,4-dioxane (4 mL) for 5 mins. Trans-N,N'-dimethylcyclohexane-1,2-diamine (24.6 µL, 0.16 mmol) was then added to the reaction, and the resulting mixture was agitated at 80° C. for 2 h. The reaction was cooled to ambient and partitioned between EtOAc (20 mL) and saturated potassium carbonate (20 mL). The organic phase was collected and distilled to dryness to give the crude product, which was purified by automated column chromatography (SiO$_2$; SNAP—10 g; 0 to 80% EtOAc in hexane) to afford the desired product as a white solid (120 mg, 0.41 mmol, 52.9%).

¹H NMR (300 MHz, DMSO-d6) Shift=8.36-8.30 (m, 1H), 7.51-7.44 (m, 1H), 7.39-7.28 (m, 2H), 4.15 (t, J=5.3 Hz, 2H), 3.69 (t, J=5.3 Hz, 2H), 3.25 (s, 3H), 2.62 (s, 3H)

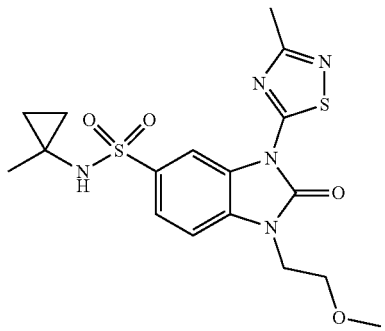

Prepared using the method described in Example 160 with 1-(2-methoxyethyl)-3-(3-methyl-1,2,4-thiadiazol-5-yl)benzimidazol-2-one (50 mg, 0.189 mmol) to yield 1-(2-methoxyethyl)-N-(1-methylcyclopropyl)-3-(3-methyl-1,2,4-thiadiazol-5-yl)-2-oxo-benzimidazole-5-sulfonamide as a white solid (20 mg, 0.047 mmol, 25%).

Example 183 N-[1-(Fluoromethyl)cyclopropyl]-1-(2-methoxyethyl)-2-oxo-3-(1,2,4-thiadiazol-5-yl)benzimidazole-5-sulfonamide

Intermediate S11 B5 1-(2-methoxyethyl)-3-(1,2,4-thiadiazol-5-yl)benzimidazol-2-one

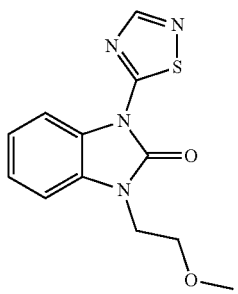 [SMILES: COCCn1c(=O)n(-c2ncns2)c2ccccc21]

Nitrogen was bubbled through a mixture of 1-(2-methoxyethyl)-1H-benzo[d]imidazol-2(3H)-one (100 mg, 0.78 mmol), 5-bromo-1,2,4-thiadiazole (180 mg, 1.09 mmol), copper iodide (14.8 mg, 0.078 mmol) and potassium carbonate (324 mg, 2.34 mmol) in 1,4-dioxane (6 mL) for 5 min. Trans-N,N-dimethylcyclohexane-1,2-diamine (24 µL, 0.16 mmol) was then added to the reaction, and the resulting mixture was agitated at 80° C. for 2 h. The reaction was cooled to ambient and partitioned between EtOAc (20 mL) and saturated potassium carbonate (20 mL). The organic phase was collected and distilled to dryness to give the crude, which was purified by automated column chromatography (SiO₂; SNAP—10 g; 0 to 80% EtOAc in hexane) to afford the desired product as a white solid (150 mg, 0.55 mmol, 69%).

¹H NMR (300 MHz, DMSO-d6) Shift=8.75 (s, 1H), 8.38-8.30 (m, 1H), 7.53-7.46 (m, 1H), 7.41-7.27 (m, 2H), 4.17 (t, J=5.3 Hz, 2H), 3.69 (t, J=5.3 Hz, 2H), 3.25 (s, 3H)

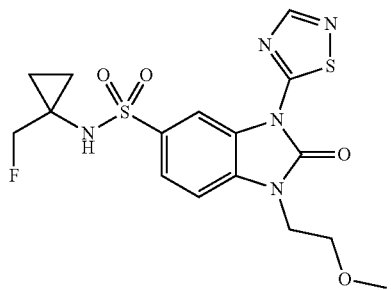 [SMILES: COCCn1c(=O)n(-c2ncns2)c2cc(S(=O)(=O)NC3(CF)CC3)ccc21]

Prepared using the method described in Example 160 with 1-(2-methoxyethyl)-3-(1,2,4-thiadiazol-5-yl)benzimidazol-2-one (25 mg, 0.091 mmol) to yield N-[1-(fluoromethyl)cyclopropyl]-1-(2-methoxyethyl)-2-oxo-3-(1,2,4-thiadiazol-5-yl)benzimidazole-5-sulfonamide as a white solid (10 mg, 0.023 mmol, 26%).

Example 184 N-[1-(Fluoromethyl)cyclopropyl]-1-(2-methoxyethyl)-3-(3-methyl-1,2,4-thiadiazol-5-yl)-2-oxo-benzimidazole-5-sulfonamide

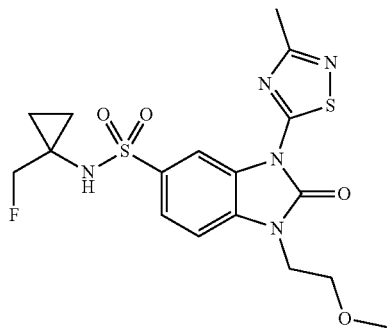 [SMILES: COCCn1c(=O)n(-c2nc(C)ns2)c2cc(S(=O)(=O)NC3(CF)CC3)ccc21]

Prepared using the method described in Example 160 with 1-(2-methoxyethyl)-3-(3-methyl-1,2,4-thiadiazol-5-yl)benzimidazol-2-one (50 mg, 0.189 mmol) to yield N-[1-(fluoromethyl)cyclopropyl]-1-(2-methoxyethyl)-3-(3-methyl-1,2,4-thiadiazol-5-yl)-2-oxo-benzimidazole-5-sulfonamide as a white solid (20 mg, 0.045 mmol, 23%).

Example 185 N-[1-(Fluoromethyl)cyclopropyl]-1-(3-methoxypropyl)-3-(3-methyl-1,2,4-thiadiazol-5-yl)-2-oxo-benzimidazole-5-sulfonamide

Intermediate S14 A N-[1-(fluoromethyl)cyclopropyl]-3-(3-methyl-1,2,4-thiadiazol-5-yl)-2-oxo-1H-benzimidazole-5-sulfonamide

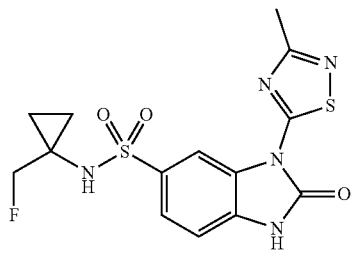 [SMILES: Cc1nsc(-n2c(=O)[nH]c3ccc(S(=O)(=O)NC4(CF)CC4)cc32)n1]

Prepared using the method described in Example 160 with 3-(3-methyl-1,2,4-thiadiazol-5-yl)-1H-benzimidazol-2-one (600 mg, 2.58 mmol) to yield N-[1-(fluoromethyl)cyclopropyl]-3-(3-methyl-1,2,4-thiadiazol-5-yl)-2-oxo-1H-benzimidazole-5-sulfonamide as a white solid (400 mg, 1.043 mmol, 40%).

$^1$H NMR (300 MHz, DMSO-d6) Shift=12.44 (br. s., 1H), 8.66 (d, J=1.7 Hz, 1H), 8.54 (s, 1H), 7.72 (dd, J=1.8, 8.3 Hz, 1H), 7.37 (d, J=8.3 Hz, 1H), 4.36-4.10 (m, 2H), 2.68-2.60 (m, 4H), 0.71 (s, 4H)

Intermediate S14 B1 N-[1-acetyl-3-(3-methyl-1,2,4-thiadiazol-5-yl)-2-oxo-benzimidazol-5-yl]sulfonyl-N-[1-(fluoromethyl)cyclopropyl]acetamide

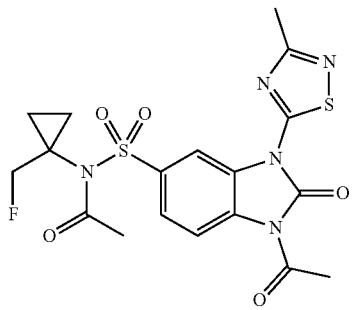 [SMILES: CC(=O)N(C1(CF)CC1)S(=O)(=O)c1ccc2c(c1)n(-c1nc(C)ns1)c(=O)n2C(C)=O]

Acetic anhydride (0.52 mL, 5.48 mmol) was added to a magnetically stirred solution of N-[1-(fluoromethyl)cyclopropyl]-3-(3-methyl-1,2,4-thiadiazol-5-yl)-2-oxo-1H-benzimidazole-5-sulfonamide (420 mg, 1.1 mmol) in pyridine (10 mL) at ambient temperature, and the resulting mixture was agitated overnight. The mixture was poured into water (80 mL) to give a suspension, which was agitated for 30 min and then filtered. The solid cake was washed with water (2×10 mL) and dried under vacuum at 40° C. to give the bis-acetylated product as a white solid (400 mg, 0.86 mmol, 78%).

$^1$H NMR (300 MHz, DMSO-d6) Shift=8.97 (d, J=1.9 Hz, 1H), 8.38 (d, J=8.7 Hz, 1H), 8.00 (dd, J=2.1, 8.7 Hz, 1H), 5.19-4.91 (m, 1H), 4.51-4.27 (m, 1H), 2.75 (s, 3H), 2.66 (s, 3H), 2.25 (s, 3H), 1.43 (s, 4H)

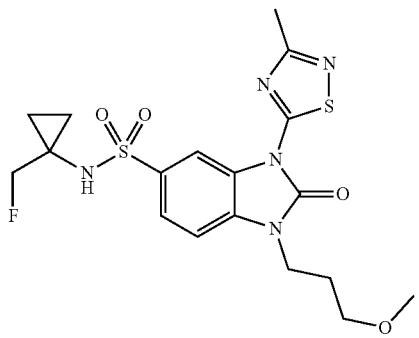 [SMILES: COCCCn1c(=O)n(-c2nc(C)ns2)c2cc(S(=O)(=O)NC3(CF)CC3)ccc21]

1-Bromo-3-methoxypropane (11.95 µL, 0.11 mmol) was added to a stirred suspension of N-[1-acetyl-3-(3-methyl-1,2,4-thiadiazol-5-yl)-2-oxo-benzimidazol-5-yl]sulfonyl-N-[1-(fluoromethyl)cyclopropyl]acetamide (50 mg, 0.11 mmol), potassium carbonate (30 mg, 0.21 mmol) and potassium iodide (18 mg, 0.11 mmol) in DMF (2 mL), and the resulting mixture was agitated at 50° C. overnight. The mixture was cooled to ambient temperature and treated with concentrated aqueous ammonia (1 mL). The resulting mixture was agitated for 4 h. The solvent was removed to give a residue, which was purified by automated column chromatography (SiO$_2$; RediSep—4 g; 0 to 80% EtOAc in hexane) to afford the desired product N-[1-(fluoromethyl)cyclopropyl]-1-(3-methoxypropyl)-3-(3-methyl-1,2,4-thiadiazol-5-yl)-2-oxo-benzimidazole-5-sulfonamide as a white solid (20 mg, 0.044 mmol, 41%).

Example 186 1-[2-(Dimethylamino)ethyl]-N-[1-(fluoromethyl)cyclopropyl]-3-(3-methyl-1,2,4-thiadiazol-5-yl)-2-oxo-benzimidazole-5-sulfonamide

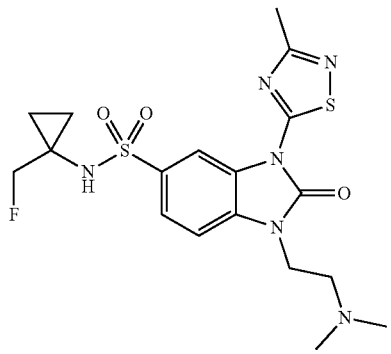 [SMILES: Cc1nsc(-n2c(=O)n(CCN(C)C)c3ccc(S(=O)(=O)NC4(CF)CC4)cc32)n1]

Prepared according to the methods described in Example 185 with (2-bromoethyl)dimethylamine hydrobromide (11.9 µL, 0.26 mmol), N-[1-acetyl-3-(3-methyl-1,2,4-thiadiazol-5-yl)-2-oxo-benzimidazol-5-yl]sulfonyl-N-[1-(fluoromethyl)cyclopropyl]acetamide (80 mg, 0.1700 mmol), potassium carbonate (47.3 mg, 0.34 mmol) and potassium iodide (28.4 mg, 0.17 mmol) to give 1-[2-(dimethylamino)ethyl]-N-[1-(fluoromethyl)cyclopropyl]-3-(3-methyl-1,2,4-thiadiazol-5-yl)-2-oxo-benzimidazole-5-sulfonamide as a white solid (10 mg, 0.02 mmol, 12%).

Example 187 N-[1-(Fluoromethyl)cyclopropyl]-1-(3-methoxypropyl)-3-(5-methyl-1,3,4-thiadiazol-2-yl)-2-oxo-benzimidazole-5-sulfonamide Intermediate S14 A2 N-[1-(fluoromethyl)cyclopropyl]-3-(5-methyl-1,3,4-thiadiazol-2-yl)-2-oxo-1H-benzimidazole-5-sulfonamide

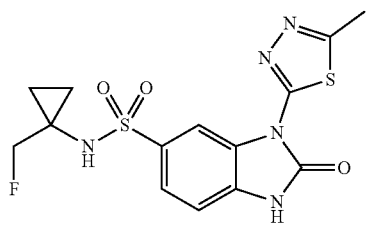 [SMILES: Cc1nnc(-n2c(=O)[nH]c3ccc(S(=O)(=O)NC4(CF)CC4)cc32)s1]

Prepared using the method described in Example 160 with 3-(5-methyl-1,3,4-thiadiazol-2-yl)-2-oxo-1H-benzimidazole-5-sulfonyl chloride (650 mg, 1.97 mmol) and 1-(fluoromethyl)cyclopropan-1-amine hydrochloride (296 mg, 2.36 mmol) to yield N-[1-(fluoromethyl)cyclopropyl]-3-(5- methyl-1,3,4-thiadiazol-2-yl)-2-oxo-1H-benzimidazole-5-sulfonamide as a white solid (400 mg, 1.043 mmol, 53%).

¹H NMR (300 MHz, DMSO-d6) Shift=12.35-12.20 (m, 1H), 8.72 (d, J=1.8 Hz, 1H), 8.74-8.70 (m, 1H), 8.50 (s, 1H), 7.96 (s, 1H), 7.70 (dd, J=1.8, 8.3 Hz, 1H), 7.34 (d, J=8.3 Hz, 1H), 4.34-4.06 (m, 2H), 2.89 (s, 3H), 2.74 (d, J=2.6 Hz, 6H), 0.68 (s, 4H)

Intermediate S14 B2 N-[1-acetyl-3-(5-methyl-1,3,4-thiadiazol-2-yl)-2-oxo-benzimidazol-5-yl]sulfonyl-N-[1-(fluoromethyl)cyclopropyl]acetamide

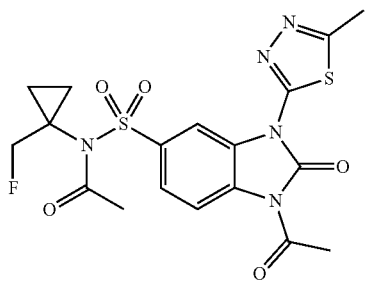 [SMILES: CC(=O)N(C1(CF)CC1)S(=O)(=O)c1ccc2c(c1)n(-c1nnc(C)s1)c(=O)n2C(C)=O]

To a magnetically stirred solution of N-[1-(fluoromethyl)cyclopropyl]-3-(5-methyl-1,3,4-thiadiazol-2-yl)-2-oxo-1H-benzimidazole-5-sulfonamide (400 mg, 1.04 mmol) in pyridine (10 mL) at 20° C. under nitrogen was added acetic anhydride (0.49 mL, 5.22 mmol), and the resulting mixture was agitated overnight. The material was poured into water (40 mL), and the resulting mixture was stirred for 30 min before being filtered. The filter-cake was washed with water (2×10 mL) and dried under vacuum at 40° C. to give the desired as a white solid (310 mg, 0.66 mmol, 63.6%).

¹H NMR (300 MHz, DMSO-d6) Shift=9.02 (d, J=2.0 Hz, 1H), 8.37 (d, J=8.7 Hz, 1H), 7.97 (dd, J=2.1, 8.7 Hz, 1H), 5.16-4.87 (m, 1H), 4.46-4.22 (m, 1H), 2.79 (s, 3H), 2.73 (s, 3H), 2.24 (s, 3H), 1.41 (br. s., 4H)

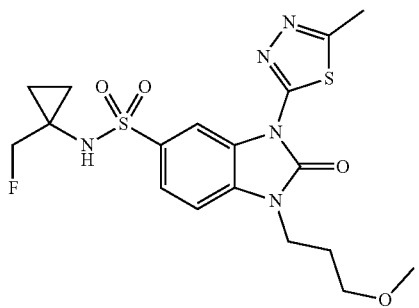 [SMILES: COCCCn1c(=O)n(-c2nnc(C)s2)c2cc(S(=O)(=O)NC3(CF)CC3)ccc21]

Prepared according to the methods described in Example 185 with N-[1-acetyl-3-(5-methyl-1,3,4-thiadiazol-2-yl)-2-oxo-benzimidazol-5-yl]sulfonyl-N-[1-(fluoromethyl)cyclopropyl]acetamide (100 mg, 0.21 mmol), potassium carbonate (89 mg, 0.64 mmol) and 1-bromo-3-methoxypropane (47.8 µL, 0.43 mmol) in DMF (2 mL) to give the desired product N-[1-(fluoromethyl)cyclopropyl]-1-(3-methoxypropyl)-3-(5-methyl-1,3,4-thiadiazol-2-yl)-2-oxo-benzimidazole-5-sulfonamide as a white solid (35 mg, 0.077 mmol, 36%).

Example 188 1-[2-(Dimethylamino)ethyl]-N-[1-(fluoromethyl)cyclopropyl]-3-(5-methyl-1,3,4-thiadiazol-2-yl)-2-oxo-benzimidazole-5-sulfonamide

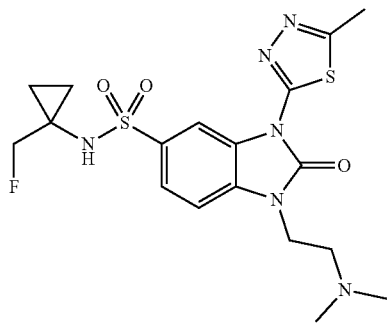 [SMILES: Cc1nnc(-n2c(=O)n(CCN(C)C)c3ccc(S(=O)(=O)NC4(CF)CC4)cc32)s1]

Prepared according to the methods described in Example 185 with N-[1-acetyl-3-(5-methyl-1,3,4-thiadiazol-2-yl)-2-oxo-benzimidazol-5-yl]sulfonyl-N-[1-(fluoromethyl)cyclopropyl]acetamide (100 mg, 0.21 mmol), potassium carbonate (89 mg, 0.64 mmol) and (2-bromoethyl)dimethylamine hydrobromide (100 mg, 0.43 mmol) in DMF (3 mL) to give the desired product 1-[2-(dimethylamino)ethyl]-N-[1-(fluoromethyl)cyclopropyl]-3-(5-methyl-1,3,4-thiadiazol-2-yl)-2-oxo-benzimidazole-5-sulfonamide as a white solid (40 mg, 0.088 mmol, 41%).

Example 189 1-Methyl-N-(1-methylcyclopropyl)-3-(5-methyl-1,3,4-oxadiazol-2-yl)-2-oxo-benzimidazole-5-sulfonamide

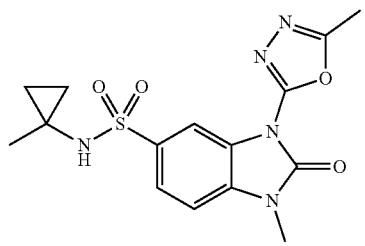

Prepared by the alkylation of 3-(5-methyl-1,3,4-oxadiazol-2-yl)-N-(1-methylcyclopropyl)-2-oxo-2,3-dihydro-1H-benzo[d]imidazole-5-sulfonamide (150 mg, 0.43 mmol) with potassium carbonate (119 mg, 0.86 mmol) and iodomethane (26.7 µL, 0.43 mmol) in DMF (2 mL) under microwave irradiation at 80° C. for 30 min. The mixture was partitioned between DCM (10 mL) and water (10 mL) and the organic phase was collected. The solvent was removed in vacuo to give a residue, which was purified by automated column chromatography (SiO₂; RediSep—4 g; 0 to 100% EtOAc in hexane) to afford the desired product as a white solid (50 mg, 0.138 mmol, 32%).

Example 190 1-Ethyl-N-(1-methylcyclopropyl)-3-(5-methyl-1,3,4-oxadiazol-2-yl)-2-oxo-benzimidazole-5-sulfonamide

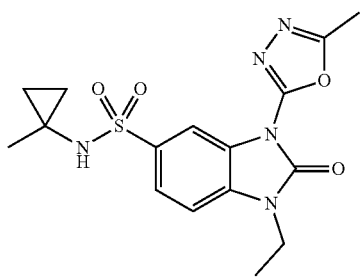

Prepared by the alkylation of 3-(5-methyl-1,3,4-oxadiazol-2-yl)-N-(1-methylcyclopropyl)-2-oxo-2,3-dihydro-1H-benzo[d]imidazole-5-sulfonamide (150 mg, 0.43 mmol), with potassium carbonate (119 mg, 0.86 mmol) and iodoethane (0.03 mL, 0.43 mmol) in DMF (2 mL) under microwave irradiation at 80° C. for 30 min to give the desired product as a white solid (40 mg, 0.106 mmol, 25%).

Example 191 1-(2-Fluoroethyl)-N-(1-methylcyclopropyl)-3-(5-methyl-1,3,4-oxadiazol-2-yl)-2-oxo-benzimidazole-5-sulfonamide

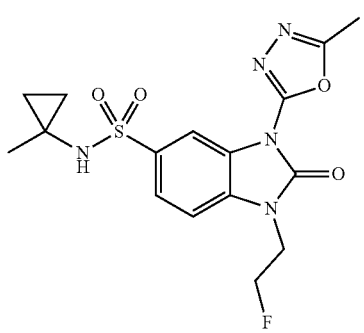

Prepared by the alkylation of 3-(5-methyl-1,3,4-oxadiazol-2-yl)-N-(1-methylcyclopropyl)-2-oxo-2,3-dihydro-1H-benzo[d]imidazole-5-sulfonamide (150 mg, 0.43 mmol), with potassium carbonate (119 mg, 0.86 mmol) and 1-bromo-2-fluoroethane (0.03 mL, 0.43 mmol) in DMF (2 mL) under microwave irradiation at 80° C. for 30 min to give the desired product as a white solid (30 mg, 0.076 mmol, 18%).

Example 192 6-Fluoro-N-(1-methylcyclopropyl)-3-(5-methyl-1,3,4-oxadiazol-2-yl)-2-oxo-1H-benzimidazole-5-sulfonamide Intermediate S13 A2 N-(4-fluoro-2-nitro-phenyl)-5-methyl-1,3,4-oxadiazol-2-amine

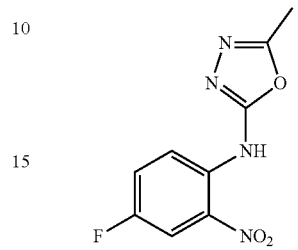

A magnetically stirred solution of 2,5-difluoronitrobenzene (1.36 mL, 12.57 mmol), 5-methyl-1,3,4-oxadiazol-2-amine (1.25 g, 12.57 mmol) and caesium carbonate (8.19 g, 25.14 mmol) in 1,4-dioxane (40 mL) was heated at 80° C. overnight. The mixture was cooled to ambient and poured into water (100 mL) to give a yellow precipitate, which was collected by filtration. The solid was washed with water (2×20 mL) and dried under vacuum at 40° C. to give the desired product N-(4-fluoro-2-nitro-phenyl)-5-methyl-1,3,4-oxadiazol-2-amine as a yellow solid (2.10 g, 8.82 mmol, 70%).

$^1$H NMR (300 MHz, DMSO-d6) Shift=10.30 (br. s., 1H), 8.18 (br. s., 1H), 8.02 (dd, J=2.8, 8.5 Hz, 1H), 7.83-7.63 (m, 1H), 2.42 (s, 3H)

Intermediate S13 B2 4-fluoro-N1-(5-methyl-1,3,4-oxadiazol-2-yl)benzene-1,2-diamine

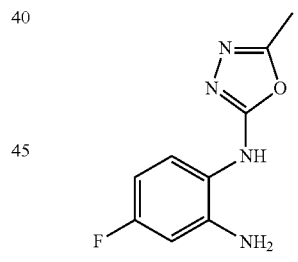

Iron powder (2.46 g, 44.08 mmol) and ammonium chloride (2.36 g, 44.08 mmol) were added to a stirred suspension of N-(4-fluoro-2-nitro-phenyl)-5-methyl-1,3,4-oxadiazol-2-amine (2.10 g, 8.82 mmol) in ethanol (80 mL) and water (80 mL), and the resulting mixture was agitated at 60° C. for 1 h. The mixture was filtered (hot) through celite and the filter cake was washed with EtOH (2×40 mL). The combined filtrates were concentrated in vacuum to approximately 80 mL to give a precipitate. The mixture was cooled to 0° C. for 1 h and then filtered to give a solid, which was washed with cold water (2×10 mL). The solid was dried under vacuum in at 40° C. to give the desired product 4-fluoro-N1-(5-methyl-1,3,4-oxadiazol-2-yl)benzene-1,2-diamine (1.2 g, 5.76 mmol, 65%) as a buff brown solid.

$^1$H NMR (300 MHz, DMSO-d6) Shift=8.92 (br. s., 1H), 7.35 (dd, J=6.1, 8.8 Hz, 1H), 6.50 (dd, J=2.9, 11.1 Hz, 1H), 6.33 (dt, J=3.0, 8.6 Hz, 1H), 5.31 (s, 2H), 2.34 (s, 3H)

Intermediate S13 C2 6-fluoro-3-(5-methyl-1,3,4-oxadiazol-2-yl)-1H-benzimidazol-2-one

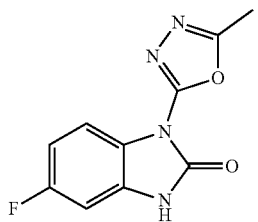 [SMILES: Cc1nnc(-n2c(=O)[nH]c3cc(F)ccc32)o1]

To a magnetically stirred solution of 4-fluoro-N1-(5-methyl-1,3,4-oxadiazol-2-yl)benzene-1,2-diamine (1.20 g, 5.76 mmol) in DMF (20 mL) at 20° C. under nitrogen was added 1,1'-carbonyldiimidazole (1.12 g, 6.92 mmol), and the resulting mixture was agitated at ambient temperature overnight. The mixture was poured into water (80 mL) to give a precipitate, which was collected by filtration, washed with water (2×10 mL) and dried under vacuum to give the desired product 6-fluoro-3-(5-methyl-1,3,4-oxadiazol-2-yl)-1H-benzimidazol-2-one as a light brown solid (1.25 g, 5.34 mmol, 93%).

$^1$H NMR (300 MHz, DMSO-d6) Shift=11.78 (s, 1H), 7.72 (dd, J=4.8, 9.5 Hz, 1H), 7.06-6.93 (m, 2H), 2.57 (s, 3H)

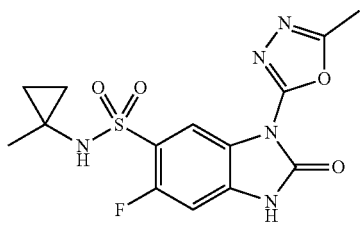

Prepared using the method described in Example 160 with 6-fluoro-3-(5-methyl-1,3,4-oxadiazol-2-yl)-1H-benzimidazol-2-one (300 mg, 1.33 mmol) and 1-methylcyclopropan-amine hydrochloride (145.5 mg, 1.35 mmol) to yield 6-fluoro-N-(1-methylcyclopropyl)-3-(5-methyl-1,3,4-oxadiazol-2-yl)-2-oxo-1H-benzimidazole-5-sulfonamide as a white solid (210 mg, 0.572 mmol, 43%).

Example 193 3-[5-(Difluoromethyl)-1,3,4-thiadiazol-2-yl]-N-[1-(fluoromethyl)cyclopropyl]-2-oxo-1-prop-2-ynyl-benzimidazole-5-sulfonamide

Intermediate S10-A4 3-[5-(difluoromethyl)-1,3,4-thiadiazol-2-yl]-1H-benzimidazol-2-one

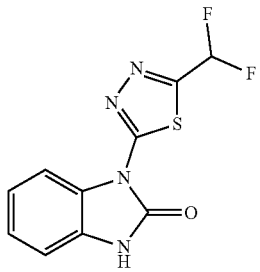 [SMILES: O=c1[nH]c2ccccc2n1-c1nnc(C(F)F)s1]

This compound was prepared by the reaction of 2-hydroxybenzimidazole (100 mg, 0.75 mmol) with 2-bromo-5-(difluoromethyl)-1,3,4-thiadiazole (176 mg, 0.82 mmol), copper(I) oxide (16 mg, 0.11 mmol), caesium carbonate (729 mg, 2.24 mmol) and N,N-dimethylglycine hydrochloride (15.61 mg, 0.11 mmol) in DMSO (2 mL) at 90° C. for 16 h. The desired product 3-[5-(difluoromethyl)-1,3,4-thiadiazol-2-yl]-1H-benzimidazol-2-one was isolated as a tan solid (100 mg, 0.372 mmol, 50%).

$^1$H NMR (300 MHz, DMSO-d6) Shift=12.02 (s, 1H), 8.32 (d, J=8.8 Hz, 1H), 7.83-7.39 (m, 1H), 7.35-7.17 (m, 3H)

Intermediate S14 A2—3-[5-(difluoromethyl)-1,3,4-thiadiazol-2-yl]-N-[1-(fluoromethyl)cyclopropyl]-2-oxo-1H-benzimidazole-5-sulfonamide

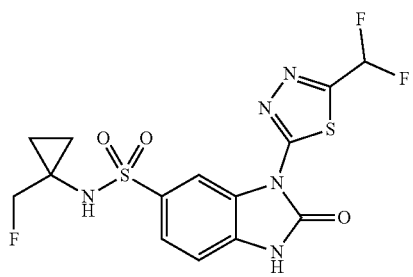 [SMILES: O=c1[nH]c2ccc(S(=O)(=O)NC3(CF)CC3)cc2n1-c1nnc(C(F)F)s1]

Prepared according to the method described in Example 160 using 3-[5-(difluoromethyl)-1,3,4-thiadiazol-2-yl]-1H-benzimidazol-2-one (600 mg, 2.24 mmol) and 1-(fluoromethyl)cyclopropan-1-amine hydrochloride (309 mg, 2.46 mmol) to afford 3-[5-(difluoromethyl)-1,3,4-thiadiazol-2-yl]-N-[1-(fluoromethyl)cyclopropyl]-2-oxo-1H-benzimidazole-5-sulfonamide as a yellow solid (377 mg, 0.899 mmol, 40%).

$^1$H NMR (300 MHz, DMSO-d6) Shift=12.47 (br. s., 1H), 8.74 (d, J=1.7 Hz, 1H), 8.54 (s, 1H), 7.84-7.44 (m, 2H), 7.38 (d, J=8.4 Hz, 1H), 4.37-4.09 (m, 2H), 0.76-0.64 (m, 4H)

Intermediate S14 B2—N-[1-acetyl-3-[5-(difluoromethyl)-1,3,4-thiadiazol-2-yl]-2-oxo-benzimidazol-5-yl]sulfonyl-N-[1-(fluoromethyl)cyclopropyl]acetamide

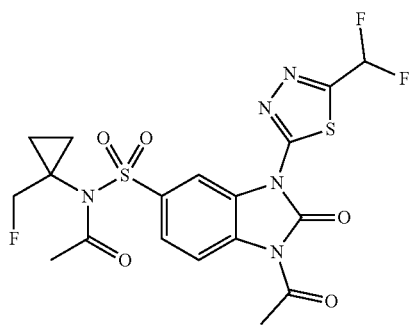 [SMILES: CC(=O)N(C1(CF)CC1)S(=O)(=O)c1ccc2c(c1)n(-c1nnc(C(F)F)s1)c(=O)n2C(C)=O]

To a magnetically stirred solution of 3-[5-(difluoromethyl)-1,3,4-thiadiazol-2-yl]-N-[1-(fluoromethyl)cyclopropyl]-2-oxo-1H-benzimidazole-5-sulfonamide (377 mg, 0.90 mmol) in pyridine (5 mL) at 20° C. under nitrogen was added acetic anhydride (0.42 mL, 4.49 mmol), and the resulting mixture was agitated overnight. The material was poured into water (40 mL), and the resulting mixture was stirred for 30 min before being filtered. The filter-cake was washed with water (2×10 mL) and dried under vacuum at 40° C. to give the desired product N-[1-acetyl-3-[5-(difluoromethyl)-1,3,4-thiadiazol-2-yl]-2-oxo-benzimidazol-5-yl]sulfonyl-N-[1-(fluoromethyl)cyclopropyl]acetamide as a yellow solid (146 mg, 0.29 mmol, 32%).

$^1$H NMR (300 MHz, DMSO-d6) Shift=8.74 (d, J=1.7 Hz, 1H), 8.54 (s, 1H), 7.84-7.44 (m, 2H), 7.38 (d, J=8.4 Hz, 1H), 5.11 (m, 1H), 5.00-4.87 (m, 1H), 4.48-4.12 (m, 4H), 2.76 (s, 6H), 0.77-0.66 (m, 4H)

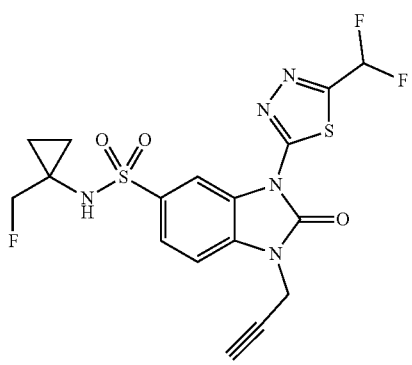 [SMILES: C#CCn1c(=O)n(-c2nnc(C(F)F)s2)c2cc(S(=O)(=O)NC3(CF)CC3)ccc21]

To a magnetically stirred solution of N-[1-acetyl-3-[5-(difluoromethyl)-1,3,4-thiadiazol-2-yl]-2-oxo-benzimidazol-5-yl]sulfonyl-N-[1-(fluoromethyl)cyclopropyl]acetamide (73 mg, 0.14 mmol) and potassium carbonate (60.12 mg, 0.43 mmol) in DMF (2 mL) was added 3-bromopropyne (25.2 µL, 0.29 mmol), and the resulting mixture was agitated at 50° C. for 16 h. The mixture was cooled to ambient temperature, treated with 4 mL of aqueous ammonia and stirred overnight. The solvent was removed in vacuo to give a residue, which was partitioned between EtOAc (50 mL) and water (50 mL). The organic layer was collected and evaporated to dryness to give the crude product as a residue, which was purified by prep. HPLC (high pH) to give the desired product 3-[5-(difluoromethyl)-1,3,4-thiadiazol-2-yl]-N-[1-(fluoromethyl)cyclopropyl]-2-oxo-1-prop-2-ynyl-benzimidazole-5-sulfonamide as a yellow solid (3 mg, 0.0066 mmol, 4.5%).

Example 194 6-Fluoro-N-[1-(fluoromethyl)cyclopropyl]-3-(5-methyl-1,3,4-oxadiazol-2-yl)-2-oxo-1H-benzimidazole-5-sulfonamide

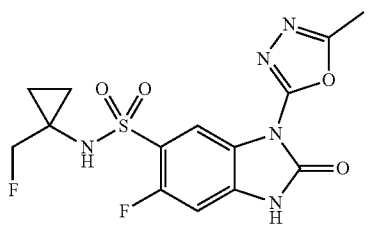 [SMILES: Cc1nnc(-n2c(=O)[nH]c3cc(F)c(S(=O)(=O)NC4(CF)CC4)cc32)o1]

Prepared using the method described in Example 160 with 6-fluoro-3-(5-methyl-1,3,4-oxadiazol-2-yl)-1H-benzimidazol-2-one (937 mg, 4.00 mmol) and 1-(fluoromethyl)cyclopropan-1-amine hydrochloride (556.1 mg, 4.51 mmol) to yield 6-fluoro-N-[1-(fluoromethyl)cyclopropyl]-3-(5-methyl-1,3,4-oxadiazol-2-yl)-2-oxo-1H-benzimidazole-5-sulfonamide as a white solid (450 mg, 1.17 mmol, 29%).

Example 195 3-[5-(Difluoromethyl)-1,3,4-oxadiazol-2-yl]-1-methyl-N-(1-methylcyclopropyl)-2-oxo-benzimidazole-5-sulfonamide Intermediate S5 D12 1-[5-(difluoromethyl)-1,3,4-oxadiazol-2-yl]-3-methyl-benzimidazol-2-one

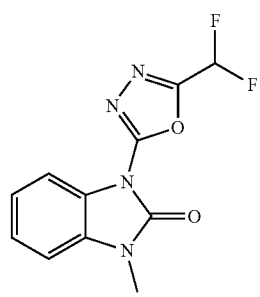 [SMILES: Cn1c(=O)n(-c2nnc(C(F)F)o2)c2ccccc21]

Prepared from 1-methyl-1,3-dihydro-2H-benzimidazol-2-one (100 mg, 0.67 mmol), 2-bromo-5-(difluoromethyl-1,3,4-oxadiazole (134.3 mg, 0.67 mmol), potassium carbonate (280 mg, 2.02 mmol), copper iodide (12.9 mg, 0.07 mmol) and trans-N,N'-dimethylcyclohexane-1,2-diamine (0.02 mL, 0.1400 mmol) in 1,4-dioxane (5 mL) at 80° C. for 2 h. Product obtained as a white solid (65 mg, 0.24 mmol, 36%).

$^1$H NMR (300 MHz, DMSO-d6) Shift=7.88 (d, J=7.6 Hz, 1H), 7.76-7.38 (m, 1H), 7.38-7.32 (m, 2H), 7.31-7.22 (m, 1H), 3.41 (s, 3H)

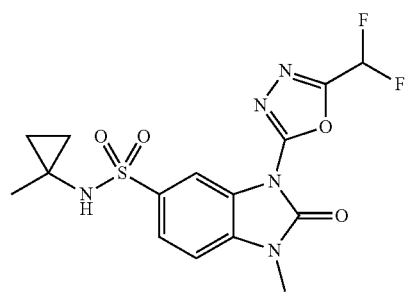 [SMILES: Cn1c(=O)n(-c2nnc(C(F)F)o2)c2cc(S(=O)(=O)NC3(C)CC3)ccc21]

Prepared using the method described in Example 160 with 1-[5-(difluoromethyl)-1,3,4-oxadiazol-2-yl]-3-methyl-benzimidazol-2-one (60 mg, 0.225 mmol) and 1-methylcyclopropanamine hydrochloride (21.2 mg, 0.20 mmol) to give 3-[5-(difluoromethyl)-1,3,4-oxadiazol-2-yl]-1-methyl-N-(1-methylcyclopropyl)-2-oxo-benzimidazole-5-sulfonamide as a white solid (20 mg, 0.05 mmol, 22%).

Example 196 3-[5-(Difluoromethyl)-1,3,4-oxadiazol-2-yl]-N-[1-(fluoromethyl)cyclopropyl]-1-methyl-2-oxo-benzimidazole-5-sulfonamide

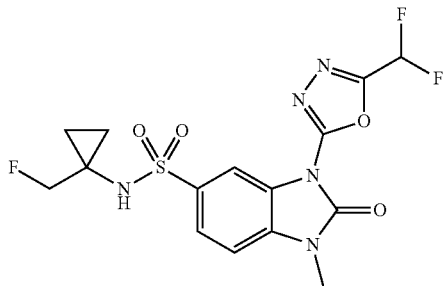 [SMILES: Cn1c(=O)n(-c2nnc(C(F)F)o2)c2cc(S(=O)(=O)NC3(CF)CC3)ccc21]

Prepared using the method described in Example 160 with 1-[5-(difluoromethyl)-1,3,4-oxadiazol-2-yl]-3-methyl-benzimidazol-2-one (60 mg, 0.225 mmol) and 1-(fluoromethyl)cyclopropan-1-amine hydrochloride (24 mg, 0.20 mmol) to give 3-[5-(difluoromethyl)-1,3,4-oxadiazol-2-yl]-N-[1-(fluoromethyl)cyclopropyl]-1-methyl-2-oxo-benzimidazole-5-sulfonamide as a white solid (21 mg, 0.05 mmol, 22%).

Example 197 6-Fluoro-1-methyl-N-(1-methylcyclopropyl)-3-(5-methyl-1,3,4-oxadiazol-2-yl)-2-oxo-benzimidazole-5-sulfonamide

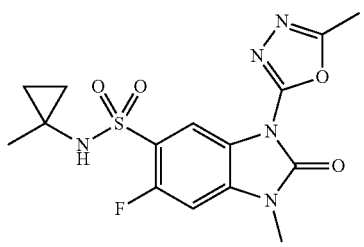

Prepared by the alkylation of 6-fluoro-N-(1-methylcyclopropyl)-3-(5-methyl-1,3,4-oxadiazol-2-yl)-2-oxo-1H-benzimidazole-5-sulfonamide (40 mg, 0.11 mmol), iodomethane (6.78 µL, 0.11 mmol) and potassium carbonate (30.1 mg, 0.22 mmol) in DMF (2 mL) under microwave irradiation at 80° C. for 45 min. The desired product 6-fluoro-1-methyl-N-(1-methylcyclopropyl)-3-(5-methyl-1,3,4-oxadiazol-2-yl)-2-oxo-benzimidazole-5-sulfonamide was isolated as a white solid (10 mg, 0.026 mmol, 24%).

Example 198 6-Fluoro-1-(2-fluoroethyl)-N-(1-methylcyclopropyl)-3-(5-methyl-1,3,4-oxadiazol-2-yl)-2-oxo-benzimidazole-5-sulfonamide

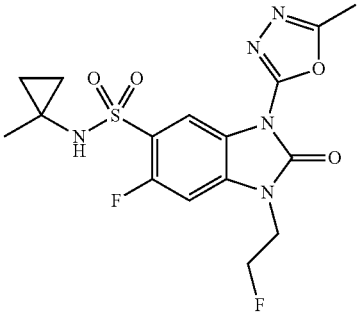

Prepared by the alkylation of 6-fluoro-N-(1-methylcyclopropyl)-3-(5-methyl-1,3,4-oxadiazol-2-yl)-2-oxo-1H-benzimidazole-5-sulfonamide (80 mg, 0.22 mmol) with 1-bromo-2-fluoroethane (16.2 µL, 0.22 mmol) and potassium carbonate (60.2 mg, 0.44 mmol) in DMF (2 mL) under microwave irradiation at 80° C. for 45 min. The desired product 6-fluoro-1-(2-fluoroethyl)-N-(1-methylcyclopropyl)-3-(5-methyl-1,3,4-oxadiazol-2-yl)-2-oxo-benzimidazole-5-sulfonamide was isolated as a white solid (25 mg, 0.061 mmol, 28%).

Example 199 3-[5-(Difluoromethyl)-1,3,4-oxadiazol-2-yl]-1-ethyl-6-fluoro-N-(1-methylcyclopropyl)-2-oxo-benzimidazole-5-sulfonamide Intermediate S5 C13
3-ethyl-5-fluoro-1H-benzimidazol-2-one

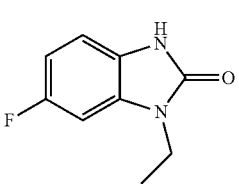

Prepared by the reaction of 1-N-ethyl-5-fluorobenzene-1,2-diamine (2.50 g, 16.21 mmol) with 1,1'-carbonyldiimidazole (3.15 g, 19.46 mmol) in DMF (40 mL) at 20° C. The desired product 3-ethyl-5-fluoro-1H-benzimidazol-2-one was obtained as a pale brown solid (1.4 g, 7.77 mmol, 47.9%).

$^1$H NMR (300 MHz, DMSO-d6) Shift=10.98-10.72 (m, 1H), 7.13 (dd, J=2.5, 9.3 Hz, 1H), 6.93 (dd, J=4.7, 8.5 Hz, 1H), 6.83-6.73 (m, 1H), 3.80 (q, J=7.2 Hz, 2H), 1.18 (t, J=7.2 Hz, 3H).

145

Intermediate S5 D13 1-[5-(difluoromethyl)-1,3,4-oxadiazol-2-yl]-3-ethyl-5-fluoro-benzimidazol-2-one

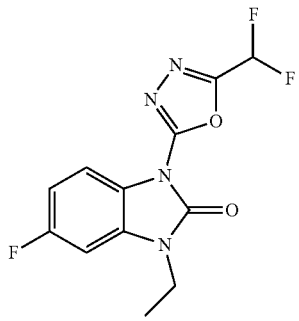 [SMILES: CCn1c(=O)n(-c2nnc(C(F)F)o2)c2ccc(F)cc21]

Prepared by the reaction of 3-ethyl-5-fluoro-1H-benzimidazol-2-one (200 mg, 1.11 mmol) with 2-bromo-5-(difluoromethyl)-1,3,4-oxadiazole (265 mg, 1.33 mmol), potassium carbonate (460 mg, 3.33 mmol), copper(I) iodide (21.1 mg, 0.11 mmol) and trans-N,N-dimethylcyclohexane-1,2-diamine (0.04 mL, 0.22 mmol) in 1,4-dioxane (6 mL) at 80° C. for 2 h. The desired product 1-[5-(difluoromethyl)-1,3,4-oxadiazol-2-yl]-3-ethyl-5-fluoro-benzimidazol-2-one was obtained as a white solid (200 mg, 0.67 mmol, 60%).

$^1$H NMR (300 MHz, DMSO-d6) Shift=7.88 (dd, J=4.8, 8.8 Hz, 1H), 7.76-7.37 (m, 2H), 7.09 (ddd, J=2.5, 8.9, 9.9 Hz, 1H), 3.95 (q, J=7.1 Hz, 2H), 1.26 (t, J=7.2 Hz, 3H).

146

Example 200 3-[5-(Difluoromethyl)-1,3,4-oxadiazol-2-yl]-1-ethyl-6-fluoro-N-[1-(fluoromethyl)cyclopropyl]-2-oxo-benzimidazole-5-sulfonamide

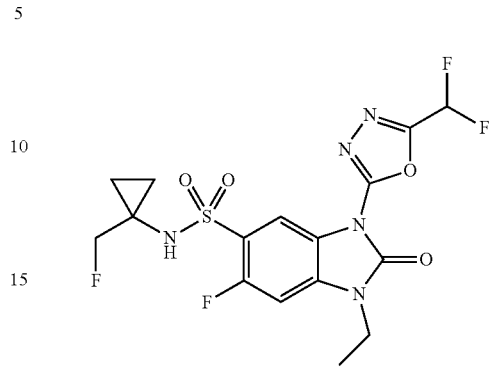

Prepared using the method described in Example 160 using 1-[5-(difluoromethyl)-1,3,4-oxadiazol-2-yl]-3-ethyl-5-fluoro-benzimidazol-2-one (100 mg, 0.335 mmol) and 1-(fluoromethyl)cyclopropan-1-amine hydrochloride (40 mg, 0.362 mmol) to give the desired product 3-[5-(difluoromethyl)-1,3,4-oxadiazol-2-yl]-1-ethyl-6-fluoro-N-[1-(fluoromethyl)cyclopropyl]-2-oxo-benzimidazole-5-sulfonamide a white solid (30 mg, 0.07 mmol, 21%).

Example 201 3-[5-(Difluoromethyl)-1,3,4-oxadiazol-2-yl]-1-ethyl-N-(1-methylcyclopropyl)-2-oxo-benzimidazole-5-sulfonamide Intermediate S5 D14 1-[5-(difluoromethyl)-1,3,4-oxadiazol-2-yl]-3-ethyl-benzimidazol-2-one

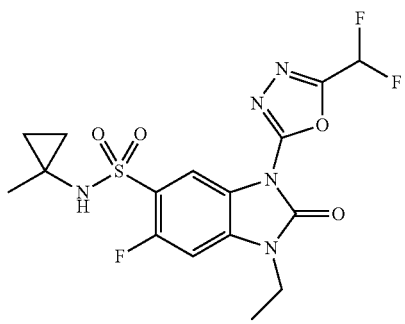

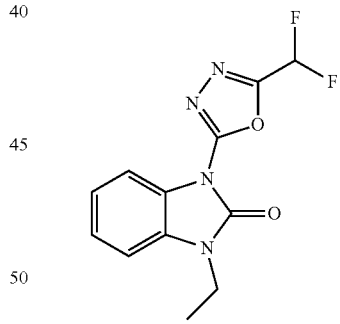

Prepared using the method described in Example 160 using 1-[5-(difluoromethyl)-1,3,4-oxadiazol-2-yl]-3-ethyl-5-fluoro-benzimidazol-2-one (100 mg, 0.335 mmol) and 1-methylcyclopropan-1-amine hydrochloride (46 mg, 0.363 mmol) to give the desired product 3-[5-(difluoromethyl)-1,3,4-oxadiazol-2-yl]-1-ethyl-6-fluoro-N-(1-methylcyclopropyl)-2-oxo-benzimidazole-5-sulfonamide as a white solid (40 mg, 0.089 mmol, 26%).

Prepared by the reaction of 1-ethyl-1,3-dihydro-2H-benzimidazol-2-one (200 mg, 1.23 mmol) with 2-bromo-5-(difluoromethyl-1,3,4-oxadiazole (245 mg, 1.23 mmol), potassium carbonate (511 mg, 3.7 mmol), copper iodide (23.5 mg, 0.12 mmol) and trans-N,N'-dimethylcyclohexane-1,2-diamine (0.04 mL, 0.2500 mmol) in 1,4-dioxane (8 mL) at 80° C. for 2 h. The desired product 1-[5-(difluoromethyl)-1,3,4-oxadiazol-2-yl]-3-ethyl-benzimidazol-2-one was obtained as a white solid (200 mg, 0.714 mmol, 58%).

$^1$H NMR (300 MHz, DMSO-d6) Shift=7.94-7.87 (m, 1H), 7.77-7.38 (m, 2H), 7.37-7.20 (m, 2H), 3.96 (q, J=7.1 Hz, 2H), 1.28 (t, J=7.2 Hz, 3H)

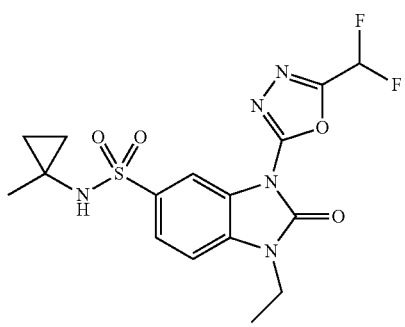 [SMILES: CCn1c(=O)n(-c2nnc(C(F)F)o2)c2cc(S(=O)(=O)NC3(C)CC3)ccc21]

Prepared using the method described in Example 160 using 1-[5-(difluoromethyl)-1,3,4-oxadiazol-2-yl]-3-ethyl-benzimidazol-2-one (100 mg, 0.357 mmol) and 1-methylcyclopropan-1-amine hydrochloride (46 mg, 0.363 mmol) to give the desired product 3-[5-(difluoromethyl)-1,3,4-oxadiazol-2-yl]-1-ethyl-N-(1-methylcyclopropyl)-2-oxo-benzimidazole-5-sulfonamide a white solid (40 mg, 0.089 mmol, 25%).

Example 202 3-[5-(Difluoromethyl)-1,3,4-oxadiazol-2-yl]-1-ethyl-N-[1-(fluoromethyl)cyclopropyl]-2-oxo-benzimidazole-5-sulfonamide

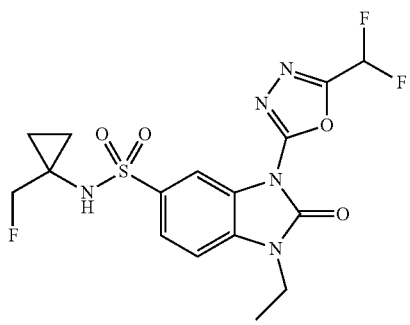 [SMILES: CCn1c(=O)n(-c2nnc(C(F)F)o2)c2cc(S(=O)(=O)NC3(CF)CC3)ccc21]

Prepared using the method described in Example 160 using 1-[5-(difluoromethyl)-1,3,4-oxadiazol-2-yl]-3-ethyl-5-fluoro-benzimidazol-2-one (100 mg, 0.357 mmol) and 1-(fluoromethyl)cyclopropan-1-amine hydrochloride (28 mg, 0.222 mmol) to give the desired product 3-[5-(difluoromethyl)-1,3,4-oxadiazol-2-yl]-1-ethyl-N-[1-(fluoromethyl)cyclopropyl]-2-oxo-benzimidazole-5-sulfonamide as a white solid (30 mg, 0.07 mmol, 20%).

Example 203 6-Fluoro-N-[1-(fluoromethyl)cyclopropyl]-1-(2-methoxyethyl)-3-(6-methylpyridazin-3-yl)-2-oxo-benzimidazole-5-sulfonamide Intermediate S5 D15 5-fluoro-3-(2-methoxyethyl)-1-(6-methylpyridazin-3-yl)benzimidazol-2-one

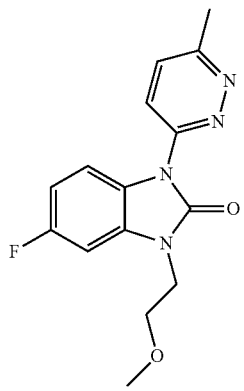 [SMILES: COCCn1c(=O)n(-c2ccc(C)nn2)c2ccc(F)cc21]

Prepared by the reaction of 5-fluoro-3-(2-methoxyethyl)-1H-benzimidazol-2-one (100 mg, 0.48 mmol) with 3-bromo-6-methylpyridazine (90.54 mg, 0.52 mmol), potassium carbonate (197 mg, 1.43 mmol), copper iodide (9.1 mg, 0.05 mmol) and trans-N,N'-dimethylcyclohexane-1,2-diamine (0.02 mL, 0.10 mmol) in DMSO (2.5 mL) at 80° C. for 3 h. The desired product 5-fluoro-3-(2-methoxyethyl)-1-(6-methylpyridazin-3-yl)benzimidazol-2-one was isolated as a white solid (41 mg, 0.136 mmol, 28%).

$^1$H NMR (300 MHz, DMSO-d6) Shift=8.29 (d, J=9.0 Hz, 1H), 7.97 (dd, J=4.9, 8.9 Hz, 1H), 7.79 (d, J=9.0 Hz, 1H), 7.35 (dd, J=2.5, 9.1 Hz, 1H), 6.98 (ddd, J=2.6, 8.9, 9.9 Hz, 1H), 4.11 (t, J=5.3 Hz, 2H), 3.67 (t, J=5.3 Hz, 2H), 3.26 (s, 3H), 2.68 (s, 3H)

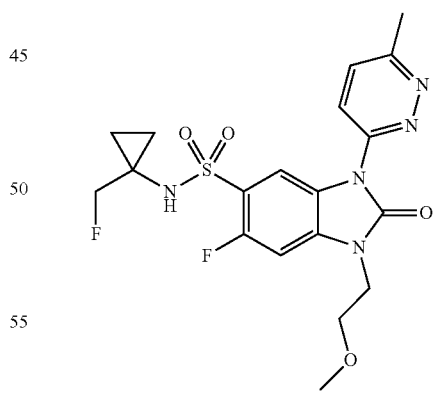

Prepared using the method described in Example 160 with 5-fluoro-3-(2-methoxyethyl)-1-(6-methylpyridazin-3-yl)benzimidazol-2-one (120 mg, 0.397 mmol) and 1-(fluoromethyl)cyclopropan-1-amine hydrochloride (55.2 mg, 0.439 mmol) to give the desired product 6-fluoro-N-[1-(fluoromethyl)cyclopropyl]-1-(2-methoxyethyl)-3-(6-methylpyridazin-3-yl)-2-oxo-benzimidazole-5-sulfonamide as a white solid (24 mg, 0.053 mmol, 13%).

149

Example 204 6-Fluoro-N-[1-(fluoromethyl)cyclopropyl]-1-methyl-3-(6-methylpyridazin-3-yl)-2-oxo-benzimidazole-5-sulfonamide Intermediate S5 D16 5-fluoro-3-methyl-1-(6-methylpyridazin-3-yl)benzimidazol-2-one

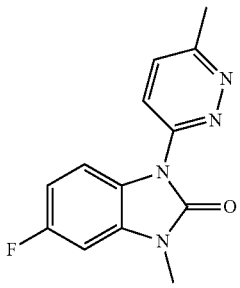 [SMILES: Cc1ccc(-n2c(=O)n(C)c3cc(F)ccc32)nn1]

Prepared by the reaction of 5-fluoro-3-methyl-1H-benzimidazol-2-one (150 mg, 0.90 mmol) with 3-bromo-6-methylpyridazine (172 mg, 0.99 mmol), potassium carbonate (374 mg, 2.71 mmol), copper iodide (17 mg, 0.09 mmol) and trans-N,N'-dimethylcyclohexane-1,2-diamine (0.03 mL, 0.18 mmol) in 1,4-dioxane (2.5 mL) at 80° C. for 16 h. The desired product 5-fluoro-3-methyl-1-(6-methylpyridazin-3-yl)benzimidazol-2-one was isolated as a yellow solid (180 mg, 0.697 mmol, 77%).

$^1$H NMR (300 MHz, DMSO-d6) Shift=8.30 (d, J=9.0 Hz, 1H), 7.99 (dd, J=4.9, 8.9 Hz, 1H), 7.78 (d, J=9.1 Hz, 1H), 7.31 (dd, J=2.5, 8.9 Hz, 1H), 6.98 (ddd, J=2.6, 8.9, 10.0 Hz, 1H), 3.41 (s, 3H), 2.67 (s, 3H)

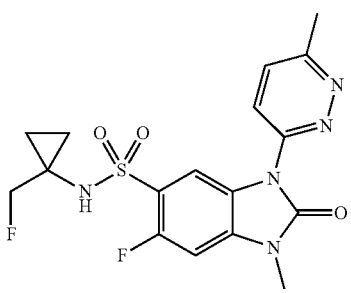 [SMILES: Cc1ccc(-n2c(=O)n(C)c3cc(F)c(S(=O)(=O)NC4(CF)CC4)cc32)nn1]

Prepared using the method described in Example 160 with 5-fluoro-3-methyl-1-(6-methylpyridazin-3-yl)benzimidazol-2-one (125 mg, 0.35 mmol) and 1-(fluoromethyl)cyclopropan-1-amine hydrochloride (48.4 mg, 0.385 mmol) to give the desired product 6-fluoro-N-[1-(fluoromethyl)cyclopropyl]-1-methyl-3-(6-methylpyridazin-3-yl)-2-oxo-benzimidazole-5-sulfonamide as a white solid (14 mg, 0.034 mmol, 10%).

150

Example 205 6-Fluoro-1-methyl-N-(1-methylcyclopropyl)-3-(6-methylpyridazin-3-yl)-2-oxo-benzimidazole-5-sulfonamide

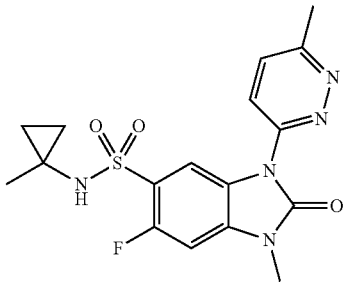 [SMILES: Cc1ccc(-n2c(=O)n(C)c3cc(F)c(S(=O)(=O)NC4(C)CC4)cc32)nn1]

Prepared using the method described in Example 160 with 5-fluoro-3-methyl-1-(6-methylpyridazin-3-yl)benzimidazol-2-one (125 mg, 0.35 mmol) and 1-methylcyclopropanamine hydrochloride (41.4 mg, 0.385 mmol) to give the desired product 6-fluoro-1-methyl-N-(1-methylcyclopropyl)-3-(6-methylpyridazin-3-yl)-2-oxo-benzimidazole-5-sulfonamide as a white solid (20 mg, 0.052 mmol, 15%).

Example 206 6-Fluoro-N-[1-(fluoromethyl)cyclopropyl]-1-methyl-2-oxo-3-[6-(trifluoromethyl)pyridazin-3-yl]benzimidazole-5-sulfonamide Intermediate S5 D17 5-fluoro-3-methyl-1-(6-(trifluoromethyl)pyridazin-3-yl)-1,3-dihydro-2H-benzo[d]imidazol-2-one

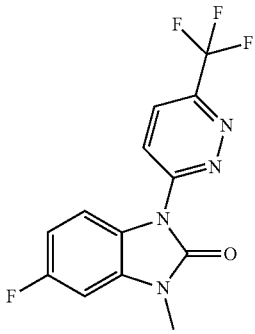 [SMILES: Cn1c(=O)n(-c2ccc(C(F)(F)F)nn2)c2ccc(F)cc21]

Prepared by the reaction of 5-fluoro-3-methyl-1H-benzimidazol-2-one (50 mg, 0.30 mmol) with 3-bromo-6-methylpyridazine (57 mg, 0.33 mmol), potassium carbonate (125 mg, 0.90 mmol), copper iodide (5.7 mg, 0.03 mmol) and trans-N,N'-dimethylcyclohexane-1,2-diamine (0.01 mL, 0.06 mmol) in 1,4-dioxane (1 mL) at 80° C. for 2 h. The desired product 5-fluoro-3-methyl-1-(6-(trifluoromethyl)pyridazin-3-yl)-1,3-dihydro-2H-benzo[d]imidazol-2-one was isolated as a white solid (40 mg, 0.128 mmol, 43%).

$^1$H NMR (300 MHz, DMSO-d6) Shift=8.82 (d, J=9.4 Hz, 1H), 8.45 (d, J=9.4 Hz, 1H), 8.24 (dd, J=4.9, 8.9 Hz, 1H), 7.36 (dd, J=2.6, 8.9 Hz, 1H), 7.04 (ddd, J=2.6, 8.9, 9.8 Hz, 1H), 3.43 (s, 3H)

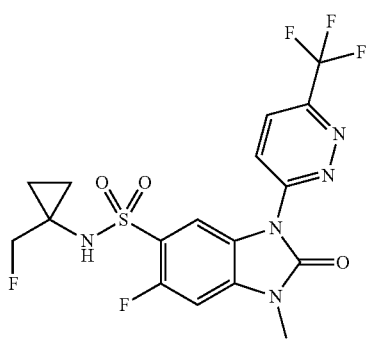 [SMILES: Cn1c(=O)n(-c2ccc(C(F)(F)F)nn2)c2cc(S(=O)(=O)NC3(CF)CC3)c(F)cc21]

Prepared using the method described in Example 160 with 5-fluoro-3-methyl-1-(6-(trifluoromethyl)pyridazin-3-yl)-1,3-dihydro-2H-benzo[d]imidazol-2-one (90 mg, 0.288 mmol) and 1-(fluoromethyl)cyclopropan-1-amine hydrochloride (40 mg, 0.321 mmol) to give the desired product 6-fluoro-N-[1-(fluoromethyl)cyclopropyl]-1-methyl-2-oxo-3-[6-(trifluoromethyl)pyridazin-3-yl]benzimidazole-5-sulfonamide as white solid (4.7 mg, 0.01 mmol, 3.5%).

Example 207 3-[5-(Difluoromethyl)-1,3,4-thiadiazol-2-yl]-1-ethyl-6-fluoro-N-(1-methylcyclopropyl)-2-oxo-benzimidazole-5-sulfonamide Intermediate S5 D18 1-[5-(difluoromethyl)-1,3,4-thiadiazol-2-yl]-3-ethyl-5-fluoro-benzimidazol-2-one

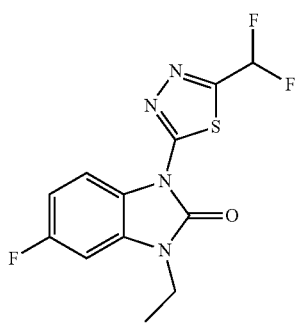

Prepared by the reaction of 3-ethyl-5-fluoro-1H-benzimidazol-2-one (200 mg, 1.11 mmol) with 2-bromo-5-(difluoromethyl)-1,3,4-oxadiazole (265 mg, 1.33 mmol), potassium carbonate (414 mg, 3.33 mmol), copper(I) iodide (19 mg, 0.10 mmol) and trans-N,N-dimethylcyclohexane-1,2-diamine (0.03 mL, 0.20 mmol) in DMSO (6 mL) at 80° C. for 2 h. The desired product 1-[5-(difluoromethyl)-1,3,4-thiadiazol-2-yl]-3-ethyl-5-fluoro-benzimidazol-2-one was isolated as a white solid (200 mg, 0.636 mmol, 64%).

$^1$H NMR (300 MHz, DMSO-d6) Shift=8.32 (dd, J=4.8, 8.9 Hz, 1H), 7.84-7.40 (m, 2H), 7.15 (ddd, J=2.6, 8.9, 9.8 Hz, 1H), 4.02 (q, J=7.2 Hz, 2H), 1.30 (t, J=7.2 Hz, 3H)

Prepared using the method described in Example 160 with 1-[5-(difluoromethyl)-1,3,4-thiadiazol-2-yl]-3-ethyl-5-fluoro-benzimidazol-2-one (100 mg, 0.318 mmol) and 1-methylcyclopropanamine hydrochloride (25 mg, 0.233 mmol) to give the desired product 3-[5-(difluoromethyl)-1,3,4-thiadiazol-2-yl]-1-ethyl-6-fluoro-N-(1-methylcyclopropyl)-2-oxo-benzimidazole-5-sulfonamide as a white solid (40 mg, 0.089 mmol, 28%).

Example 208 3-[5-(Difluoromethyl)-1,3,4-thiadiazol-2-yl]-1-ethyl-6-fluoro-N-[1-(fluoromethyl)cyclopropyl]-2-oxo-benzimidazole-5-sulfonamide Prepared using the method described in Example 160 with 1-[5-(difluoromethyl)-1,3,4-thiadiazol-2-yl]-3-ethyl-5-fluoro-benzimidazol-2-one (100 mg, 0.318 mmol) and 1-(fluoromethyl)cyclopropan-1-amine hydrochloride (36 mg, 0.291 mmol) to give the desired product 3-[5-(difluoromethyl)-1,3,4-thiadiazol-2-yl]-1-ethyl-6-fluoro-N-[1-(fluoromethyl)cyclopropyl]-2-oxo-benzimidazole-5-sulfonamide as white solid (55 mg, 0.118 mmol, 37%).

Example 209 3-[5-(Difluoromethyl)-1,3,4-oxadiazol-2-yl]-6-fluoro-1-methyl-N-(1-methylcyclopropyl)-2-oxo-benzimidazole-5-sulfonamide Intermediate S5 D19 1-[5-(difluoromethyl)-1,3,4-oxadiazol-2-yl]-5-fluoro-3-methyl-benzimidazol-2-one

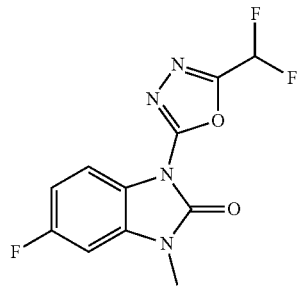 [SMILES: Cn1c(=O)n(-c2nnc(C(F)F)o2)c2ccc(F)cc21]

Prepared by the reaction of 5-fluoro-3-methyl-1H-benzimidazol-2-one (204 mg, 1.23 mmol) with 2-bromo-5-(difluoromethyl-1,3,4-oxadiazole (244 mg, 1.23 mmol), potassium carbonate (509 mg, 3.68 mmol), copper iodide (23 mg, 0.12 mmol) and trans-N,N'-dimethylcyclohexane-1,2-diamine (0.04 mL, 0.25 mmol) in 1,4-dioxane (8 mL) at 80° C. for 2 h. The desired product 1-[5-(difluoromethyl)-1,3,4-oxadiazol-2-yl]-5-fluoro-3-methyl-benzimidazol-2-one was obtained as a white solid (80 mg, 0.283 mmol, 23%).

$^1$H NMR (300 MHz, DMSO-d6) Shift=7.86 (dd, J=4.7, 8.8 Hz, 1H), 7.75-7.35 (m, 2H), 7.09 (ddd, J=2.5, 8.9, 9.8 Hz, 1H), 3.40 (s, 3H)

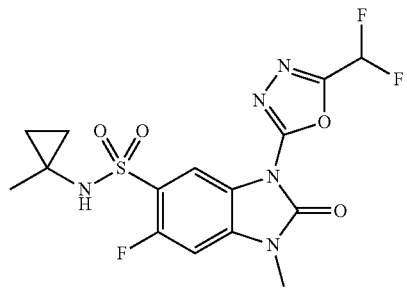 [SMILES: Cn1c(=O)n(-c2nnc(C(F)F)o2)c2cc(S(=O)(=O)NC3(C)CC3)c(F)cc21]

Prepared using the method described in Example 160 with 1-[5-(difluoromethyl)-1,3,4-oxadiazol-2-yl]-5-fluoro-3-methyl-benzimidazol-2-one (40 mg, 0.141 mmol) and 1-methylcyclopropanamine hydrochloride (17 mg, 0.157 mmol) to give the desired product 3-[5-(difluoromethyl)-1,3,4-oxadiazol-2-yl]-6-fluoro-1-methyl-N-(1-methylcyclopropyl)-2-oxo-benzimidazole-5-sulfonamide as a white solid (10 mg, 0.024 mmol, 17%).

Example 210 3-[5-(Difluoromethyl)-1,3,4-oxadiazol-2-yl]-6-fluoro-N-[1-(fluoromethyl)cyclopropyl]-1-methyl-2-oxo-benzimidazole-5-sulfonamide

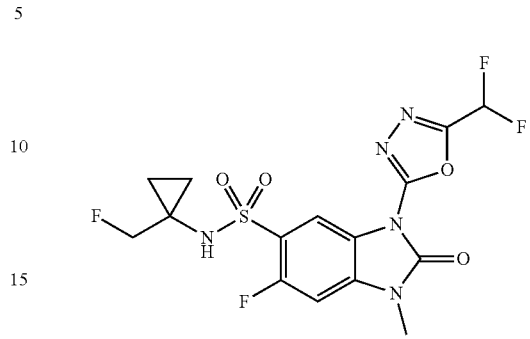

Prepared using the method described in Example 160 with 1-[5-(difluoromethyl)-1,3,4-oxadiazol-2-yl]-5-fluoro-3-methyl-benzimidazol-2-one (40 mg, 0.141 mmol) and 1-(fluoromethyl)cyclopropan-1-amine hydrochloride (26 mg, 0.209 mmol) to give the desired product 3-[5-(difluoromethyl)-1,3,4-oxadiazol-2-yl]-6-fluoro-N-[1-(fluoromethyl)cyclopropyl]-1-methyl-2-oxo-benzimidazole-5-sulfonamide as a white solid (15 mg, 0.044 mmol, 24%).

Example 211 3-[5-(Difluoromethyl)-1,3,4-oxadiazol-2-yl]-6-fluoro-1-(2-fluoroethyl)-N-(1-methylcyclopropyl)-2-oxo-benzimidazole-5-sulfonamide Intermediate S5 A20
5-fluoro-N-(2-fluoroethyl)-2-nitro-aniline

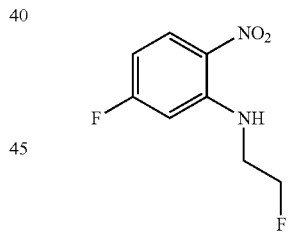

To a magnetically stirred solution of 2,4-difluoronitrobenzene (2.17 mL, 19.8 mmol) and 2-fluoroethylamine hydrochloride (1.97 g, 19.8 mmol) in ethanol (40 mL) at 0° C. under nitrogen was added N,N-diisopropylethylamine (6.54 mL, 39.6 mmol) and the resulting mixture was agitated at ambient temperature overnight. The mixture was poured into water (200 mL) to give a suspension, which was stirred for 30 min and filtered. The solid was washed with water (2×20 mL) and dried under vacuum at 40° C. for 3 h to give the desired product 5-fluoro-N-(2-fluoroethyl)-2-nitro-aniline as a yellow solid (3.4 g, 16.82 mmol, 84.9%).

$^1$H NMR (300 MHz, DMSO-d6) Shift=8.39 (br. s., 1H), 8.23-8.13 (m, 1H), 6.98 (dd, J=2.6, 12.3 Hz, 1H), 6.57 (ddd, J=2.6, 7.4, 9.7 Hz, 1H), 4.73 (t, J=4.9 Hz, 1H), 4.57 (t, J=4.9 Hz, 1H), 3.81-3.72 (m, 1H), 3.71-3.63 (m, 1H).

Intermediate S5 B20
4-fluoro-N2-(2-fluoroethyl)benzen-1,2-diamine

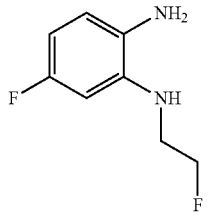 [SMILES: Nc1ccc(F)cc1NCCF]

To a magnetically stirred suspension of 5-fluoro-N-(2-fluoroethyl)-2-nitro-aniline (3.3 g, 16.32 mmol) in ethanol (60 mL) and water (60 mL) at 20° C. was added iron powder (4.5 mg, 81 mmol) and ammonium chloride (4.4 g, 81.62 mmol), and the resulting mixture was agitated at 60° C. for 2 h. The mixture was filtered hot through a pad of celite and the cake was washed with warm ethanol (2×20 mL). The combined filtrates were then evaporated to dryness to give a residue, which was partitioned between DCM (50 mL) and water (50 mL). The DCM layer was collected and evaporated to dryness to give the desired product 4-fluoro-N2-(2-fluoroethyl)benzene-1,2-diamine as a dark purple foam (2.50 g, 14.52 mmol, 89%).

$^1$H NMR (300 MHz, DMSO-d6) Shift=6.50 (dd, J=6.0, 8.4 Hz, 1H), 6.29 (dd, J=2.8, 11.7 Hz, 1H), 6.19 (dt, J=2.8, 8.5 Hz, 1H), 4.94 (t, J=5.1 Hz, 1H), 4.67 (t, J=5.0 Hz, 1H), 4.51 (t, J=5.0 Hz, 1H), 4.38 (s, 2H), 3.41 (q, J=5.2 Hz, 1H), 3.31 (q, J=5.2 Hz, 1H).

Intermediate S5 C20
5-fluoro-3-(2-fluoroethyl)-1H-benzimidazol-2-one

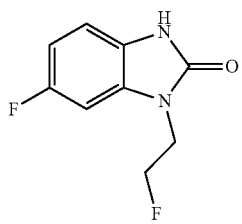 [SMILES: O=c1[nH]c2ccc(F)cc2n1CCF]

To a magnetically stirred solution of 4-fluoro-N2-(2-fluoroethyl)benzene-1,2-diamine (3.0 g, 17.4 mmol) in THF (80 mL) at 20° C. under nitrogen was added 1,1'-carbonyldiimidazole (3.39 g, 20.91 mmol), and the resulting mixture was agitated at ambient temperature for 2 h. The solvent was removed in vacuo to give a residue, which was partitioned between DCM (100 mL) and water (50 mL). The organic phase was collected and distilled to dryness to give a residue, which was purified by automated column chromatography (SiO$_2$; RediSep—40 g; 0 to 100% EtOAc in hexane) to afford the desired product 5-fluoro-3-(2-fluoroethyl)-1H-benzimidazol-2-one as a light pink solid (2.0 g, 10.09 mmol, 58%).

$^1$H NMR (300 MHz, DMSO-d6) Shift=11.12-10.84 (m, 1H), 7.13 (dd, J=2.4, 9.3 Hz, 1H), 6.95 (dd, J=4.8, 8.5 Hz, 1H), 6.81 (ddd, J=2.4, 8.3, 10.4 Hz, 1H), 4.74 (t, J=4.9 Hz, 1H), 4.58 (t, J=4.8 Hz, 1H), 4.15 (t, J=4.8 Hz, 1H), 4.07 (t, J=4.8 Hz, 1H)

Intermediate S5 D20 1-[5-(difluoromethyl)-1,3,4-oxadiazol-2-yl]-5-fluoro-3-(2-fluoroethyl)benzimidazol-2-one

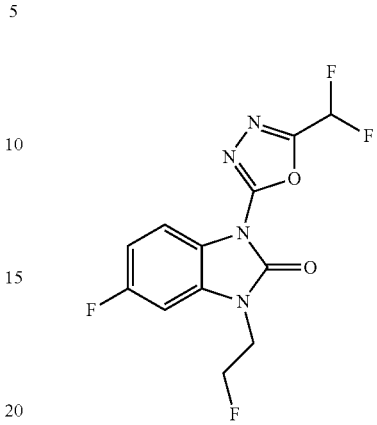

Prepared by the reaction 5-fluoro-3-(2-fluoroethyl)-1H-benzimidazol-2-one (200 mg, 1.01 mmol) with potassium carbonate (418.46 mg, 3.03 mmol), copper(I) iodide (19 mg, 0.10 mmol), 2-bromo-5-(difluoromethyl-1,3,4-oxadiazole (241 mg, 1.21 mmol) and trans-N,N'-dimethylcyclohexane-1,2-diamine (0.03 mL, 0.20 mmol) in 1,4-dioxane (6 mL) at 80° C. for 2 h. The desired compound 1-[5-(difluoromethyl)-1,3,4-oxadiazol-2-yl]-5-fluoro-3-(2-fluoroethyl)benzimidazol-2-one was isolated as a white solid (200 mg, 0.633 mmol, 63%).

$^1$H NMR (300 MHz, DMSO-d6) Shift=7.89 (dd, J=4.7, 8.9 Hz, 1H), 7.80-7.36 (m, 2H), 7.11 (ddd, J=2.6, 8.9, 9.8 Hz, 1H), 4.82 (t, J=4.7 Hz, 1H), 4.66 (t, J=4.7 Hz, 1H), 4.32 (t, J=4.7 Hz, 1H), 4.23 (t, J=4.7 Hz, 1H)

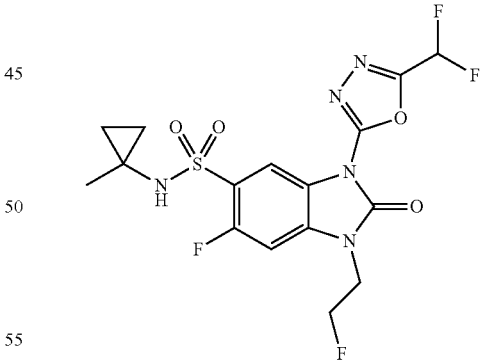

Prepared using the method described in Example 160 with 1-[5-(difluoromethyl)-1,3,4-oxadiazol-2-yl]-5-fluoro-3-(2-fluoroethyl)benzimidazol-2-one (100 mg, 0.316 mmol) and 1-methylcyclopropan-1-amine hydrochloride (25 mg, 0.232 mmol) to give the desired product 3-[5-(difluoromethyl)-1,3,4-oxadiazol-2-yl]-6-fluoro-1-(2-fluoroethyl)-N-(1-methylcyclopropyl)-2-oxo-benzimidazole-5-sulfonamide as a white solid (30 mg, 0.067 mmol, 21%).

Example 212 3-[5-(Difluoromethyl)-1,3,4-oxadiazol-2-yl]-6-fluoro-1-(2-fluoroethyl)-N-[1-(fluoromethyl)cyclopropyl]-2-oxo-benzimidazole-5-sulfonamide

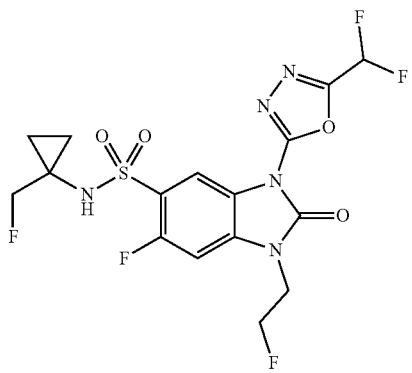 [SMILES: O=c1n(CCF)c2cc(F)c(S(=O)(=O)NC3(CF)CC3)cc2n1-c1nnc(C(F)F)o1]

Prepared using the method described in Example 160 with 1-[5-(difluoromethyl)-1,3,4-oxadiazol-2-yl]-5-fluoro-3-(2-fluoroethyl)benzimidazol-2-one (100 mg, 0.316 mmol) and 1-(fluoromethyl)cyclopropan-1-amine hydrochloride (29 mg, 0.232 mmol) to give the desired product 3-[5-(difluoromethyl)-1,3,4-oxadiazol-2-yl]-6-fluoro-1-(2-fluoroethyl)-N-[1-(fluoromethyl)cyclopropyl]-2-oxo-benzimidazole-5-sulfonamide as a white solid (30 mg, 0.064 mmol, 20%).

Example 213 3-[5-(Difluoromethyl)-1,3,4-thiadiazol-2-yl]-6-fluoro-N-[1-(fluoromethyl)cyclopropyl]-2-oxo-1-prop-2-ynyl-benzimidazole-5-sulfonamide Intermediate S13 A3—5-(difluoromethyl)-N-(4-fluoro-2-nitro-phenyl)-1,3,4-thiadiazol-2-amine

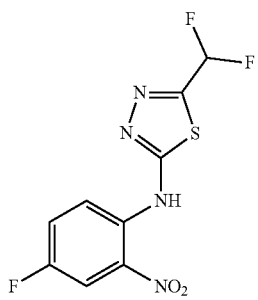 [SMILES: O=[N+]([O-])c1cc(F)ccc1Nc1nnc(C(F)F)s1]

To a magnetically stirred solution of 2,5-difluoronitrobenzene (1.87 mL, 15.7 mmol) and caesium carbonate (15.36 g, 47.1 mmol) in DMSO (50 mL) under nitrogen was added 5-(difluoromethyl)-1,3,4-thiadiazol-2-amine (2.49 g, 16.5 mmol), and the resulting mixture was stirred at 65° C. for 4 h. The mixture was cooled to ambient temperature and partitioned between water (250 mL) and EtOAc (100 mL). The organic phase was distilled to dryness and the resulting residue purified by automated column chromatography (100 g SNAP—0-100% EtOAc in hexane) to afford 5-(difluoromethyl)-N-(4-fluoro-2-nitro-phenyl)-1,3,4-thiadiazol-2-amine as a yellow solid (1.15 g, 3.95 mmol, 25%).

$^1$H NMR (300 MHz, DMSO-d6) Shift=10.77 (s, 1H), 8.35-8.16 (m, 1H), 8.09-7.99 (m, 1H), 7.72 (ddd, J=3.0, 7.7, 9.2 Hz, 1H), 7.61-7.20 (m, 1H)

Intermediate S13 B3—N1-[5-(difluoromethyl)-1,3,4-thiadiazol-2-yl]-4-fluoro-benzene-1,2-diamine

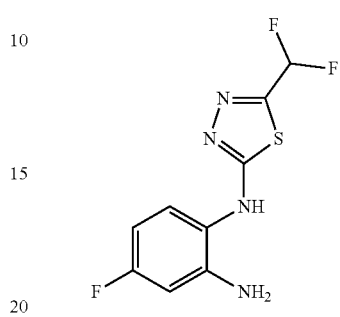

Iron powder (1.10 g, 19.73 mmol) and ammonium chloride (1.05 g, 19.7 mmol) were added to a stirred suspension of 5-(difluoromethyl)-N-(4-fluoro-2-nitro-phenyl)-1,3,4-thiadiazol-2-amine (1.14 g, 3.95 mmol) in ethanol (40 mL) and water (40 mL), and the resulting mixture was agitated at 60° C. for 1 h. The mixture was filtered (hot) through celite and the filter cake was washed with EtOH (2×40 mL). The combined filtrates were concentrated in vacuum to approximately 20 mL. The aqueous solution was then extracted with EtOAc (3×50 mL). The combined organic layers were dried over MgSO$_4$ and evaporated to afford a residue, which was purified by automated column chromatography (40 g SNAP—0 to 100% EtOAc in hexane) to afford N1-[5-(difluoromethyl)-1,3,4-thiadiazol-2-yl]-4-fluoro-benzene-1,2-diamine as a tan solid (727 mg, 2.79 mmol, 71%).

$^1$H NMR (300 MHz, DMSO-d6) Shift=9.56 (s, 1H), 7.52-6.89 (m, 2H), 6.45 (dd, J=2.9, 11.2 Hz, 1H), 6.26 (dt, J=2.9, 8.5 Hz, 1H), 5.35 (s, 2H)

Intermediate S13 C3—3-[5-(difluoromethyl)-1,3,4-thiadiazol-2-yl]-6-fluoro-1H-benzimidazol-2-one

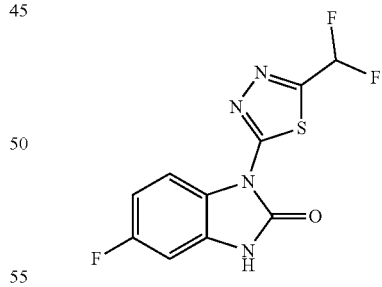

To a magnetically stirred solution of N1-[5-(difluoromethyl)-1,3,4-thiadiazol-2-yl]-4-fluoro-benzene-1,2-diamine (727 mg, 2.79 mmol) in DMF (8 mL) at 20° C. under nitrogen was added 1,1'-carbonyldiimidazole (543 mg, 3.35 mmol), and the resulting mixture was agitated at ambient temperature for 2 h. The solvent was removed in vacuo and to the resulting brown residue was added water (40 mL). A beige precipitate formed which was collected and washed with water to afford 3-[5-(difluoromethyl)-1,3,4-thiadiazol-2-yl]-6-fluoro-1H-benzimidazol-2-one as a pale brown solid (671 mg, 2.34 mmol, 84%).

¹H NMR (300 MHz, DMSO-d6) Shift=12.18 (br. s., 1H), 8.26 (dd, J=4.8, 9.5 Hz, 1H), 7.92-7.30 (m, 1H), 7.22-6.94 (m, 2H)

Intermediate S14 A3—3-[5-(difluoromethyl)-1,3,4-thiadiazol-2-yl]-6-fluoro-N-[1-(fluoromethyl)cyclopropyl]-2-oxo-1H-benzimidazole-5-sulfonamide

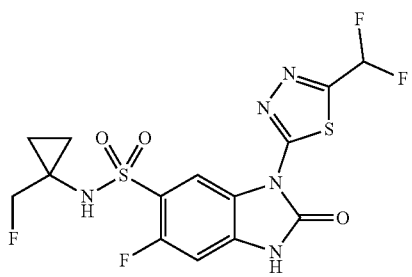 [SMILES: O=c1[nH]c2cc(F)c(S(=O)(=O)NC3(CF)CC3)cc2n1-c1nnc(C(F)F)s1]

Prepared according to the method described for Example 160 with 3-[5-(difluoromethyl)-1,3,4-thiadiazol-2-yl]-6-fluoro-1H-benzimidazol-2-one (671 mg, 2.34 mmol) and 1-(fluoromethyl)cyclopropan-1-amine hydrochloride (170 mg, 1.35 mmol) to afford 3-[5-(difluoromethyl)-1,3,4-thiadiazol-2-yl]-6-fluoro-N-[1-(fluoromethyl)cyclopropyl]-2-oxo-1H-benzimidazole-5-sulfonamide as an orange solid (250 mg, 0.572 mmol, 24%).
¹H NMR (300 MHz, DMSO-d6) Shift=12.81-12.38 (m, 1H), 8.78 (s, 1H), 8.68 (d, J=6.4 Hz, 1H), 7.64 (s, 2H), 7.33 (d, J=9.8 Hz, 1H), 4.41-4.00 (m, 2H), 0.76 (d, J=4.1 Hz, 4H).

Intermediate S14 B3—N-[1-acetyl-3-[5-(difluoromethyl)-1,3,4-thiadiazol-2-yl]-6-fluoro-2-oxo-benzimidazol-5-yl]sulfonyl-N-[1-(fluoromethyl)cyclopropyl]acetamide

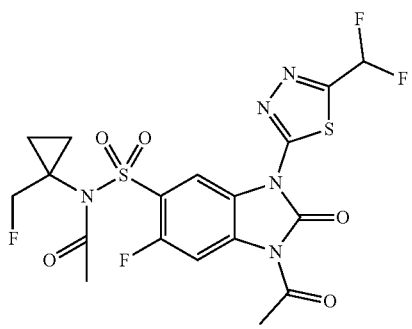 [SMILES: CC(=O)N(C1(CF)CC1)S(=O)(=O)c1cc2c(cc1F)n(C(C)=O)c(=O)n2-c1nnc(C(F)F)s1]

To a magnetically stirred solution of 3-[5-(difluoromethyl)-1,3,4-thiadiazol-2-yl]-6-fluoro-N-[1-(fluoromethyl)cyclopropyl]-2-oxo-1H-benzimidazole-5-sulfonamide (250 mg, 0.57 mmol) in pyridine (3 mL) at 20° C. under nitrogen was added acetic anhydride (0.27 mL, 2.86 mmol), and the resulting mixture was agitated overnight. The material was poured into water (25 mL) and the aqueous was extracted with DCM (2×50 mL). The DCM was passed through a hydrophobic frit and concentrated to dryness. The resulting solid was dissolved in the smallest amount of DCM and precipitated by the addition of hexane. The solid was collected via suction filtration and washed with hexane. The solid was air dried to afford N-[1-acetyl-3-[5-(difluoromethyl)-1,3,4-thiadiazol-2-yl]-6-fluoro-2-oxo-benzimidazol-5-yl]sulfonyl-N-[1-(fluoromethyl)cyclopropyl]acetamide as a brown solid (150 mg, 0.28 mmol, 50%).
¹H NMR (300 MHz, DMSO-d6) Shift=8.78 (d, J=6.6 Hz, 1H), 7.83-7.45 (m, 1H), 7.36 (d, J=10.5 Hz, 1H), 5.22-5.06 (m, 1H), 5.03-4.89 (m, 1H), 4.37-4.26 (m, 1H), 4.20-4.09 (m, 3H), 2.32-2.25 (m, 6H), 0.89-0.69 (m, 4H)

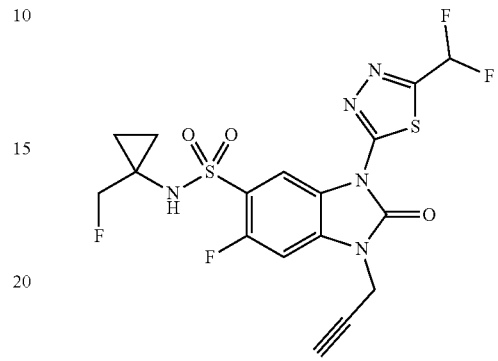

To a magnetically stirred solution of N-[1-acetyl-3-[5-(difluoromethyl)-1,3,4-thiadiazol-2-yl]-6-fluoro-2-oxo-benzimidazol-5-yl]sulfonyl-N-[1-(fluoromethyl)cyclopropyl]acetamide (70 mg, 0.13 mmol) and potassium carbonate (55.6 mg, 0.40 mmol) in DMF (2 mL) at 20° C. under nitrogen was added 3-bromopropyne (23.3 µL, 0.27 mmol), and the resulting mixture was agitated at 50° C. for 16 h. Mixture cooled to ambient temperature and treated with 4 mL of aqueous ammonia. The mixture was diluted with water to induce a precipitate. The mixture was stirred overnight then the solid was collected and purified by prep. HPLC (high pH) to give the desired product 3-[5-(difluoromethyl)-1,3,4-thiadiazol-2-yl]-6-fluoro-N-[1-(fluoromethyl)cyclopropyl]-2-oxo-1-prop-2-ynyl-benzimidazole-5-sulfonamide as a yellow solid (7.4 mg, 0.016 mmol, 12%).

Example 214 2-[3-[5-(Difluoromethyl)-1,3,4-thiadiazol-2-yl]-6-fluoro-5-[[1-(fluoromethyl)cyclopropyl]sulfamoyl]-2-oxo-benzimidazol-1-yl]acetamide

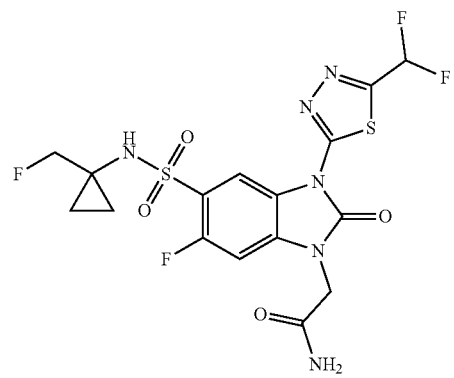 [SMILES: NC(=O)Cn1c(=O)n(-c2nnc(C(F)F)s2)c2cc(S(=O)(=O)NC3(CF)CC3)c(F)cc21]

Isolated as an impurity during the preparation of Example 215.

Example 215 1-(Cyanomethyl)-3-[5-(difluoromethyl)-1,3,4-thiadiazol-2-yl]-6-fluoro-N-[1-(fluoromethyl)cyclopropyl]-2-oxo-benzimidazole-5-sulfonamide Intermediate S10 B5—2-[3-[5-(difluoromethyl)-1,3,4-thiadiazol-2-yl]-6-fluoro-2-oxo-benzimidazol-1-yl]acetonitrile

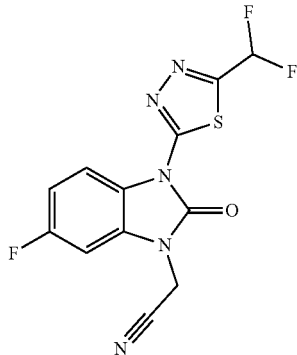 [SMILES: N#CCn1c(=O)n(-c2nnc(C(F)F)s2)c2ccc(F)cc21]

To a magnetically stirred solution of 3-[5-(difluoromethyl)-1,3,4-thiadiazol-2-yl]-6-fluoro-1H-benzimidazol-2-one (168 mg, 0.59 mmol) and potassium carbonate (243 mg, 1.76 mmol) in DMF (4 mL) was added bromoacetonitrile (81.7 µL, 1.17 mmol), and the resulting mixture was agitated at 50° C. for 1 h. Water (50 mL) was added which induced a precipitate that was collected via suction filtration. The solid was dissolved up in EtOAc, dried over MgSO₄ and evaporated to afford 2-[3-[5-(difluoromethyl)-1,3,4-thiadiazol-2-yl]-6-fluoro-2-oxo-benzimidazol-1-yl]acetonitrile as a light brown solid (147 mg, 0.452 mmol, 77%).

$^1$H NMR (300 MHz, DMSO-d6) Shift=8.41-8.31 (m, 1H), 7.63 (s, 2H), 7.30-7.18 (m, 1H), 5.30 (s, 2H)

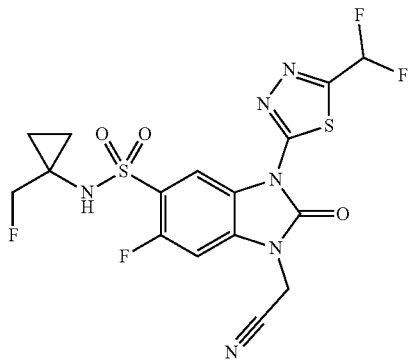 [SMILES: N#CCn1c(=O)n(-c2nnc(C(F)F)s2)c2cc(S(=O)(=O)NC3(CF)CC3)c(F)cc21]

Prepared according to the method described in Example 160 using 2-[3-[5-(difluoromethyl)-1,3,4-thiadiazol-2-yl]-6-fluoro-2-oxo-benzimidazol-1-yl]acetonitrile (148 mg, 0.455 mmol) and 1-(fluoromethyl)cyclopropan-1-amine hydrochloride (112 mg, 0.897 mmol) to give the desired 2-[3-[5-(difluoromethyl)-1,3,4-thiadiazol-2-yl]-6-fluoro-2-oxo-benzimidazol-1-yl]acetonitrile (2.6 mg, 0.005 mmol, 1%)

Example 216 3-[5-(Difluoromethyl)-1,3,4-thiadiazol-2-yl]-6-fluoro-1-(2-fluoroethyl)-N-[1-(fluoromethyl)cyclopropyl]-2-oxo-benzimidazole-5-sulfonamide

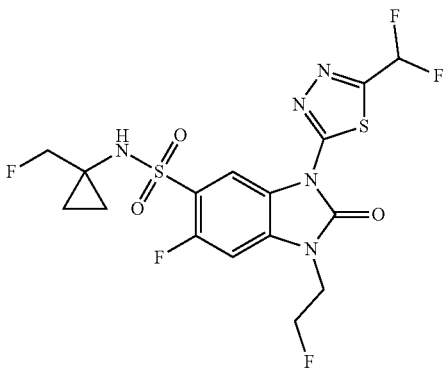 [SMILES: O=c1n(CCF)c2cc(F)c(S(=O)(=O)NC3(CF)CC3)cc2n1-c1nnc(C(F)F)s1]

1-[5-(Difluoromethyl)-1,3,4-thiadiazol-2-yl]-5-fluoro-3-(2-fluoroethyl)benzimidazol-2-one was prepared by the reaction of 5-fluoro-3-(2-fluoroethyl)-1H-benzimidazol-2-one (250 mg, 1.26 mmol) with potassium carbonate (523 mg, 3.79 mmol), copper(I) iodide (24 mg, 0.13 mmol), 2-bromo-5-(difluoromethyl)-1,3,4-thiadiazole (298 mg, 1.21 mmol) and trans-N,N-dimethylcyclohexane-1,2-diamine (0.04 mL, 0.25 mmol) in DMSO (3 mL) at 80° C. for 2 h. The mixture was cooled to ambient temperature and filtered through celite washing with EtOAc (100 mL). The organic phase was collected and washed with water (3×50 mL), dried over MgSO4 and distilled to dryness. The resulting residue was purified by automated column chromatography (12 g SNAP—0-100% EtOAc in hexane) to afford the desired compound 1-[5-(difluoromethyl)-1,3,4-thiadiazol-2-yl]-5-fluoro-3-(2-fluoroethyl)benzimidazol-2-one as a pale green solid (241 mg, 0.725 mmol, 57%).

$^1$H NMR (300 MHz, DMSO-d6) Shift=8.34 (dd, J=4.9, 8.9 Hz, 1H), 7.82-7.42 (m, 2H), 7.17 (ddd, J=2.6, 9.3, 10.6 Hz, 1H), 4.85 (t, J=4.6 Hz, 1H), 4.69 (t, J=4.7 Hz, 1H), 4.38 (t, J=4.7 Hz, 1H), 4.29 (t, J=4.7 Hz, 1H)

The title compound was prepared using the method described in Example 160 with 1-[5-(difluoromethyl)-1,3,4-thiadiazol-2-yl]-5-fluoro-3-(2-fluoroethyl)benzimidazol-2-one (120 mg, 0.363 mmol) and 1-(fluoromethyl)cyclopropan-1-amine hydrochloride (73 mg, 0.58 mmol) to give the desired product 3-[5-(difluoromethyl)-1,3,4-thiadiazol-2-yl]-6-fluoro-1-(2-fluoroethyl)-N-[1-(fluoromethyl)cyclopropyl]-2-oxo-benzimidazole-5-sulfonamide as a white solid (24 mg, 0.05 mmol, 17%).

Example 217 3-[5-(Difluoromethyl)-1,3,4-thiadiazol-2-yl]-6-fluoro-1-(2-fluoroethyl)-N-(1-methylcyclopropyl)-2-oxo-benzimidazole-5-sulfonamide

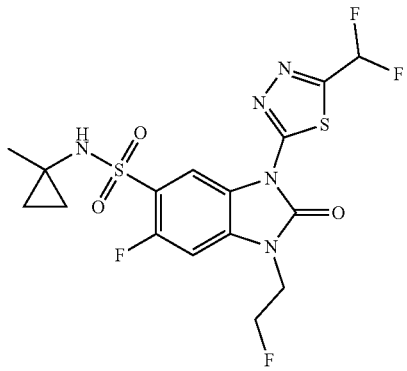 [SMILES: CC1(NS(=O)(=O)c2cc3c(cc2F)n(CCF)c(=O)n3-c2nnc(C(F)F)s2)CC1]

Prepared using the method described in Example 160 with 1-[5-(difluoromethyl)-1,3,4-thiadiazol-2-yl]-5-fluoro-3-(2-fluoroethyl)benzimidazol-2-one (120 mg, 0.363 mmol), which was prepared as described in Example 216, and 1-methylcyclopropan-1-amine hydrochloride (62 mg, 0.58 mmol) to give the desired product 3-[5-(difluoromethyl)-1,3,4-3-[5-(difluoromethyl)-1,3,4-thiadiazol-2-yl]-6-fluoro-1-(2-fluoroethyl)-N-(1-methylcyclopropyl)-2-oxo-benzimidazole-5-sulfonamide as a white solid (42 mg, 0.09 mmol, 31%).

Example 218 Ethyl 3-methyl-5-[(1-methylcyclopropyl)sulfamoyl]benzofuran-2-carboxylate

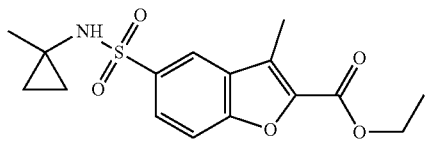 [SMILES: CCOC(=O)c1oc2ccc(S(=O)(=O)NC3(C)CC3)cc2c1C]

To a solution of N,N-diisopropylethylamine (0.12 mL, 0.70 mmol) in THF (5 mL) cooled in an ice bath, was added a mixture of 1-methylcyclopropanamine hydrochloride (0.04 mL, 0.34 mmol) and ethyl 5-(chlorosulfonyl)-3-methyl-1-benzofuran-2-carboxylate (100 mg, 0.33 mmol) in DCM (3 mL) and the mixture stirred overnight at ambient temperature. The mixture was diluted with water, extracted twice with DCM. The extracts were evaporated to dryness and the crude product mixture was purified by prep HPLC (high pH) to give the desired product (47 mg, 0.14 mmol, 42%) as a white powder.

PARG Assays (Biological Activity)
PARG assay

PARG In vitro assays were conducted in a total volume of 15 ul in a standard 384 well format. 5 ul of Human Full Length PARG (Produced internally by Astra Zeneca), used at a final reaction concentration of 80 μM, was added to 5 ul of Ribosylated PARP substrate (also produced internally by Astra Zeneca) at final reaction concentration of 4.5 nM in assay buffer (50 mM Tris pH7.4, 0.1 mg/ml BSA, 3 mM EDTA, 0.4 mM EGTA, 1 mM DTT, 0.01% Tween 20, 50 mM KCl). The reaction was incubated at room temperature for 10 minutes and then 5 ul detection reagent was added. Detection Reagent consists of 42 nM MAb Anti-6HIS XL665 (CisBio: 61 HISXLB) and 2.25 nM Streptavidin Europium Cryptate (CisBio: 610SAKLB), both at 3× working stock concentrations (final concentrations of 14 nM and 0.75 nM respectively), in a detection buffer of 50 mM Tris pH7.4, BSA at 0.1 mg/ml and KF at 100 mM. Following incubation at room temperature for 60 minutes in the dark, TR-FRET signal was measured at Ex 340 and Em 665 and Em 620. A ratio was calculated as Em665/EM620x104 for each well and used to calculate percent inhibition for test compounds.

PARG Cell Assays

This method is based on the detection of endogenous levels of poly (ADP) ribose chains present in the nucleus of HeLa cell line using indirect immunofluorescence. MMS stimulation increases PAR chains for up to 25 mins. After that point, PARG is active and breaks down the PAR chains, until by one hour after stimulation no PAR chains are detectable. Inhibition of PARG maintains PAR chains.

Briefly, following compound treatment and treatment with the DNA damaging agent methylmethanesulfonate (MMS), the cell monolayer is fixed, then permeabilised and incubated with a mouse monoclonal antibody raised against multimers of poly(ADP) ribose. After an overnight incubation, excess antibody is removed by washing and an Alexafluor 488-linked secondary antibody which recognises the mouse monoclonal is added together with a nuclear stain (Hoechst 33342). Images of the cells are then captured and analysed on a High Content Screening platform and the total intensity of the nuclear fluorescent signal at 488 nM is quantified. An increase in fluorescence indicates that more PAR chains are present and therefore the magnitude of PARG inhibition.

HeLa cells, seeded in 384-well plates, at 4000/well in 30 μL RPMI 1640 media, supplemented with 10% FBS and 2 mM Glutamax, were incubated overnight at 37° C., 5% CO2.

The following day, cells were dosed in quadruplicate with compound (10 point dose response) and incubated for 1 h at 37° C., 5% CO2.

At the end of the 1 h dosing period, MMS was added to duplicates at a final concentration of 50 pig/mL, for a further hour.

Media was tipped off and the cells fixed with 50 μL ice-cold 95% MetOH/PBS for 15 mins at −20° C. Following a PBS wash, 50 μL PBS/0.1% Triton was added to the cells for 20 mins. Following another PBS wash, anti-PAR antibody (Calbiochem AM80) was diluted 1:4000 in a buffer (PBS+0.5% FBS+0.05% Tween20) and added to the cells and incubated overnight at 4° C.

The following day, cells were washed three times with PBS and then incubated for 1 hr with secondary antibody (Alexa Fluor® 488 goat anti mouse IgG (H+L)) diluted 1:1000 and Hoechst diluted 1:5000 in buffer (5% FBS in PBS+0.05% Tween20).

Cells were washed three times with PBS and the plate sealed with a light-proof seal.

Images of the cells were captured on a ThermoFisher Celllnsight and the mean total intensity of spots fluorescent at 485 nm in the nucleus was reported.

TABLE 1

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 1 | | A1 | | 9.410 |
| Example 2 | | A1 | | 4.995 |
| Example 3 | | A2 | | 8.283 |
| Example 4 | | A2 | | 2.906 |
| Example 5 | | A2 | | 6.761 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 6 | | A10 | 8.319 | |
| Example 7 | | A10 | 9.787 | |
| Example 8 | | A10 | 4.506 | |
| Example 9 | | A10 | 4.040 | |
| Example 10 | | A10 | 8.418 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 11 | | A2 | 4.672 | |
| Example 12 | | A2 | 8.294 | |
| Example 13 | | A2 | 7.117 | |
| Example 14 | | Scheme 8 | 4.278 | |
| Example 15 | | A10 | 6.593 | |
| Example 16 | | A10 | 3.385 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 17 | | A10 | 4.781 | |
| Example 18 | | A10 | 7.560 | |
| Example 19 | | A10 | 5.358 | |
| Example 20 | | A10 | 3.500 | |
| Example 21 | | Scheme 8 | 5.233 | |
| Example 22 | | A10 | 9.181 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 23 | | A10 | | 8.832 |
| Example 24 | | A2 | | 2.797 |
| Example 25 | | Scheme 8 | | 8.918 |
| Example 26 | | A13 | | 6.991 |
| Example 27 | | A2 | | 0.925 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 28 | 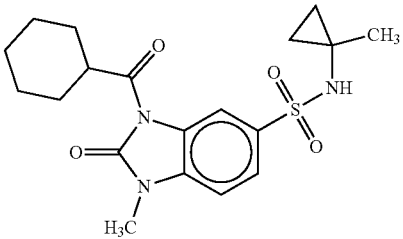 | A2 | | 0.352 |
| Example 29 | 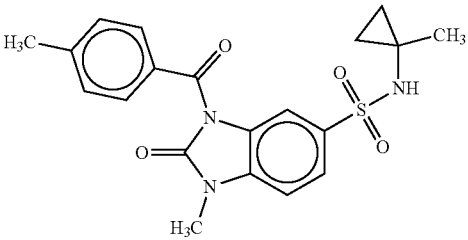 | A2 | | 4.456 |
| Example 30 | 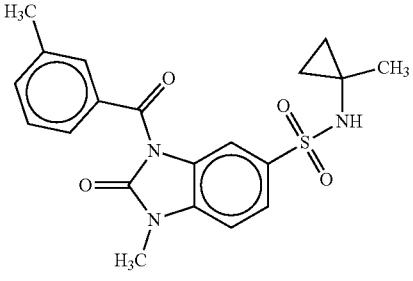 | A2 | | 9.568 |
| Example 31 | 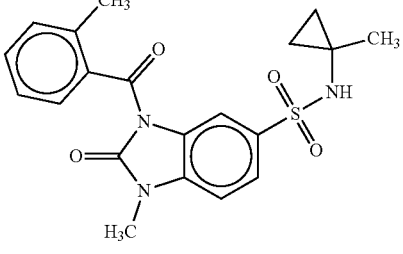 | A2 | | 4.912 |
| Example 32 | 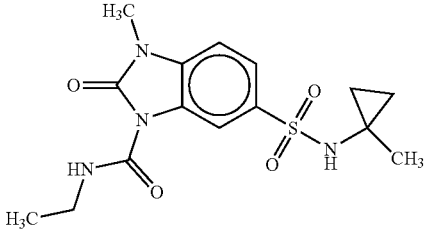 | A2 | | 6.859 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 33 | 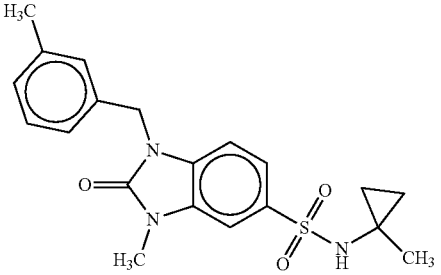 | A4 | 6.312 | |
| Example 34 | 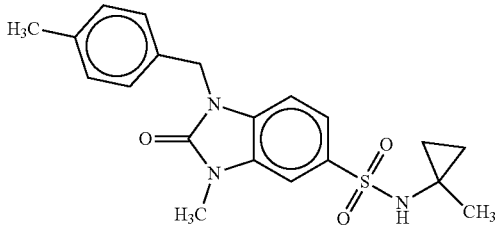 | A4 | 6.205 | |
| Example 35 | 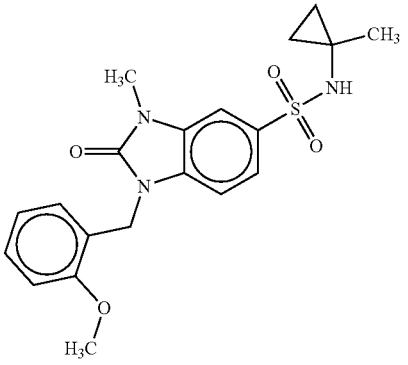 | A4 | 7.694 | |
| Example 36 | 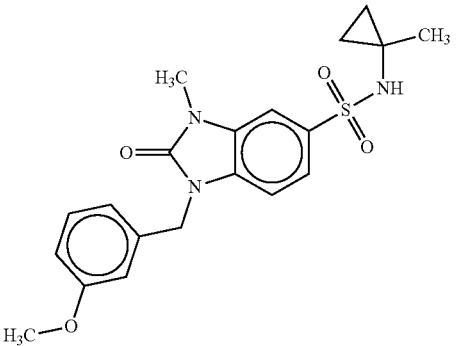 | A4 | 6.166 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 37 | | A4 | 3.145 | |
| Example 38 | | A4 | 5.715 | |
| Example 39 | | A4 | 3.737 | |
| Example 40 | | A4 | 6.303 | |
| Example 41 | | A4 | 5.769 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 42 | | A4 | 2.347 | |
| Example 43 | | A4 | 5.245 | |
| Example 44 | | A4 | 3.354 | |
| Example 45 | | A4 | 3.204 | |
| Example 46 | | A4 | 9.747 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 47 | | A4 | 5.718 | |
| Example 48 | | A4 | 7.833 | |
| Example 49 | | A4 | 5.071 | |
| Example 50 | | A4 | 4.913 | |
| Example 51 | | A4 | 5.262 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 52 | | A14 | 5.158 | |
| Example 53 | | A14 | 2.857 | |
| Example 54 | | A14 | 9.071 | |
| Example 55 | | A3 | 7.047 | |
| Example 56 | | One pot sulfonyl chloride formation/ sulphonamide synthesis | 8.296 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 57 | | A13 | | 5.634 |
| Example 58 | | A4 | | 4.645 |
| Example 59 | | A4 | | 2.656 |
| Example 60 | | A4 | | 5.962 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean ($\mu$M) |
|---|---|---|---|---|
| Example 61 | | A4 | 6.062 | |
| Example 62 | | A4 | 5.901 | |
| Example 63 | | A4 | 4.172 | |
| Example 64 | | A4 | 8.501 | |
| Example 65 | | A4 | 9.799 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 66 | | A3 | | 1.349 |
| Example 67 | | Wittig reaction and acid deprotection | | 4.454 |
| Example 68 | | A14 | | 0.902 |
| Example 69 | | Wittig reaction and acid deprotection | | 3.214 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 70 | 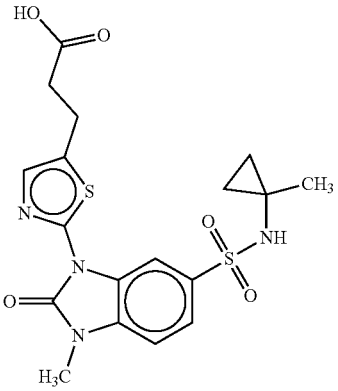 | Hydrogenation | 0.804 | |
| Example 71 | 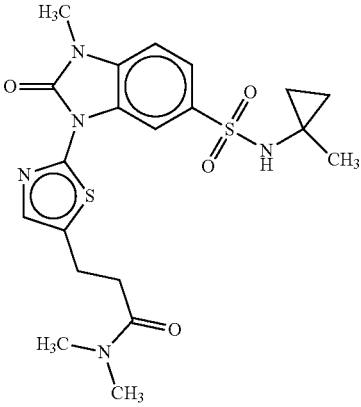 | Amide formation | 7.053 | |
| Example 72 | 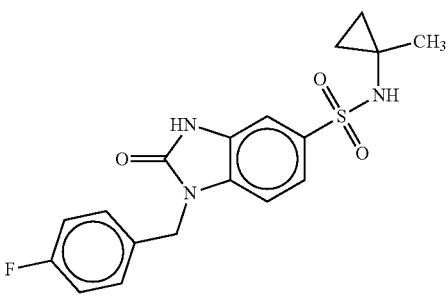 | Intermediate S3-D1 | 8.300 | |
| Example 73 | 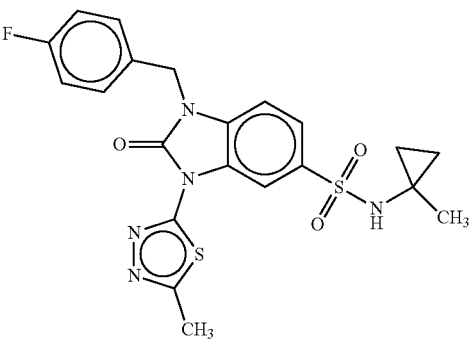 | A14 | 0.636 | 0.107 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 74 | 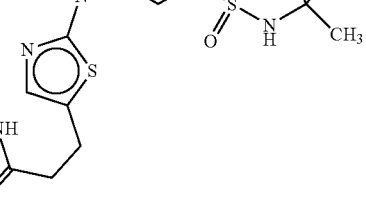 | Amide formation | 9.731 | |
| Example 75 | 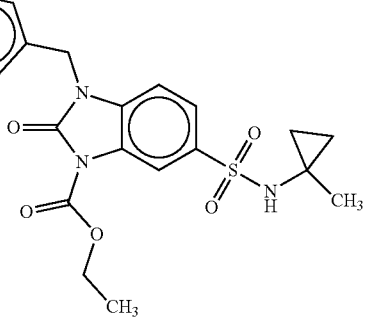 | A3 | 0.925 | |
| Example 76 | 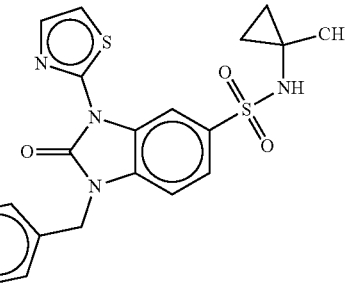 | A14 | 2.714 | |
| Example 77 | 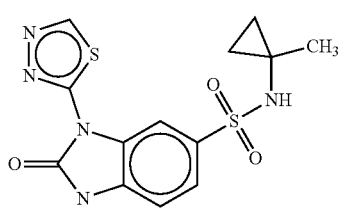 | A14 | 5.002 | |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 78 | 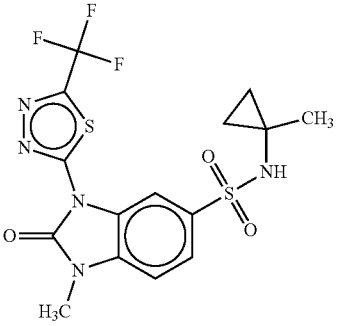 | A14 | 0.717 | |
| Example 79 | 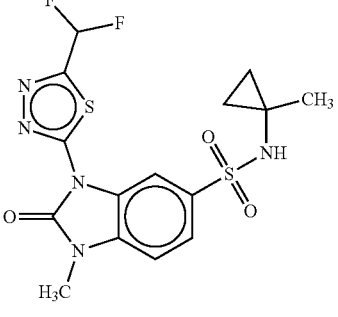 | A14 | 0.652 | |
| Example 80 | 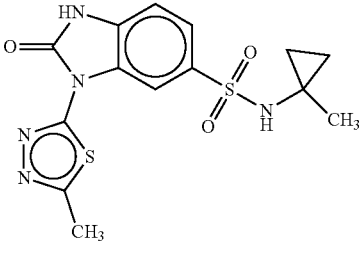 | Intermediate S4-C2 | 0.732 | |
| Example 81 | 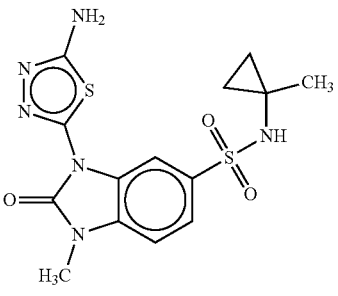 | Amine deprotection | 1.552 | |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 82 | 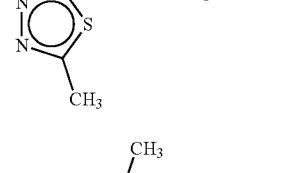 | A5 | 0.155 | 0.193 |
| Example 83 | 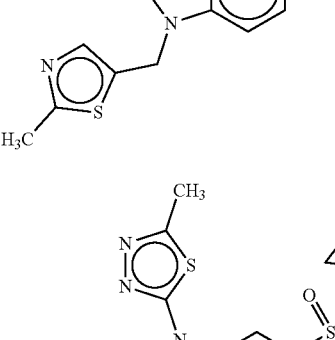 | A11 | 0.151 | 0.127 |
| Example 84 | 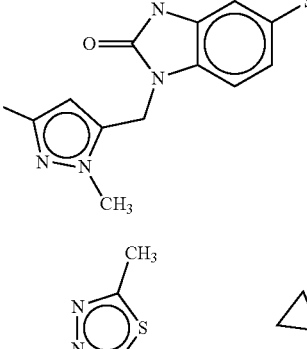 | A11 | 0.359 | 0.271 |
| Example 85 | 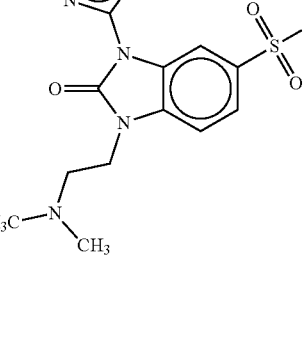 | A5 | 0.684 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 86 | | A5 | 0.403 | 0.277 |
| Example 87 | | A11 | 0.068 | 0.109 |
| Example 88 | | A11 | 0.053 | 0.038 |
| Example 89 | | Intermediate S3-D2 | 9.266 | |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 90 | 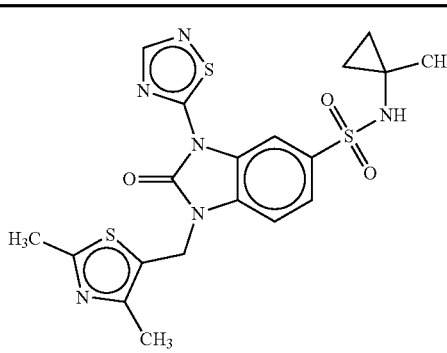 | A15 | 0.040 | 0.063 |
| Example 91 | 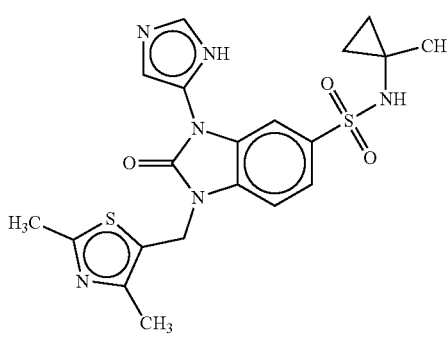 | A15 | 3.041 | |
| Example 92 | 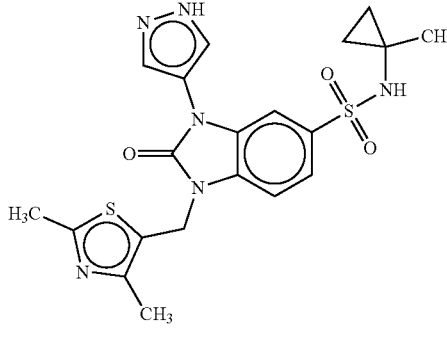 | A15 | 3.315 | |
| Example 93 | 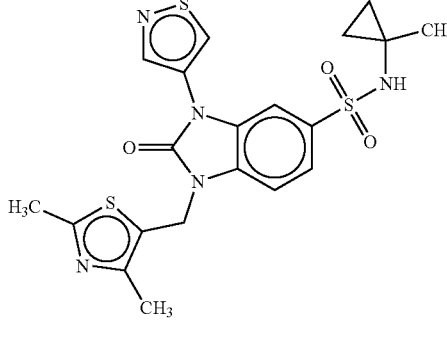 | A15 | 1.340 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 94 | | Intermediate S4-C1 | 1.455 | |
| Example 95 | | A15 | 0.740 | |
| Example 96 | | A15 | 7.029 | |
| Example 97 | | A15 | 0.816 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 98 | | A15 | 0.359 | 0.694 |
| Example 99 | | A11 | 0.202 | 0.342 |
| Example 100 | | A5 | 0.265 | 0.194 |
| Example 101 | | A12 | 0.246 | 0.390 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 102 | 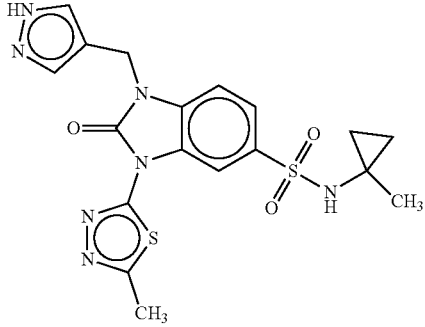 | A12 | 0.212 | 0.508 |
| Example 103 | 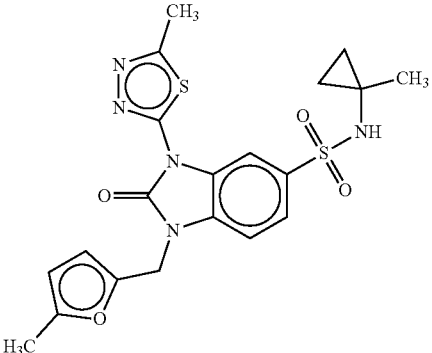 | A12 | 0.284 | 0.221 |
| Example 104 | 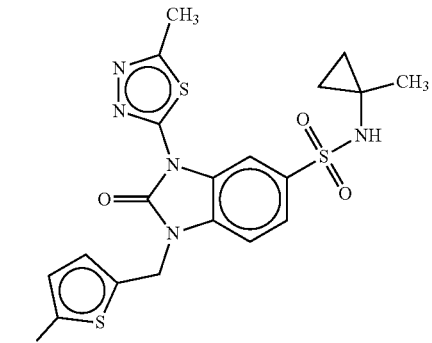 | A12 | 0.280 | 0.245 |
| Example 105 | 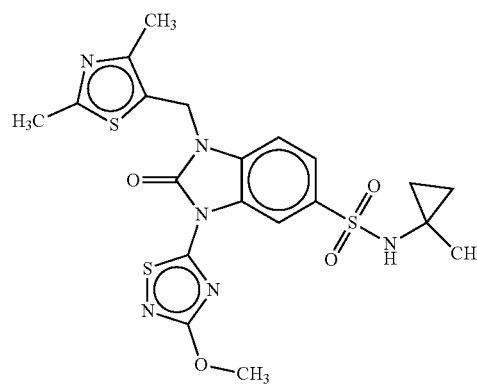 | A12 | 0.269 | 0.246 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 106 | 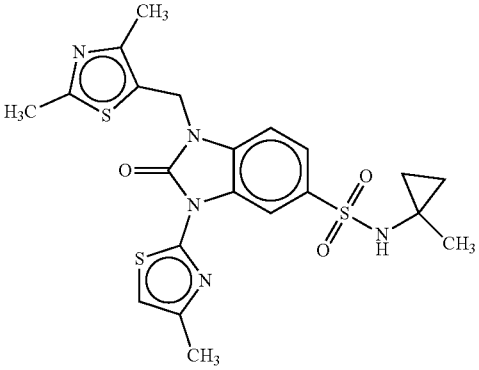 | A15 | 1.516 | |
| Example 107 | 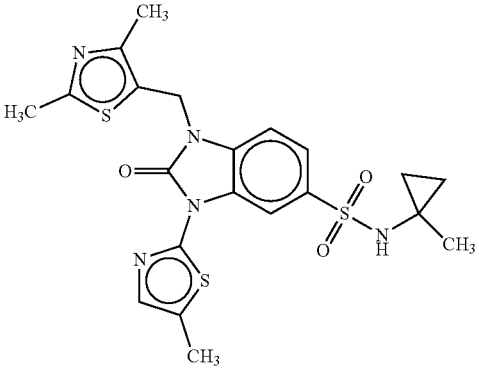 | A15 | 0.086 | 0.159 |
| Example 108 | 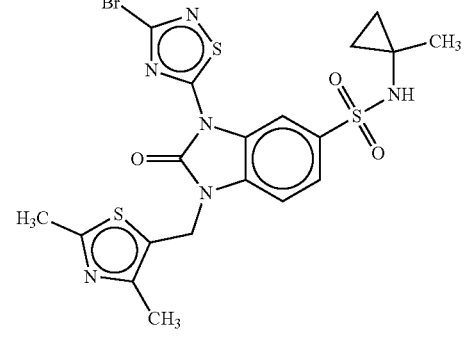 | A15 | 0.069 | 0.067 |
| Example 109 | 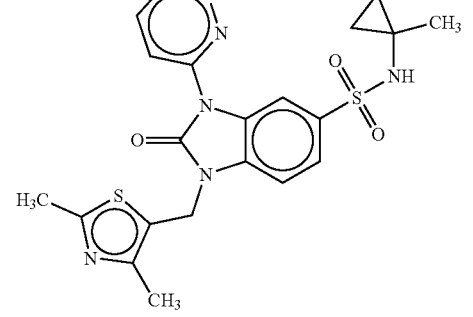 | A15 | 0.878 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 110 | | A15 | 0.234 | |
| Example 111 | | A15 | 0.147 | 0.507 |
| Example 112 | | A3 | 0.140 | 0.850 |
| Example 113 | | A13 | 0.632 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 114 | | Scheme 5 | 0.679 | |
| Example 115 | | Scheme 7 | 2.320 | |
| Example 116 | | Scheme 5 | 0.245 | 0.197 |
| Example 117 | | A3 | 0.275 | 24.670 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 118 | 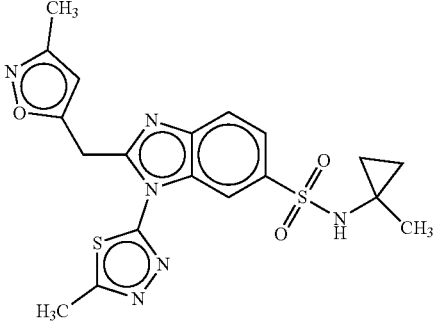 | Scheme 9 | | 0.671 |
| Example 119 | 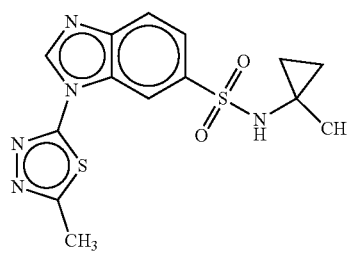 | Scheme 9 | | 1.034 |
| Example 120 | 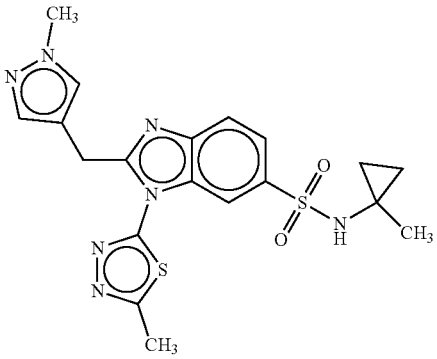 | Scheme 9 | | 0.867 |
| Example 121 | 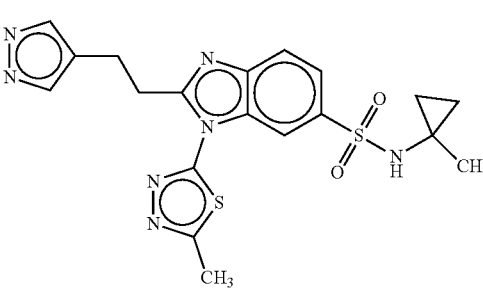 | Scheme 9 | | 1.018 |
| Example 122 | 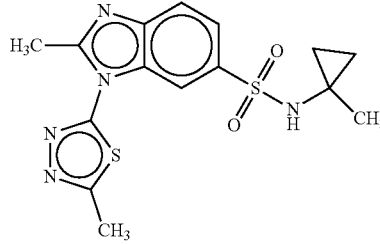 | Scheme 9 | | 1.529 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 123 | | Scheme 5 | | 0.734 |
| Example 124 | | Scheme 9 | | 7.677 |
| Example 125 | | Scheme 9 | | 2.556 |
| Example 126 | | Scheme 7 | | 4.275 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 127 | | Scheme 7 | 6.046 | |
| Example 128 | | Scheme 7 | 2.108 | |
| Example 129 | | Scheme 7 | 0.371 | 0.251 |
| Example 130 | | Scheme 7 | 0.218 | 0.1352 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 131 | | Scheme 7 | 0.261 | 0.2284 |
| Example 132 | | Scheme 7 | 7.422 | |
| Example 133 | | A6 | 1.135 | |
| Example 134 | | A6 | 0.910 | |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 135 | 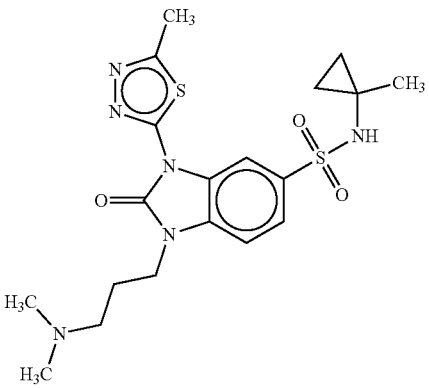 | A7 | 0.512 | 0.371 |
| Example 136 | 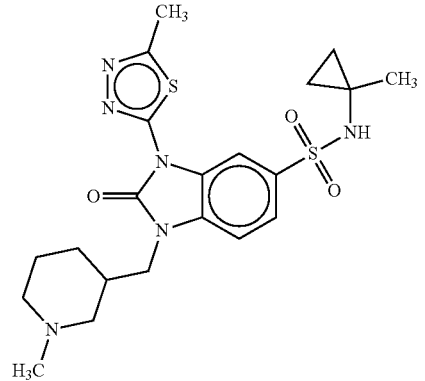 | A7 | 0.567 | |
| Example 137 | 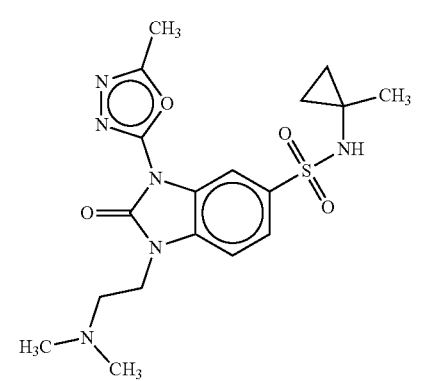 | A6 | 2.284 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 138 | | A7 | | 1.020 |
| Example 139 | | A6 | | 1.154 |
| Example 140 | | A7 | | 1.969 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 141 | | A7 | 1.116 | |
| Example 142 | | A7 | 3.800 | |
| Example 143 | | A7 | 0.441 | 0.343 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 144 | | Scheme 7 | 0.595 | |
| Example 145 | | Scheme 7 | 0.134 | 0.0466 |
| Example 146 | | Scheme 6 | 1.192 | |
| Example 147 | | A6 | 0.461 | 0.437 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 148 | 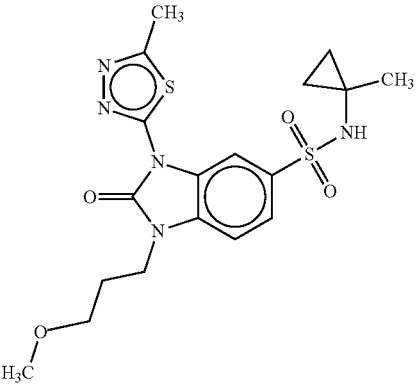 | A7 | 0.373 | 0.238 |
| Example 149 | 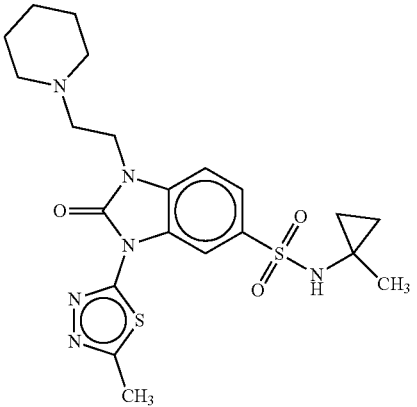 | A7 | 0.735 | |
| Example 150 | 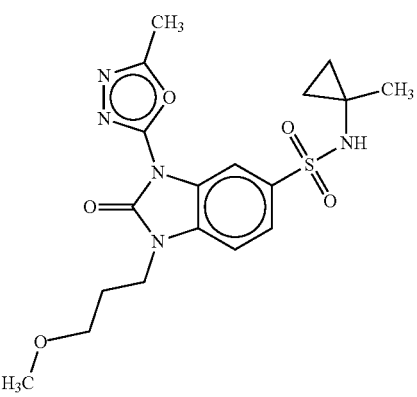 | A8 | 0.904 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 151 | | A8 | 1.156 | |
| Example 152 | | A8 | 0.275 | 0.194 |
| Example 153 | | A8 | 1.121 | |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 154 | | A8 | 0.614 | 9.082 |
| Example 155 | | A9 | 0.464 | 0.166 |
| Example 156 | | Scheme 5 | 0.686 | 0.589 |
| Example 157 | | Scheme 10 | 1.166 | 3.495 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 158 | 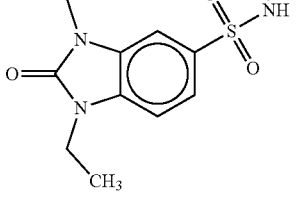 | Scheme 10 | 1.037 | 0.486 |
| Example 159 | 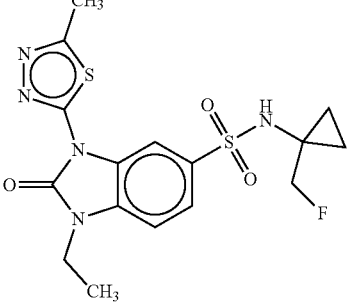 | Scheme 10 | 0.590 | 0.349 |
| Example 160 | 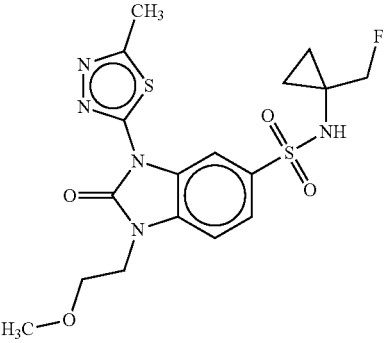 | Scheme 11 | 0.616 | 0.453 |
| Example 161 | 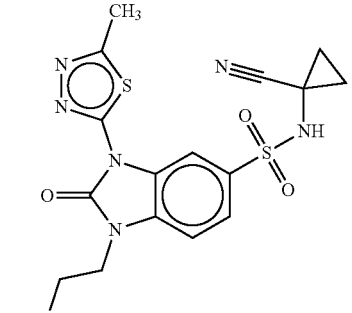 | Scheme 11 | 0.616 | 0.491 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 162 | | Scheme 11 | 0.260 | 0.176 |
| Example 163 | | Scheme 11 | 0.090 | 0.104 |
| Example 164 | | Scheme 11 | 0.203 | 0.109 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 165 | 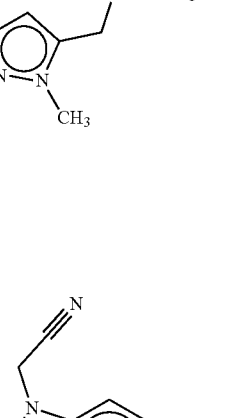 | Scheme 11 | 0.234 | 0.127 |
| Example 166 | 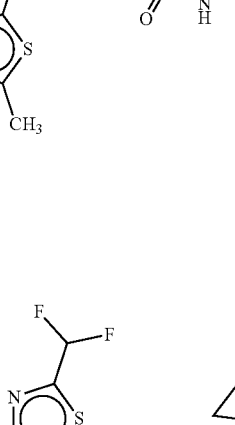 | Sulfonyl chloride formation/ sulfonamide synthesis | 0.784 | 0.291 |
| Example 167 | 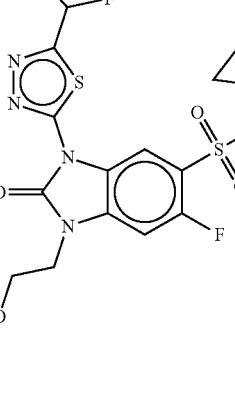 | Benzimidazolone N1-alkylation | 0.074 | 0.046 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean ($\mu$M) |
|---|---|---|---|---|
| Example 168 | | Example 160 | 0.099 | 0.032 |
| Example 169 | | Example 160 | 0.355 | 0.036 |
| Example 170 | | Scheme 12 | 0.092 | 0.089 |
| Example 171 | | Example 160 | 7.113 | 1.555 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 172 | | Example 160 | 12.030 | 2.087 |
| Example 173 | | Example 160 | 0.141 | 0.064 |
| Example 174 | | Example 160 | 0.091 | 0.041 |
| Example 175 | | Example 160 | 0.250 | 0.551 |
| Example 176 | | Example 160 | 6.021 | 1.787 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 177 | 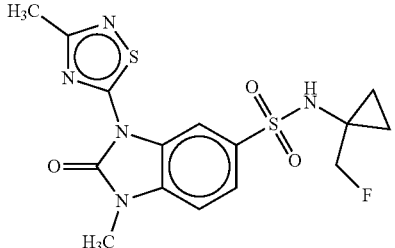 | Example 160 | 12.160 | 2.539 |
| Example 178 | 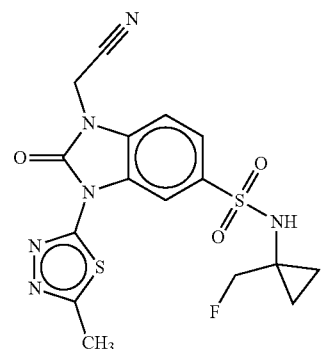 | Example 160 | 0.682 | 0.903 |
| Example 179 | 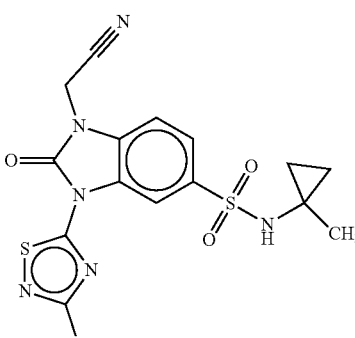 | Example 160 | 1.147 | 1.162 |
| Example 180 | 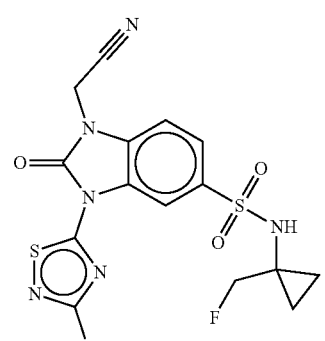 | Example 160 | 1.130 | 1.935 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 181 | | Example 160 | 0.291 | 0.109 |
| Example 182 | | Example 160 | 0.309 | 0.537 |
| Example 183 | | Example 160 | 0.549 | 0.376 |
| Example 184 | | Example 160 | 1.394 | 0.701 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 185 | | Benzimidazolone N1-alkylation | 3.780 | 0.740 |
| Example 186 | | Example 185 | 4.228 | 3.118 |
| Example 187 | | Example 185 | 0.427 | 0.201 |
| Example 188 | | Example 185 | 0.610 | 0.347 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 189 | | Benzimidazolone N1-alkylation | 1.793 | 1.226 |
| Example 190 | | Benzimidazolone N1-alkylation | 0.934 | 0.404 |
| Example 191 | | Benzimidazolone N1-alkylation | 0.967 | 0.807 |
| Example 192 | | Example 160 | 1.455 | 11.680 |

257
258
TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 193 | 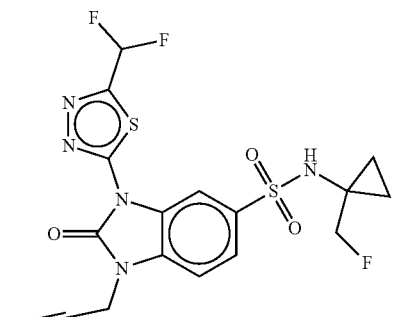 | Benzimidazolone N1-alkylation | 0.153 | 0.040 |
| Example 194 | 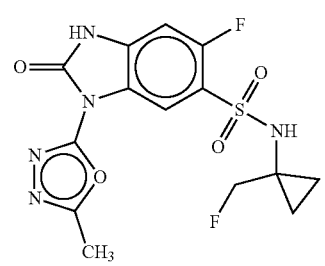 | Example 160 | 1.240 | >30 |
| Example 195 | 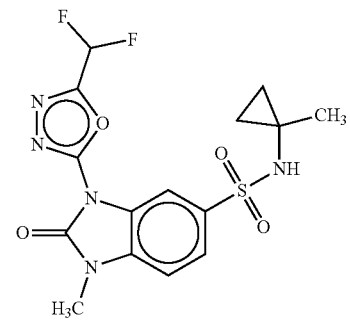 | Example 160 | 1.009 | 0.457 |
| Example 196 | 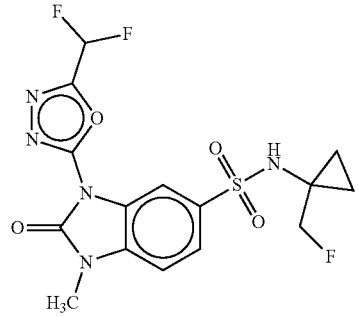 | Example 160 | 0.789 | 0.469 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 197 | | Benzimidazolone N1-alkylation | 0.759 | 0.538 |
| Example 198 | | Benzimidazolone N1-alkylation | 0.419 | 0.297 |
| Example 199 | | Example 160 | 0.314 | 0.145 |
| Example 200 | | Example 160 | 0.112 | 0.126 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean ($\mu$M) |
|---|---|---|---|---|
| Example 201 | | Example 160 | 0.759 | 0.189 |
| Example 202 | | Example 160 | 0.421 | 0.240 |
| Example 203 | | Example 160 | 4.833 | 3.704 |
| Example 204 | | Example 160 | 6.190 | 4.229 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 205 | | Example 160 | 6.687 | 5.756 |
| Example 206 | | Example 160 | 3.974 | 0.970 |
| Example 207 | | Example 160 | 0.133 | 0.024 |
| Example 208 | | Example 160 | 0.054 | 0.029 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (µM) |
|---|---|---|---|---|
| Example 209 | | Example 160 | 0.930 | 0.219 |
| Example 210 | | Example 160 | 0.349 | 0.224 |
| Example 211 | | Example 160 | 0.401 | 0.135 |
| Example 212 | | Example 160 | 0.129 | 0.110 |

TABLE 1-continued
Method of synthesis and PARG activity (Biochem and Cell Activity)
| EXAMPLE | COMPOUNDS | METHOD | PARG_EC50_ENZYME | PARG Cell IC50 Geomean (μM) |
|---|---|---|---|---|
| Example 213 | 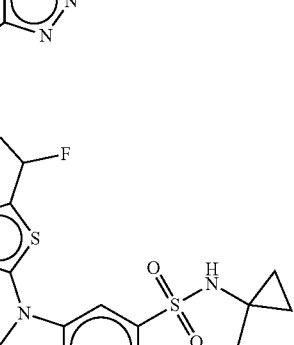 | Benzimidazolone N1-alkylation | 0.029 | 0.016 |
| Example 214 | 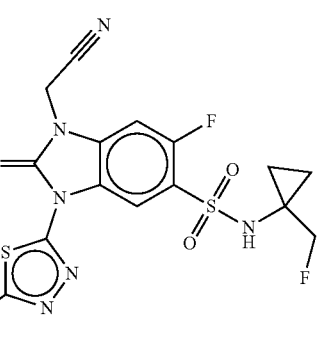 | Example 215 | 0.165 | 1.525 |
| Example 215 | 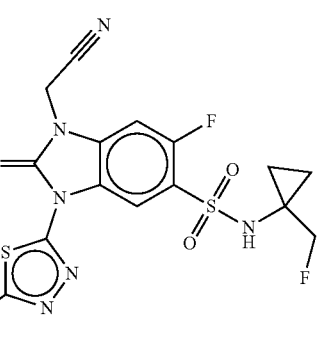 | Example 160 | 0.170 | 0.086 |
| Example 216 | 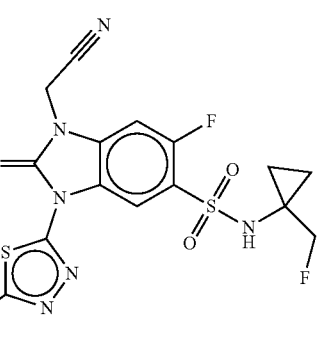 | Example 160 | 0.051 | 0.033 |

TABLE 1-continued

Method of synthesis and PARG activity (Biochem and Cell Activity)

| EXAMPLE | COMPOUNDS | METHOD | PARG_EC50_ENZYME | PARG Cell IC50 Geomean (μM) |
|---|---|---|---|---|
| Example 217 | | Example 160 | 0.156 | 0.036 |
| Example 218 | | Sulfonamide synthesis | 15.82 | 2.810 |

TABLE 2

LCMS data

| | | High pH | | | | | Low pH | | |
|---|---|---|---|---|---|---|---|---|---|
| Example | LC-MS Method | LC-MS Purity | Adduct | Observed MW | RT (min) | LC-MS Method | LC-MS Purity | Adduct | Observed MW | RT (min) |
| Example 1 | B | >95 | [M + H]+ | 440.0 | 0.80 | B | >95 | [M + H]+ | 439.9 | 0.80 |
| Example 2 | A | >95 | [M + H]+ | 336.6 | 0.96 | A | >95 | [M + H]+ | 336.6 | 1.02 |
| Example 3 | A | >95 | [M + H]+ | 372.6 | 1.08 | A | >95 | [M + H]+ | 372.6 | 1.09 |
| Example 4 | A | 85-90 | [M + H]+ | 398.6 | 1.17 | A | 90-95 | [M + H]+ | 398.6 | 1.19 |
| Example 5 | B | >95 | [M + H]+ | 373.0 | 0.60 | B | >95 | [M + H]+ | 373.0 | 0.62 |
| Example 6 | A | 90-95 | [M − H]− | 370.5 | 1.02 | A | 90-95 | [M + H]+ | 372.5 | 1.01 |
| Example 7 | A | 90-95 | [M + H]+ | 338.6 | 1.06 | A | 90-95 | [M + H]+ | 338.6 | 1.05 |
| Example 8 | A | >95 | [M + H]+ | 350.6 | 1.09 | A | >95 | [M + H]+ | 350.6 | 1.09 |
| Example 9 | A | >95 | [M + H]+ | 350.5 | 1.08 | A | >95 | [M + H]+ | 350.5 | 1.08 |
| Example 10 | A | >95 | [M + H]+ | 366.6 | 0.89 | A | >95 | [M + H]+ | 366.6 | 0.86 |
| Example 11 | A | 90-95 | [M + H]+ | 350.6 | 1.09 | A | 90-95 | [M + H]+ | 350.6 | 1.10 |
| Example 12 | A | >95 | [M + H]+ | 378.6 | 1.22 | A | >95 | [M + H]+ | 378.6 | 1.22 |
| Example 13 | B | >95 | [M + H]+ | 373.0 | 0.59 | B | >95 | [M + H]+ | 373.0 | 0.64 |
| Example 14 | A | >95 | [M + H]+ | 380.6 | 0.87 | A | >95 | [M + H]+ | 380.6 | 0.86 |
| Example 15 | A | 90-95 | [M + H]+ | 352.6 | 1.12 | A | 90-95 | [M − H]− | 350.5 | 1.13 |
| Example 16 | A | >95 | [M + H]+ | 364.6 | 1.15 | A | >95 | [M + H]+ | 364.6 | 1.16 |
| Example 17 | A | >95 | [M + H]+ | 320.5 | 0.93 | A | >95 | [M + H]+ | 320.6 | 0.92 |
| Example 18 | A | 90-95 | [M + H]+ | 322.6 | 0.95 | A | >95 | [M + H]+ | 322.6 | 0.95 |
| Example 19 | A | >95 | [M − H]− | 348.6 | 1.06 | A | >95 | [M + H]+ | 350.6 | 1.06 |
| Example 20 | A | 90-95 | [M − H]− | 374.6 | 1.07 | A | <85 | [M − H]− | 374.6 | 1.09 |
| Example 21 | A | >95 | [M − H]− | 377.5 | 0.78 | A | >95 | [M − H]− | 377.5 | 0.82 |
| Example 22 | A | 90-95 | [M + H]+ | 368.5 | 0.89 | A | 90-95 | [M − H]− | 366.5 | 0.88 |
| Example 23 | A | 90-95 | [M + H]+ | 376.5 | 0.88 | A | 90-95 | [M − H]− | 374.5 | 0.85 |
| Example 24 | A | 85-90 | [M − H]− | 322.5 | 0.97 | A | 85-90 | [M − H]− | 322.5 | 0.97 |
| Example 25 | A | >95 | [M − H]− | 391.5 | 0.88 | A | >95 | [M − H]− | 391.5 | 0.87 |
| Example 26 | A | >95 | [M + H]+ | 364.4 | 1.02 | A | 90-95 | [M + H]+ | 364.4 | 1.02 |
| Example 27 | A | 90-95 | [M + H]+ | 386.5 | 1.09 | A | >95 | [M − H]− | 384.5 | 1.10 |
| Example 28 | A | >95 | [M + H]+ | 392.6 | 1.28 | A | >95 | [M + H]+ | 392.6 | 1.30 |
| Example 29 | A | >95 | [M + H]+ | 400.5 | 1.15 | A | >95 | [M + H]+ | 400.5 | 1.16 |
| Example 30 | A | >95 | [M + H]+ | 400.5 | 1.15 | A | >95 | [M + H]+ | 400.5 | 1.16 |
| Example 31 | A | >95 | [M + H]+ | 400.4 | 1.14 | A | >95 | [M + H]+ | 400.5 | 1.15 |
| Example 32 | A | >95 | [M + H]+ | 353.5 | 1.03 | A | >95 | [M + H]+ | 353.5 | 1.03 |
| Example 33 | B | >95 | [M + H]+ | 386.1 | 0.78 | B | >95 | [M + H]+ | 386.1 | 0.78 |
| Example 34 | B | >95 | [M + H]+ | 386.1 | 0.78 | B | >95 | [M + H]+ | 386.0 | 0.78 |

TABLE 2-continued

LCMS data

| | High pH | | | | Low pH | | | |
|---|---|---|---|---|---|---|---|---|
| Example | LC-MS Method | LC-MS Purity | Adduct | Observed MW | RT (min) | LC-MS Method | LC-MS Purity | Adduct | Observed MW | RT (min) |
| Example 35 | B | >95 | [M + H]+ | 402.1 | 0.76 | B | >95 | [M + H]+ | 402.1 | 0.76 |
| Example 36 | B | >95 | [M + H]+ | 402.1 | 0.74 | B | >95 | [M + H]+ | 402.0 | 0.74 |
| Example 37 | B | >95 | [M + H]+ | 402.1 | 0.74 | B | >95 | [M + H]+ | 402.1 | 0.74 |
| Example 38 | B | >95 | [M + H]+ | 406.0 | 0.79 | B | >95 | [M + H]+ | 406.0 | 0.79 |
| Example 39 | B | >95 | [M + H]+ | 406.0 | 0.79 | B | >95 | [M + H]+ | 406.0 | 0.79 |
| Example 40 | B | >95 | [M + H]+ | 390.0 | 0.75 | B | >95 | [M + H]+ | 390.0 | 0.75 |
| Example 41 | B | >95 | [M + H]+ | 390.0 | 0.75 | B | >95 | [M + H]+ | 390.0 | 0.75 |
| Example 42 | B | >95 | [M + H]+ | 390.0 | 0.75 | B | >95 | [M + H]+ | 390.0 | 0.75 |
| Example 43 | B | >95 | [M + H]+ | 397.0 | 0.71 | B | >95 | [M + H]+ | 397.0 | 0.71 |
| Example 44 | B | >95 | [M − H]− | 395.0 | 0.70 | B | >95 | [M + H]+ | 414.1 | 0.71 |
| Example 45 | B | >95 | [M + H]+ | 397.0 | 0.70 | B | >95 | [M + H]+ | 397.1 | 0.70 |
| Example 46 | B | >95 | [M + H]+ | 440.0 | 0.82 | B | >95 | [M + H]+ | 440.0 | 0.82 |
| Example 47 | B | >95 | [M + H]+ | 408.0 | 0.74 | B | >95 | [M + H]+ | 408.0 | 0.74 |
| Example 48 | B | >95 | [M + H]+ | 440.0 | 0.85 | B | >95 | [M + H]+ | 440.0 | 0.85 |
| Example 49 | B | >95 | [M + H]+ | 400.1 | 0.82 | B | >95 | [M + H]+ | 400.1 | 0.82 |
| Example 50 | B | >95 | [M + H]+ | 432.1 | 0.75 | B | >95 | [M + H]+ | 432.1 | 0.75 |
| Example 51 | B | >95 | [M + H]+ | 408.0 | 0.77 | B | >95 | [M − H]− | 406.0 | 0.77 |
| Example 52 | A | 90-95 | [M + H]+ | 348.4 | 1.00 | A | >95 | [M + H]+ | 384.5 | 1.00 |
| Example 53 | A | >95 | [M − H]− | 363.5 | 1.10 | A | >95 | [M + H]+ | 365.5 | 1.08 |
| Example 54 | A | >95 | [M + H]+ | 392.5 | 1.00 | A | >95 | [M + H]+ | 392.5 | 1.01 |
| Example 55 | A | >95 | [M + H]+ | 339.5 | 0.95 | A | >95 | [M + H]+ | 339.5 | 0.94 |
| Example 56 | A | >95 | [M + H]+ | 314.5 | 0.88 | A | >95 | [M + H]+ | 314.5 | 0.87 |
| Example 57 | A | >95 | [M + H]+ | 358.5 | 1.07 | A | >95 | [M + H]+ | 358.5 | 1.06 |
| Example 58 | B | >95 | [M + H]+ | 415.0 | 0.72 | B | >95 | [M + H]+ | 415.0 | 0.72 |
| Example 59 | B | >95 | [M − H]− | 413.0 | 0.58 | B | >95 | [M + H]+ | 415.0 | 0.58 |
| Example 60 | B | >95 | [M − H]− | 419.0 | 0.57 | B | >95 | [M − H]− | 419.0 | 0.57 |
| Example 61 | B | >95 | [M + H]+ | 432.1 | 0.59 | B | >95 | [M + H]+ | 432.1 | 0.59 |
| Example 62 | B | >95 | [M − H]− | 404.9 | 0.70 | B | 90-95 | [M − H]− | 404.9 | 0.69 |
| Example 63 | B | >95 | [M + H]+ | 446.0 | 0.61 | B | >95 | [M + H]+ | 446.1 | 0.61 |
| Example 64 | B | >95 | [M + H]+ | 376.0 | 0.60 | B | >95 | [M + H]+ | 376.0 | 0.60 |
| Example 65 | B | >95 | [M + H]+ | 392.9 | 0.62 | B | >95 | [M + H]+ | 393.0 | 0.63 |
| Example 66 | A | >95 | [M − H]− | 416.5 | 0.95 | A | >95 | [M − H]− | 416.5 | 0.93 |
| Example 67 | A | >95 | [M − H]− | 416.5 | 0.71 | A | >95 | [M − H]− | 416.5 | 0.95 |
| Example 68 | A | >95 | [M + H]+ | 380.4 | 0.99 | A | >95 | [M + H]+ | 380.4 | 0.99 |
| Example 69 | A | >95 | [M − H]− | 433.4 | 0.74 | A | >95 | [M − H]− | 433.4 | 1.00 |
| Example 70 | A | >95 | [M − H]− | 435.4 | 0.72 | A | >95 | [M − H]− | 435.4 | 0.98 |
| Example 71 | A | >95 | [M + H]+ | 464.5 | 1.01 | A | >95 | [M + H]+ | 464.5 | 1.01 |
| Example 72 | A | >95 | [M + H]+ | 376.4 | 1.02 | A | >95 | [M + H]+ | 376.4 | 0.99 |
| Example 73 | A | >95 | [M + H]+ | 474.4 | 1.21 | A | >95 | [M + H]+ | 474.4 | 1.22 |
| Example 74 | A | >95 | [M + H]+ | 450.5 | 0.93 | A | >95 | [M + H]+ | 450.5 | 0.94 |
| Example 75 | A | >95 | [M + H]+ | 448.5 | 1.17 | A | >95 | [M + H]+ | 448.5 | 1.18 |
| Example 76 | A | 90-95 | [M − H]− | 457.5 | 1.27 | A | >95 | [M − H]− | 457.5 | 1.28 |
| Example 77 | A | >95 | [M + H]+ | 366.4 | 0.95 | A | >95 | [M + H]+ | 366.4 | 0.95 |
| Example 78 | A | >95 | [M + H]+ | 434.4 | 1.21 | A | >95 | [M + H]+ | 434.4 | 1.22 |
| Example 79 | A | >95 | [M + H]+ | 416.4 | 1.12 | A | >95 | [M + H]+ | 416.4 | 1.13 |
| Example 80 | A | >95 | [M + H]+ | 366.5 | 0.73 | A | >95 | [M + H]+ | 366.5 | 0.89 |
| Example 81 | A | 90-95 | [M + H]+ | 381.5 | 0.85 | A | 90-95 | [M + H]+ | 381.5 | 0.86 |
| Example 82 | A | >95 | [M + H]+ | 420.5 | 1.14 | A | >95 | [M + H]+ | 420.5 | 1.15 |
| Example 83 | A | >95 | [M + H]+ | 477.5 | 1.04 | A | >95 | [M + H]+ | 477.5 | 1.00 |
| Example 84 | A | >95 | [M + H]+ | 474.6 | 0.99 | A | >95 | [M + H]+ | 474.6 | 1.00 |
| Example 85 | A | >95 | [M + H]+ | 437.6 | 1.00 | A | >95 | [M + H]+ | 437.3 | 0.72 |
| Example 86 | A | >95 | [M + H]+ | 486.6 | 1.17 | A | >95 | [M + H]+ | 486.6 | 1.19 |
| Example 87 | A | >95 | [M + H]+ | 491.6 | 1.04 | A | >95 | [M + H]+ | 491.6 | 1.03 |
| Example 88 | A | >95 | [M + H]+ | 527.5 | 1.14 | A | >95 | [M + H]+ | 527.5 | 1.17 |
| Example 89 | A | 90-95 | [M + H]+ | 393.5 | 0.86 | A | 90-95 | [M + H]+ | 393.5 | 0.86 |
| Example 90 | A | >95 | [M + H]+ | 477.5 | 1.10 | A | >95 | [M + H]+ | 477.5 | 1.12 |
| Example 91 | A | >95 | [M − H]− | 457.5 | 0.88 | A | >95 | [M − H]− | 457.6 | 0.90 |
| Example 92 | A | >95 | [M + H]+ | 459.5 | 0.89 | A | >95 | [M + H]+ | 459.4 | 0.91 |
| Example 93 | A | >95 | [M − H]− | 474.6 | 1.06 | A | 90-95 | [M − H]− | 474.6 | 1.09 |
| Example 94 | A | >95 | [M + H]+ | 350.6 | 0.67 | A | 85-90 | [M + H]+ | 350.6 | 0.82 |
| Example 95 | A | >95 | [M + H]+ | 476.6 | 1.07 | A | >95 | [M + H]+ | 476.6 | 1.10 |
| Example 96 | A | >95 | [M + H]+ | 473.6 | 1.01 | A | >95 | [M + H]+ | 473.6 | 1.04 |
| Example 97 | A | >95 | [M + H]+ | 476.6 | 0.97 | A | >95 | [M + H]+ | 476.6 | 1.00 |
| Example 98 | A | >95 | [M + H]+ | 366.5 | 1.05 | A | >95 | [M + H]+ | 366.5 | 1.08 |
| Example 99 | A | 90-95 | [M + H]+ | 475.6 | 0.96 | A | 90-95 | [M + H]+ | 475.6 | 0.98 |
| Example 100 | A | >95 | [M + H]+ | 404.5 | 1.05 | A | >95 | [M + H]+ | 404.5 | 1.08 |
| Example 101 | A | >95 | [M + H]+ | 447.6 | 0.98 | A | >95 | [M + H]+ | 447.6 | 0.98 |
| Example 102 | A | >95 | [M + H]+ | 446.6 | 0.92 | A | >95 | [M + H]+ | 446.6 | 0.91 |
| Example 103 | A | >95 | [M + H]+ | 460.6 | 1.18 | A | >95 | [M + H]+ | 460.6 | 1.19 |
| Example 104 | A | >95 | [M + H]+ | 476.6 | 1.23 | A | >95 | [M + H]+ | 476.6 | 1.24 |
| Example 105 | A | 90-95 | [M + H]+ | 507.4 | 1.15 | A | >95 | [M + H]+ | 507.4 | 1.18 |
| Example 106 | A | >95 | [M + H]+ | 490.3 | 1.18 | A | >95 | [M + H]+ | 490.3 | 1.20 |
| Example 107 | A | >95 | [M + H]+ | 490.4 | 1.19 | A | >95 | [M + H]+ | 490.4 | 1.21 |

TABLE 2-continued

LCMS data

| | High pH | | | | Low pH | | | |
|---|---|---|---|---|---|---|---|---|
| Example | LC-MS Method | LC-MS Purity | Adduct | Observed MW | RT (min) | LC-MS Method | LC-MS Purity | Adduct | Observed MW | RT (min) |
|---|---|---|---|---|---|---|---|---|---|---|
| Example 108 | A | >95 | [M + H]+ | 555.3 | 1.21 | A | >95 | [M + H]+ | 555.3 | 1.23 |
| Example 109 | A | >95 | [M + H]+ | 471.4 | 0.97 | A | >95 | [M + H]+ | 471.4 | 0.98 |
| Example 110 | A | 90-95 | [M + H]+ | 477.3 | 1.01 | A | >95 | [M + H]+ | 477.4 | 1.02 |
| Example 111 | A | >95 | [M + H]+ | 476.3 | 1.12 | A | >95 | [M + H]+ | 476.4 | 1.14 |
| Example 112 | A | >95 | [M + H]+ | 465.4 | 1.03 | A | >95 | [M + H]+ | 465.4 | 1.03 |
| Example 113 | A | >95 | [M]+ | 459.4 | 1.14 | A | >95 | [M]+ | 459.4 | 1.15 |
| Example 114 | A | >95 | [M + H]+ | 398.3 | 1.07 | A | >95 | [M + H]+ | 398.3 | 1.08 |
| Example 115 | A | >95 | [M + H]+ | 349.3 | 1.05 | A | >95 | [M + H]+ | 349.3 | 1.07 |
| Example 116 | A | >95 | [M + H]+ | 398.3 | 1.00 | A | >95 | [M + H]+ | 398.3 | 1.01 |
| Example 117 | A | >95 | [M + H]+ | 489.4 | 0.84 | A | >95 | [M + H]+ | 489.4 | 0.84 |
| Example 118 | A | >95 | [M + H]+ | 445.3 | 0.96 | A | >95 | [M + H]+ | 445.3 | 0.97 |
| Example 119 | A | >95 | [M]+ | 350.3 | 0.89 | A | >95 | [M]+ | 350.3 | 0.90 |
| Example 120 | A | >95 | [M + H]+ | 444.3 | 0.88 | A | >95 | [M + H]+ | 444.3 | 0.89 |
| Example 121 | A | >95 | [M + H]+ | 458.3 | 0.91 | A | >95 | [M + H]+ | 458.4 | 0.92 |
| Example 122 | A | >95 | [M + H]+ | 364.3 | 0.90 | A | >95 | [M + H]+ | 364.3 | 0.90 |
| Example 123 | A | >95 | [M + H]+ | 448.2 | 1.18 | A | 90-95 | [M + H]+ | 448.2 | 1.20 |
| Example 124 | A | >95 | [M + H]+ | 421.3 | 0.79 | A | 90-95 | [M + H]+ | 421.3 | 0.77 |
| Example 125 | A | >95 | [M + H]+ | 394.3 | 0.81 | A | >95 | [M + H]+ | 394.3 | 0.66 |
| Example 126 | A | >95 | [M + H]+ | 439.3 | 1.27 | A | >95 | [M + H]+ | 439.3 | 1.30 |
| Example 127 | A | >95 | [M + H]+ | 457.3 | 1.26 | A | >95 | [M + H]+ | 457.3 | 1.29 |
| Example 128 | A | >95 | [M + H]+ | 403.3 | 1.26 | A | >95 | [M + H]+ | 403.3 | 1.29 |
| Example 129 | A | >95 | [M + H]+ | 474.3 | 1.11 | A | >95 | [M + H]+ | 474.3 | 1.12 |
| Example 130 | A | >95 | [M + H]+ | 417.2 | 1.11 | A | >95 | [M + H]+ | 417.2 | 1.13 |
| Example 131 | A | >95 | [M + H]+ | 471.3 | 1.20 | A | >95 | [M + H]+ | 471.3 | 1.23 |
| Example 132 | A | >95 | [M + H]+ | 448.3 | 1.20 | A | >95 | [M + H]+ | 448.3 | 1.22 |
| Example 133 | C | >95 | [M + H]+ | 435.2 | 1.45 | A | >95 | [M + H]+ | 435.3 | 0.67 |
| Example 134 | C | >95 | [M + H]+ | 408.3 | 1.54 | A | >95 | [M + H]+ | 408.3 | 0.92 |
| Example 135 | C | >95 | [M + H]+ | 451.3 | 1.01 | A | >95 | [M + H]+ | 451.3 | 0.74 |
| Example 136 | C | 90-95 | [M + H]+ | 477.3 | 1.63 | A | 90-95 | [M + H]+ | 477.4 | 0.77 |
| Example 137 | C | 90-95 | [M + H]+ | 421.3 | 1.51 | A | >95 | [M + H]+ | 421.3 | 0.65 |
| Example 138 | C | 90-95 | [M + H]+ | 461.4 | 1.58 | A | >95 | [M + H]+ | 461.4 | 0.70 |
| Example 139 | C | 90-95 | [M + H]+ | 461.4 | 1.49 | A | >95 | [M + H]+ | 461.4 | 0.70 |
| Example 140 | C | 90-95 | [M + H]+ | 461.4 | 1.70 | A | >95 | [M + H]+ | 461.4 | 0.70 |
| Example 141 | C | >95 | [M + H]+ | 463.4 | 1.48 | A | >95 | [M + H]+ | 463.4 | 0.68 |
| Example 142 | C | >95 | [M + H]+ | 447.4 | 0.96 | A | >95 | [M + H]+ | 447.4 | 0.68 |
| Example 143 | C | >95 | [M + H]+ | 477.3 | 1.70 | A | >95 | [M + H]+ | 477.3 | 0.77 |
| Example 144 | A | >95 | [M + H]+ | 391.3 | 1.00 | A | >95 | [M + H]+ | 391.3 | 1.02 |
| Example 145 | A | 90-95 | [M + H]+ | 453.3 | 1.19 | A | >95 | [M + H]+ | 453.3 | 1.22 |
| Example 146 | A | 85-90 | [M + H]+ | 458.3 | 1.29 | A | >95 | [M + H]+ | 458.3 | 1.32 |
| Example 147 | C | >95 | [M + H]+ | 424.2 | 1.58 | A | >95 | [M + H]+ | 424.3 | 1.03 |
| Example 148 | C | 90-95 | [M + H]+ | 438.3 | 1.70 | A | >95 | [M + H]+ | 438.3 | 1.07 |
| Example 149 | C | >95 | [M + H]+ | 476.8 | 1.69 | A | 90-95 | [M + H]+ | 477.3 | 0.77 |
| Example 150 | C | >95 | [M + H]+ | 422.3 | 1.58 | A | >95 | [M + H]+ | 422.2 | 0.94 |
| Example 151 | C | >95 | [M + H]+ | 421.2 | 1.35 | A | >95 | [M + H]+ | 421.1 | 0.75 |
| Example 152 | C | >95 | [M + H]+ | 479.2 | 1.60 | A | >95 | [M + H]+ | 479.2 | 0.77 |
| Example 153 | C | >95 | [M + H]+ | 463.2 | 1.94 | A | >95 | [M + H]+ | 463.2 | 0.74 |
| Example 154 | C | >95 | [M + H]+ | 437.2 | 1.45 | A | >95 | [M + H]+ | 437.1 | 0.83 |
| Example 155 | C | >95 | [M + H]+ | 463.2 | 1.72 | A | >95 | [M + H]+ | 463.3 | 0.74 |
| Example 156 | A | >95 | [M + H]+ | 398.1 | 0.95 | A | >95 | [M + H]+ | 398.1 | 0.95 |
| Example 157 | A | >95 | [M + H]+ | 377.0 | 0.60 | A | >95 | [M + H]+ | 377.0 | 0.82 |
| Example 158 | A | >95 | [M + H]+ | 405.0 | 0.91 | A | >95 | [M + H]+ | 405.0 | 0.96 |
| Example 159 | A | >95 | [M + H]+ | 412.1 | 1.02 | A | >95 | [M + H]+ | 412.1 | 1.01 |
| Example 160 | A | >95 | [M + H]+ | 442.1 | 0.99 | A | >95 | [M + H]+ | 442.1 | 0.98 |
| Example 161 | A | >95 | [M + H]+ | 435.1 | 0.87 | A | >95 | [M + H]+ | 435.1 | 0.94 |
| Example 162 | A | >95 | [M + H]+ | 471.1 | 1.01 | A | >95 | [M + H]+ | 471.1 | 1.07 |
| Example 163 | A | >95 | [M + H]+ | 378.1 | 1.12 | A | >95 | [M + H]+ | 378.1 | 1.05 |
| Example 164 | A | >95 | [M + H]+ | 528.1 | 1.08 | A | >95 | [M + H]+ | 528.1 | 1.08 |
| Example 165 | A | >95 | [M + H]+ | 521.1 | 0.98 | A | >95 | [M + H]+ | 521.1 | 1.04 |
| Example 166 | A | >95 | [M + H]+ | 405.0 | 0.98 | A | >95 | [M + H]+ | 405.0 | 0.98 |
| Example 167 | A | >95 | [M + H]+ | 496.4 | 1.13 | A | >95 | [M + H]+ | 496.1 | 1.13 |
| Example 168 | A | 90-95 | [M + H]+ | 478.1 | 1.16 | A | 90-95 | [M + H]+ | 478.1 | 1.17 |
| Example 169 | A | >95 | [M + H]+ | 460.1 | 1.14 | A | >95 | [M + H]+ | 460.1 | 1.15 |
| Example 170 | A | >95 | [M + H]+ | 505.2 | 1.10 | A | >95 | [M + H]+ | 505.2 | 0.82 |
| Example 171 | A | 90-95 | [M + H]+ | 460.1 | 1.14 | A | >95 | [M + H]+ | 460.1 | 1.15 |
| Example 172 | A | 90-95 | [M + H]+ | 416.1 | 1.05 | A | 90-95 | [M + H]+ | 416.1 | 1.06 |
| Example 173 | A | >95 | [M + H]+ | 434.1 | 1.12 | A | >95 | [M + H]+ | 434.1 | 1.09 |
| Example 174 | A | >95 | [M + H]+ | 452.1 | 1.08 | A | >95 | [M + H]+ | 452.1 | 1.09 |
| Example 175 | A | >95 | [M + H]+ | 384.0 | 1.00 | A | >95 | [M + H]+ | 384.0 | 1.00 |
| Example 176 | A | >95 | [M + H]+ | 380.2 | 1.08 | A | >95 | [M + H]+ | 380.1 | 1.08 |
| Example 177 | A | 85-90 | [M + H]+ | 398.1 | 1.03 | A | 85-90 | [M + H]+ | 398.2 | 1.03 |
| Example 178 | A | 90-95 | [M + H]+ | 423.1 | 0.94 | A | 90-95 | [M + H]+ | 423.1 | 0.94 |
| Example 179 | A | >95 | [M + H]+ | 405.1 | 1.06 | A | >95 | [M + H]+ | 405.1 | 1.06 |
| Example 180 | A | >95 | [M + H]+ | 423.1 | 1.02 | A | >95 | [M + H]+ | 423.1 | 1.02 |

TABLE 2-continued

| | LCMS data | | | | | | | | | |
|---|---|---|---|---|---|---|---|---|---|---|
| | High pH | | | | | Low pH | | | | |
| Example | LC-MS Method | LC-MS Purity | Adduct | Observed MW | RT (min) | LC-MS Method | LC-MS Purity | Adduct | Observed MW | RT (min) |
| Example 181 | A | 90-95 | [M + H]+ | 434.1 | 1.10 | A | 90-95 | [M + H]+ | 434.1 | 1.07 |
| Example 182 | A | >95 | [M + H]+ | 424.2 | 1.10 | A | >95 | [M + H]+ | 424.2 | 1.11 |
| Example 183 | A | >95 | [M + H]+ | 428.2 | 1.03 | A | >95 | [M + H]+ | 428.2 | 1.03 |
| Example 184 | A | 90-95 | [M + H]+ | 442.2 | 1.06 | A | 90-95 | [M + H]+ | 442.1 | 1.06 |
| Example 185 | A | >95 | [M + H]+ | 456.3 | 1.09 | A | >95 | [M + H]+ | 456.2 | 1.10 |
| Example 186 | A | >95 | [M + H]+ | 455.0 | 1.04 | A | >95 | [M + H]+ | 455.2 | 0.75 |
| Example 187 | A | >95 | [M + H]+ | 456.2 | 1.01 | A | >95 | [M + H]+ | 456.2 | 1.02 |
| Example 188 | A | >95 | [M + H]+ | 455.2 | 0.96 | A | >95 | [M + H]+ | 455.2 | 0.69 |
| Example 189 | A | >95 | [M + H]+ | 364.2 | 0.89 | A | >95 | [M + H]+ | 364.2 | 0.86 |
| Example 190 | A | 90-95 | [M + H]+ | 378.2 | 0.95 | A | 90-95 | [M + H]+ | 378.2 | 0.93 |
| Example 191 | A | 90-95 | [M + H]+ | 396.2 | 0.92 | A | 90-95 | [M + H]+ | 396.2 | 0.90 |
| Example 192 | A | >95 | [M + H]+ | 368.1 | 0.68 | A | >95 | [M + H]+ | 368.1 | 0.81 |
| Example 193 | A | >95 | [M − H]− | 456.1 | 1.14 | A | >95 | [M + H]+ | 458.1 | 1.12 |
| Example 194 | A | 90-95 | [M + H]+ | 386.1 | 0.65 | A | 90-95 | [M + H]+ | 386.1 | 0.76 |
| Example 195 | A | 85-90 | [M + H]+ | 400.2 | 1.01 | A | 90-95 | [M + H]+ | 400.2 | 1.00 |
| Example 196 | A | 90-95 | [M + H]+ | 418.1 | 0.98 | A | 90-95 | [M + H]+ | 418.1 | 0.95 |
| Example 197 | A | >95 | [M + H]+ | 382.1 | 0.90 | A | >95 | [M + H]+ | 382.1 | 0.88 |
| Example 198 | A | >95 | [M + H]+ | 414.2 | 0.94 | A | >95 | [M + H]+ | 414.2 | 0.91 |
| Example 199 | A | >95 | [M + H]+ | 432.1 | 1.07 | A | 90-95 | [M + H]+ | 432.1 | 1.07 |
| Example 200 | A | >95 | [M + H]+ | 450.1 | 1.03 | A | >95 | [M + H]+ | 450.1 | 1.03 |
| Example 201 | A | 90-95 | [M + H]+ | 414.1 | 1.06 | A | 90-95 | [M + H]+ | 414.1 | 1.05 |
| Example 202 | A | >95 | [M + H]+ | 432.2 | 1.02 | A | >95 | [M + H]+ | 432.2 | 1.00 |
| Example 203 | A | >95 | [M − H]− | 452.2 | 0.95 | A | >95 | [M + H]+ | 454.2 | 0.95 |
| Example 204 | A | >95 | [M + H]+ | 408.2 | 0.91 | A | >95 | [M + H]+ | 410.2 | 0.91 |
| Example 205 | A | >95 | [M − H]− | 390.2 | 0.95 | A | >95 | [M + H]+ | 392.2 | 0.95 |
| Example 206 | A | >95 | [M − H]− | 462.2 | 1.12 | A | >95 | [M + H]+ | 464.2 | 1.12 |
| Example 207 | A | >95 | [M + H]+ | 448.2 | 1.20 | A | >95 | [M + H]+ | 448.2 | 1.20 |
| Example 208 | A | >95 | [M + H]+ | 466.1 | 1.16 | A | >95 | [M + H]+ | 466.1 | 1.15 |
| Example 209 | A | >95 | [M + H]+ | 418.1 | 1.01 | A | >95 | [M + H]+ | 418.1 | 1.01 |
| Example 210 | A | 90-95 | [M + H]+ | 436.1 | 0.98 | A | 90-95 | [M + H]+ | 436.1 | 0.97 |
| Example 211 | A | >95 | [M + H]+ | 450.2 | 1.04 | A | >95 | [M + H]+ | 450.1 | 1.04 |
| Example 212 | A | >95 | [M − H]− | 468.1 | 1.00 | A | >95 | [M + H]+ | 468.2 | 1.00 |
| Example 213 | A | >95 | [M − H]− | 474.1 | 1.13 | A | >95 | [M + H]+ | 476.1 | 1.12 |
| Example 214 | A | >95 | [M − H]− | 493.1 | 0.93 | A | >95 | [M + H]+ | 495.1 | 0.93 |
| Example 215 | A | >95 | [M − H]− | 475.1 | 1.07 | A | >95 | [M − H]− | 475.1 | 1.06 |
| Example 216 | A | >95 | [M − H]− | 482.1 | 1.12 | A | >95 | [M + H]+ | 484.2 | 1.11 |
| Example 217 | A | >95 | [M − H]− | 464.1 | 1.13 | A | >95 | [M + H]+ | 466.1 | 1.14 |
| Example 218 | A | >95 | [M + H]+ | 338.1 | 1.21 | A | >95 | [M + H]+ | 338.2 | 1.20 |

TABLE 3

$^1$H NMR data

| Example | NMR Purity | $^1$H NMR |
|---|---|---|
| Example 73 | >95 | $^1$H NMR (300 MHz, CDCl$_3$) δ = 9.03 (d, J = 4.9 Hz, 1H), 7.85 (dd, J = 1.8, 8.3 Hz, 1H), 7.40-7.34 (m, 2H), 7.12-7.03 (m, 3H), 5.16 (s, 2H), 5.04 (s, 1H), 2.83 (s, 3H), 1.25 (s, 3H), 0.85-0.77 (m, 2H), 0.56-0.42 (m, 2H) |
| Example 82 | >95 | $^1$H NMR (300 MHz, CDCl$_3$) δ = 9.04 (d, J = 3.9 Hz, 1H), 7.93 (dd, J = 2.0, 8.5 Hz, 1H), 7.24 (d, J = 8.6 Hz, 1H), 5.00 (s, 1H), 3.90 (d, J = 7.1 Hz, 2H), 2.81 (s, 3H), 1.34-1.28 (m, 1H), 1.26 (s, 3H), 0.88-0.81 (m, 2H), 0.69-0.60 (m, 2H), 0.57-0.47 (m, 4H) |
| Example 83 | >95 | $^1$H NMR (300 MHz, CDCl$_3$) δ = 9.03 (d, J = 1.6 Hz, 1H), 7.91 (dd, J = 1.9, 8.4 Hz, 1H), 7.71 (s, 1H), 7.22 (d, J = 8.6 Hz, 1H), 5.32 (s, 2H), 5.01 (s, 1H), 2.82 (s, 3H), 2.67 (s, 3H), 1.22 (s, 3H), 0.82 (s, 2H), 0.55-0.45 (m, 2H) |
| Example 84 | >95 | $^1$H NMR (300 MHz, CDCl$_3$) δ = 9.04 (d, J = 1.7 Hz, 1H), 7.89 (dd, J = 1.6, 8.6 Hz, 1H), 7.21 (d, J = 8.5 Hz, 1H), 6.10 (s, 1H), 5.17 (s, 2H), 5.02 (s, 1H), 3.90 (s, 3H), 2.82 (s, 3H), 2.23 (s, 3H), 1.25 (s, 3H), 0.87-0.76 (m, 2H), 0.55-0.45 (m, 2H) |
| Example 86 | >95 | $^1$H NMR (300 MHz, CDCl$_3$) δ = 9.02 (d, J = 1.7 Hz, 1H), 7.84 (dd, J = 1.6, 8.3 Hz, 1H), 7.32 (d, J = 8.7 Hz, 2H), 7.11 (d, J = 8.0 Hz, 1H), 6.89 (d, J = 8.6 Hz, 2H), 5.13 (s, 2H), 5.01 (s, 1H), 3.80 (s, 3H), 2.82 (s, 3H), 1.23 (s, 3H), 0.87-0.76 (m, 2H), 0.54-0.43 (m, 2H) |
| Example 87 | >95 | $^1$H NMR (300 MHz, CDCl$_3$) δ = 9.04 (d, J = 1.8 Hz, 1H), 7.91 (dd, J = 1.8, 8.4 Hz, 1H), 7.18 (d, J = 8.2 Hz, 1H), 5.25 (s, 2H), 4.99 (s, 1H), 2.82 (s, 3H), 2.62 (s, 3H), 2.57 (s, 3H), 1.25 (s, 3H), 0.86-0.79 (m, 2H), 0.54-0.48 (m, 2H) |
| Example 88 | >95 | $^1$H NMR (300 MHz, CDCl$_3$) δ = 9.05 (s, 1H), 7.94 (d, J = 8.0 Hz, 1H), 7.23 (d, J = 7.9 Hz, 1H), 6.97 (t, J = 53.8 Hz, 1H), 5.28 (s, 2H), 5.06 (br. s., 1H), 2.62 (s, 3H), 2.58 (s, 3H), 1.25 (s, 3H), 0.82 (br. s., 2H), 0.56-0.46 (m, 2H) |

TABLE 3-continued

¹H NMR data

| Example | NMR Purity | ¹H NMR |
|---|---|---|
| Example 90 | >95 | ¹H NMR (300 MHz, CDCl₃) δ = 9.02 (s, 1H), 8.54 (s, 1H), 7.92 (d, J = 7.1 Hz, 1H), 7.22 (d, J = 8.2 Hz, 1H), 5.28 (s, 2H), 4.99 (s, 1H), 2.63 (s, 3H), 2.59 (s, 3H), 1.26 (s, 3H), 0.84-0.78 (m, 2H), 0.55-0.47 (m, 2H) |
| Example 98 | >95 | ¹H NMR (300 MHz, CDCl₃) δ = 9.01 (s, 1H), 8.54 (s, 1H), 7.95 (d, J = 8.3 Hz, 1H), 7.22 (d, J = 8.1 Hz, 1H), 4.97 (s, 1H), 3.61 (s, 3H), 1.25 (s, 3H), 0.87-0.79 (m, 2H), 0.56-0.48 (m, 2H) |
| Example 99 | >95 | ¹H NMR (300 MHz, CDCl₃) δ = 8.46 (s, 1H), 7.88 (d, J = 8.8 Hz, 1H), 7.16 (d, J = 8.4 Hz, 1H), 5.21 (s, 2H), 5.04 (s, 1H), 2.66 (s, 3H), 2.62 (s, 3H), 2.57 (s, 3H), 1.24 (s, 3H), 0.85-0.75 (m, 2H), 0.56-0.45 (m, 2H) |
| Example 100 | >95 | ¹H NMR (300 MHz, CDCl₃) δ = 9.05 (d, J = 4.2 Hz, 1H), 7.96 (dd, J = 2.1, 8.4 Hz, 1H), 7.39 (d, J = 8.1 Hz, 1H), 5.02 (s, 1H), 4.82 (d, J = 2.5 Hz, 2H), 2.82 (s, 3H), 2.42 (t, J = 2.6 Hz, 1H), 1.26 (s, 4H), 0.87-0.81 (m, 3H), 0.54-0.48 (m, 3H) |
| Example 101 | >95 | ¹H NMR (300 MHz, CDCl₃) δ = 9.05 (d, J = 1.7 Hz, 1H), 7.90 (dd, J = 1.8, 8.4 Hz, 1H), 7.67 (d, J = 0.8 Hz, 1H), 7.31-7.27 (m, 1H), 7.14 (s, 1H), 5.33 (s, 2H), 5.00 (s, 1H), 2.82 (s, 3H), 1.25 (s, 3H), 0.87-0.78 (m, 2H), 0.53-0.47 (m, 2H) |
| Example 102 | >95 | ¹H NMR (300 MHz, DMSO-d₆) δ = 12.84 (br. s, 1H), 8.77 (d, J = 1.7 Hz, 1H), 8.14 (br. s., 1H), 7.83 (br. s, 1H), 7.74 (dd, J = 1.9, 8.4 Hz, 1H), 7.62 (d, J = 8.4 Hz, 1H), 5.09 (s, 2H), 2.76 (s, 3H), 1.07 (s, 3H), 0.70-0.52 (m, 2H), 0.44-0.28 (m, 2H) |
| Example 103 | >95 | ¹H NMR (300 MHz, CDCl₃) δ = 9.01 (s, 1H), 7.90 (d, J = 8.6 Hz, 1H), 7.34 (d, J = 8.2 Hz, 1H), 6.34 (d, J = 3.4 Hz, 1H), 5.93 (br, s, 1H), 5.10 (s, 2H), 4.97 (br. s, 1H), 2.81 (s, 3H), 2.24 (s, 3H), 1.24 (s, 3H), 0.89-0.78 (m, 2H), 0.55-0.43 (m, 2H) |
| Example 104 | >95 | ¹H NMR (300 MHz, CDCl₃) δ = 9.01 (d, J = 1.7 Hz, 1H), 7.89 (dd, J = 1.9, 8.3 Hz, 1H), 7.24 (d, J = 8.3 Hz, 1H), 6.95 (d, J = 3.4 Hz, 1H), 6.62 (d, J = 2.4 Hz, 1H), 5.26 (s, 2H), 5.13 (s, 1H), 2.81 (s, 3H), 2.43 (s, 3H), 1.24 (s, 3H), 0.86-0.78 (m, 2H), 0.53-0.45 (m, 2H) |
| Example 105 | 90-95 | ¹H NMR (300 MHz, CDCl₃) δ = 8.87 (s, 1H), 7.92 (d, J = 8.6 Hz, 1H), 7.20 (d, J = 8.3 Hz, 1H), 5.25 (s, 2H), 5.02 (s, 1H), 4.15 (s, 3H), 2.62 (s, 3H), 2.57 (s, 3H), 1.24 (s, 3H), 0.85-0.77 (m, 2H), 0.54-0.46 (m, 2H) |
| Example 107 | >95 | ¹H NMR (300 MHz, CDCl₃) δ = 9.04 (d, J = 1.1 Hz, 1H), 7.84 (dd, J = 1.6, 8.1 Hz, 1H), 7.31 (s, 1H), 7.14 (d, J = 8.3 Hz, 1H), 5.24 (s, 2H), 4.91 (s, 1H), 2.61 (s, 3H), 2.57 (s, 3H), 2.50 (s, 3H), 1.24 (s, 3H), 0.87-0.78 (m, 2H), 0.54-0.46 (m, 2H) |
| Example 108 | >95 | ¹H NMR (300 MHz, CDCl₃) δ = 8.85 (d, J = 1.8 Hz, 1H), 7.94 (dd, J = 1.8, 8.4 Hz, 1H), 7.23 (d, J = 8.3 Hz, 1H), 5.27 (s, 2H), 5.02 (s, 1H), 2.62 (s, 3H), 2.58 (s, 3H), 1.29 (s, 3H), 0.90-0.80 (m, 2H), 0.61-0.50 (m, 2H) |
| Example 111 | >95 | ¹H NMR (300 MHz, CDCl₃) δ = 9.13 (d, J = 1.9 Hz, 1H), 7.86 (dd, J = 1.9, 8.4 Hz, 1H), 7.70 (d, J = 3.6 Hz, 1H), 7.21 (d, J = 3.6 Hz, 1H), 7.16 (d, J = 8.5 Hz, 1H), 5.26 (s, 2H), 4.96-4.88 (m, 1H), 2.63 (s, 3H), 2.59 (s, 3H), 1.25 (s, 3H), 0.83 (d, J = 1.9 Hz, 2H), 0.51 (d, J = 2.1 Hz, 2H) |
| Example 112 | >95 | ¹H NMR (300 MHz, CDCl₃) δ = 8.42 (s, 1H), 7.82 (d, J = 8.5 Hz, 1H), 7.06 (d, J = 8.0 Hz, 1H), 5.14 (s, 2H), 4.91 (s, 1H), 4.57 (q, J = 7.1 Hz, 2H), 2.61 (s, 3H), 2.55 (s, 3H), 1.51 (t, J = 7.2 Hz, 3H), 1.24 (s, 3H), 0.83-0.75 (m, 2H), 0.54-0.45 (m, 2H) |
| Example 116 | >95 | ¹H NMR (300 MHz, DMSO-d₆) δ = 8.71 (d, J = 6.5 Hz, 1H), 8.37 (br. s, 1H), 7.63 (d, J = 10.3 Hz, 1H), 3.46 (s, 3H), 2.75 (s, 3H), 1.13 (s, 3H), 0.78-0.55 (m, 2H), 0.49-0.34 (m, 2H) |
| Example 117 | >95 | ¹H NMR (300 MHz, DMSO-d₆) δ = 8.90 (s, 1H), 8.31 (s, 1H), 8.17 (s, 1H), 7.78 (d, J = 9.4 Hz, 1H), 7.62 (d, J = 9.2 Hz, 1H), 5.70 (s, 2H), 2.74 (d, J = 4.8 Hz, 3H), 2.61 (s, 3H), 1.10 (s, 3H), 0.62 (br. s., 2H), 0.39 (br. s., 2H) |
| Example 129 | >95 | ¹H NMR (300 MHz, CDCl₃) δ = 8.76 (d, J = 1.6 Hz, 1H), 7.81 (dd, J = 1.4, 8.6 Hz, 1H), 7.64 (d, J = 8.5 Hz, 1H), 7.51 (s, 1H), 4.95 (s, 1H), 4.20 (s, 2H), 2.82 (s, 3H), 2.70 (s, 3H), 2.47 (s, 3H), 1.22 (s, 3H), 0.87-0.78 (m, 2H), 0.52-0.46 (m, 2H) |
| Example 130 | >95 | ¹H NMR (300 MHz, CDCl₃) δ = 8.67 (br. s., 1H), 8.64-8.55 (m, 2H), 7.91 (d, J = 8.2 Hz, 1H), 5.08-4.95 (m, 1H), 2.88 (s, 3H), 2.53 (br. s., 1H), 1.37-1.27 (m, 2H), 1.19 (s, 3H), 1.08 (dd, J = 3.5, 7.8 Hz, 2H), 0.85-0.75 (m, 2H), 0.53-0.42 (m, 2H) |
| Example 131 | >95 | ¹H NMR (300 MHz, CDCl₃) δ = 8.70 (s, 1H), 8.54 (d, J = 8.3 Hz, 1H), 8.27 (s, 1H), 8.04-7.87 (m, 3H), 7.27-7.18 (m, 2H), 5.06 (s, 1H), 2.88 (s, 3H), 1.23 (s, 3H), 0.86-0.77 (m, 2H), 0.54-0.46 (m, 2H) |
| Example 135 | >95 | ¹H NMR (300 MHz, DMSO-d₆) δ = 8.76 (d, J = 1.8 Hz, 1H), 7.99 (br. s., 1H), 7.76 (dd, J = 1.8, 8.3 Hz, 1H), 7.59 (d, J = 8.4 Hz, 1H), 4.02 (t, J = 6.9 Hz, 2H), 2.76-2.73 (m, 3H), 2.29-2.23 (m, 2H), 2.07 (s, 6H), 1.91-1.82 (m, 2H), 1.08 (s, 3H), 0.64-0.56 (m, 2H), 0.38-0.30 (m, 2H) |
| Example 143 | >95 | ¹H NMR (400 MHz, CDCl₃) δ = 9.02 (d, J = 1.8 Hz, 1H), 7.92 (dd, J = 1.8, 8.3 Hz, 1H), 7.21 (d, J = 8.5 Hz, 1H), 5.28 (br. s, 1H), 4.33 (dd, J = 4.3, 14.2 Hz, 1H), 3.90 (dd, J = 9.4, 14.2 Hz, 1H), 2.91 (td, J = 4.1, 11.8 Hz, 1H), 2.80 (s, 3H), 2.55-2.46 (m, 4H), 2.25-2.17 (m, 1H), 1.77-1.53 (m, 5H), 1.43-1.30 (m, 1H), 1.24 (s, 3H), 0.89-0.76 (m, 2H), 0.56-0.43 (m, 2H) |
| Example 145 | >95 | ¹H NMR (300 MHz, CDCl₃) δ = 8.77 (s, 1H), 8.68-8.58 (m, 2H), 7.96 (d, J = 8.6 Hz, 1H), 7.09 (t, J = 53.2 Hz, 1H), 5.01 (br. s, 1H), 2.62-2.43 (m, 1H), 1.35 (td, J = 3.9, 7.7 Hz, 2H), 1.22 (s, 3H), 1.11 (qd, J = 3.8, 7.6 Hz, 2H), 0.86-0.77 (m, 2H), 0.55-0.46 (m, 2H) |
| Example 147 | >95 | ¹H NMR (400 MHz, CDCl₃) δ = 9.02 (d, J = 1.6 Hz, 1H), 7.91 (dd, J = 1.8, 8.4 Hz, 1H), 7.33 (d, J = 8.4 Hz, 1H), 5.01 (s, 1H), 4.19 (t, J = 5.1 Hz, 2H), 3.85-3.77 (m, 1H), 3.75 (t, J = 5.3 Hz, 2H), 3.34 (s, 3H), 2.82 (s, 3H), 1.25 (s, 3H), 0.91-0.80 (m, 2H), 0.53-0.48 (m, 2H) |

TABLE 3-continued

¹H NMR data

| Example | NMR Purity | ¹H NMR |
|---|---|---|
| Example 148 | 90-95 | ¹H NMR (400 MHz, CDCl₃) δ = 9.03 (d, J = 1.8 Hz, 1H), 7.93 (dd, J = 1.9, 8.5 Hz, 1H), 7.29-7.27 (m, 1H), 5.00 (s, 1H), 4.13 (t, J = 6.7 Hz, 2H), 3.41 (t, J = 5.6 Hz, 2H), 3.32 (s, 3H), 2.81 (s, 3H), 2.09 (quin, J = 6.1 Hz, 2H), 1.26-1.20 (m, 3H), 0.86-0.80 (m, 2H), 0.54-0.46 (m, 2H) |
| Example 152 | >95 | ¹H NMR (400 MHz, CDCl₃) δ = 9.02 (d, J = 1.9 Hz, 1H), 7.91 (dd, J = 1.9, 8.3 Hz, 1H), 7.21 (d, J = 8.4 Hz, 1H), 5.22 (s, 1H), 4.13 (t, J = 6.5 Hz, 2H), 3.64 (t, J = 4.5 Hz, 4H), 2.81 (s, 3H), 2.75 (t, J = 6.4 Hz, 2H), 2.54 (t, J = 4.7 Hz, 4H), 1.23 (s, 3H), 0.88-0.78 (m, 2H), 0.55-0.44 (m, 2H) |
| Example 154 | >95 | ¹H NMR (400 MHz, DMSO-d₆) δ = 8.76 (d, J = 1.9 Hz, 1H), 8.16 (s, 1H), 7.76 (dd, J = 1.9, 8.4 Hz, 1H), 7.61 (d, J = 8.4 Hz, 1H), 7.46 (br. s., 1H), 6.94 (br. s., 1H), 4.18 (t, J = 7.2 Hz, 2H), 2.75 (s, 3H), 2.58 (t, J = 7.1 Hz, 2H), 1.09 (s, 3H), 0.64-0.57 (m, 2H), 0.42-0.32 (m, 2H) |
| Example 155 | >95 | ¹H NMR (400 MHz, CDCl₃) δ = 9.02 (d, J = 1.9 Hz, 1H), 7.91 (dd, J = 1.9, 8.4 Hz, 1H), 7.29 (d, J = 8.4 Hz, 1H), 5.18 (s, 1H), 4.05 (dd, J = 4.8, 14.3 Hz, 1H), 3.97 (dd, J = 7.2, 14.3 Hz, 1H), 3.10 (ddd, J = 2.6, 7.0, 9.5 Hz, 1H), 2.80 (s, 3H), 2.79-2.73 (m, 1H), 2.45 (s, 3H), 2.38-2.26 (m, 1H), 2.00-1.86 (m, 1H), 1.85-1.71 (m, 3H), 1.24 (s, 3H), 0.89-0.78 (m, 2H), 0.55-0.44 (m, 2H) |
| Example 156 | >95 | ¹H NMR (300 MHz, DMSO-d6) Shift = 8.74 (d, J = 1.6 Hz, 1H), 8.63-8.39 (m, 1H), 7.84-7.73 (m, 1H), 7.61-7.51 (m, 1H), 4.29 (s, 1H), 4.13 (s, 1H), 3.49 (s, 3H), 2.75 (s, 3H), 0.69 (br s, 4H) |
| Example 157 | >95 | ¹H NMR (300 MHz, DMSO-d6) Shift = 12.36 (br s, 1H), 9.18 (br s, 1H), 8.77 (s, 1H), 7.78 (br d, J = 8.1 Hz, 1H), 7.39 (br d, J = 8.0 Hz, 1H), 2.75 (br s, 3H), 1.39 (br s, 2H), 1.24 (br s, 2H) |
| Example 158 | >95 | ¹H NMR (300 MHz, DMSO-d6) Shift = 8.85-8.77 (m, 1H), 8.42-8.37 (m, 1H), 8.45-8.37 (m, 2H), 7.90-7.77 (m, 1H), 7.74-7.64 (m, 1H), 4.06 (br d, J = 6.6 Hz, 3H), 2.76 (s, 3H), 1.38 (br s, 2H), 1.33-1.28 (m, 2H), 1.25-1.20 (m, 2H) |
| Example 159 | >95 | ¹H NMR (300 MHz, DMSO-d6) Shift = 8.76 (s, 1H), 8.42 (s, 2H), 7.81-7.73 (m, 1H), 7.67-7.59 (m, 1H), 4.30 (s, 1H), 4.14 (s, 1H), 4.09-3.97 (m, 2H), 2.75 (s, 3H), 1.31 (s, 3H), 0.69 (s, 4H) |
| Example 160 | >95 | ¹H NMR (300 MHz, CDCL3) Shift = 9.10-9.02 (m, 1H), 7.95-7.84 (m, 1H), 7.40-7.33 (m, 1H), 5.50-5.36 (m, 1H), 4.35-4.27 (m, 1H), 4.24-4.16 (m, 2H), 4.17-4.10 (m, 1H), 3.76 (br s, 2H), 3.35 (s, 3H), 2.82 (br s, 3H), 1.04 (br s, 2H), 0.80 (br s, 2H) |
| Example 161 | >95 | ¹H NMR (300 MHz, DMSO-d6) Shift = 9.25-9.18 (m, 1H), 8.81 (d, J = 1.8 Hz, 1H), 7.87-7.79 (m, 1H), 7.69 (s, 1H), 4.20 (t, J = 5.1 Hz, 2H), 3.68 (t, J = 5.2 Hz, 2H), 3.23 (s, 3H), 2.76 (s, 3H), 1.41 (s, 2H), 1.27-1.21 (m, 2H) |
| Example 162 | >95 | ¹H NMR (300 MHz, DMSO-d6) Shift = 9.26 (s, 1H), 8.84 (s, 1H), 7.94-7.61 (m, 3H), 4.23 (br s, 2H), 3.70 (br s, 2H), 3.24 (s, 3H), 1.42 (br s, 2H), 1.24 (br s, 2H) |
| Example 163 | >95 | ¹H NMR (300 MHz, CDCL3) Shift = 9.08 (s, 1H), 8.00-7.88 (m, 1H), 7.40 (br d, J = 8.5 Hz, 1H), 7.26-6.88 (m, 1H), 5.43 (s, 1H), 4.29 (s, 1H), 4.23 (br t, J = 4.8 Hz, 2H), 4.13 (s, 1H), 3.78 (br t, J = 4.8 Hz, 2H), 3.36 (s, 3H), 1.05 (br s, 2H), 0.81 (br s, 2H) |
| Example 164 | >95 | ¹H NMR (300 MHz, DMSO-d6) Shift = 8.80 (d, J = 1.5 Hz, 1H), 7.87-7.43 (m, 1H), 6.13 (s, 1H), 5.30 (s, 2H), 4.31 (s, 1H), 4.14 (s, 1H), 3.82 (s, 3H), 2.06 (s, 3H), 0.70 (br s, 4H) |
| Example 165 | >95 | ¹H NMR (300 MHz, DMSO-d6) Shift = 8.85 (s, 1H), 8.45-8.25 (m, 1H), 7.91-7.80 (m, 1H), 7.74-7.64 (m, 1H), 7.92-7.38 (m, 1H), 6.07 (s, 1H), 5.33 (s, 2H), 3.81 (s, 3H), 2.04 (s, 3H), 1.44-1.35 (m, 2H), 1.23 (br s, 2H) |
| Example 166 | >95 | ¹H NMR (300 MHz, DMSO-d6) Shift = 8.55 (d, J = 1.7 Hz, 1H), 8.14 (s, 1H), 7.60 (dd, J = 1.8, 8.4 Hz, 1H), 7.47 (d, J = 8.4 Hz, 1H), 5.08 (s, 2H), 2.52 (s, 3H), 0.85 (s, 3H), 0.42-0.31 (m, 2H), 0.18-0.07 (m, 2H) |
| Example 167 | >95 | ¹H NMR (300 MHz, DMSO-d6) Shift = 8.81 (s, 1H), 8.72 (d, J = 6.5 Hz, 1H), 7.86-7.43 (m, 2H), 4.41-4.09 (m, 4H), 3.68 (t, J = 5.2 Hz, 2H), 3.26 (s, 3H), 0.83-0.69 (m, 4H) |
| Example 168 | >95 | ¹H NMR (300 MHz, DMSO-d6) Shift = 8.75 (d, J = 6.4 Hz, 1H), 8.43 (s, 1H), 7.90-7.40 (m, 2H), 4.19 (t, J = 5.2 Hz, 2H), 3.68 (t, J = 5.2 Hz, 2H), 3.26 (s, 3H), 1.16 (s, 3H), 0.73-0.63 (m, 2H), 0.49-0.38 (m, 2H) |
| Example 169 | >95 | ¹H NMR (300 MHz, DMSO-d6) Shift = 8.79 (d, J = 1.7 Hz, 1H), 8.19 (s, 1H), 7.86-7.43 (m, 3H), 4.20 (t, J = 5.2 Hz, 2H), 3.69 (t, J = 5.2 Hz, 2H), 3.25 (s, 3H), 1.10 (s, 3H), 0.68-0.56 (m, 2H), 0.45-0.33 (m, 2H) |
| Example 170 | >95 | ¹H NMR (300 MHz, DMSO-d6) Shift = 8.78 (d, J = 1.8 Hz, 1H), 7.86-7.45 (m, 3H), 4.34-4.13 (m, 4H), 4.06 (t, J = 6.6 Hz, 3H), 2.30 (t, J = 6.5 Hz, 2H), 2.10 (s, 6H), 1.88 (t, J = 6.6 Hz, 2H), 0.70 (s, 4H) |
| Example 171 | >95 | ¹H NMR (300 MHz, DMSO-d6) Shift = 8.65 (d, J = 6.4 Hz, 1H), 8.41 (s, 1H), 7.67 (d, J = 10.3 Hz, 1H), 3.48 (s, 3H), 2.64 (s, 3H), 1.16 (s, 3H), 0.73-0.61 (m, 2H), 0.48-0.37 (m, 2H) |
| Example 172 | 90-95 | ¹H NMR (300 MHz, DMSO-d6) Shift = 8.79 (s, 1H), 8.63 (d, J = 6.4 Hz, 1H), 7.68 (d, J = 10.3 Hz, 1H), 4.24 (d, J = 49.0 Hz, 2H), 3.48 (s, 3H), 2.64 (s, 3H), 0.81-0.73 (m, 4H) |
| Example 173 | >95 | ¹H NMR (300 MHz, DMSO-d6) Shift = 8.72 (d, J = 6.4 Hz, 1H), 8.44 (s, 1H), 7.85-7.43 (m, 2H), 3.49 (s, 3H), 1.14 (s, 3H), 0.73-0.61 (m, 2H), 0.48-0.37 (m, 2H) |
| Example 174 | >95 | ¹H NMR (300 MHz, DMSO-d6) δ = 8.82 (s, 1H), 8.70 (d, J = 6.4 Hz, 1H), 7.85-7.46 (m, 2HH), 4.30 (s, 1H), 4.14 (s, 1H), 3.50 (s, 3H), 0.80-0.71 (m, 4H) |
| Example 175 | >95 | ¹H NMR (300 MHz, DMSO-d6) Shift = 8.82 (s, 1H), 8.74 (d, J = 1.7 Hz, 1H), 8.54 (s, 1H), 7.81 (dd, J = 1.9, 8.4 Hz, 1H), 7.61 (d, J = 8.4 Hz, 1H), 4.21 (d, J = 49.3 Hz, 2H), 3.52 (s, 3H), 0.73-0.64 (m, 4H) |

TABLE 3-continued

¹H NMR data

| Example | NMR Purity | ¹H NMR |
|---|---|---|
| Example 176 | >95 | ¹H NMR (300 MHz, DMSO-d6) Shift = 8.71 (d, J = 1.7 Hz, 1H), 8.17 (s, 1H), 7.81 (dd, J = 1.8, 8.3 Hz, 1H), 7.59 (d, J = 8.4 Hz, 1H), 3.51 (s, 3H), 2.65 (s, 3H), 1.10 (s, 3H), 0.70-0.59 (m, 2H), 0.46-0.35 (m, 2H) |
| Example 177 | 90-95 | ¹H NMR (300 MHz, DMSO-d6) Shift = 8.69 (d, J = 1.7 Hz, 1H), 8.56 (s, 1H), 7.80 (dd, J = 1.8, 8.4 Hz, 1H), 7.59 (d, J = 8.4 Hz, 1H), 4.34-4.12 (m, 2H), 3.50 (s, 3H), 2.64 (s, 3H), 0.71 (s, 4H) |
| Example 178 | 90-95 | ¹H NMR (300 MHz, DMSO-d6) Shift = 8.78 (d, J = 1.7 Hz, 1H), 8.60 (s, 1H), 7.96 (s, 1H), 7.84 (dd, J = 1.8, 8.4 Hz, 1H), 7.72 (d, J = 8.5 Hz, 1H), 5.33 (s, 2H), 4.32-4.13 (m, 2H), 2.77 (s, 3H), 0.74-0.67 (m, 4H) |
| Example 179 | >95 | ¹H NMR (300 MHz, DMSO-d6) Shift = 8.75 (d, J = 1.6 Hz, 1H), 8.24 (s, 1H), 7.88 (dd, J = 1.8, 8.4 Hz, 1H), 7.75 (d, J = 8.4 Hz, 1H), 5.35 (s, 2H), 2.66 (s, 3H), 1.13 (s, 3H), 0.71-0.59 (m, 2H), 0.47-0.36 (m, 2H) |
| Example 180 | >95 | ¹H NMR (300 MHz, DMSO-d6) Shift = 8.74 (d, J = 1.7 Hz, 1H), 8.63 (s, 1H), 7.87 (dd, J = 1.8, 8.4 Hz, 1H), 7.75 (d, J = 8.5 Hz, 1H), 5.36 (s, 2H), 4.35-4.14 (m, 2H), 2.66 (s, 3H), 0.74 (s, 4H) |
| Example 181 | >95 | ¹H NMR (300 MHz, DMSO-d6) Shift = 8.76 (d, J = 1.8 Hz, 1H), 8.57 (s, 1H), 7.85-7.44 (m, 3H), 4.35-4.08 (m, 2H), 3.52 (s, 3H), 0.74-0.64 (m, 4H) |
| Example 182 | >95 | ¹H NMR (300 MHz, DMSO-d6) Shift = 8.73 (d, J = 1.8 Hz, 1H), 8.18 (s, 1H), 7.79 (dd, J = 1.8, 8.4 Hz, 1H), 7.65 (d, J = 8.5 Hz, 1H), 4.19 (t, J = 5.2 Hz, 2H), 3.70 (t, J = 5.2 Hz, 2H), 3.25 (s, 3H), 2.65 (s, 3H), 1.12 (s, 3H), 0.70-0.60 (m, 2H), 0.46-0.36 (m, 2H) |
| Example 183 | >95 | ¹H NMR (300 MHz, DMSO-d6) Shift = 8.82 (s, 1H), 8.76 (d, J = 1.7 Hz, 1H), 8.54 (s, 1H), 7.79 (dd, J = 1.8, 8.4 Hz, 1H), 7.66 (d, J = 8.5 Hz, 1H), 4.33-4.10 (m, 4H), 3.70 (t, J = 5.3 Hz, 2H), 3.25 (s, 3H), 0.70 (s, 4H) |
| Example 184 | >95 | ¹H NMR (300 MHz, DMSO-d6) Shift = 8.72 (d, J = 1.7 Hz, 1H), 8.57 (s, 1H), 7.79 (dd, J = 1.8, 8.4 Hz, 1H), 7.65 (d, J = 8.5 Hz, 1H), 4.37-4.13 (m, 4H), 3.70 (t, J = 5.2 Hz, 2H), 3.25 (s, 3H), 2.65 (s, 3H), 0.73 (s, 4H) |
| Example 185 | >95 | ¹H NMR (300 MHz, DMSO-d6) Shift = 8.71 (d, J = 1.8 Hz, 1H), 8.57 (s, 1H), 7.80 (dd, J = 1.8, 8.4 Hz, 1H), 7.60 (d, J = 8.4 Hz, 1H), 4.35-4.12 (m, 2H), 4.06 (t, J = 6.9 Hz, 2H), 3.38 (t, J = 5.8 Hz, 2H), 3.18 (s, 3H), 2.65 (s, 3H), 1.97 (quin, J = 6.4 Hz, 2H), 0.72 (s, 4H) |
| Example 186 | >95 | ¹H NMR (300 MHz, DMSO-d6) Shift = 8.72 (d, J = 1.6 Hz, 1H), 7.79 (dd, J = 1.7, 8.4 Hz, 1H), 7.67 (d, J = 8.4 Hz, 1H), 4.35-4.14 (m, 2H), 4.11 (t, J = 6.2 Hz, 2H), 2.68-2.59 (m, 5H), 2.20 (s, 6H), 0.73 (s, 4H) |
| Example 187 | >95 | ¹H NMR (300 MHz, DMSO-d6) Shift = 8.76 (d, J = 1.7 Hz, 1H), 8.53 (s, 1H), 7.77 (dd, J = 1.8, 8.3 Hz, 1H), 7.56 (d, J = 8.4 Hz, 1H), 4.33-4.11 (m, 2H), 4.05 (t, J = 6.7 Hz, 2H), 3.38 (t, J = 5.9 Hz, 2H), 3.18 (s, 3H), 2.75 (s, 3H), 1.96 (quin, J = 6.3 Hz, 2H), 0.69 (s, 4H) |
| Example 188 | >95 | ¹H NMR (300 MHz, DMSO-d6) Shift = 8.76 (d, J = 1.7 Hz, 1H), 8.54 (s, 1H), 7.76 (dd, J = 1.8, 8.3 Hz, 1H), 7.63 (d, J = 8.4 Hz, 1H), 4.33-4.13 (m, 2H), 4.10 (t, J = 6.5 Hz, 2H), 2.75 (s, 3H), 2.66-2.59 (m, 3H), 2.20 (s, 6H), 0.70 (s, 4H) |
| Example 189 | >95 | ¹H NMR (300 MHz, DMSO-d6) Shift = 8.24 (d, J = 1.6 Hz, 1H), 8.11 (s, 1H), 7.75 (dd, J = 1.8, 8.3 Hz, 1H), 7.50 (d, J = 8.3 Hz, 1H), 3.33 (s, 3H), 2.60 (s, 3H), 1.07 (s, 3H), 0.65-0.56 (m, 2H), 0.41-0.32 (m, 2H) |
| Example 190 | 90-95 | ¹H NMR (300 MHz, DMSO-d6) Shift = 8.25 (d, J = 1.6 Hz, 1H), 8.11 (s, 1H), 7.73 (dd, J = 1.8, 8.4 Hz, 1H), 7.56 (d, J = 8.3 Hz, 1H), 3.97 (q, J = 7.1 Hz, 2H), 2.59 (s, 3H), 1.27 (t, J = 7.2 Hz, 3H), 1.07 (s, 3H), 0.64-0.56 (m, 2H), 0.41-0.32 (m, 2H) |
| Example 191 | 90-95 | ¹H NMR (300 MHz, DMSO-d6) Shift = 8.27 (d, J = 1.7 Hz, 1H), 8.13 (s, 1H), 7.74 (dd, J = 1.8, 8.4 Hz, 1H), 7.58 (d, J = 8.4 Hz, 1H), 4.84 (t, J = 4.7 Hz, 1H), 4.72-4.64 (m, 1H), 4.35 (t, J = 4.6 Hz, 1H), 4.29-4.22 (m, 1H), 2.60 (s, 3H), 1.08 (s, 3H), 0.61 (s, 2H), 0.43-0.34 (m, 2H) |
| Example 192 | >95 | ¹H NMR (300 MHz, DMSO-d6) Shift = 12.20 (s, 1H), 8.34 (s, 1H), 8.19 (d, J = 6.4 Hz, 1H), 7.96 (s, 1H), 7.21 (d, J = 9.8 Hz, 1H), 2.89 (s, 3H), 1.12 (s, 3H), 0.71-0.60 (m, 2H), 0.45-0.35 (m, 2H) |
| Example 193 | 85-90 | ¹H NMR (300 MHz, DMSO-d6) Shift = 8.80 (d, J = 1.7 Hz, 1H), 8.61 (s, 1H), 7.90-7.45 (m, 3H), 4.94 (d, J = 2.3 Hz, 2H), 4.31 (s, 1H), 4.15 (s, 1H), 3.51 (t, J = 2.4 Hz, 1H), 0.75-0.66 (m, 4H), |
| Example 194 | >95 | ¹H NMR (300 MHz, DMSO-d6) Shift = 12.22 (br. s., 1H), 8.72 (s, 1H), 8.16 (d, J = 6.4 Hz, 1H), 7.96 (s, 1H), 7.22 (d, J = 9.8 Hz, 1H), 4.35-4.02 (m, 2H), 2.89 (s, 3H), 0.78-0.66 (m, 4H) |
| Example 195 | 90-95 | ¹H NMR (300 MHz, DMSO-d6) Shift = 8.34 (d, J = 1.6 Hz, 1H), 8.15 (s, 1H), 7.82-7.41 (m, 3H), 3.45 (s, 3H), 1.09 (s, 3H), 0.66-0.56 (m, 2H), 0.43-0.33 (m, 2H) |
| Example 196 | >95 | ¹H NMR (300 MHz, DMSO-d6) Shift = 8.54 (s, 1H), 8.32 (d, J = 1.8 Hz, 1H), 7.82-7.40 (m, 3H), 4.32-4.12 (m, 2H), 3.45 (s, 3H), 0.74-0.64 (m, 4H) |
| Example 197 | >95 | ¹H NMR (300 MHz, DMSO-d6) Shift = 8.36 (s, 1H), 8.21 (d, J = 6.3 Hz, 1H), 7.58 (d, J = 10.2 Hz, 1H), 3.41 (s, 3H), 2.60 (s, 3H), 1.12 (s, 3H), 0.71-0.59 (m, 2H), 0.45-0.37 (m, 2H) |
| Example 198 | >95 | ¹H NMR (300 MHz, DMSO-d6) Shift = 8.24 (d, J = 6.3 Hz, 1H), 7.63 (d, J = 10.2 Hz, 1H), 4.82 (t, J = 4.5 Hz, 1H), 4.66 (t, J = 4.5 Hz, 1H), 4.36-4.30 (m, 1H), 4.24 (t, J = 4.6 Hz, 1H), 2.60 (s, 3H), 1.13 (s, 3H), 0.69-0.62 (m, 2H), 0.45-0.38 (m, 2H) |
| Example 199 | >95 | ¹H NMR (300 MHz, DMSO-d6) Shift = 8.42 (s, 1H), 8.31 (d, J = 6.3 Hz, 1H), 7.80-7.40 (m, 2H), 3.97 (q, J = 7.2 Hz, 2H), 1.28 (t, J = 7.1 Hz, 4H), 1.14 (s, 3H), 0.71-0.62 (m, 2H), 0.46-0.38 (m, 2H) |

TABLE 3-continued

¹H NMR data

| Example | NMR Purity | ¹H NMR |
|---|---|---|
| Example 200 | >95 | ¹H NMR (300 MHz, DMSO-d6) Shift = 8.28 (d, J = 6.3 Hz, 1H), 7.78-7.40 (m, 2H), 4.33-4.11 (m, 2H), 3.98 (d, J = 7.1 Hz, 2H), 1.28 (t, J = 7.2 Hz, 3H), 0.75 (br. s., 4H) |
| Example 201 | >95 | ¹H NMR (300 MHz, DMSO-d6) Shift = 8.35 (d, J = 1.7 Hz, 1H), 8.16 (s, 1H), 7.81-7.41 (m, 3H), 4.00 (q, J = 7.1 Hz, 2H), 1.29 (t, J = 7.2 Hz, 3H), 1.10 (s, 3H), 0.66-0.57 (m, 2H), 0.42-0.34 (m, 2H) |
| Example 202 | >95 | ¹H NMR (300 MHz, DMSO-d6) Shift = 8.54 (s, 1H), 8.34 (d, J = 1.6 Hz, 1H), 7.80-7.41 (m, 3H), 4.35-4.11 (m, 2H), 4.00 (q, J = 7.2 Hz, 2H), 1.29 (t, J = 7.2 Hz, 4H), 0.70 (br. s., 4H) |
| Example 203 | >95 | ¹H NMR (300 MHz, DMSO-$d_6$) Shift = 8.68 (s, 1H), 8.45 (d, J = 6.6 Hz, 1H), 8.33 (d, J = 9.1 Hz, 1H), 7.83 (d, J = 9.2 Hz, 1H), 7.57 (d, J = 10.4 Hz, 1H), 4.30 (s, 1H), 4.19-4.07 (m, 3H), 3.68 (t, J = 5.1 Hz, 2H), 3.26 (s, 3H), 2.69 (s, 3H), 0.81-0.65 (m, 4H). |
| Example 204 | >95 | ¹H NMR (300 MHz, DMSO-$d_6$) Shift = 8.67 (s, 1H), 8.46 (d, J = 6.6 Hz, 1H), 8.34 (d, J = 9.1 Hz, 1H), 7.82 (d, J = 9.2Hz, 1H), 7.56 (d, J = 10.2 Hz, 1H), 4.29 (s, 1H), 4.12 (s, 1H), 3.45 (s, 3H), 2.69 (s, 3H), 0.79-0.69 (m, 4H). |
| Example 205 | >95 | ¹H NMR (300 MHz, DMSO-$d_6$) Shift = 8.48 (d, J = 6.7 Hz, 1H), 8.38-8.27 (m, 2H), 7.82 (d, J = 91. Hz, 1H), 7.55 (d, J = 10.3 Hz, 1H), 3.45 (s, 3H), 2.69 (s, 3H), 1.20 (s, 3H), 0.66 (dd, J = 5.0, 7.8 Hz, 2H), 0.40 (dd, J = 4.8, 7.8 Hz, 2H). |
| Example 206 | >95 | ¹H NMR (300 MHz, DMSO-$d_6$) Shift = 8.84 (d, J = 9.5 Hz, 1H), 8.76-8.66 (m, 2H), 8.49 (d, J = 9.4 Hz, 1H), 7.61 (d, J = 10.2 Hz, 1H), 4.30 (s, 1H), 4.13 (s, 1H), 0.80-0.71 (m, 4H). |
| Example 207 | >95 | ¹H NMR (300 MHz, DMSO-$d_6$) Shift = 8.74 (d, J = 6.5 Hz, 1H), 8.44 (s, 1H), 7.85-7.44 (m, 2H), 4.04 (q, J = 7.1 Hz, 2H), 1.31 (t, J = 7.2 Hz, 3H), 1.15 (s, 3H), 0.72-0.63 (m, 2H), 0.47-0.39 (m, 2H) |
| Example 208 | >95 | ¹H NMR (300 MHz, DMSO-d6) Shift = 8.82 (s, 1H), 8.72 (d, J = 6.4 Hz, 1H), 7.84-7.44 (m, 2H), 4.34-4.13 (m, 2H), 4.04 (q, J = 7.0 Hz, 2H), 1.09 (t, J = 7.0 Hz, 3H), 0.76 (br. s., 4H) |
| Example 209 | >95 | ¹H NMR (300 MHz, DMSO-d6) Shift = 8.41 (s, 1H), 8.29 (d, J = 6.3 Hz, 1H), 7.79-7.41 (m, 2H), 3.43 (s, 3H), 1.13 (s, 3H), 0.71-0.62 (m, 2H), 0.46-0.38 (m, 2H) |
| Example 210 | >95 | ¹H NMR (300 MHz, DMSO-d6) Shift = 8.41 (s, 1H), 8.29 (d, J = 6.3 Hz, 1H), 7.79-7.41 (m, 2H), 3.43 (s, 3H), 1.13 (s, 3H), 0.71-0.62 (m, 2H), 0.46-0.38 (m, 2H) |
| Example 211 | >95 | ¹H NMR (300 MHz, DMSO-d6) Shift = 8.47-8.41 (m, 1H), 8.35-8.28 (m, 1H), 7.60 (s, 2H), 4.83 (t, J = 4.6 Hz, 1H), 4.68 (t, J = 4.5 Hz, 1H), 4.39-4.31 (m, 1H), 4.29-4.21 (m, 1H), 1.16-1.12 (m, 3H), 0.71-0.62 (m, 2H), 0.46-0.38 (m, 2H) |
| Example 212 | >95 | ¹H NMR (300 MHz, DMSO-d6) Shift = 8.81 (s, 1H), 8.30 (d, J = 6.3 Hz, 1H), 7.79-7.41 (m, 2H), 4.83 (t, J = 4.6 Hz, 1H), 4.68 (t, J = 4.6 Hz, 1H), 4.41-4.11 (m, 4H), 0.76 (br. s., 4H) |
| Example 213 | >95 | ¹H NMR (300 MHz, DMSO-$d_6$) Shift = 8.87 (s, 1H), 8.74 (d, J = 6.4 Hz, 1H), 7.85-7.45 (m, 2H), 4.92 (d, J = 2.5 Hz, 2H), 4.32 (s, 2H), 4.31 (s, 1H), 4.15 (s, 1H), 3.52 (t, J = 2.4 Hz, 1H), 0.82-0.70 (m, 4H). |
| Example 214 | >95 | ¹H NMR (300 MHz, DMSO-$d_6$) Shift = 8.84 (br. s, 1H), 8.74 (d, J = 6.4 Hz, 1H), 7.85-7.43 (m, 4H), 4.66 (s, 1H), 4.32 (s, 2H), 4.16 (s, 1H), 0.81-0.70 (m, 4H). |
| Example 215 | >95 | ¹H NMR (300 MHz, DMSO-$d_6$) Shift = 8.89 (br. s, 1H), 8.75 (d, J = 6.3 Hz, 1H), 7.90-7.46 (m, 2H), 5.33 (s, 2H), 4.31 (s, 1H), 4.15 (s, 1H), 0.85-0.69 (m, 4H). |
| Example 216 | >95 | ¹H NMR (300 MHz, DMSO-$d_6$) Shift = 8.84 (s, 1H), 8.74 (d, J = 6.4 Hz, 1H), 7.85-7.44 (m, 2HH), 4.86 (t, J = 4.5 Hz, 1H), 4.70 (t, J = 4.5 Hz, 1H), 4.41 (t, J = 4.5 Hz, 1H), 4.36-4.37 (m, 2H), 4.15 (s, 1H), 0.82-0.72 (m, 4H). |
| Example 217 | >95 | ¹H NMR (300 MHz, DMSO-$d_6$) Shift = 8.76 (d, J = 6.5 Hz, 1H), 8.46 (s, 1H), 7.85-7.44 (m, 2HH), 4.86 (t, J = 4.5 Hz, 1H), 4.70 (t, J = 4.5 Hz, 1H), 4.41 (t, J = 4.5 Hz, 1H), 4.32 (t, J = 4.5 Hz, 1H), 1.16 (s, 3H), 0.68 (dd, J = 4.8, 7.8 Hz, 2H) , 0.43 (dd, J = 4.8, 8.0 Hz, 2H). |
| Example 218 | 90-95 | ¹H NMR (300 MHz, DMSO-$d_6$) Shift = 8.26-8.24 (m, 1H), 8.11 (s, 1H), 7.93-7.90 (m, 2H), 4.39 (q, J = 7.2 Hz, 2H), 2.61 (s, 3H), 1.36 (t, J = 7.1 Hz, 3H), 1.04 (s, 3H), 0.62-0.57 (m, 2H), 0.40-0.35 (m, 2H). |

ARH3 and PARP1 Assays (Selectivity Data)

ARH3 Assay

ARH3 In vitro selectivity assays were conducted in a total volume of 15 ul in a standard 384 well format. 5 ul of Human Full Length ARH3 (Enzo Life Sciences: ALX-201-292), used at a final reaction concentration of 17.5 nM, was added to 5 ul of Ribosylated PARP substrate (also produced internally by Astra Zeneca) at final reaction concentration of 4.5 nM in assay buffer (50 mM Tris pH7.4, 0.1 mg/ml BSA, 3 mM EDTA, 0.4 mM EGTA, 1 mM DTT, 0.01% Tween 20, 50 mM KCl). The reaction was incubated at room temperature for 30 minutes and then 5 ul detection reagent was added. Detection Reagent consists of 42 nM MAb Anti-6HIS XL665 (CisBio: 61HISXLB) and 2.25 nM Streptavidin Europium Cryptate (CisBio: 610SAKLB), both at 3× working stock concentrations (final concentrations of 14 nM and 0.75 nM respectively), in a detection buffer of 50 mM Tris pH7.4, BSA at 0.1 mg/ml and KF at 100 mM. Following incubation at room temperature for 60 minutes in the dark, TR-FRET signal was measured at Ex 340 and Em 665 and Em 620. A ratio was calculated as Em665/EM620x104 for each well and used to calculate percent inhibition for test compounds.

PARP1 Assay

PARP1 In vitro selectivity assays were conducted as a 10 ul reaction volume in a NUNC Maxisorp 384-well assay plate pre-coated in-house with Histones. 5 ul of Human High specific Activity PARP1 (Trevigen: 4668-100-01) was used at a final reaction concentration of 0.02 units/ml in 1×PARP Buffer (Trevigen: 4671-096-02) with 5 ul of 1×PARP cocktail, which is a mixture of 10×PARP Cocktail (Trevigen: 4671-096-03), 10× Activate DNA (Trevigen: 4671-096-06)

and 20×PARP Buffer (as above). The reaction was incubated at room temperature for 60 minutes to allow histones on the coated plate to become PARylated. The wells were then washed with PBS/0.1% Triton $X_{100}$. PARP1 activity was then detected by measuring the extent of PARylation. Firstly, 10 ul of Streptavidin-HRP (Trevigen: 4800-30-06), diluted 1 in 250 in 1×PARG Assay Buffer (Trevigen: 4680-096-02), was added to each well and incubated at room temperature for 60 minutes. Secondly, following another wash with PBS/0.1% Triton X100, Peroxy Glow Reagents A and B (Trevigen: 4675-096-01 and 4675-096-02) were mixed in equal quantities immediately before use and 100 ul was added to each well. Luminescence signal was then measured immediately.

TABLE 4

ARH3 and PARP1 activity data (Selectivity data)

| Example | ARH3 Biochem IC50 (µM) | PARP1 Biochem IC50 (µM) |
| --- | --- | --- |
| Example 73 | >100 | >150 |
| Example 79 | >100 | >150 |
| Example 82 | >100 | >150 |
| Example 83 | >100 | >150 |
| Example 87 | 76.7 | >150 |
| Example 88 | >100 | >150 |
| Example 90 | >100 | >150 |
| Example 14 | >150 | >150 |
| Example 118 | >150 | >150 |
| Example 119 | >150 | >150 |
| Example 129 | >16.7 (showed interference at top concentration of 150 uM) | >150 |
| Example 145 | >150 | >150 |
| Example 146 | >16.7 (showed interference at top concentration of 150 uM) | >150 |
| Example 174 | >50 | >150 |
| Example 200 | >150 | |
| Example 208 | >150 | >150 |
| Example 211 | >150 | |
| Example 212 | >150 | |
| Example 213 | >150 | |
| Example 216 | >150 | |

REFERENCES

[1] Ame, J. C., E. Fouquerel, L. R. Gauthier, D. Biard, F. D. Boussin, F. Dantzer, G. de Murcia and V. Schreiber (2009). "Radiation-induced mitotic catastrophe in PARG-deficient cells." J Cell Sci 122(Pt 12): 1990-2002.

[2] Barber, L. J., S. Sandhu, L. Chen, J. Campbell, I. Kozarewa, K. Fenwick, I. Assiotis, D. N. Rodrigues, J. S. Reis Filho, V. Moreno, J. Mateo, L. R. Molife, J. De Bono, S. Kaye, C. J. Lord and A. Ashworth (2013). "Secondary mutations in BRCA2 associated with clinical resistance to a PARP inhibitor." J Pathol 229(3): 422-429.

[3] Blenn, C., P. Wyrsch and F. R. Althaus (2011). "The ups and downs of tannins as inhibitors of poly(ADP-ribose) glycohydrolase." Molecules 16(2): 1854-1877.

[4] Caiafa, P., T. Guastafierro and M. Zampieri (2009). "Epigenetics: poly(ADP-ribosyl)ation of PARP-1 regulates genomic methylation patterns." FASEB J 23(3): 672-678.

[5] Curtin, N. J. and C. Szabo (2013). "Therapeutic applications of PARP inhibitors: anticancer therapy and beyond." Mol Aspects Med 34(6): 1217-1256.

[6] Dahl, M., V. Maturi, P. Lonn, P. Papoutsoglou, A. Zieba, M. Vanlandewijck, L. P. van der Heide, Y. Watanabe, O. Soderberg, M. O. Hottiger, C. H. Heldin and A. Moustakas (2014). "Fine-tuning of Smad protein function by poly(ADP-ribose) polymerases and poly(ADP-ribose) glycohydrolase during transforming growth factor beta signaling." PLoS One 9(8): e103651.

[7] Drost, R. and J. Jonkers (2014). "Opportunities and hurdles in the treatment of BRCA1-related breast cancer." Oncogene 33(29): 3753-3763.

[8] Erdelyi, K., P. Bai, I. Kovacs, E. Szabo, G. Mocsar, A. Kakuk, C. Szabo, P. Gergely and L. Virag (2009). "Dual role of poly(ADP-ribose) glycohydrolase in the regulation of cell death in oxidatively stressed A549 cells." FASEB J 23(10): 3553-3563.

[9] Fathers, C., R. M. Drayton, S. Solovieva and H. E. Bryant (2012). "Inhibition of poly(ADP-ribose) glycohydrolase (PARG) specifically kills BRCA2-deficient tumor cells." Cell Cycle 11(5): 990-997.

[10] Fisher, A. E., H. Hochegger, S. Takeda and K. W. Caldecott (2007). "Poly(ADP-ribose) polymerase 1 accelerates single-strand break repair in concert with poly (ADP-ribose) glycohydrolase." Mol Cell Biol 27(15): 5597-5605.

[11] Frizzell, K. M., M. J. Gamble, J. G. Berrocal, T. Zhang, R. Krishnakumar, Y. Cen, A. A. Sauve and W. L. Kraus (2009). "Global analysis of transcriptional regulation by poly(ADP-ribose) polymerase-1 and poly(ADP-ribose) glycohydrolase in MCF-7 human breast cancer cells." J Biol Chem 284(49): 33926-33938.

[12] Fujihara, H., H. Ogino, D. Maeda, H. Shirai, T. Nozaki, N. Kamada, K. Jishage, S. Tanuma, T. Takato, T. Ochiya, T. Sugimura and M. Masutani (2009). "Poly(ADP-ribose) Glycohydrolase deficiency sensitizes mouse ES cells to DNA damaging agents." Curr Cancer Drug Targets 9(8): 953-962.

[13] Guastafierro, T., A. Catizone, R. Calabrese, M. Zampieri, O. Martella, M. G. Bacalini, A. Reale, M. Di Girolamo, M. Miccheli, D. Farrar, E. Klenova, F. Ciccarone and P. Caiafa (2013). "ADP-ribose polymer depletion leads to nuclear Ctcf re-localization and chromatin rearrangement(1)." Biochem J 449(3): 623-630.

[14] Ji, Y. and A. V. Tulin (2009). "Poly(ADP-ribosyl)ation of heterogeneous nuclear ribonucleoproteins modulates splicing." Nucleic Acids Res 37(11): 3501-3513.

[15] Le May, N., I. Iltis, J. C. Ame, A. Zhovmer, D. Biard, J. M. Egly, V. Schreiber and F. Coin (2012). "Poly (ADP-ribose) glycohydrolase regulates retinoic acid receptor-mediated gene expression." Mol Cell 48(5): 785-798.

[16] Mashimo, M., J. Kato and J. Moss (2014). "Structure and function of the ARH family of ADP-ribosyl-acceptor hydrolases." DNA Repair (Amst).

[17] Mortusewicz, O., E. Fouquerel, J. C. Ame, H. Leonhardt and V. Schreiber (2011). "PARG is recruited to DNA damage sites through poly(ADP-ribose)- and PCNA-dependent mechanisms." Nucleic Acids Res 39(12): 5045-5056.

[18] Nakadate, Y., Y. Kodera, Y. Kitamura, T. Tachibana, T. Tamura and F. Koizumi (2013). "Silencing of poly(ADP-ribose) glycohydrolase sensitizes lung cancer cells to radiation through the abrogation of DNA damage checkpoint." Biochem Biophys Res Commun 441(4): 793-798.

[19] Shirai, H., H. Fujimori, A. Gunji, D. Maeda, T. Hirai, A. R. Poetsch, H. Harada, T. Yoshida, K. Sasai, R. Okayasu and M. Masutani (2013). "Parg deficiency confers radio-sensitization through enhanced cell death in mouse ES cells exposed to various forms of ionizing radiation." Biochem Biophys Res Commun 435(1): 100-106.

[20] Shirai, H., A. R. Poetsch, A. Gunji, D. Maeda, H. Fujimori, H. Fujihara, T. Yoshida, H. Ogino and M. Masutani (2013). "PARG dysfunction enhances DNA double strand break formation in S-phase after alkylation DNA damage and augments different cell death pathways." Cell Death Dis 4: e656.

[21] Sun, Y., T. Zhang, B. Wang, H. Li and P. Li (2012). "Tannic acid, an inhibitor of poly(ADP-ribose) glycohydrolase, sensitizes ovarian carcinoma cells to cisplatin." Anticancer Drugs 23(9): 979-990.

[22] Zhou, Y., X. Feng and D. W. Koh (2010). "Enhanced DNA accessibility and increased DNA damage induced by the absence of poly(ADP-ribose) hydrolysis." Biochemistry 49(34): 7360-7366.

[23] Zhou, Y., X. Feng and D. W. Koh (2011). "Synergistic cytotoxicity of N-methyl-N'-nitro-N-nitrosoguanidine and absence of poly(ADP-ribose) glycohydrolase involves chromatin decondensation." Int J Oncol 39(1): 121-127.

The invention claimed is:
1. A compound, or a pharmaceutically acceptable salt or solvate thereof, having the structural formula (II) shown below:

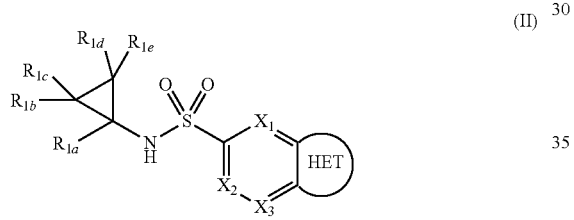

(II)

wherein:
$R_{1a}$ is selected from, fluoro, chloro, cyano, formyl, (1-2C) alkyl, (1-2C) haloalkyl, (2C)alkenyl, and (2C)alkynyl;
$R_{1b}$, $R_{1c}$, $R_{1d}$, and $R_{1e}$ are each independently selected from H, fluoro and methyl;
$X_1$ is selected from $CR_2$ or N; wherein $R_2$ is H or fluoro;
$X_2$ is selected from $CR_3$ or N; wherein $R_3$ is H or fluoro;
$X_3$ is selected from $CR_4$ or N; wherein $R_4$ is H, halo, cyano, (1-2C)alkyl, (1-2C) haloalkyl, (1-2C)alkoxy, (1-2C)haloalkoxy and (2C)alkynyl; or
$R_4$ is selected from a group of the formula:
-$L_4$-$L_{4C}$-$Q_{4C}$
wherein
$L_4$ is absent or (1-3C)alkylene optionally substituted by (1-2C)alkyl or oxo;
$L_{4C}$ is absent or selected from O, S, SO, $SO_2$, $N(R_{4b})$, C(O), C(O)O, OC(O), C(O)N($R_{4b}$), N($R_{4b}$)C(O), N($R_{4b}$)C(O)N($R_{4c}$), S(O)$_2$N($R_{4b}$), and N($R_{4b}$)SO$_2$, wherein $R_{4b}$ and $R_{4c}$ are each independently selected from hydrogen and (1-2C)alkyl; and
$Q_{4C}$ is hydrogen, (1-6C)alkyl, (3-6C)cycloalkyl, aryl, heterocyclyl or heteroaryl; and wherein $Q_{4C}$ is optionally substituted by one or more substituents selected from halo, trifluoromethyl, trifluoromethoxy, amino, cyano, hydroxy, amino, carboxy, carbamoyl, sulphamoyl, (1-4C)alkyl, $NR_{4d}R_{4e}$, $OR_{4d}$, $C(O)R_{4d}$, $C(O)OR_{4d}$, $OC(O)R_{4d}$, $C(O)N(R_{4e})R_{4d}$, $N(R_{4e})C(O)R_{4d}$, $S(O)_yR_{4d}$ (where y is 0, 1 or 2), $SO_2N(R_{4e})R_{4d}$, $N(R_{4e})SO_2R_{4d}$ and $(CH_2)_zNR_{4e}R_{4d}$ (where z is 1, 2 or 3), wherein $R_{4d}$ and $R_{4e}$ are each independently selected from H and (1-4C)alkyl;

HET is a fused 5-membered saturated, partially saturated or unsaturated heterocyclic ring of formula:

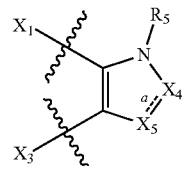

wherein
bond a is a single bond;
$R_5$ is H, (1-4C)alkyl or a group of the formula:
-$L_1$-$L_5$-$Q_5$
wherein
$L_1$ is absent or selected from (1-3C)alkylene optionally substituted by (1-2C)alkyl or oxo, or a (2-3C)alkenylene or (2-3C)alkynylene linker that is optionally substituted by (1-2C)alkyl;
$L_5$ is absent or selected from C(O), C(O)O, OC(O), C(O)N($R_a$), N($R_a$)C(O), N($R_a$)C(O)N($R_b$), S(O)$_2$N ($R_a$), and N($R_a$)SO$_2$, wherein $R_a$ and $R_b$ are each independently selected from hydrogen or (1-2C)alkyl; and
$Q_5$ is selected from hydrogen, (1-4C)alkyl, aryl, 5-6 membered heteroaryl, (4-6C)cycloalkyl, (4-6C)cycloalkenyl, (2C)alkenyl and 5-6 membered heterocyclyl;
and wherein $Q_5$ is optionally substituted by one or more substituents selected from (1-4C)alkyl, halo, amino, cyano, carboxy, carbamoyl, sulphamoyl, trifluoromethoxy, haloalkyl, $NR_cR_d$, $OR_c$, $C(O)R_c$, $C(O)OR_c$, $OC(O)R_c$, $C(O)N(R_c)R_d$, $N(R_c)C(O)R_d$, $S(O)_yR_c$ (where y is 0, 1 or 2), $SO_2N(R_c)R_d$, $N(R_c)SO_2R_d$ or $(CH_2)_z NR_cR_d$ (where z is 1, 2 or 3), wherein $R_c$ and $R_d$ are each independently selected from H or (1-4C)alkyl;
or $Q_5$ is optionally substituted by a group of the formula;
—$W_5$—$Y_5$—$Z_5$
wherein
$W_5$ is absent or selected from (1-3C)alkylene optionally substituted by (1-2C)alkyl or oxo, or a (2-3C)alkenylene or (2-3C)alkynylene linker that is optionally substituted by (1-2C)alkyl;
$Y_5$ is absent or selected from C(O), C(O)O, OC(O), C(O)N($R_e$), N($R_e$)C(O), N($R_e$)C(O)N($R_f$), S(O)$_2$N($R_e$), and N($R_e$)SO$_2$, wherein $R_e$ and $R_f$ are each independently selected from hydrogen and (1-2C)alkyl; and
$Z_5$ is selected from hydrogen, (1-4C)alkyl, phenyl, 5 or 6-membered heterocyclyl and a 5-6 membered heteroaryl; and wherein $Z_5$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl and sulphamoyl;
$X_4$ is selected from C(=O), C(=NH), C(=S), $CHR_{6c}$ and N—$R_{6N}$;
wherein
$R_{6C}$ is selected from hydrogen, cyano, halo and a group of the formula:
-$L_6$-$L_{6C}$-Q6C wherein L$_6$ is absent or (1-3C)alkylene optionally substituted by (1-2C)alkyl or oxo;

L$_{6C}$ is absent or selected from O, S, SO, SO$_2$, N(R$_g$), C(O), C(O)O, OC(O), C(O)N(R$_g$), N(R$_g$)C(O), N(R$_g$)C(O)N(R$_h$), S(O)$_2$N(R$_g$), and N(R$_g$)SO$_2$, wherein R$_g$ and R$_h$ are each independently selected from hydrogen and (1-2C)alkyl; and Q$_{6C}$ is hydrogen, (1-4C)alkyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, carboxy, carbamoyl, sulphamoyl, NR$_i$R$_j$, OR$_i$, C(O)R$_i$, C(O)OR$_i$, OC(O)R$_i$, C(O)N(R)R$_i$R$_j$, N(R$_i$)C(O)R$_j$, S(O)$_y$R$_i$ (where y is 0, 1 or 2), SO$_2$N(R$_i$)R$_j$, N(R$_i$)SO$_2$R$_j$ and (CH$_2$)$_z$NR$_i$R$_j$ (where z is 1, 2 or 3), wherein R$_i$ and R$_j$ are each independently selected from H and (1-4C)alkyl;

R$_{6N}$ is selected from hydrogen and a group of the formula:
-L$_6$-L$_{6N}$-Q$_{6N}$
wherein L$_6$ is absent or (1-3C)alkylene optionally substituted by (1-2C)alkyl or oxo;

L$_{6N}$ is absent or selected from O, S, SO, SO$_2$, N(R$_k$), C(O), C(O)O, OC(O), C(O)N(R$_k$), N(R$_k$)C(O), N(R$_k$)C(O)N(R$_l$), S(O)$_2$N(R$_k$) and, or N(R$_k$)SO$_2$, wherein R$_k$ and R$_l$ are each independently selected from hydrogen and (1-2C)alkyl; and Q$_{6N}$ is hydrogen, cyano, (1-6C)alkyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, carboxy, carbamoyl, sulphamoyl, NR$_m$R$_n$, OR$_m$, C(O)R$_m$, C(O)OR$_m$, OC(O)R$_m$, C(O)N(R$_m$)R$_n$, N(R$_m$)C(O)R$_n$, S(O)$_y$R$_m$ (where y is 0, 1 or 2), SO$_2$N(R$_m$)R$_n$, N(R$_m$)SO$_2$R$_n$ and (CH$_2$)$_z$NR$_m$R$_n$ (where z is 1, 2 or 3), wherein R$_m$ and R$_n$ are each independently selected from H and (1-4C)alkyl;

X$_5$ is selected from C(=O), C(=NH), C(=S), CHR$_{7c}$ and N—R$_{7N}$;
wherein

R$_{7c}$ is selected from, cyano, halo and a group of the formula:
-L$_7$-L$_{7C}$-Q$_{7C}$
wherein L$_7$ is absent or (1-3C)alkylene optionally substituted by (1-2C)alkyl or oxo;

L$_{7C}$ is absent or selected from O, S, SO, SO$_2$, N(R$_o$), C(O), C(O)O, OC(O), C(O)N(R$_o$), N(R$_o$)C(O), N(R$_o$)C(O)N(R$_p$), S(O)$_2$N(R$_o$), and N(R$_o$)SO$_2$, wherein R$_o$ and R$_p$ are each independently selected from hydrogen and (1-2C)alkyl; and Q$_{7C}$ is hydrogen, cyano, (1-6C)alkyl, (2C)alkynyl, (2-3C)alkenyl, (3-6C)cycloalkyl, aryl, heterocyclyl or heteroaryl; and wherein Q$_{7C}$ is optionally substituted by one or more substituents selected from (1-4C)alkyl, halo, trifluoromethyl, trifluoromethoxy, amino, cyano, nitro, hydroxy, amino, carboxy, carbamoyl, sulphamoyl, NR$_q$R$_r$, OR$_q$, C(O)N$_q$, C(O)OR$_q$, OC(O)R$_q$, C(O)N(R$_q$)R$_r$, N(R$_q$)C(O)R$_r$, S(O)$_y$R$_q$ (where y is 0, 1 or 2), SO$_2$N(R$_q$)R$_r$, N(R$_q$)SO$_2$R$_r$ or (CH$_2$)$_z$NR$_q$R$_r$, (where z is 1, 2 or 3), wherein R$_q$ and R$_r$ are each independently selected from H or (1-4C)alkyl; or Q$_{7C}$ is optionally substituted by a group of the formula:
-W$_{7C}$-L$_{7'}$-Z$_{7C}$ wherein W$_{7C}$ is absent or (1-3C)alkylene substituted by (1-2C)alkyl or oxo;

L$_{7'}$ is absent or selected from C(O), C(O)O, OC(O), C(O)N(R$_s$), N(R$_s$)C(O), N(R$_s$)C(O)N(R$_t$), S(O)$_2$N(R$_s$), and N(R$_s$)SO$_2$, wherein R$_s$ and R$_t$ are each independently selected from hydrogen or (1-2C)alkyl; and Z$_{7C}$ is phenyl or 5-6 membered heteroaryl; each of which is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl and sulphamoyl;

R$_{7N}$ is selected from hydrogen and a group of the formula:
-L$_7$-L$_{7N}$-Q$_{7N}$
wherein L$_7$ is absent or (1-3C)alkylene optionally substituted by (1-2C)alkyl;

L$_{7N}$ is absent or selected from O, S, SO, SO$_2$, N(R$_u$), C(O), C(O)O, OC(O), C(O)N(R$_u$), N(R$_u$)C(O), N(R$_u$)C(O)N(R$_v$), S(O)$_2$N(R$_u$), and N(R$_u$)SO$_2$, wherein R$_u$ and R$_v$ are each independently selected from hydrogen and (1-2C)alkyl; and Q$_{7N}$ is hydrogen, cyano, (1-6C)alkyl, (2C)alkynyl, (2-3C)alkenyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl, NR$_w$R$_x$, OR$_w$, C(O)R$_w$, C(O)OR$_w$, OC(O)R$_w$, C(O)N(R$_w$)R$_x$, N(R$_w$)C(O)R$_x$, S(O)$_y$R$_w$ (where y is 0, 1 or 2), SO$_2$N(R$_w$)R$_x$, N(R$_w$)SO$_2$R$_x$ and (CH$_2$)$_z$NR$_w$R$_x$ (where z is 1, 2 or 3), wherein R$_w$ and R$_x$ are each independently selected from H and (1-4C)alkyl; or Q$_{7N}$ is optionally substituted by a group of the formula:
-W$_{7N}$-L$_{7'}$-Z$_{7N}$
wherein W$_{7N}$ is absent or (1-3C)alkylene optionally substituted by (1-3C)alkyl;

L$_{7'}$ is absent or selected from C(O), C(O)O, OC(O), C(O)N(R$_y$), N(R$_y$)C(O), N(R$_y$)C(O)N(R$_z$), S(O)$_2$N(R$_y$), and N(R$_y$)SO$_2$, wherein R$_y$ and R$_z$ are each independently selected from hydrogen or (1-2C)alkyl; and Z$_{7N}$ is phenyl or 5-6 membered heteroaryl; each of which is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl and or sulphamoyl;

with the proviso that:

(i) Only one or two of R$_{1b-e}$ can be selected from any substituent other than H;

(ii) only one or two of X$_1$, X$_2$ or X$_3$ can be N;

(iii) Het may only comprise up to 2 ring nitrogen atoms; and (iv) only one of X$_4$ or X$_5$ can be selected from C(=O), C(=NH) or C(=S).

2. A compound according to claim 1, wherein R$_{1a}$ is selected from cyano or (1-2C)alkyl.

3. A compound according to claim 1, wherein X$_1$ is CR$_2$; wherein R$_2$ is H or fluoro.

4. A compound according to claim 3, wherein X$_1$ is C—H.

5. A compound according to claim 1, wherein X$_2$ is CR$_3$; wherein R$_3$ is H or fluoro.

6. A compound according to claim 1, wherein X$_3$ is selected from CR$_4$ or N; wherein R$_4$ is H, halo, cyano or (1-2C)haloalkyl.

7. A compound according to claim 6, wherein $X_3$ is C—H, C—F or $CF_3$.

8. A compound according to claim 1, wherein $R_{1b}$, $R_{1c}$, $R_{1d}$ and $R_{1e}$ are H.

9. A compound according to claim 1, wherein $R_5$ is H, (1-4C)alkyl or a group of the formula:

-$L_1$-$L_5$-$Q_5$ wherein $L_1$ is absent or selected from (1-3C)alkylene optionally substituted by (1-2C)alkyl and oxo;

$L_5$ is absent or selected from C(O), C(O)O, OC(O), C(O)N($R_a$), and N($R_a$)C(O), wherein $R_a$ is selected from hydrogen and (1-2C)alkyl; and $Q_5$ is selected from hydrogen, (1-4C)alkyl, aryl, 5-6 membered heteroaryl, (4-6C)cycloalkyl, (4-6C)cycloalkenyl, (2C)alkenyl and 5-6 membered heterocyclyl;

and wherein $Q_5$ is optionally substituted by one or more substituents selected from (1-4C)alkyl, halo, amino, cyano, amino, carboxy, carbamoyl, sulphamoyl, trifluoromethoxy, haloalkyl, $NR_cR_d$, $OR_c$, C(O)$R_c$, C(O)O$R_c$, OC(O)$R_c$, C(O)N($R_c$)$R_d$, and N($R_c$)C(O)$R_d$, wherein $R_c$ and $R_d$ are each independently selected from H and (1-4C)alkyl;

or $Q_5$ is optionally substituted by a group of the formula;

—$W_5$—$Y_5$—$Z_5$ wherein $W_5$ is absent or selected from (1-3C)alkylene optionally substituted by (1-2C)alkyl or oxo, or a (2-3C)alkenylene or (2-3C)alkynylene linker that is optionally substituted by (1-2C)alkyl;

$Y_5$ is absent or selected from C(O), C(O)O, OC(O), C(O)N($R_e$), N($R_e$)C(O), N($R_e$)C(O)N($R_f$), S(O)$_2$N($R_e$), and N($R_e$)SO$_2$, wherein $R_e$ and $R_f$ are each independently selected from hydrogen and (1-2C)alkyl; and $Z_5$ is selected from hydrogen, (1-4C)alkyl, phenyl, 5 or 6-membered heterocyclyl and a 5-6 membered heteroaryl; and wherein $Z_5$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, hydroxyl, carboxy, carbamoyl and sulphamoyl.

10. A compound of claim 1, wherein $R_5$ is H, (1-4C)alkyl or a group of the formula:

-$L_1$-$L_5$-$Q_5$ wherein $L_1$ is absent or (1-3C)alkylene optionally substituted by (1-2C)alkyl or oxo;

$L_5$ is absent or selected from C(O), C(O)O, OC(O), C(O)N($R_a$), and N($R_a$)C(O), wherein $R_a$ and $R_b$ are each independently selected from hydrogen and (1-2C)alkyl; and $Q_5$ is selected from hydrogen, (1-4C)alkyl, aryl, 5-6 membered heteroaryl, (4-6C)cycloalkyl, (4-6C)cycloalkenyl, (2C)alkenyl and 5-6 membered heterocyclyl;

and wherein $Q_5$ is optionally substituted by one or more substituents selected from (1-4C)alkyl, halo, amino, cyano, amino, haloalkyl, $NR_cR_d$, $OR_c$, and C(O)$R_c$, wherein $R_c$ and $R_d$ are each independently selected from H and (1-2C)alkyl;

or $Q_5$ is optionally substituted by a group of the formula;

—$W_5$—$Y_5$—$Z_5$ wherein $W_5$ is absent or (1-3C)alkylene;

$Y_5$ is absent or selected from C(O), C(O)O, OC(O), and C(O)N($R_e$), wherein $R_e$ and $R_f$ are each independently selected from hydrogen or and (1-2C)alkyl; and $Z_5$ is selected from hydrogen, (1-4C)alkyl, phenyl, or a 5-6 membered heteroaryl; and wherein $Z_5$ is optionally substituted by one or more substituents selected from (1-2C)alkyl or and halo.

11. A compound of claim 1, wherein $X_4$ is selected from C(=O), C(=NH), C(=S), and CHR$_{6C}$;

wherein $R_{6c}$ is selected from hydrogen, cyano, halo or a group of the formula:

-$L_6$-$L_{6C}$-$Q_{6C}$ wherein $L_6$ is absent or (1-3C)alkylene optionally substituted by (1-2C)alkyl or oxo;

$L_{6C}$ is absent or selected from O, S, SO, SO$_2$, N($R_g$), C(O), C(O)O, OC(O), C(O)N($R_g$), N($R_g$)C(O), N($R_g$)C(O)N($R_h$), S(O)$_2$N($R_g$), and N($R_g$)SO$_2$, wherein $R_g$ and $R_h$ are each independently selected from hydrogen or (1-2C)alkyl; and $Q_{6C}$ is hydrogen, (1-4C)alkyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, carboxy, carbamoyl, sulphamoyl, $NR_i R_j$, $OR_i$, C(O)$R_i$, C(O)O$R_i$, OC(O)$R_i$, C(O)N($R_i$)$R_j$, N($R_i$)C(O)$R_j$, S(O)$_y R_i$ (where y is 0, 1 or 2), SO$_2$N($R_i$)$R_j$, N($R_i$)SO$_2R_j$ and (CH$_2$)$_z$ NR$_i$ R$_j$ (where z is 1, 2 or 3), wherein $R_i$ and $R_j$ are each independently selected from H and (1-4C)alkyl.

12. A compound according to claim 1, wherein $X_4$ is selected from C(=O) and CHR$_{6C}$;

wherein $R_{6c}$ is selected from hydrogen, or a group of the formula:

-$L_6$-$L_{6C}$-$Q_{6C}$ wherein $L_{6C}$ is absent or (1-3C)alkylene optionally substituted by (1-2C)alkyl or oxo;

$L_{6C}$ is absent or selected from O, S, SO, SO$_2$, N($R_g$), C(O), C(O)O, OC(O), C(O)N($R_g$), N($R_g$)C(O), N($R_g$)C(O)N($R_h$), S(O)$_2$N($R_g$), and N($R_g$)SO$_2$, wherein $R_g$ is selected from hydrogen or (1-2C)alkyl; and $Q_{6C}$ is hydrogen, (1-4C)alkyl, (3-6C)cycloalkyl, aryl, heterocyclyl or heteroaryl, each of which is optionally substituted by one or more substituents selected from (1-2C)alkyl, halo and trifluoromethyl.

13. A compound according to claim 1, wherein $X_5$ is selected from C(=O), C(=NH), C(=S), CHR$_{7C}$ and N—R$_{7N}$;

wherein $R_{7C}$ is selected from, cyano, halo and a group of the formula:

-$L_7$-$L_{7C}$-$Q_{7C}$ wherein $L_7$ is absent or (1-3C)alkylene optionally substituted by (1-2C)alkyl or oxo;

$L_{7C}$ is absent or selected from O, S, SO, SO$_2$, N($R_0$), C(O), C(O)O, OC(O), C(O)N($R_0$), and N($R_0$)C(O), wherein $R_o$ is selected from hydrogen and (1-2C)alkyl; and $Q_{7C}$ is hydrogen, cyano, (1-4C)alkyl, (2C)alkynyl, (2-3C)alkenyl, (3-6C)cycloalkyl, aryl, heterocyclyl or heteroaryl; and wherein $Q_{7C}$ is optionally substituted by one or more substituents selected from (1-2C)alkyl, halo, trifluoromethyl, trifluoromethoxy, amino, cyano, hydroxy, carboxy, carbamoyl and sulphamoyl;

R$_{7N}$ is selected from hydrogen or a group of the formula:
-L$_7$-Q$_{7N}$
wherein
L$_7$ is absent or (1-3C)alkylene optionally substituted by (1-2C)alkyl;
Q$_{7N}$ is hydrogen, cyano, (1-6C)alkyl, (2C)alkynyl, (2-3C)alkenyl, (3-6C)cycloalkyl, aryl, heterocyclyl or heteroaryl, each of which is optionally substituted by one or more substituents selected from (1-4C)alkyl, halo, trifluoromethyl, trifluoromethoxy, amino, cyano, hydroxy, amino, carboxy, carbamoyl, sulphamoyl, NR$_w$R$_x$, OR$_w$, C(O)R$_w$, C(O)OR$_w$, OC(O)R$_w$, C(O)N(R$_w$)R$_x$, and N(R$_w$)C(O)R$_x$, wherein R$_w$ and R$_x$ are each independently selected from H or and (1-4C)alkyl.

14. A compound according to claim 1, wherein X$_5$ is selected from C(=O), CHR$_{7C}$, and N—R$_{7N}$;
wherein
R$_{7C}$ is a group of the formula:
-L$_7$-L$_{7C}$-Q$_{7C}$
wherein
L$_7$ is absent or (1-3C)alkylene optionally substituted by (1-2C)alkyl or oxo;
L$_{7C}$ is absent or selected from O, S, N(R$_0$), C(O), C(O)O, C(O)N(R$_0$), and N(R$_0$)C(O), wherein R$_o$ is selected from hydrogen and (1-2C)alkyl; and
Q$_{7C}$ is hydrogen, cyano, (1-2C)alkyl, (2C)alkynyl, (2-3C)alkenyl, (3-6C)cycloalkyl, aryl, heterocyclyl or heteroaryl; and wherein Q$_{7C}$ is optionally substituted by one or more substituents selected from (1-2C)alkyl, halo, trifluoromethyl, amino or cyano;
R$_{7N}$ is selected from hydrogen and a group of the formula:
-L$_7$Q$_{7N}$
wherein
L$_7$ is absent or (1-3C)alkylene optionally substituted by (1-2C)alkyl;
Q$_{7N}$ is hydrogen, cyano, (1-6C)alkyl, (2C)alkynyl, (2-3C)alkenyl, (3-6C)cycloalkyl, aryl, heterocyclyl or heteroaryl, each of which is optionally substituted by one or more substituents selected from (1-2C)alkyl, halo, trifluoromethyl, amino, cyano, carbamoylNR$_w$ R$_x$, OR$_w$, C(O)N(R$_w$)R$_x$, and N(R$_w$)c(o)r$_x$, wherein R$_w$ and r$_x$ are each independently selected from H or (1-2C) alkyl.

15. A compound selected from one of the following:
1-[(2,6-dichlorophenyl)methyl]-3-methyl-N-(1-methylcyclopropyl)-2-oxo-benzimidazole-5-sulfonamide;
1-(cyclopropylmethyl)-3-methyl-N-(1-methylcyclopropyl)-2-oxo-benzimidazole-5-sulfonamide;
1-benzyl-3-methyl-N-(1-methylcyclopropyl)-2-oxo-benzimidazol e-5-sulfonamide;
1-(cyclopropylmethyl)-N-(1-methylcyclopropyl)-2-oxo-3-phenyl-benzimidazole-5-sulfonamide;
3-methyl-N-(1-methylcyclopropyl)-2-oxo-1-(3-pyridylmethyl)benzimidazole-5-sulfonamide;
1-[(2,2-difluorocyclopropyl)methyl]-3-methyl-N-(1-methylcyclopropyl)-2-oxo-benzimidazole-5-sulfonamide;
1-isobutyl-3-methyl-N-(1-methylcyclopropyl)-2-oxo-benzimidazole-5-sulfonamide;
3-methyl-N-(1-methylcyclopropyl)-1-[(2-methylcyclopropyl)methyl]-2-oxo-benzimidazole-5-sulfonamide;
3-methyl-N-(1-methylcyclopropyl)-1-[(1-methylcyclopropyl)methyl]-2-oxo-benzimidazole-5-sulfonamide;
3-methyl-N-(1-methylcyclopropyl)-1-[(3-methyloxetan-3-yl)methyl]-2-oxo-benzimidazole-5-sulfonamide;
1-(cyclobutylmethyl)-3-methyl-N-(1-methylcyclopropyl)-2-oxo-benzimidazole-5-sulfonamide;
1-(cyclohexylmethyl)-3-methyl-N-(1-methylcyclopropyl)-2-oxo-benzimidazole-5-sulfonamide;
3-methyl-N-(1-methylcyclopropyl)-2-oxo-1-(4-pyridylmethyl)benzimidazole-5-sulfonamide;
1-(2,2-dimethylpropyl)-3-methyl-N-(1-methylcyclopropyl)-2-oxo-benzimidazole-5-sulfonamide;
1-(cyclopentylmethyl)-3-methyl-N-(1-methylcyclopropyl)-2-oxo-benzimidazole-5-sulfonamide;
3-methyl-N-(1-methylcyclopropyl)-2-oxo-1-prop-2-ynyl-benzimidazole-5-sulfonamide;
1-allyl-3-methyl-N-(1-methylcyclopropyl)-2-oxo-benzimidazol e-5-sulfonamide;
1-(2-cyclopropylethyl)-3-methyl-N-(1-methylcyclopropyl)-2-oxo-benzimidazole-5-sulfonamide;
3-methyl-N-(1-methylcyclopropyl)-1-[(5-methyl-2-furyl)methyl]-2-oxo-benzimidazole-5-sulfonamide;
2-[3-methyl-5-[(1-methylcyclopropyl)sulfamoyl]-2-oxo-benzimidazol-1-yl]ethyl acetate;
3-methyl-N-(1-methylcyclopropyl)-1-[(1-methylpyrazol-3-yl)methyl]-2-oxo-benzimidazole-5-sulfonamide;
3-acetyl-1-methyl-N-(1-methylcyclopropyl)-2-oxo-benzimidazole-5-sulfonamide;
1-methyl-N-(1-methylcyclopropyl)-2-oxo-3-(3-thienyl)benzimidazole-5-sulfonamide;
3-benzoyl-1-methyl-N-(1-methylcyclopropyl)-2-oxo-benzimidazole-5-sulfonamide;
3-(cyclohexanecarbonyl)-1-methyl-N-(1-methylcyclopropyl)-2-oxo-benzimidazole-5-sulfonamide;
1-methyl-3-(4-methylbenzoyl)-N-(1-methylcyclopropyl)-2-oxo-benzimidazole-5-sulfonamide;
1-methyl-3-(3-methylbenzoyl)-N-(1-methylcyclopropyl)-2-oxo-benzimidazole-5-sulfonamide;
1-methyl-3-(2-methylbenzoyl)-N-(1-methylcyclopropyl)-2-oxo-benzimidazole-5-sulfonamide;
N-ethyl-3-methyl-6-(1-methylcyclopropyl)sulfamoyl]-2-oxo-benzimidazole-1-carboxamide;
3-methyl-N-(1-methylcyclopropyl)-1-(m-tolylmethyl)-2-oxo-benzimidazole-5-sulfonamide;
3-methyl-N-(1-methylcyclopropyl)-2-oxo-1-(p-tolylmethyl)benzimidazol e-5-sulfonamide;
1-[(2-methoxyphenyl)methyl]-3-methyl-N-(1-methylcyclopropyl)-2-oxo-benzimidazole-5-sulfonamide;
1-[(3-methoxyphenyl)methyl]-3-methyl-N-(1-methylcyclopropyl)-2-oxo-benzimidazole-5-sulfonamide;
1-[(4-methoxyphenyl)methyl]-3-methyl-N-(1-methylcyclopropyl)-2-oxo-benzimidazole-5-sulfonamide;
1-[(3-chlorophenyl)methyl]-3-methyl-N-(1-methylcyclopropyl)-2-oxo-benzimidazole-5-sulfonamide;
1-[(4-chlorophenyl)methyl]-3-methyl-N-(1-methylcyclopropyl)-2-oxo-benzimidazole-5-sulfonamide;
1-[(2-fluorophenyl)methyl]-3-methyl-N-(1-methylcyclopropyl)-2-oxo-benzimidazole-5-sulfonamide;
1-[(3-fluorophenyl)methyl]-3-methyl-N-(1-methylcyclopropyl)-2-oxo-benzimidazole-5-sulfonamide;
1-[(4-fluorophenyl)methyl]-3-methyl-N-(1-methylcyclopropyl)-2-oxo-benzimidazole-5-sulfonamide;
1-[(2-cyanophenyl)methyl]-3-methyl-N-(1-methylcyclopropyl)-2-oxo-benzimidazole-5-sulfonamide;
1-[(3-cyanophenyl)methyl]-3-methyl-N-(1-methylcyclopropyl)-2-oxo-benzimidazole-5-sulfonamide;
1-[(4-cyanophenyl)methyl]-3-methyl-N-(1-methylcyclopropyl)-2-oxo-benzimidazole-5-sulfonamide;
3-methyl-N-(1-methylcyclopropyl)-2-oxo-1-[[2-(trifluoromethyl)phenyl]-methyl]benzimidazole-5-sulfonamide;
1-[(2,6-difluorophenyl)methyl]-3-methyl-N-(1-methylcyclopropyl)-2-oxo-benzimidazole-5-sulfonamide;

1-[(3,5-dichlorophenyl)methyl]-3-methyl-N-(1-methyl-cyclopropyl)-2-oxo-benzimidazole-5-sulfonamide;
1-[(3,5-dimethylphenyl)methyl]-3-methyl-N-(1-methyl-cyclopropyl)-2-oxo-benzimidazole-5-sulfonamide;
1-[(3,5-dimethoxyphenyl)methyl]-3-methyl-N-(1-methylcyclopropyl)-2-oxo-benzimidazole-5-sulfonamide;
1-[(3,5-difluorophenyl)methyl]-3-methyl-N-(1-methyl-cyclopropyl)-2-oxo-benzimidazole-5-sulfonamide;
3-(2-furyl)-1-methyl-N-(1-methylcyclopropyl)-2-oxo-benzimidazole-5-sulfonamide;
1-methyl-N-(1-methylcyclopropyl)-2-oxo-3-thiazol-2-yl-benzimidazole-5-sulfonamide;
3-(5-formyl-2-thienyl)-1-methyl-N-(1-methylcyclopropyl)-2-oxo-benzimidazole-5-sulfonamide;
N,3-dimethyl-6-[(1-methylcyclopropyl)sulfamoyl]-2-oxo-benzimidazole-1-carboxamide;
6-fluoro-1,3-dimethyl-N-(1-methylcyclopropyl)-2-oxo-benzimidazole-5-sulfonamide;
3-methyl-N-(1-methylcyclopropyl)-2-oxo-1-phenyl-benzimidazole-5-sulfonamide;
1-[(4-cyano-3-fluoro-phenyl)methyl]-3-methyl-N-(1-methylcyclopropyl)-2-oxo-benzimidazole-5-sulfonamide;
4-[[3-methyl-5-[(1-methylcyclopropyl)sulfamoyl]-2-oxo-benzimidazol-1-yl]methyl]benzamide;
N-methyl-5[3-methyl-5-[(1-methylcyclopropyl)sulfamoyl]-2-oxo-benzimidazol-1-yl]methyl]-1,2,4-oxadiazole-3-carboxamide;
3-[[3-methyl-5-[(1-methylcyclopropyl)sulfamoyl]-2-oxo-benzimidazol-1-yl]methyl]benzamide;
3-methyl-N-(1-methylcyclopropyl)-1-[(5-nitro-2-furyl)methyl]-2-oxo-benzimidazole-5-sulfonamide;
N-[44[3-methyl-5-[(1-methylcyclopropyl)sulfamoyl]-2-oxo-benzimidazol-1-yl]methyl]phenyl]acetamide;
3-methyl-N-(1-methylcyclopropyl)-1-[(2-methylpyrazol-3-yl)methyl]-2-oxo-benzimidazole-5-sulfonamide;
3-methyl-N-(1-methylcyclopropyl)-1-[(2-methylthiazol-5-yl)methyl]-2-oxo-benzimidazole-5-sulfonamide;
ethyl 3-methyl-6-[(1-methylcyclopropyl)sulfamoyl]-2-oxo-benzimidazole-1-carboxylate;
(E)-3-[5-[3-methyl-6-[(1-methylcyclopropyl)sulfamoyl]-2-oxo-benzimidazol-1-y1]-2-furyl]prop-2-enoic acid;
1-methyl-N-(1-methylcyclopropyl)-3-(5-methyl-1,3,4-thiadiazol-2-yl)-2-oxo-benzimidazole-5-sulfonamide;
(E)-3-[2-[3-methyl-6-[(1-methylcyclopropyl)sulfamoyl]-2-oxo-benzimidazol-1-ylithiazol-5-yl]prop-2-enoic acid;
3-[2-[3-methyl-6-[(1-methylcyclopropyl)sulfamoyl]-2-oxo-benzimidazol-1-yl]propanoic acid;
N,N-dim ethyl-3-[2-[3-methyl-6-[(1-methylcyclopropyl)sulfamoyl]-2-oxo-benzimidazol-1-ylithiazol-5-yl]propanamide;
1-[(4-fluorophenyl)methyl]-N-(1-methylcyclopropyl)-2-oxo-3H-benzimidazole-5-sulfonamide;
1-[(4-fluorophenyl)methyl]-N-(1-methylcyclopropyl)-3-(5-methyl-1,3,4-thiadiazol-2-yl)-2-oxo-benzimidazole-5-sulfonamide;
N-methyl-3-[2-[3-methyl-6-[(1-methylcyclopropyl)sulfamoyl]-2-oxo-benzimidazol-1-ylithiazol-5-yl]propanamide;
ethyl 3-[(4-fluorophenyl)methyl]-6-[(1-methylcyclopropyl)sulfamoyl]-2-oxo-benzimidazole-1-carboxylate;
1-[(4-fluorophenyl)methyl]-N-(1-methylcyclopropyl)-2-oxo-3-thiazol-2-yl-benzimidazole-5-sulfonamide;
1-methyl-N-(1-methylcyclopropyl)-2-oxo-3-(1,3,4-thiadiazol-2-yl)benzimidazole-5-sulfonamide;
1-methyl-N-(1-methylcyclopropyl)-2-oxo-3-[5-(trifluoromethyl)-1,3,4-thiadiazol-2-yl]benzimidazole-5-sulfonamide;
3-[5-(difluoromethyl)-1,3,4-thiadiazol-2-yl]-1-methyl-N-(1-methylcyclopropyl)-2-oxo-benzimidazole-5-sulfonamide;
N-(1-methylcyclopropyl)-3-(5-methyl-1,3,4-thiadiazol-2-yl)-2-oxo-1H-benzimidazole-5-sulfonamide;
3-(5-amino-1,3,4-thiadiazol-2-yl)-1-methyl-N-(1-methylcyclopropyl)-2-oxo-benzimidazole-5-sulfonamide;
1-(cyclopropylmethyl)-N-(1-methylcyclopropyl)-3-(5-methyl-1,3,4-thiadiazol-2-yl)-2-oxo-benzimidazole-5-sulfonamide;
N-(1-methylcyclopropyl)-3-(5-methyl-1,3,4-thiadiazol-2-yl)-1-[(2-methylthiazol-5-yl)methyl]-2-oxo-benzimidazole-5-sulfonamide;
1-[(2,5-dimethylpyrazol-3-yl)methyl]-N-(1-methylcyclopropyl)-3-(5-methyl-1,3,4-thiadiazol-2-yl)-2-oxo-benzimidazole-5-sulfonamide;
1-[2-(dimethylamino)ethyl]-N-(1-methylcyclopropyl)-3-(5-methyl-1,3,4-thiadiazol-2-yl)-2-oxo-benzimidazole-5-sulfonamide;
1-[(4-methoxyphenyl)methyl]-N-(1-methylcyclopropyl)-3-(5-methyl-1,3,4-thiadiazol-2-yl)-2-oxo-benzimidazole-5-sulfonamide;
1-[(2,4-dimethylthiazol-5-yl)methyl]-N-(1-methylcyclopropyl)-3-(5-methyl-1,3,4-thiadiazol-2-yl)-2-oxo-benzimidazole-5-sulfonamide;
3-[5-(difluoromethyl)-1,3,4-thiadiazol-2-yl]-1-[(2,4-dimethylthiazol-5-yl)methyl]-N-(1-methylcyclopropyl)-2-oxo-benzimidazole-5-sulfonamide;
1-[(2,4-dimethylthiazol-5-yl)methyl]-N-(1-methylcyclopropyl)-2-oxo-3H-benzimidazole-5-sulfonamide;
1-[(2,4-dimethylthiazol-5-yl)methyl]-N-(1-methylcyclopropyl)-2-oxo-3-(1,2,4-thiadiazol-5-yl)benzimidazole-5-sulfonamide;
1-[(2,4-dimethylthiazol-5-yl)methyl]-3-(1H-imidazol-5-yl)-N-(1-methylcyclopropyl)-2-oxo-benzimidazole-5-sulfonamide;
1-[(2,4-dimethylthiazol-5-yl)methyl]-N-(1-methylcyclopropyl)-2-oxo-3-(1H-pyrazol-4-yl)benzimidazole-5-sulfonamide;
1-[(2,4-dimethylthiazol-5-yl)methyl]-3-isothiazol-4-yl-N-(1-methylcyclopropyl)-2-oxo-benzimidazole-5-sulfonamide;
N-(1-methylcyclopropyl)-3-(5-methyl-1,3,4-oxadiazol-2-yl)-2-oxo-1H-benzimidazole-5-sulfonamide;
1-[(2,4-dimethylthiazol-5-yl)methyl]-N-(1-methylcyclopropyl)-2-oxo-3-thiazol-4-yl-benzimidazole-5-sulfonamide;
1-[(2,4-dimethylthiazol-5-yl)methyl]-N-(1-methylcyclopropyl)-3-(1-methylpyrazol-3-yl)-2-oxo-benzimidazole-5-sulfonamide;
1-[(2,4-dimethylthiazol-5-yl)methyl]-N-(1-methylcyclopropyl)-2-oxo-3-thiazol-5-yl-benzimidazole-5-sulfonamide;
1-methyl-N-(1-methylcyclopropyl)-2-oxo-3-(1,2,4-thiadiazol-5-yl)benzimidazole-5-sulfonamide;
1-[(2,4-dimethylthiazol-5-yl)methyl]-N-(1-methylcyclopropyl)-3-(5-methyl-1,3,4-oxadiazol-2-yl)-2-oxo-benzimidazole-5-sulfonamide;
N-(1-methylcyclopropyl)-3-(5-methyl-1,3,4-thiadiazol-2-yl)-2-oxo-1-prop-2-ynyl-benzimidazole-5-sulfonamide;
N-(1-methylcyclopropyl)-3-(5-methyl-1,3,4-thiadiazol-2-yl)-1-(oxazol-2-ylmethyl)-2-oxo-benzimidazole-5-sulfonamide;

N-(1-methylcyclopropyl)-3-(5-methyl-1,3,4-thiadiazol-2-yl)-2-oxo-1-(1H-pyrazol-4-ylmethyl)benzimidazole-5-sulfonamide;

N-(1-methylcyclopropyl)-1-[(5-methyl-2-furyl)methyl]-3-(5-methyl-1,3,4-thiadiazol-2-yl)-2-oxo-benzimidazole-5-sulfonamide;

N-(1-methylcyclopropyl)-3-(5-methyl-1,3,4-thiadiazol-2-yl)-1-[(5-methyl-2-thienyl)methyl]-2-oxo-benzimidazole-5-sulfonamide;

1-[(2,4-dimethylthiazol-5-yl)methyl]-3-(3-methoxy-1,2,4-thiadiazol-5-yl)-N-(1-methylcyclopropyl)-2-oxo-benzimidazole-5-sulfonamide;

1-[(2,4-dimethylthiazol-5-yl)methyl]-N-(1-methylcyclopropyl)-3-(4-methylthiazol-2-yl)-2-oxo-benzimidazole-5-sulfonamide;

1-[(2,4-dimethylthiazol-5-yl)methyl]-N-(1-methylcyclopropyl)-3-(5-methylthiazol-2-yl)-2-oxo-benzimidazole-5-sulfonamide;

3-(3-bromo-1,2,4-thiadiazol-5-yl)-1-[(2,4-dimethylthiazol-5-yl)methyl]-N-(1-methylcyclopropyl)-2-oxo-benzimidazole-5-sulfonamide;

1-[(2,4-dimethylthiazol-5-yl)methyl]-N-(1-methylcyclopropyl)-2-oxo-3-pyridazin-3-yl-benzimidazole-5-sulfonamide;

1-[(2,4-dimethylthiazol-5-yl)methyl]-N-(1-methylcyclopropyl)-2-oxo-3-(1,3,4-thiadiazol-2-yl)benzimidazole-5-sulfonamide;

1-[(2,4-dimethylthiazol-5-yl)methyl]-N-(1-methylcyclopropyl)-2-oxo-3-thiazol-2-yl-benzimidazole-5-sulfonamide;

ethyl 3-[(2,4-dimethylthiazol-5-yl)methyl]-6-[(1-methylcyclopropyl)sulfamoyl]-2-oxo-benzimidazole-1-carboxylate;

3-(cyclopenten-1-yl)-1-[(2,4-dimethylthiazol-5-yl)methyl]-N-(1-methylcyclopropyl)-2-oxo-benzimidazole-5-sulfonamide;

7-fluoro-1-methyl-N-(1-methylcyclopropyl)-3-(5-methyl-1,3,4-thiadiazol-2-yl)-2-oxo-benzimidazole-5-sulfonamide;

6-fluoro-1-methyl-N-(1-methylcyclopropyl)-3-(5-methyl-1,3,4-thiadiazol-2-yl)-2-oxo-benzimidazole-5-sulfonamide;

N-methyl-54[5-[(1-methylcyclopropyl)sulfamoyl]-3-(5-methyl-1,3,4-oxadiazol-2-yl)-2-oxo-benzimidazol-1-yl]methyl]-1,2,4-oxadiazole-3-carboxamide;

1-methyl-N-(1-methylcyclopropyl)-3-(5-methyl-1,3,4-thiadiazol-2-yl)-2-oxo-7-(trifluoromethyl)benzimidazole-5-sulfonamide;

1-[3-(dimethylamino)propyl]-N-(1-methylcyclopropyl)-3-(5-methyl-1,3,4-oxadiazol-2-yl)-2-oxo-benzimidazole-5-sulfonamide;

1-(2-methoxyethyl)-N-(1-methylcyclopropyl)-3-(5-methyl-1,3,4-oxadiazol-2-yl)-2-oxo-benzimidazole-5-sulfonamide;

1-[3-(dimethylamino)propyl]-N-(1-methylcyclopropyl)-3-(5-methyl-1,3,4-thiadiazol-2-yl)-2-oxo-benzimidazole-5-sulfonamide;

N-(1-methylcyclopropyl)-1-[(1-methyl-3-piperidyl)methyl]-3-(5-methyl-1,3,4-thiadiazol-2-yl)-2-oxo-benzimidazole-5-sulfonamide;

1-[2-(dimethylamino)ethyl]-N-(1-methylcyclopropyl)-3-(5-methyl-1,3,4-oxadiazol-2-yl)-2-oxo-benzimidazole-5-sulfonamide;

N-(1-methylcyclopropyl)-3-(5-methyl-1,3,4-oxadiazol-2-yl)-1-[(1-methyl-2-piperidyl)methyl]-2-oxo-benzimidazole-5-sulfonamide;

N-(1-methylcyclopropyl)-3-(5-methyl-1,3,4-oxadiazol-2-yl)-1-[(1-methyl-3-piperidyl)methyl]-2-oxo-benzimidazole-5-sulfonamide;

N-(1-methylcyclopropyl)-3-(5-methyl-1,3,4-oxadiazol-2-yl)-2-oxo-1-[2-(1-piperidyl)ethyl]benzimidazole-5-sulfonamide;

N-(1-methylcyclopropyl)-3-(5-methyl-1,3,4-oxadiazol-2-yl)-1-(2-morpholinoethyl)-2-oxo-benzimidazole-5-sulfonamide;

N-(1-methylcyclopropyl)-3-(5-methyl-1,3,4-oxadiazol-2-yl)-2-oxo-1-(2-pyrrolidin-1-ylethyl)benzimidazole-5-sulfonamide;

N-(1-methylcyclopropyl)-1-[(1-methyl-2-piperidyl)methyl]-3-(5-methyl-1,3,4-thiadiazol-2-yl)-2-oxo-benzimidazole-5-sulfonamide;

1-(2-methoxyethyl)-N-(1-methylcyclopropyl)-3-(5-methyl-1,3,4-thiadiazol-2-yl)-2-oxo-benzimidazole-5-sulfonamide;

1-(3-methoxypropyl)-N-(1-methylcyclopropyl)-3-(5-methyl-1,3,4-thiadiazol-2-y1)-2-oxo-benzimidazole-5-sulfonamide;

N-(1-methylcyclopropyl)-3-(5-methyl-1,3,4-thiadiazol-2-yl)-2-oxo-1-[2-(1-piperidyl)ethyl]benzimidazole-5-sulfonamide;

1-(3-methoxypropyl)-N-(1-methylcyclopropyl)-3-(5-methyl-1,3,4-oxadiazol-2-y1)-2-oxo-benzimidazole-5-sulfonamide;

3-[5-[(1-methylcyclopropyl)sulfamoyl]-3-(5-methyl-1,3,4-oxadiazol-2-yl)-2-oxo-benzimidazol-1-yl]propanamide;

N-(1-methylcyclopropyl)-3-(5-methyl-1,3,4-thiadiazol-2-yl)-1-(2-morpholinoethyl)-2-oxo-benzimidazole-5-sulfonamide;

N-(1-methylcyclopropyl)-3-(5-methyl-1,3,4-thiadiazol-2-yl)-2-oxo-1-(2-pyrrolidin-1-yl ethyl)benzimidazol e-5-sulfonamide;

3-[5-[(1-methylcyclopropyl)sulfamoyl]-3-(5-methyl-1,3,4-thiadiazol-2-yl)-2-oxo-benzimidazol-1-yl]propanamide;

N-(1-methylcyclopropyl)-1-[(1-methylpyrrolidin-2-yl)methyl]-3-(5-methyl-1,3,4-thiadiazol-2-yl)-2-oxo-benzimidazol e-5-sulfonamide;

N-[1-(fluoromethyl)cyclopropyl]—1-methyl-3-(5-methyl-1,3,4-thiadiazol-2-yl)-2-oxo-benzimidazole-5-sulfonamide;

N-(1-cyanocyclopropyl)-3-(5-methyl-1,3,4-thiadiazol-2-yl)-2-oxo-1H-benzimidazole-5-sulfonamide;

N-(1-cyanocyclopropyl)-1-ethyl-3-(5-methyl-1,3,4-thiadiazol-2-yl)-2-oxo-benzimidazole-5-sulfonamide;

1-ethyl-N-[1-(fluoromethyl)cyclopropyl]-3-(5-methyl-1,3,4-thiadiazol-2-yl)-2-oxo-benzimidazole-5-sulfonamide;

N— [1-(fluoromethyl)cyclopropyl]—1-(2-methoxyethyl)-3-(5-methyl-1,3,4-thiadiazol-2-yl)-2-oxo-benzimidazol e-5-sulfonamide;

N-(1-cyanocyclopropyl)-1-(2-methoxyethyl)-3-(5-methyl-1,3,4-thiadiazol-2-yl)-2-oxo-benzimidazole-5-sulfonamide;

N-(1-cyanocyclopropyl)-3-[5-(difluoromethyl)-1,3,4-thiadiazol-2-yl]—1-(2-methoxyethyl)-2-oxo-benzimidazol e-5-sulfonamide;

3-[5-(difluoromethyl)-1,3,4-thiadiazol-2-yl]-N— [1-(fluoromethyl)cyclopropyl]—1-(2-methoxyethyl)-2-oxo-benzimidazol e-5-sulfonamide;

3-[5-(difluoromethyl)-1,3,4-thiadiazol-2-yl]—1-[(2,5-dimethylpyrazol-3-yl)methyl]-N— [1-(fluoromethyl)cyclopropyl]-2-oxo-benzimidazole-5- sulfonamide;

N-(1-cyanocyclopropyl)-3-[5-(difluoromethyl)-1,3,4-thiadiazol-2-yl]—1-[(2,5-dimethylpyrazol-3-yl)methyl]-2-oxo-benzimidazole-5-sulfonamide;
1-(cyanomethyl)-N-(1-methylcyclopropy1)-3-(5-methyl-1,3,4-thiadiazol-2-yl)-2-oxo-benzimidazol e-5-sulfonamide;
3-[5-(difluoromethyl)-1,3,4-thiadiazol-2-yl]-6-fluoro-N4 1-(fluoromethyl)cyclopropyl]—1-(2-methoxyethyl)-2-oxo-benzimidazole-5-sulfonamide;
3-[5-(difluoromethyl)-1,3,4-thiadiazol-2-yl]-6-fluoro-1-(2-methoxyethyl)-N-(1-methylcyclopropyl)-2-oxo-benzimidazol e-5-sulfonamide;
3-[5-(difluoromethyl)-1,3,4-thiadiazol-2-yl]—1-(2-methoxyethyl)-N-(1-methylcyclopropyl)-2-oxo-benzimidazol e-5-sulfonamide;
3-[5-(difluoromethyl)-1,3,4-thiadiazol-2-yl]—1-[3-(dimethylamino)propyl]-N-[1-(fluoromethyl)cyclopropyl]-2-oxo-benzimidazole-5-sulfonamide;
6-fluoro-1-methyl-N-(1-methylcyclopropyl)-3-(3-methyl-1,2,4-thiadiazol-5-yl)-2-oxo-benzimidazole-5-sulfonamide;
6-fluoro-N-[1-(fluoromethyl)cyclopropyl]—1-methyl-3-(3-methyl-1,2,4-thiadiazol-5-yl)-2-oxo-benzimidazole-5-sulfonamide;
3-[5-(difluoromethyl)-1,3,4-thiadiazol-2-yl]-6-fluoro-1-methyl-N-(1-methylcyclopropyl)-2-oxo-benzimidazole-5-sulfonamide;
3-[5-(difluoromethyl)-1,3,4-thiadiazol-2-yl]-6-fluoro-N4 1-(fluoromethyl)cyclopropyl]—1-methyl-2-oxo-benzimidazole-5-sulfonamide;
N-[1-(fluoromethyl)cyclopropyl]-1-methyl-2-oxo-3-(1,2,4-thiadiazol-5-yl)benzimidazol e-5-sulfonamide;
1-methyl-N-(1-methylcyclopropyl)-3-(3-methyl-1,2,4-thiadiazol-5-yl)-2-oxo-benzimidazole-5-sulfonamide;
N-[1-(fluoromethyl)cyclopropyl]—1-methyl-3-(3-methyl-1,2,4-thiadiaz 01-5-yl)-2-oxo-benzimidazol e-5-sulfonamide;
1-(cyanomethyl)-N-[1-(fluoromethyl)cyclopropyl]-3-(5-methyl-1,3,4-thiadiazol-2-yl)-2-oxo-benzimidazole-5-sulfonamide;
1-(cyanomethyl)-N-(1-methylcyclopropyl)-3-(3-methyl-1,2,4-thiadiazol-5-yl)-2-oxo-benzimidazole-5-sulfonamide;
1-(cyanomethyl)-N-[1-(fluoromethyl)cyclopropyl]-3-(3-methyl-1,2,4-thiadiazol-5-yl)-2-oxo-benzimidazole-5-sulfonamide;
3-[5-(difluoromethyl)-1,3,4-thiadiazol-2-yl]-N-[1-(fluoromethyl)cyclopropyl]-1-methyl-2-oxo-benzimidazole-5-sulfonamide;
1-(2-methoxyethyl)-N-(1-methylcyclopropyl)-3-(3-methyl-1,2,4-thiadiazol-5-yl)-2-oxo-benzimidazole-5-sulfonamide;
N-[1-(fluoromethyl)cyclopropyl]-1-(2-methoxyethyl)-2-oxo-3-(1,2,4-thiadiazol-5-yl)benzimidazole-5-sulfonamide;
N-[1-(fluoromethyl)cyclopropyl]-1-(2-methoxyethyl)-3-(3-methyl-1,2,4-thiadiazol-5-yl)-2-oxo-benzimidazole-5-sulfonamide;
N-[1-(fluoromethyl)cyclopropyl]-1-(3-methoxypropyl)-3-(3-methyl-1,2,4-thiadiazol-5-yl)-2-oxo-benzimidazole-5-sulfonamide;
1-[2-(dimethylamino)ethyl]-N-[1-(fluoromethyl)cyclopropyl]-3-(3-methyl-1,2,4-thiadiazol-5-yl)-2-oxo-benzimidazole-5-sulfonamide;
N-[1-(fluoromethyl)cyclopropyl]-1-(3-methoxypropyl)-3-(5-methyl-1,3,4-thiadiazol-2-yl)-2-oxo-benzimidazole-5-sulfonamide;
1-[2-(dimethylamino)ethyl]-N-[1-(fluoromethyl)cyclopropyl]-3-(5-methyl-1,3,4-thiadiazol-2-yl)-2-oxo-benzimidazole-5-sulfonamide;
1-methyl-N-(1-methylcyclopropyl)-3-(5-methyl-1,3,4-oxadiazol-2-yl)-2-oxo-benzimidazole-5-sulfonamide;
1-ethyl-N-(1-methylcyclopropyl)-3-(5-methyl-1,3,4-oxadiazol-2-yl)-2-oxo-benzimidazole-5-sulfonamide;
1-(2-fluoroethyl)-N-(1-methylcyclopropyl)-3-(5-methyl-1,3,4-oxadiazol-2-yl)-2-oxo-benzimidazole-5-sulfonamide;
6-fluoro-N-(1-methylcyclopropyl)-3-(5-methyl-1,3,4-oxadiazol-2-yl)-2-oxo-1H-benzimidazole-5-sulfonamide;
3-[5-(difluoromethyl)-1,3,4-thiadiazol-2-yl]-N-[1-(fluoromethyl)cyclopropyl]-2-oxo-1-prop-2-ynyl-benzimidazole-5-sulfonamide;
6-fluoro-N-[1-(fluoromethyl)cyclopropyl]-3-(5-methyl-1,3,4-oxadiazol-2-yl)-2-oxo-1H-benzimidazole-5-sulfonamide;
3-[5-(difluoromethyl)-1,3,4-oxadiazol-2-yl]-1-methyl-N-(1-methylcyclopropyl)-2-oxo-benzimidazole-5-sulfonamide;
3-[5-(difluoromethyl)-1,3,4-oxadiazol-2-yl]-N-[1-(fluoromethyl)cyclopropyl]-1-methyl-2-oxo-benzimidazole-5-sulfonamide;
6-fluoro-1-methyl-N-(1-methylcyclopropyl)-3-(5-methyl-1,3,4-oxadiazol-2-yl)-2-oxo-benzimidazole-5-sulfonamide;
6-fluoro-1-(2-fluoroethyl)-N-(1-methylcyclopropyl)-3-(5-methyl-1,3,4-oxadiazol-2-yl)-2-oxo-benzimidazole-5-sulfonamide;
3-[5-(difluoromethyl)-1,3,4-oxadiazol-2-yl]-1-ethyl-6-fluoro-N-(1-methylcyclopropyl)-2-oxo-benzimidazole-5-sulfonamide;
3-[5-(difluoromethyl)-1,3,4-oxadiazol-2-yl]-1-ethyl-6-fluoro-N-[1-(fluoromethyl)cyclopropyl]-2-oxo-benzimidazole-5-sulfonamide;
3-[5-(difluoromethyl)-1,3,4-oxadiazol-2-yl]-1-ethyl-N-(1-methylcyclopropyl)-2-oxo-benzimidazole-5-sulfonamide;
3-[5-(difluoromethyl)-1,3,4-oxadiazol-2-yl]-1-ethyl-N-[1-(fluoromethyl)cyclopropyl]-2-oxo-benzimidazole-5-sulfonamide;
6-fluoro-N-[1-(fluoromethyl)cyclopropyl]-1-(2-methoxyethyl)-3-(6-methylpyridazin-3-yl)-2-oxo-benzimidazole-5-sulfonamide;
6-fluoro-N-[1-(fluoromethyl)cyclopropyl]-1-methyl-3-(6-methylpyridazin-3-yl)-2-oxo-benzimidazole-5-sulfonamide;
6-fluoro-1-methyl-N-(1-methylcyclopropyl)-3-(6-methylpyridazin-3-yl)-2-oxo-benzimidazole-5-sulfonamide;
6-fluoro-N-[1-(fluoromethyl)cyclopropyl]-1-methyl-2-oxo-3-[6-(trifluoromethyl)pyridazin-3-yl]benzimidazole-5-sulfonamide;
3-[5-(difluoromethyl)-1,3,4-thiadiazol-2-yl]-1-ethyl-6-fluoro-N-(1-methylcyclopropyl)-2-oxo-benzimidazole-5-sulfonamide;
3-[5-(difluoromethyl)-1,3,4-thiadiazol-2-yl]-1-ethyl-6-fluoro-N-[1-(fluoromethyl)cyclopropyl]-2-oxo-benzimidazole-5-sulfonamide;
3-[5-(difluoromethyl)-1,3,4-oxadiazol-2-yl]-6-fluoro-1-methyl-N-(1-methylcyclopropyl)-2-oxo-benzimidazole-5-sulfonamide;
3-[5-(difluoromethyl)-1,3,4-oxadiazol-2-yl]-6-fluoro-N-[1-(fluoromethyl)cyclopropyl]-1-methyl-2-oxo-benzimidazole-5-sulfonamide;

3-[5-(difluoromethyl)-1,3,4-oxadiazol-2-yl]-6-fluoro-1-(2-fluoroethyl)-N-(1-methylcyclopropyl)-2-oxo-benzimidazole-5-sulfonamide;

3-[5-(difluoromethyl)-1,3,4-oxadiazol-2-yl]-6-fluoro-1-(2-fluoroethyl)-N-[1-(fluoromethyl)cyclopropyl]-2-oxo-benzimidazole-5-sulfonamide;

3-[5-(difluoromethyl)-1,3,4-thiadiazol-2-yl]-6-fluoro-N41-(fluoromethyl)cyclopropyl]-2-oxo-1-prop-2-ynyl-benzimidazole-5-sulfonamide;

2-[3-[5-(difluoromethyl)-1,3,4-thiadiazol-2-yl]-6-fluoro-5-[[1-(fluoromethyl)cyclopropyl]sulfamoyl]-2-oxo-benzimidazol-1-yl]acetamide;

1-(cyanomethyl)-3-[5-(difluoromethyl)-1,3,4-thiadiazol-2-yl]-6-fluoro-N-[1-(fluoromethyl)cyclopropyl]-2-oxo-benzimidazole-5-sulfonamide;

3-[5-(Difluoromethyl)-1,3,4-thiadiazol-2-yl]-6-fluoro-1-(2-fluoroethyl)-N-[1-(fluoromethyl)cyclopropyl]-2-oxo-benzimidazole-5-sulfonamide; and 3-[5-(Difluoromethyl)-1,3,4-thiadiazol-2-yl]-6-fluoro-1-(2-fluoroethyl)-N-(1-methylcyclopropyl)-2-oxo-benzimidazole-5-sulfonamide.

16. A pharmaceutical composition comprising a compound according to claim 1, or a pharmaceutically acceptable salt or solvate thereof, in admixture with a pharmaceutically acceptable diluent or carrier.

* * * * *

UNITED STATES PATENT AND TRADEMARK OFFICE
CERTIFICATE OF CORRECTION

| | | |
|---|---|---|
| PATENT NO. | : 10,995,073 B2 | Page 1 of 1 |
| APPLICATION NO. | : 16/662997 | |
| DATED | : May 4, 2021 | |
| INVENTOR(S) | : McGonagle et al. | |

It is certified that error appears in the above-identified patent and that said Letters Patent is hereby corrected as shown below:

On the Title Page

Left Column, item (72) Inventors:
Please delete "Bodhan Waszkowycz" and insert --Bohdan Waszkowycz--

Signed and Sealed this
Fourth Day of January, 2022

Drew Hirshfeld
*Performing the Functions and Duties of the
Under Secretary of Commerce for Intellectual Property and
Director of the United States Patent and Trademark Office*